US009145414B2

(12) United States Patent
Sakamoto et al.

(10) Patent No.: US 9,145,414 B2
(45) Date of Patent: Sep. 29, 2015

(54) 1,2,4-TRIAZINE-6-CARBOXAMIDE DERIVATIVE

(71) Applicant: TAIHO PHARMACEUTICAL CO., LTD., Chiyoda-ku (JP)

(72) Inventors: Toshihiro Sakamoto, Moriya (JP); Takashi Mita, Tsukuba (JP); Kazuaki Shibata, Tsukuba (JP); Yoshio Ogino, Tsukuba (JP); Hideya Komatani, Toride (JP)

(73) Assignee: TAIHO PHARMACEUTICAL CO., LTD., Chiyoda-ku (JP)

( * ) Notice: Subject to any disclaimer, the term of this patent is extended or adjusted under 35 U.S.C. 154(b) by 0 days.

(21) Appl. No.: 14/348,339

(22) PCT Filed: Sep. 28, 2012

(86) PCT No.: PCT/JP2012/075204
§ 371 (c)(1),
(2) Date: Aug. 4, 2014

(87) PCT Pub. No.: WO2013/047813
PCT Pub. Date: Apr. 4, 2013

(65) Prior Publication Data
US 2014/0343038 A1   Nov. 20, 2014

(30) Foreign Application Priority Data
Sep. 30, 2011   (JP) ................................. 2011-217750

(51) Int. Cl.
*C07D 401/12* (2006.01)
*C07D 401/14* (2006.01)
*C07D 403/12* (2006.01)
*C07D 403/14* (2006.01)
*C07D 405/12* (2006.01)
*C07D 405/14* (2006.01)
*C07D 409/12* (2006.01)
*C07D 409/14* (2006.01)
*C07D 413/12* (2006.01)
*C07D 417/12* (2006.01)
*C07D 417/14* (2006.01)
*C07D 471/04* (2006.01)
*C07D 495/04* (2006.01)
*A61K 31/53* (2006.01)
*A61K 31/535* (2006.01)
*A61P 35/00* (2006.01)

(52) U.S. Cl.
CPC .............. *C07D 471/04* (2013.01); *A61K 31/53* (2013.01); *A61K 31/535* (2013.01); *C07D 401/12* (2013.01); *C07D 401/14* (2013.01); *C07D 403/12* (2013.01); *C07D 403/14* (2013.01); *C07D 405/12* (2013.01); *C07D 405/14* (2013.01); *C07D 409/12* (2013.01); *C07D 409/14* (2013.01); *C07D 413/12* (2013.01); *C07D 417/12* (2013.01); *C07D 417/14* (2013.01); *C07D 495/04* (2013.01)

(58) Field of Classification Search
CPC .. C07D 401/12; C07D 401/14; C07D 403/12; C07D 403/14; C07D 405/12; C07D 405/14; C07D 409/12; C07D 409/14; C07D 413/12; C07D 417/12; C07D 417/14; C07D 471/04; C07D 495/04; A61K 31/53; A61K 31/535
USPC .......................................... 544/182; 514/242
See application file for complete search history.

(56) References Cited

U.S. PATENT DOCUMENTS 6,432,963 B1    8/2002  Hisamichi et al.
6,797,706 B1 *  9/2004  Hisamichi et al. ............ 514/183

FOREIGN PATENT DOCUMENTS

EP        1 184 376 A1      3/2002
WO     WO 99/31073 A1       6/1999
WO     WO 00/75113 A1      12/2000
(Continued)

OTHER PUBLICATIONS

Witzig et al., Hematology Am Soc Hematol Educ Program. 2010;2010:265-70.*
Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Gautschi et al., Clin. Cancer Res., 14(6), 1639-1648, 2008.*
Mountzios et al., Cancer Treatments Reviews, 34, 175-182, 2008.*
Pyne et al. Cancer Res 2011 ;71:6576-6582.*
Hulikal, V. Deuterium Labeled Compounds in Drug Discovery Process-Abstract, www.hwb.gov.in/htmldocs/nahwd2010/L15.pdf.*
International Search Report and Written Opinion issued Oct. 30, 2012 in PCT/JP2012/075204.
Linfeng Chen, et al., "SYK-dependent tonic B-cell receptor signaling is a rational treatment target in diffuse large B-cell lymphoma" Blood, vol. 111, No. 4, Feb. 15, 2008, pp. 2230-2237.

(Continued)

*Primary Examiner* — Venkataraman Balasubramanian
(74) *Attorney, Agent, or Firm* — Oblon, McClelland, Maier & Neustadt, L.L.P.

(57) ABSTRACT

The present invention provides a compound represented by the following general formula (I) or a salt thereof which has a Syk inhibitory effect (in the formula $R_1$ represents a hydrogen atom or an optionally substituted $C_1$-$C_6$ alkyl group; A represents a hydrogen atom, an optionally substituted $C_1$-$C_8$ alkyl group, an optionally substituted $C_2$-$C_6$ alkenyl group, an optionally substituted $C_2$-$C_6$ alkynyl group, an optionally substituted $C_3$-$C_{10}$ cycloalkyl group, an optionally substituted $C_6$-$C_{14}$ aromatic hydrocarbon group, an optionally substituted 4- to 10-membered unsaturated heterocyclic group, or an optionally substituted 4- to 10-membered saturated heterocyclic group, or optionally forms a 4- to 10-membered unsaturated heterocyclic ring or a 4- to 10-membered saturated heterocyclic ring together with $R_1$ and the nitrogen atom bonded thereto; $R_2$ represents a hydrogen atom or an optionally substituted $C_1$-$C_6$ alkyl group; and B represents an optionally substituted unsaturated heterocyclic group).

10 Claims, No Drawings

(56) References Cited

FOREIGN PATENT DOCUMENTS

| WO | WO 00/76980 A1 | 12/2000 |
|---|---|---|
| WO | WO 2013/192049 A2 | 12/2013 |

OTHER PUBLICATIONS

Maike Buchner, et al., "Spleen Tyrosine Kinase is Overexpressed and Represents a Potential Therapeutic Target in Chronic Lymphocytic Leukemia" Cancer Research, vol. 69, No. 13, Jul. 1, 2009, pp. 5424-5432.

Omer N. Pamuk, et al., "Spleen tyrosine kinase inhibition in the treatment of autoimmune, allergic and autoinflammatory diseases" Arthritis Research & Therapy, vol. 12, No. 6, 2010, 11 Pages.

Sylvia Braselmann, et al., "R406, an Orally Available Spleen Tyrosine Kinase Inhibitor Blocks Fc Receptor Signaling and Reduces Immune Complex-Mediated Inflammation" Journal of Pharmacology and Experimental Therapeutics, vol. 319, No. 3, 2006, pp. 998-1008.

Jonathan W. Friedberg, et al., "Inhibition of Syk with fostamatinib disodium has significant clinical activity in non-Hodgkin lymphoma and chronic lymphocytic leukemia" Blood, vol. 115, No. 13, Apr. 1, 2010, pp. 2578-2585.

Friedberg, J.W., et al., blood 2010 115: 2578-2585 doi:10 1182/blood-2009-08-236471 originally published online Nov. 17, 2009, "inhibition if Syk with fostamatinib disodium has significant clinical activity in non-Hodgkin lymphoma and chronic lymphocytic leukemia".

Hahn CK, et al., Cancer Cell 16, Oct. 6, 2009;16(4):281-94. DOI 10.1016/j. ccr. 2009. 08.018. "Proteomic and genetic approaches identify Syk as an AML target".

Gioia, R., Blood. Jul. 5, 2011, 118:2211-2221. doi: 10.1182/blood-2010-10-313692. Originally published online Jul. 5, 2011, "Quantitative phosphoproteomics revealed interplay between Syk and Lyn in the resistance to nilotinib in chronic myeloid leukemia cells".

Suljagic M., blood 2010 116: 4894-4905, doi:10.1182/blood-2010-03-275180 originally published online Aug. 17, 2010, "The Syk inhibitor fostamatinib disodium (R788) inhibits tumor growth in the E TCL transgenic mouse model of CLL by blocking antigen-dependent B-cell receptor signaling".

Buchner, M., et al., Cancer Res 2009; 69:(13), Jul. 1, 2009, 5424-5432, "Spleen Tyrosine Kinase is Overexposed and Represents a Potential Therapeutic Target in Chronic Lymphocytic Leukemia".

B. Streubel, et al., Leukemia (2006) 20, 313-318, "Novel t(5;9)(q33;q22) fuses ITK to SYK in unspecified peripheral T-cell lymphoma".

Konstanze Pechloff, et al., JEM vol. 207 No. 5 1031-1044, "The fusion kinase ITK-SYK mimics a T cell receptor signal and drives oncogenesis in conditional mouse models of peripheral T cell lymphoma", 2010.

Extended European Search Report issued Feb. 25, 2015, in Patent Application No. 12836932.9.

* cited by examiner

1,2,4-TRIAZINE-6-CARBOXAMIDE DERIVATIVE

FIELD OF THE INVENTION

The present invention relates to a novel 1,2,4-triazine-6-carboxamide derivative having a Syk (spleen tyrosine kinase) inhibitory effect and a pharmaceutical composition comprising the same as an active ingredient.

BACKGROUND OF THE INVENTION

Syk, a non-receptor tyrosine kinase constituting the Syk family with ZAP70, is expressed in a wide range of immune-related cells including B cells, macrophages, neutrophils, and mast cells and involved in their functions. Syk binds to the ITAM domains of immunoreceptors such as Fc receptor family (FcR) or B cell receptor (BCR) expressed in these cells and plays a role in transducing downstream signals from these receptors. In B cells, Syk is activated by BCR after antigen stimulation. The activated Syk activates various downstream signaling pathways such as PI3K, $Ca^{2+}$-NFAT, and RAS-MAPK pathways and finally plays an important role in B cell activation, differentiation, and maturation.

In recent years, it has become increasingly evident that these B cell receptor signals and Syk functions play an important role in the growth or survival of B cell-derived blood cancer such as B cell lymphoma or chronic lymphatic leukemia (CLL). Specifically, the B cell receptor signals in diffuse large B cell lymphoma (DLBCL) are chronically activated in an antigen-independent manner, and the activated signals are essential for the growth or survival of cancer cells (Non Patent Document 1). The high expression or activation of Syk reportedly plays an important role in the survival of CLL (Non Patent Document 2). According to the further reports, the treatment of these blood cancer cells with compounds having a Syk inhibitory effect is effective for inhibiting their growth or inducing cell death (Non Patent Documents 1 and 2). Thus, from these pieces of information, the inhibition of Syk is expected to produce therapeutic effects on B cell lymphoma or CLL. Also, it has been suggested that Syk is involved in malignant transformation to peripheral T cell lymphoma (PTCL), myelodysplastic syndrome (MDS), and blood cancer of origin other than B cells, such as acute myeloid leukemia (AML). Accordingly, Syk inhibitors are expected to be able to serve as therapeutic agents effective not only for B cell-derived cancer but for T cell lymphoma or AML.

The Syk inhibitors have also been reported to be able to serve as therapeutic agents for cancer as well as autoimmune diseases (rheumatoid arthritis, systemic lupus erythematosus, nephrotic syndrome, etc.), allergic diseases (bronchial asthma, allergic rhinitis, atopic dermatitis, contact dermatitis, urticaria, food allergy, conjunctivitis, etc.), chronic obstructive pulmonary disease (COPD), and the like (Non Patent Document 3).

R406 (Rigel Pharmaceuticals, Inc.), which is a Syk inhibitor currently under development (Non Patent Document 4), has low selectivity for Syk and reportedly has adverse effects attributed to its inhibition of kinases other than Syk (Non Patent Document 5).

Heteroaromatic carboxamide derivatives have also been reported as other Syk inhibitors (Patent Document 1) and however, still have insufficient Syk inhibitory activity. Alternatively, Patent Document 2 has reported 1,2,4-triazine-6-carboxamide derivatives and however, has no mention about Syk inhibitory activity.

CITATION LIST

Patent Documents

[Patent Document 1] International Publication No. WO2000/075113
[Patent Document 2] International Publication No. WO2000/076980

Non-Patent Documents

[Non Patent Document 1] Blood. 2008; 111 (4): 2230-7.
[Non Patent Document 2] Cancer Res. 2009; 69 (13): 5424-32.
[Non Patent Document 3] Arthritis Res Ther. 2010; 12 (6): 222.
[Non Patent Document 4] J Pharmacol Exp Ther. 2006; 319 (3): 998-1008.
[Non Patent Document 5] Blood. 2010; 115 (13): 2578-85.

SUMMARY OF THE INVENTION

Problems to be Solved by the Invention

As described above, Syk inhibitors are expected to have therapeutic effects on various diseases including cancer (particularly, blood cancer), autoimmune diseases, and allergic diseases. Unfortunately, selective and strong Syk inhibitors have not yet been found.

Thus, an object of the present invention is to provide a novel compound which inhibits Syk selectively and strongly or a salt thereof.

Means for Solving the Problems

The present inventors have conducted diligent studies to attain the object and consequently completed the present invention by finding that a compound group which has 1,2,4-triazine-6-carboxamide as a basic structure and has an unsaturated heterocyclic group via N at position 5 of the triazine ring has excellent inhibitory activity against Syk with high selectivity and a cancer cell growth inhibitory effect and is useful as a pharmaceutical agent for treating cancer.

Specifically, the present invention provides a compound represented by the following general formula (I) or a salt thereof:

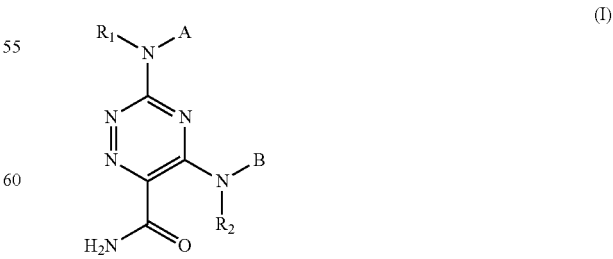

wherein
$R_1$ represents a hydrogen atom or an optionally $R_a$-substituted $C_1$-$C_6$ alkyl group;

A represents an optionally $R_a$-substituted $C_1$-$C_8$ alkyl group, an optionally $R_a$-substituted $C_2$-$C_6$ alkenyl group, an optionally $R_a$-substituted $C_2$-$C_6$ alkynyl group, an optionally $R_b$-substituted $C_3$-$C_{10}$ cycloalkyl group, an optionally $R_b$-substituted $C_6$-$C_{14}$ aromatic hydrocarbon group, an optionally $R_b$-substituted 4- to 10-membered saturated heterocyclic group, or an optionally $R_b$-substituted 4- to 10-membered unsaturated heterocyclic group, or optionally forms a 4- to 10-membered saturated heterocyclic ring or a 4- to 10-membered unsaturated heterocyclic ring together with $R_1$ and the nitrogen atom bonded thereto;

$R_a$ represents a heavy hydrogen atom, a halogen atom, a cyano group, a nitro group, —C(=O)$OR_x$, —C(=O)$SR_x$, —C(=S)$OR_x$, —N($R_x$)($R_y$), —$NR_x$C(=O)$R_y$, —$NR_x$SO$_2R_y$, —$NR_x$C(=O)$OR_y$, —$NR_x$C(=O)N($R_y$)($R_z$), —$NR_x$SO$_2$N($R_y$)($R_z$), —N($R_x$)—$OR_y$, =$NR_x$, =N—$OR_x$, —$OR_x$, —OC(=O)$R_x$, —OC(=S)$R_x$, —OC(=O)$OR_x$, —OC(=O) N($R_x$)($R_y$), —OC(=S)$OR_x$, —$SR_x$, —SO$_2R_x$, —SO$_2$N($R_x$)($R_y$), a $C_3$-$C_{10}$ cycloalkyl group, a $C_6$-$C_{14}$ aromatic hydrocarbon group, a 4- to 10-membered saturated heterocyclic group, or a 4- to 10-membered unsaturated heterocyclic group (wherein the $C_3$-$C_{10}$ cycloalkyl group, the $C_6$-$C_{14}$ aromatic hydrocarbon group, the 4- to 10-membered saturated heterocyclic group, and the 4- to 10-membered unsaturated heterocyclic group are each independently optionally substituted by 1 to 3 substituent(s) selected from the group consisting of a heavy hydrogen atom, a halogen atom, a hydroxyl group, a cyano group, a nitro group, an amino group, an oxo group, an oxide group, an imino group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group);

$R_b$ represents a heavy hydrogen atom, a halogen atom, a cyano group, a nitro group, an oxo group, an oxide group, —C(=O)$OR_x$, —C(=O)$SR_x$, —C(=S)$OR_x$, —N($R_x$)($R_y$), —$NR_x$C(=O)$R_y$, —$NR_x$SO$_2R_y$, —$NR_x$C(=O)$OR_y$, —$NR_x$C(=O) N($R_y$)($R_z$), —$NR_x$SO$_2$N($R_y$)($R_x$), —N($R_x$)—$OR_y$, =$NR_x$, =N—$OR_x$, —$OR_x$, —OC(=O)$R_x$, —OC(=S)$R_x$, —OC(=O)$OR_x$, —OC(=O)N($R_x$)($R_y$), —OC(=S)$OR_x$, —$SR_x$, —SO$_2R_x$, —SO$_2$N($R_x$)($R_y$), a $C_1$-$C_6$ alkyl group, a $C_1$-$C_6$ haloalkyl group, a $C_1$-$C_6$ deuterated alkyl group, a $C_2$-$C_6$ alkenyl group, or a $C_2$-$C_6$ alkynyl group;

$R_2$ represents a hydrogen atom or an optionally $R_a$-substituted $C_1$-$C_6$ alkyl group;

B represents an optionally $R_c$-substituted unsaturated heterocyclic group;

$R_c$ represents a heavy hydrogen atom, a halogen atom, a cyano group, a nitro group, an oxo group, an oxide group, —C(=O)$R_x$, —C(=O)$OR_x$, —C(=O)N($R_x$)($R_y$), —C(=O)$SR_x$, —C(=S)$OR_x$, —N($R_x$)($R_y$), —$NR_x$C(=O)$R_y$, —$NR_x$SO$_2R_y$, —$NR_x$C(=O)$OR_x$, —$NR_x$C(=O)N($R_y$)($R_z$), —$NR_x$SO$_2$N($R_y$)($R_z$), —N($R_x$)—$OR_y$, =$NR_x$, =N—$OR_x$, —$OR_x$, —OC(=O)$R_x$, —OC(=S)$R_x$, —OC(=O) $OR_x$, —OC(=O) N($R_x$)($R_y$), —OC(=S) $OR_x$, —$SR_x$, —SO$_2R_x$, —SO$_2$N($R_x$)($R_y$), a $C_1$-$C_6$ alkyl group, a $C_1$-$C_6$ haloalkyl group, a $C_1$-$C_6$ deuterated alkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, a 4- to 10-membered saturated heterocyclic group, or a 4- to 10-membered unsaturated heterocyclic group (wherein the $C_1$-$C_6$ alkyl group, the $C_1$-$C_6$ haloalkyl group, the $C_1$-$C_6$ deuterated alkyl group, the $C_2$-$C_6$ alkenyl group, and the $C_2$-$C_6$ alkynyl group are each independently optionally substituted by 1 to 3 substituent(s) selected from the group consisting of a cyano group, a nitro group, —N($R_x$)($R_y$), and —$OR_x$, and the $C_3$-$C_{10}$ cycloalkyl group, the $C_6$-$C_{14}$ aromatic hydrocarbon group, the 4- to 10-membered saturated heterocyclic group, and the 4- to 10-membered unsaturated heterocyclic group are each independently optionally substituted by 1 to 3 substituent(s) selected from the group consisting of $R_d$, an oxo group, an oxide group, a $C_1$-$C_6$ alkyl group, a $C_1$-$C_6$ haloalkyl group, a $C_1$-$C_6$ deuterated alkyl group, a $C_2$-$C_6$ alkenyl group, and a $C_2$-$C_6$ alkynyl group);

$R_d$ represents a heavy hydrogen atom, a halogen atom, a cyano group, a nitro group, —C(=O)$R_x$, —C(=O)$OR_x$, —C(=O)N($R_x$)($R_y$), —C(=O)$SR_x$, —C(=S)$OR_x$, —N($R_x$)($R_y$), —$NR_x$C(=O)$R_y$, —$NR_x$SO$_2R_y$, —$NR_x$C(=O)$OR_y$, —$NR_x$C(=O) N($R_y$)($R_z$), —$NR_x$SO$_2$N($R_y$)($R_z$), —N($R_x$)—$OR_y$, =$NR_x$, =N—$OR_x$, —$OR_x$, —OC(=O)$R_x$, —OC(=S)$R_x$, —OC(=O)$OR_x$, —OC(=O)N($R_x$)($R_y$), —OC(=S)$OR_x$, —$SR_x$, —SO$_2R_x$, or —SO$_2$N($R_x$)($R_y$); and $R_x$, $R_y$, and $R_z$ are the same as or different from each other and each represent a hydrogen atom, a $C_1$-$C_6$ alkyl group, a $C_1$-$C_6$ haloalkyl group, a $C_1$-$C_6$ deuterated alkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, a 4- to 10-membered saturated heterocyclic group, or a 4- to 10-membered unsaturated heterocyclic group.

The present invention also provides pharmaceutical agents such as a Syk inhibitor and an antitumor agent comprising the compound represented by the general formula (I) as an active ingredient.

The present invention further provides a pharmaceutical agent comprising the compound represented by the general formula (1) or the salt thereof.

The present invention further provides a pharmaceutical composition comprising the compound represented by the general formula (1) or the salt thereof and a pharmaceutically acceptable carrier.

The present invention further provides the compound represented by the general formula (1) or the salt thereof for use in the treatment of tumor.

The present invention further provides use of the compound represented by the general formula (1) or the salt thereof for production of an antitumor agent.

The present invention further provides a method for treating tumor, comprising administering the compound represented by the general formula (1) or the salt thereof.

Effects of the Invention

The present invention provides a novel compound represented by the general formula (I) or a salt thereof which is useful as a Syk inhibitor.

The compound of the present invention or the salt thereof has been shown to have excellent Syk inhibitory activity and exhibit a growth inhibitory effect on cancer cell lines. The compound of the present invention or the salt thereof also advantageously has few adverse effects attributed to other kinases, by virtue of its excellent selectivity for Syk. Thus, the compound of the present invention or the salt thereof is useful as a preventive and/or therapeutic agent for tumor, particularly, cancer.

DETAILED DESCRIPTION OF THE INVENTION

The compound represented by the general formula (I) of the present invention has a 1,2,4-triazine skeleton and has an unsaturated heterocyclic group via N at position 5 thereof. This compound is a novel compound which is not described in any of the literatures in Citation List or the like.

In the present specification, specific examples of the "halogen atom" include a chlorine atom, a bromine atom, a fluorine atom, and an iodine atom.

In the present specification, the "$C_1$-$C_8$ alkyl group" refers to a linear or branched alkyl group having 1 to 8 carbon atoms. Specific examples thereof include a methyl group, an ethyl group, a n-propyl group, an isopropyl group, a n-butyl group, an isobutyl group, a sec-butyl group, a tert-butyl group, a pentyl group, a hexyl group, a heptyl group, and an octyl group.

In the present specification, the "$C_1$-$C_6$ alkyl group" refers to a linear or branched alkyl group having 1 to 6 carbon atoms. Specific examples thereof include a methyl group, an ethyl group, a n-propyl group, an isopropyl group, a n-butyl group, an isobutyl group, a sec-butyl group, a tert-butyl group, a pentyl group, and a hexyl group.

In the present specification, the "$C_1$-$C_6$ haloalkyl group" refers to a group in which one to all hydrogen atoms in the $C_1$-$C_6$ alkyl group are replaced with the halogen atom(s). Specific examples thereof include a monofluoromethyl group, a difluoromethyl group, a trifluoromethyl group, a 1-fluoroethyl group, a 2-fluoroethyl group, a 1,1-difluoroethyl group, a 1,2-difluoroethyl group, and a 2,2-difluoroethyl group.

In the present specification, the "$C_1$-$C_6$ deuterated alkyl group" refers to a group in which one to all hydrogen atoms in the $C_1$-$C_6$ alkyl group are replaced with heavy hydrogen atom(s). Specific examples thereof include a methyl-d1 group, a methyl-d2 group, a methyl-d3 group, an ethyl-d1 group, an ethyl-d2 group, an ethyl-d3 group, an ethyl-d4 group, and an ethyl-d5 group.

In the present specification, the "$C_1$-$C_6$ alkylamino group" refers to a group in which one or two hydrogen atoms in an amino group are replaced with the $C_1$-$C_6$ alkyl group(s). Specific examples thereof include a methylamino group, an ethylamino group, a dimethylamino group, a diethylamino group, and an ethylmethylamino group.

In the present specification, the "$C_2$-$C_6$ alkenyl group" refers to a linear or branched alkenyl group having 2 to 6 carbon atoms containing at least one carbon-carbon double bond. Specific examples thereof include a vinyl group, an allyl group, a methylvinyl group, a propenyl group, a butenyl group, a pentenyl group, and a hexenyl group.

In the present specification, the "$C_2$-$C_6$ alkynyl group" refers to a linear or branched alkynyl group having 2 to 6 carbon atoms containing at least one carbon-carbon triple bond. Specific examples thereof include an ethynyl group and a 2-propynyl group.

In the present specification, the "$C_1$-$C_6$ alkoxy group" refers to a linear or branched alkoxy group having 1 to 6 carbon atoms. Specific examples thereof include a methoxy group, an ethoxy group, a n-propoxy group, an isopropoxy group, a n-butoxy group, an isobutoxy group, and a tert-butoxy group.

In the present specification, the "$C_2$-$C_7$ alkanoyl group" refers to a group in which a hydrogen atom in a carbonyl group is replaced with the $C_1$-$C_6$ alkyl group. Specific examples thereof include an acetyl group, a n-propanoyl group, an isopropanoyl group, a n-butyroyl group, and a tert-butyroyl group.

In the present specification, the "$C_3$-$C_{10}$ cycloalkyl group" refers to a monocyclic or polycyclic cycloalkyl group having 3 to 10 carbon atoms. Specific examples thereof include a cyclopropyl group, a cyclobutyl group, a cyclopentyl group, a cyclohexyl group, a cycloheptyl group, and a decalyl group.

In the present specification, the "$C_6$-$C_{14}$ aromatic hydrocarbon group" refers to a monocyclic or polycyclic aromatic hydrocarbon group having 6 to 14 carbon atoms. Specific examples thereof include a phenyl group and a naphthyl group.

In the present specification, the "4- to 10-membered saturated heterocyclic group" refers to a 4- to 10-membered monocyclic or polycyclic fully saturated heterocyclic group. Specific examples thereof include an azetidinyl group, a pyrrolidinyl group, a piperidinyl group, a piperazinyl group, a hexamethyleneimino group, a morpholino group, a thiomorpholino group, a homopiperazinyl group, a tetrahydrofuranyl group, and a tetrahydropyranyl group.

In the present specification, the "4- to 10-membered unsaturated heterocyclic group" refers to a 4- to 10-membered monocyclic or polycyclic fully unsaturated or partially saturated heterocyclic group. Specific examples of the fully unsaturated heterocyclic group include an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, a triazolopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, and a quinoxalyl group. Examples of the partially saturated heterocyclic group include a 3,4-methylenedioxyphenyl group, an ethylenedioxyphenyl group, a dihydrobenzofuranyl group, and an oxetanyl group.

In the present specification, $R_a$ is a heavy hydrogen atom, a halogen atom, a cyano group, a nitro group, —C(=O)O$R_x$, —C(=O)S$R_x$, —C(=S)O$R_x$, —N($R_x$)($R_y$), —$NR_x$C(=O)$R_y$, —$NR_x$SO$_2$$R_y$, —$NR_x$C(=O)O$R_y$, —$NR_x$C(=O)N($R_y$)($R_z$), —$NR_x$SO$_2$N($R_y$)($R_z$), —N($R_x$)—O$R_y$, =N$R_x$, =N—O$R_x$, —O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —SO$_2$$R_x$, —SO$_2$N($R_x$)($R_y$), a $C_3$-$C_{10}$ cycloalkyl group, a $C_6$-$C_{14}$ aromatic hydrocarbon group, a 4- to 10-membered saturated heterocyclic group, or a 4- to 10-membered unsaturated heterocyclic group (wherein the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of a heavy hydrogen atom, a halogen atom, a hydroxyl group, a cyano group, a nitro group, an amino group, an oxo group, an oxide group, an imino group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group; the number of these substituents is not particularly limited and is preferably 1 to 3).

In the present specification, $R_b$ is a heavy hydrogen atom, a halogen atom, a cyano group, a nitro group, an oxo group, an oxide group, —C(=O)O$R_x$, —C(=O)S$R_x$, —C(=S)O$R_x$, —N($R_x$)($R_y$), —$NR_x$C(=O)$R_y$, —$NR_x$SO$_2$$R_y$, —$NR_x$C(=O)O$R_y$, —$NR_x$C(=O) N($R_y$)($R_z$), —$NR_x$SO$_2$N($R_y$)($R_z$), —N($R_x$)—O$R_y$, =N$R_x$, =N—O$R_x$, —O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —SO$_2$$R_x$, —SO$_2$N($R_x$)($R_y$), a $C_1$-$C_6$ alkyl group, a $C_1$-$C_6$ haloalkyl group, a $C_1$-$C_6$ deuterated alkyl group, a $C_2$-$C_6$ alkenyl group, or a $C_2$-$C_6$ alkynyl group.

In the present specification, $R_c$ is a heavy hydrogen atom, a halogen atom, a cyano group, a nitro group, an oxo group, an oxide group, —C(=O)$R_x$, —C(=O)O$R_x$, —C(=O)N($R_x$)($R_y$), —C(=O)S$R_x$, —C(=S)O$R_x$, —N($R_x$)($R_y$), —$NR_x$C(=O) $R_y$, —$NR_x$SO$_2$$R_y$, —$NR_x$C(=O)O$R_y$, —$NR_x$C(=O) N($R_y$)($R_z$), —$NR_x$SO$_2$N($R_y$)($R_z$), —N($R_x$)—O$R_y$, =N$R_x$, =N—O$R_x$, —O$R_x$, —OC(=O)$R_x$, —OC(=S)$R_x$, —OC(=O)O$R_x$, —OC(=O)N($R_x$)($R_y$), —OC(=S)O$R_x$, —S$R_x$, —SO$_2$R$_x$, —SO$_2$N(R$_x$)(R$_y$), a C$_1$-C$_6$ alkyl group, a C$_1$-C$_6$ haloalkyl group, a C$_1$-C$_6$ deuterated alkyl group, a C$_2$-C$_6$ alkenyl group, a C$_2$-C$_6$ alkynyl group, a C$_3$-C$_{10}$cycloalkyl group, a C$_6$-C$_{14}$ aromatic hydrocarbon group, a 4- to 10-membered unsaturated heterocyclic group, or a 4- to 10-membered saturated heterocyclic group (wherein the C$_1$-C$_6$ alkyl group, the C$_1$-C$_6$ haloalkyl group, the C$_1$-C$_6$ deuterated alkyl group, the C$_2$-C$_6$alkenyl group, and the C$_2$-C$_6$ alkynyl group are each optionally substituted by R$_d$, and the C$_3$-C$_{10}$ cycloalkyl group, the C$_6$-C$_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of R$_d$, an oxo group, an oxide group, a C$_1$-C$_6$ alkyl group, a C$_1$-C$_6$ haloalkyl group, a C$_1$-C$_6$ deuterated alkyl group, a C$_1$-C$_6$ alkoxy group, a C$_2$-C$_6$alkenyl group, and a C$_2$-C$_6$ alkynyl group; the number of these substituents is not particularly limited and is preferably 1 to 3).

In the present specification, R$_d$ is a heavy hydrogen atom, a halogen atom, a cyano group, a nitro group, —C(=O)R$_x$, —C(=O)OR$_x$, —C(=O)N(R$_x$)(R$_y$), —C(=O)SR$_x$, —C(=S)OR$_x$, —C(=O) ON(R$_x$)(R$_y$), —N(R$_x$)(R$_y$), —NR$_x$C(=O)R$_y$, —NR$_x$SO$_2$R$_y$, —NR$_x$C(=O)OR$_y$, —NR$_x$C(=O)N(R$_y$)(R$_z$), —NR$_x$SO$_2$N(R$_y$)(R$_z$), —N(R$_x$)—OR$_y$, =NR$_x$, =N—OR$_x$, —OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —SO$_2$R$_x$, or —SO$_2$N(R$_x$)(R$_y$)

In the present specification, R$_x$, R$_y$, and R$_z$ are the same as or different from each other and each represent a hydrogen atom, a C$_1$-C$_6$ alkyl group, a C$_1$-C$_6$ haloalkyl group, a C$_1$-C$_6$ deuterated alkyl group, a C$_2$-C$_6$ alkenyl group, a C$_2$-C$_6$ alkynyl group, a C$_3$-C$_{10}$ cycloalkyl group, a C$_6$-C$_{14}$ aromatic hydrocarbon group, a 4- to 10-membered unsaturated heterocyclic group, or a 4- to 10-membered saturated heterocyclic group.

In the present specification, R$_{xx}$ and R$_{yy}$ are the same as or different from each other and each represent a hydrogen atom, a C$_1$-C$_6$ alkyl group, a C$_1$-C$_6$ haloalkyl group, or a C$_3$-C$_{10}$ cycloalkyl group.

In the general formula (I), R$_1$ is preferably a hydrogen atom or a C$_1$-C$_6$ alkyl group, particularly preferably a hydrogen atom.

In the general formula (I), the "C$_1$-C$_8$ alkyl group" in the "optionally R$_a$-substituted C$_1$-C$_8$ alkyl group" represented by A is preferably a methyl group, an ethyl group, a n-propyl group, an isopropyl group, a n-butyl group, an isobutyl group, a sec-butyl group, a tert-butyl group, a pentyl group, a hexyl group, a heptyl group, or an octyl group.

In the general formula (I), R$_a$ in the "optionally R$_a$-substituted C$_1$-C$_8$ alkyl group" represented by A is preferably a halogen atom, —N(R$_x$)(R$_y$), —OR$_x$, a C$_3$-C$_{10}$ cycloalkyl group, a C$_6$-C$_{14}$ aromatic hydrocarbon group, a 4- to 10-membered unsaturated heterocyclic group, or a 4- to 10-membered saturated heterocyclic group (wherein the C$_3$-C$_{10}$ cycloalkyl group, the C$_6$-C$_{14}$ aromatic hydrocarbon group, the 4- to 10-membered unsaturated heterocyclic group, and the 4- to 10-membered saturated heterocyclic group are each optionally substituted by 1 to 3 identical or different substituents selected from the group consisting of a heavy hydrogen atom, a halogen atom, a hydroxyl group, a cyano group, a nitro group, an amino group, an oxo group, an oxide group, an imino group, a C$_1$-C$_6$ alkyl group, a C$_1$-C$_6$ haloalkyl group, a C$_1$-C$_6$ deuterated alkyl group, a C$_1$-C$_6$ alkoxy group, a C$_2$-C$_6$ alkenyl group, and a C$_2$-C$_6$alkynyl group);

more preferably a halogen atom, an amino group, a C$_1$-C$_6$alkylamino group, a hydroxyl group, a C$_1$-C$_6$ alkoxy group, a C$_3$-C$_{10}$cycloalkyl group, a C$_6$-C$_{14}$ aromatic hydrocarbon group, or a 4- to 10-membered saturated heterocyclic group (wherein the C$_3$-C$_{10}$cycloalkyl group and the 4- to 10-membered saturated heterocyclic group are each optionally substituted by an amino group);

further preferably a halogen atom, an amino group, a C$_1$-C$_6$alkoxy group, a C$_3$-C$_{10}$ cycloalkyl group, or a C$_6$-C$_{14}$ aromatic hydrocarbon group (wherein the C$_3$-C$_{10}$ cycloalkyl group is optionally substituted by an amino group);

particularly preferably an amino group, a C$_1$-C$_6$ alkoxy group, a C$_3$-C$_{10}$ cycloalkyl group, or a C$_6$-C$_{14}$ aromatic hydrocarbon group (wherein the C$_3$-C$_{10}$ cycloalkyl group is optionally substituted by an amino group).

In this context, the number of R$_a$ is not particularly limited and is preferably 1 to 5.

In the general formula (I), the "C$_2$-C$_6$ alkenyl group" in the "optionally R$_a$-substituted C$_2$-C$_6$ alkenyl group" represented by A is preferably a C$_2$-C$_4$ alkenyl group. In the general formula (I), R$_a$ in the "optionally R$_a$-substituted C$_2$-C$_6$ alkenyl group" represented by A is preferably a halogen atom. In this context, the number of R$_a$ is not particularly limited and is preferably 1 to 3.

In the general formula (I), the "C$_2$-C$_6$ alkynyl group" in the "optionally R$_a$-substituted C$_2$-C$_6$ alkynyl group" represented by A is preferably a C$_2$-C$_4$ alkynyl group. In the general formula (I), R$_a$ in the "optionally R$_a$-substituted C$_2$-C$_6$ alkynyl group" represented by A is preferably a halogen atom. In this context, the number of R$_a$ is not particularly limited and is preferably 1 to 3.

In the general formula (I), the "C$_3$-C$_{10}$ cycloalkyl group" in the "optionally R$_b$-substituted C$_3$-C$_{10}$ cycloalkyl group" represented by A is preferably a C$_4$-C$_7$ cycloalkyl group, more preferably a cyclopentyl group, a cyclohexyl group, or a cycloheptyl group, particularly preferably a cyclohexyl group. In the general formula (I), R$_b$ in the "optionally R$_b$-substituted C$_3$-C$_{10}$ cycloalkyl group" represented by A is preferably —N(R$_x$)(R$_y$) or —OR$_x$, more preferably —N(R$_{xx}$)(R$_{yy}$) or —OR$_{xx}$, further preferably a hydroxyl group, an amino group, or a C$_1$-C$_6$ alkylamino group, still further preferably an amino group or a C$_1$-C$_6$ alkylamino group, particularly preferably an amino group. In this context, the number of R$_b$ is not particularly limited and is preferably 1 to 3.

In the general formula (I), the "C$_6$-C$_{14}$ aromatic hydrocarbon group" in the "optionally R$_b$-substituted C$_6$-C$_{14}$ aromatic hydrocarbon group" represented by A is preferably a phenyl group. In the general formula (I), R$_b$ in the "optionally R$_b$-substituted C$_6$-C$_{14}$ aromatic hydrocarbon group" represented by A is preferably —N(R$_x$)(R$_y$), more preferably —N(R$_{xx}$)(R$_{yy}$), particularly preferably an amino group. In this context, the number of R$_b$ is not particularly limited and is preferably 1 to 3.

In the general formula (I), the 4- to 10-membered saturated heterocyclic group in the "optionally R$_b$-substituted 4- to 10-membered saturated heterocyclic group" represented by A is preferably a 4- to 6-membered monocyclic saturated heterocyclic group, more preferably a 4- to 6-membered monocyclic saturated heterocyclic group having 1 to 3 heteroatoms selected from N, S, and O, further preferably a 4- to 6-membered monocyclic saturated heterocyclic group having 1 heteroatom selected from N and O, still further preferably an azetidinyl group, a pyrrolidinyl group, a piperidinyl group, a tetrahydrofuranyl group, or a tetrahydropyranyl group, particularly preferably a piperidinyl group or a tetrahydropyranyl group. In the general formula (I), R$_b$ in the "optionally R$_b$-substituted 4- to 10-membered saturated heterocyclic group" represented by A is preferably a $C_1$-$C_6$ alkyl group, —N($R_x$)($R_y$), or —$OR_x$, more preferably a $C_1$-$C_6$ alkyl group, —N($R_{xx}$)($R_{yy}$), or —$OR_{xx}$, further preferably a $C_1$-$C_6$ alkyl group, a hydroxyl group, or an amino group, still further preferably a hydroxyl group or an amino group, particularly preferably an amino group. In this context, the number of $R_b$ is not particularly limited and is preferably 1 to 3.

In the general formula (I), the 4- to 10-membered unsaturated heterocyclic group in the "optionally $R_b$-substituted 4- to 10-membered unsaturated heterocyclic group" represented by A is preferably a 4- to 6-membered unsaturated heterocyclic group, more preferably a 4- to 6-membered monocyclic unsaturated heterocyclic group having 1 to 3 heteroatoms selected from N, S, and O, particularly preferably a pyrrolyl group or a pyridyl group. In the general formula (I), $R_b$ in the "optionally $R_b$-substituted 4- to 10-membered unsaturated heterocyclic group" represented by A is preferably —N($R_x$)($R_y$), more preferably —N($R_{xx}$)($R_{yy}$), particularly preferably an amino group. In this context, the number of $R_b$ is not particularly limited and is preferably 1 to 3.

In the general formula (I), A is preferably a $C_1$-$C_8$ alkyl group optionally substituted by 1 to 5 identical or different $R_a$, a $C_3$-$C_{10}$cycloalkyl group optionally substituted by 1 to 3 identical or different $R_b$, or a 4- to 10-membered saturated heterocyclic group optionally substituted by 1 to 3 identical or different $R_b$;

more preferably a $C_1$-$C_8$ alkyl group optionally substituted by 1 to 5 identical or different substituents selected from the group consisting of a halogen atom, —N($R_x$)($R_y$), —$OR_x$, a $C_3$-$C_{10}$ cycloalkyl group, a $C_6$-$C_{14}$ aromatic hydrocarbon group, a 4- to 10-membered unsaturated heterocyclic group, and a 4- to 10-membered saturated heterocyclic group (wherein the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by 1 to 3 identical or different substituents selected from the group consisting of a heavy hydrogen atom, a halogen atom, a hydroxyl group, a cyano group, a nitro group, an amino group, an oxo group, an oxide group, an imino group, a $C_1$-$C_6$ alkyl group, a $C_1$-$C_6$haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group); a $C_3$-$C_{10}$ cycloalkyl group optionally substituted by 1 to 3 identical or different substituents selected from the group consisting of —N($R_x$)($R_y$) and —$OR_x$; or a 4- to 10-membered saturated heterocyclic group optionally substituted by 1 to 3 identical or different substituents selected from the group consisting of a $C_1$-$C_6$ alkyl group, —N($R_x$)($R_y$), and —$OR_x$;

further preferably a $C_1$-$C_8$ alkyl group optionally substituted by 1 to 5 identical or different substituents selected from the group consisting of a halogen atom, an amino group, a $C_1$-$C_6$alkylamino group, a hydroxyl group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group and the 4- to 10-membered saturated heterocyclic group are each optionally substituted by an amino group); a $C_3$-$C_{10}$ cycloalkyl group optionally substituted by 1 to 3 identical or different substituents selected from the group consisting of a hydroxyl group, an amino group, and a $C_1$-$C_6$alkylamino group; or a 4- to 10-membered saturated heterocyclic group optionally substituted by 1 to 3 identical or different substituents selected from a $C_1$-$C_6$ alkyl group, a hydroxyl group, and an amino group;

still further preferably a $C_1$-$C_8$ alkyl group optionally substituted by 1 to 5 identical or different substituents selected from the group consisting of a halogen atom, an amino group, a $C_1$-$C_6$ alkylamino group, a hydroxyl group, a $C_1$-$C_6$ alkoxy group, a $C_3$-$C_{10}$cycloalkyl group, and a $C_6$-$C_{14}$ aromatic hydrocarbon group (wherein the $C_3$-$C_{10}$ cycloalkyl group and the 4- to 10-membered saturated heterocyclic group are each optionally substituted by an amino group); a $C_3$-$C_{10}$ cycloalkyl group optionally substituted by 1 to 3 identical or different substituents selected from the group consisting of an amino group and a $C_1$-$C_6$ alkylamino group; or a 4- to 10-membered saturated heterocyclic group optionally substituted by 1 to 3 identical or different substituents selected from a hydroxyl group and an amino group;

still further preferably a $C_1$-$C_8$ alkyl group optionally substituted by 1 to 5 identical or different substituents selected from the group consisting of a halogen atom, an amino group, a $C_1$-$C_6$alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by 1 to 3 identical or different substituents selected from a hydroxyl group and an amino group;

still further preferably a $C_1$-$C_8$ alkyl group optionally substituted by 1 to 5 identical or different substituents selected from the group consisting of an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by an amino group;

still further preferably a $C_1$-$C_8$ alkyl group optionally substituted by 1 to 5 identical or different substituents selected from the group consisting of an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_5$-$C_7$ cycloalkyl group optionally substituted by an amino group; or an optionally amino group-substituted 4- to 6-membered monocyclic saturated heterocyclic group having 1 heteroatom selected from N and O;

particularly preferably a $C_1$-$C_8$ alkyl group optionally substituted by 1 to 5 identical or different substituents selected from the group consisting of an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_5$-$C_7$ cycloalkyl group optionally substituted by an amino group; or a tetrahydropyranyl group or a piperidinyl group optionally substituted by an amino group.

In the general formula (I), the suitable combination of $R_1$ and A is preferably $R_1$ being a hydrogen atom or a $C_1$-$C_6$ alkyl group and A being a $C_1$-$C_8$ alkyl group optionally substituted by 1 to 5 identical or different $R_a$, a $C_3$-$C_{10}$ cycloalkyl group optionally substituted by 1 to 3 identical or different $R_b$, or a 4- to 10-membered saturated heterocyclic group optionally substituted by 1 to 3 identical or different $R_b$, or $R_1$ and A forming a 4- to 10-membered unsaturated heterocyclic ring or a 4- to 10-membered saturated heterocyclic ring together with the nitrogen atom bonded thereto (wherein the 4- to 10-membered unsaturated heterocyclic ring and the 4- to 10-membered saturated heterocyclic ring are each optionally substituted by $R_b$);

more preferably $R_1$ being a hydrogen atom or a $C_1$-$C_6$ alkyl group and A being a $C_1$-$C_8$ alkyl group optionally substituted by 1 to 5 identical or different substituents selected from the group consisting of a halogen atom, —N($R_x$)($R_y$), —$OR_x$, a $C_3$-$C_{10}$ cycloalkyl group, a $C_6$-$C_{14}$ aromatic hydrocarbon group, a 4- to 10-membered unsaturated heterocyclic group, and a 4- to 10-membered saturated heterocyclic group (wherein the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by 1 to 3 identical or different substituents selected from the group consisting of a heavy hydrogen atom, a halogen atom, a hydroxyl group, a cyano group, a nitro group, an amino group, an oxo group, an oxide group, an imino group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group); a $C_3$-$C_{10}$ cycloalkyl group optionally substituted by 1 to 3 identical or different substituents selected from the group consisting of —N($R_x$)($R_y$) and —O$R_x$; or a 4- to 10-membered saturated heterocyclic group optionally substituted by 1 to 3 identical or different substituents selected from the group consisting of a $C_1$-$C_6$ alkyl group, —N($R_x$)($R_y$), —O$R_x$, or $R_1$ and A forming a 4- to 10-membered saturated heterocyclic ring together with the nitrogen atom bonded thereto (wherein the 4- to 10-membered saturated heterocyclic ring is optionally substituted by 1 to 3 identical or different substituents selected from the group consisting of —N($R_x$)($R_y$) and —O$R_x$);

further preferably $R_1$ being a hydrogen atom or a $C_1$-$C_6$ alkyl group and A being a $C_1$-$C_8$ alkyl group optionally substituted by 1 to 5 identical or different substituents selected from the group consisting of a halogen atom, an amino group, a $C_1$-$C_6$ alkylamino group, a hydroxyl group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group and the 4- to 10-membered saturated heterocyclic group are each optionally substituted by an amino group); a $C_3$-$C_{10}$ cycloalkyl group optionally substituted by 1 to 3 identical or different substituents selected from the group consisting of a hydroxyl group, an amino group, and a $C_1$-$C_6$ alkylamino group; or a 4- to 10-membered saturated heterocyclic group optionally substituted by 1 to 3 identical or different substituents selected from a $C_1$-$C_6$ alkyl group, a hydroxyl group, and an amino group, or $R_1$ and A forming a 4- to 10-membered saturated heterocyclic ring together with the nitrogen atom bonded thereto (wherein the 4- to 10-membered saturated heterocyclic ring is optionally substituted by 1 to 3 identical or different substituents selected from the group consisting of an amino group and a hydroxyl group);

still further preferably $R_1$ being a hydrogen atom or a $C_1$-$C_6$ alkyl group and A being a $C_1$-$C_8$ alkyl group optionally substituted by 1 to 5 identical or different substituents selected from the group consisting of a halogen atom, an amino group, a $C_1$-$C_6$ alkylamino group, a hydroxyl group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group and the 4- to 10-membered saturated heterocyclic group are each optionally substituted by an amino group); a $C_3$-$C_{10}$ cycloalkyl group optionally substituted by 1 to 3 identical or different substituents selected from the group consisting of an amino group and a $C_1$-$C_6$ alkylamino group; or a 4- to 10-membered saturated heterocyclic group optionally substituted by 1 to 3 identical or different substituents selected from a hydroxyl group and an amino group, or $R_1$ and A forming a 4- to 10-membered saturated heterocyclic ring together with the nitrogen atom bonded thereto (wherein the 4- to 10-membered saturated heterocyclic ring is optionally substituted by 1 to 3 identical or different substituents selected from the group consisting of an amino group and a hydroxyl group);

still further preferably $R_1$ being a hydrogen atom or a $C_1$-$C_6$ alkyl group and A being a $C_1$-$C_8$ alkyl group optionally substituted by 1 to 5 identical or different substituents selected from the group consisting of a halogen atom, an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by 1 to 3 identical or different substituents selected from a hydroxyl group and an amino group, or $R_1$ and A forming a 4- to 10-membered saturated heterocyclic ring together with the nitrogen atom bonded thereto;

still further preferably $R_1$ being a hydrogen atom and A being a $C_1$-$C_8$ alkyl group optionally substituted by 1 to 5 identical or different substituents selected from the group consisting of an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by an amino group;

still further preferably $R_1$ being a hydrogen atom and A being a $C_1$-$C_8$ alkyl group optionally substituted by 1 to 5 identical or different substituents selected from the group consisting of an amino group and a $C_1$-$C_6$ alkoxy group; a $C_3$-$C_{10}$ cycloalkyl group optionally substituted by an amino group; or a 4- to 10-membered saturated heterocyclic group optionally substituted by an amino group;

still further preferably $R_1$ being a hydrogen atom and A being a $C_1$-$C_8$ alkyl group optionally substituted by 1 to 5 identical or different substituents selected from the group consisting of an amino group and a $C_1$-$C_6$ alkoxy group; a $C_5$-$C_7$ cycloalkyl group optionally substituted by an amino group; or an optionally amino group-substituted 4- to 6-membered monocyclic saturated heterocyclic group having 1 heteroatom selected from N and O;

particularly preferably $R_1$ being a hydrogen atom and A being a $C_1$-$C_8$ alkyl group optionally substituted by 1 to 5 identical or different substituents selected from the group consisting of an amino group and a $C_1$-$C_6$ alkoxy group; a $C_5$-$C_7$ cycloalkyl group optionally substituted by an amino group; or a tetrahydropyranyl group or a piperidinyl group optionally substituted by an amino group.

The particularly preferred form of A is represented by any of the following structural formulas (1) to (9) wherein the form represented by the structural formula (1), (3), (4), (5), (8), or (9) is more preferred, and the form represented by the structural formula (1), (4), or (8) is particularly preferred:

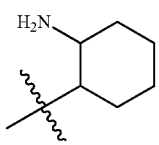

(1)

-continued (2)
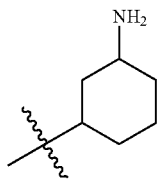

(3)
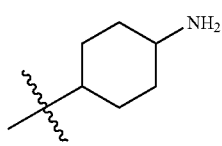

(4)
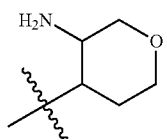

(5)
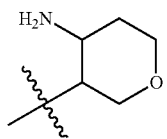

(6)
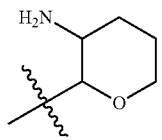

(7)
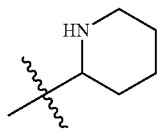

(8)
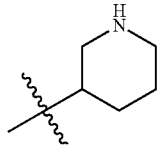

(9)
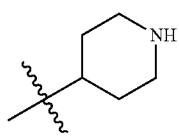

In the general formula (I), $R_2$ is preferably a hydrogen atom or a $C_1$-$C_6$ alkyl group, particularly preferably a hydrogen atom.

In the general formula (I), the "unsaturated heterocyclic group" in the "optionally $R_c$-substituted unsaturated heterocyclic group" represented by B is preferably a 4- to 10-membered monocyclic or bicyclic fully unsaturated or partially saturated heterocyclic group (except for a 3,4-methylenedioxyphenyl group) having 1 to 4 heteroatoms selected from N, S, and O, more preferably a 5- or 6-membered monocyclic fully unsaturated or partially saturated heterocyclic group having 1 to 3 heteroatoms selected from N, S, and O or a 9- or 10-membered bicyclic fully unsaturated or partially saturated heterocyclic group (except for a 3,4-methylenedioxyphenyl group) having 1 to 3 heteroatoms selected from N, S, and O, particularly preferably a 5- or 6-membered monocyclic fully unsaturated heterocyclic group having 1 to 3 heteroatoms selected from N, S, and O or a 9- or 10-membered bicyclic fully unsaturated heterocyclic group having 1 to 3 heteroatoms selected from N, S, and O. Specifically, the unsaturated heterocyclic ring in B is preferably an imidazolyl group, a thienyl group, a furyl group, a pyrrolyl group, an oxazolyl group, an isoxazolyl group, a thiazolyl group, an isothiazolyl group, a thiadiazolyl group, a pyrazolyl group, a triazolyl group, a tetrazolyl group, a pyridyl group, a pyrazyl group, a pyrimidinyl group, a pyridazinyl group, an indolyl group, an isoindolyl group, an indazolyl group, an imidazopyridyl group, a triazolopyridyl group, a thienopyridyl group, a benzimidazolyl group, a benzoxazolyl group, a benzothiazolyl group, a benzothienyl group, a benzofuranyl group, a purinyl group, a quinolyl group, an isoquinolyl group, a quinazolinyl group, a quinoxalyl group, or a naphthyridinyl group; more preferably a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzoxazolyl group, a benzothiazolyl group, a benzothienyl group, a benzofuranyl group, a quinolyl group, or a naphthyridinyl group; further preferably a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzothiazolyl group, a benzothienyl group, a benzofuranyl group, or a quinolyl group; still further preferably a thienyl group, a thiazolyl group, an isothiazolyl group, a pyrazolyl group, a pyridyl group, an indolyl group, an indazolyl group, a thienopyridyl group, a benzimidazolyl group, a benzothiazolyl group, a benzothienyl group, a benzofuranyl group, or a quinolyl group; particularly preferably a thienyl group, an indolyl group, an indazolyl group, a benzothienyl group, or a quinolyl group.

In the general formula (I), $R_c$ in the "optionally $R_c$-substituted unsaturated heterocyclic group" represented by B is preferably a halogen atom, a cyano group, an oxide group, a $C_1$-$C_6$alkyl group, —C(=O)$R_x$, —C(=O)O$R_x$, —C(=O)N($R_x$)($R_y$), a $C_3$-$C_{10}$ cycloalkyl group, a $C_6$-$C_{14}$ aromatic hydrocarbon group, a 4- to 10-membered unsaturated heterocyclic group, or a 4- to 10-membered saturated heterocyclic group (wherein the $C_1$-$C_6$ alkyl group is optionally substituted by $R_d$, and the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of $R_d$, an oxo group, an oxide group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$alkenyl group, and a $C_2$-$C_6$ alkynyl group);

more preferably a halogen atom; a cyano group; an oxide group; a $C_1$-$C_6$ alkyl group optionally substituted by 1 to 5 identical or different substituents selected from the group consisting of a heavy hydrogen atom, a halogen atom, —O$R_x$, a $C_6$-$C_{14}$ aromatic hydrocarbon group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a $C_1$-$C_6$ alkyl group and —O$R_x$; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, —C(=O)R$_x$, and —OR$_x$; or a 4- to 10-membered saturated heterocyclic group optionally substituted by an oxo group;

further preferably a halogen atom; a cyano group; an oxide group; a C$_1$-C$_6$ alkyl group optionally substituted by 1 to 5 identical or different substituents selected from the group consisting of a heavy hydrogen atom, a halogen atom, a hydroxyl group, a C$_1$-C$_6$ alkoxy group, a C$_6$-C$_{14}$ aromatic hydrocarbon group, and a 4- to 10-membered unsaturated heterocyclic group; —C(=O)R$_x$; —C(=O)OR$_x$; —C(=O)N(R$_x$)(R$_y$); —OR$_x$; a C$_3$-C$_{10}$ cycloalkyl group optionally substituted by 1 to 3 identical or different substituents selected from the group consisting of a hydroxyl group and a C$_1$-C$_6$ alkyl group; a C$_6$-C$_{14}$ aromatic hydrocarbon group; a 4- to 10-membered unsaturated heterocyclic group optionally substituted by 1 to 3 identical or different substituents selected from the group consisting of a C$_1$-C$_6$ alkyl group, a C$_1$-C$_6$ alkoxy group, and a C$_2$-C$_7$ alkanoyl group; or a 4- to 10-membered saturated heterocyclic group optionally substituted by an oxo group;

still further preferably a halogen atom; a cyano group; a C$_1$-C$_6$ alkyl group optionally substituted by 1 to 5 identical or different substituents selected from the group consisting of a heavy hydrogen atom, a halogen atom, a hydroxyl group, a C$_1$-C$_6$ alkoxy group, a C$_6$-C$_{14}$ aromatic hydrocarbon group, and a 4- to 10-membered unsaturated heterocyclic group; —C(=O)R$_x$; —C(=O)OR$_x$; —C(=O)N(R$_x$)(R$_y$); —OR$_x$; a C$_3$-C$_{10}$ cycloalkyl group optionally substituted by 1 to 3 identical or different substituents selected from the group consisting of a hydroxyl group and a C$_1$-C$_6$ alkyl group; a C$_6$-C$_{14}$ aromatic hydrocarbon group; a 4- to 10-membered unsaturated heterocyclic group optionally substituted by 1 to 3 identical or different substituents selected from the group consisting of a C$_1$-C$_6$ alkyl group, a C$_1$-C$_6$ alkoxy group, and a C$_2$-C$_7$ alkanoyl group; or a 4- to 10-membered saturated heterocyclic group optionally substituted by an oxo group;

still further preferably a halogen atom; a cyano group; a C$_1$-C$_6$ alkyl group optionally substituted by 1 to 5 identical or different substituents selected from the group consisting of a heavy hydrogen atom, a halogen atom, a hydroxyl group, a C$_1$-C$_6$ alkoxy group, and a 4- to 10-membered unsaturated heterocyclic group; —C(=O)R$_x$; —C(=O)OR$_x$; —C(=O)N(R$_x$)(R$_y$); —OR$_x$; a C$_3$-C$_{10}$ cycloalkyl group optionally substituted by 1 to 3 identical or different substituents selected from the group consisting of a hydroxyl group and a C$_1$-C$_6$ alkyl group; a C$_6$-C$_{14}$ aromatic hydrocarbon group; a 4- to 10-membered unsaturated heterocyclic group optionally substituted by 1 to 3 identical or different substituents selected from the group consisting of a C$_1$-C$_6$ alkyl group, a C$_1$-C$_6$ alkoxy group, and a C$_2$-C$_7$ alkanoyl group; or a 4- to 10-membered saturated heterocyclic group optionally substituted by an oxo group;

still further preferably a halogen atom; a C$_1$-C$_6$ alkyl group optionally substituted by 1 to 5 identical or different substituents selected from the group consisting of a heavy hydrogen atom, a halogen atom, and a hydroxyl group; a C$_3$-C$_{10}$ cycloalkyl group optionally substituted by 1 to 3 identical or different substituents selected from the group consisting of a hydroxyl group and a C$_1$-C$_6$ alkyl group; a C$_6$-C$_{14}$ aromatic hydrocarbon group; a 4- to 10-membered unsaturated heterocyclic group optionally substituted by 1 to 3 identical or different substituents selected from the group consisting of a C$_1$-C$_6$ alkyl group and a C$_2$-C$_7$ alkanoyl group; or a 4- to 10-membered saturated heterocyclic group;

particularly preferably a halogen atom; a C$_1$-C$_6$ alkyl group optionally substituted by 1 to 5 identical or different substituents selected from the group consisting of a heavy hydrogen atom, a halogen atom, and a hydroxyl group; a C$_3$-C$_{10}$ cycloalkyl group optionally substituted by 1 to 3 hydroxyl groups; a C$_6$-C$_{14}$ aromatic hydrocarbon group; a 4- to 10-membered unsaturated heterocyclic group optionally substituted by 1 to 3 C$_1$-C$_6$ alkyl groups; or a 4- to 10-membered saturated heterocyclic group.

In the general formula (I), the "Re-substituted unsaturated heterocyclic group" represented by B is preferably an optionally R$_c$-substituted 4- to 10-membered monocyclic or bicyclic fully unsaturated or partially saturated heterocyclic group having 1 to 4 heteroatoms selected from N, S, and O;

more preferably an optionally Re-substituted 5- or 6-membered monocyclic fully unsaturated or partially saturated heterocyclic group (except for a 3,4-methylenedioxyphenyl group) having 1 to 3 heteroatoms selected from N, S, and O or an optionally R$_c$-substituted 9- or 10-membered bicyclic fully unsaturated or partially saturated heterocyclic group (except for a 3,4-methylenedioxyphenyl group) having 1 to 3 heteroatoms selected from N, S, and O;

further preferably an optionally R$_c$-substituted 5- or 6-membered monocyclic fully unsaturated heterocyclic group having 1 to 3 heteroatoms selected from N, S, and O or an optionally R$_c$-substituted 9- or 10-membered bicyclic fully unsaturated heterocyclic group (except for a 3,4-methylenedioxyphenyl group) having 1 to 3 heteroatoms selected from N, S, and O;

still further preferably a 5- or 6-membered monocyclic fully unsaturated heterocyclic group having 1 to 3 heteroatoms selected from N, S, and O or a 9- or 10-membered bicyclic fully unsaturated heterocyclic group having 1 to 3 heteroatoms selected from N, S, and O, wherein the unsaturated heterocyclic group is optionally substituted by 1 to 5 identical or different substituents selected from the group consisting of a halogen atom, a cyano group, an oxide group, a C$_1$-C$_6$ alkyl group, —C(=O)R$_x$, —C(=O)OR$_x$, —C(=O)N(R$_x$)(R$_y$), a C$_3$-C$_{10}$ cycloalkyl group, a C$_6$-C$_{14}$ aromatic hydrocarbon group, a 4- to 10-membered unsaturated heterocyclic group, and a 4- to 10-membered saturated heterocyclic group (wherein the C$_1$-C$_6$ alkyl group is optionally substituted by R$_d$, and the C$_3$-C$_{10}$ cycloalkyl group, the C$_6$-C$_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of R$_d$, an oxo group, an oxide group, a C$_1$-C$_6$ alkyl group, a C$_1$-C$_6$ haloalkyl group, a C$_1$-C$_6$ deuterated alkyl group, a C$_1$-C$_6$ alkoxy group, a C$_2$-C$_6$ alkenyl group, and a C$_2$-C$_6$ alkynyl group);

still further preferably a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzoxazolyl group, a benzothiazolyl group, a benzothienyl group, a benzofuranyl group, a quinolyl group, or a naphthyridinyl group optionally substituted by 1 to 5 identical or different substituents selected from the group consisting of: a halogen atom; a cyano group; an oxide group; a C$_1$-C$_6$ alkyl group optionally substituted by 1 to 5 identical or different substituents selected from the group consisting of a heavy hydrogen atom, a halogen atom, a hydroxyl group, a C$_1$-C$_6$ alkoxy group, a C$_6$-C$_{14}$ aromatic hydrocarbon group, and a 4- to 10-membered unsaturated heterocyclic group; —C(=O)R$_x$; —C(=O)OR$_x$; —C(=O)N(R$_x$)(R$_y$); —OR$_x$; a C$_3$-C$_{10}$ cycloalkyl group optionally substituted by 1 to 3 identical or different substituents selected from the group consisting of a hydroxyl group and a C$_1$-C$_6$ alkyl group; a C$_6$-C$_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a $C_2$-$C_7$ alkanoyl group; and a 4- to 10-membered saturated heterocyclic group optionally substituted by an oxo group;

still further preferably a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzothiazolyl group, a benzothienyl group, a benzofuranyl group, or a quinolyl group optionally substituted by 1 to 5 identical or different substituents selected from the group consisting of: a halogen atom; a cyano group; a $C_1$-$C_6$ alkyl group optionally substituted by 1 to 5 identical or different substituents selected from the group consisting of a heavy hydrogen atom, a halogen atom, a hydroxyl group, a $C_1$-$C_6$ alkoxy group, a $C_6$-$C_{14}$ aromatic hydrocarbon group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a hydroxyl group and a $C_1$-$C_6$ alkyl group; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a $C_2$-$C_7$ alkanoyl group; and a 4- to 10-membered saturated heterocyclic group optionally substituted by an oxo group;

still further preferably a thienyl group, a thiazolyl group, an isothiazolyl group, a pyrazolyl group, a pyridyl group, an indolyl group, an indazolyl group, a thienopyridyl group, a benzimidazolyl group, a benzothiazolyl group, a benzothienyl group, a benzofuranyl group, or a quinolyl group optionally substituted by 1 to 5 identical or different substituents selected from the group consisting of: a halogen atom; a cyano group; a $C_1$-$C_6$ alkyl group optionally substituted by 1 to 5 identical or different substituents selected from the group consisting of a heavy hydrogen atom, a halogen atom, a hydroxyl group, a $C_1$-$C_6$ alkoxy group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a hydroxyl group and a $C_1$-$C_6$ alkyl group; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a $C_2$-$C_7$ alkanoyl group; and a 4- to 10-membered saturated heterocyclic group optionally substituted by an oxo group;

particularly preferably a thienyl group, an indolyl group, an indazolyl group, a benzothienyl group, or a quinolyl group optionally substituted by 1 to 5 identical or different substituents selected from the group consisting of: a halogen atom; a $C_1$-$C_6$ alkyl group optionally substituted by 1 to 5 identical or different substituents selected from the group consisting of a heavy hydrogen atom, a halogen atom, and a hydroxyl group; a $C_3$-$C_{10}$ cycloalkyl group optionally substituted by 1 to 3 hydroxyl groups; a $C_6$-$C_{14}$ aromatic hydrocarbon group; a 4- to 10-membered unsaturated heterocyclic group optionally substituted by 1 to 3 $C_1$-$C_6$ alkyl groups; and a 4- to 10-membered saturated heterocyclic group.

The preferred form of the "unsaturated heterocyclic group" represented by B is represented by any of the structural formulas as shown below. As described above, the "unsaturated heterocyclic group" may have any of the substituents listed above.

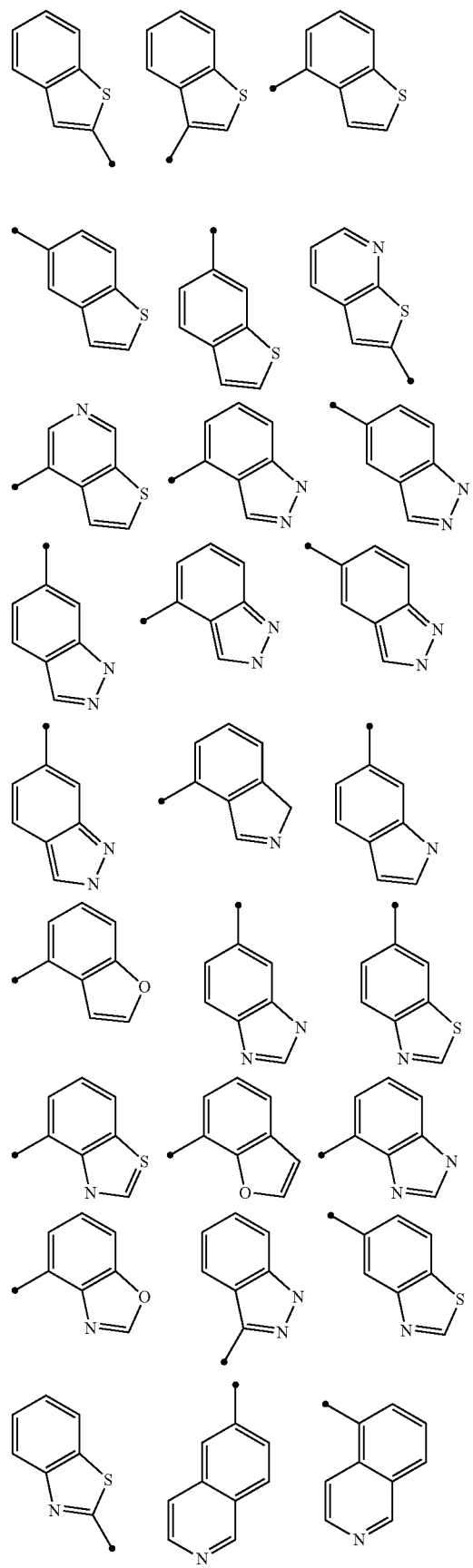

-continued

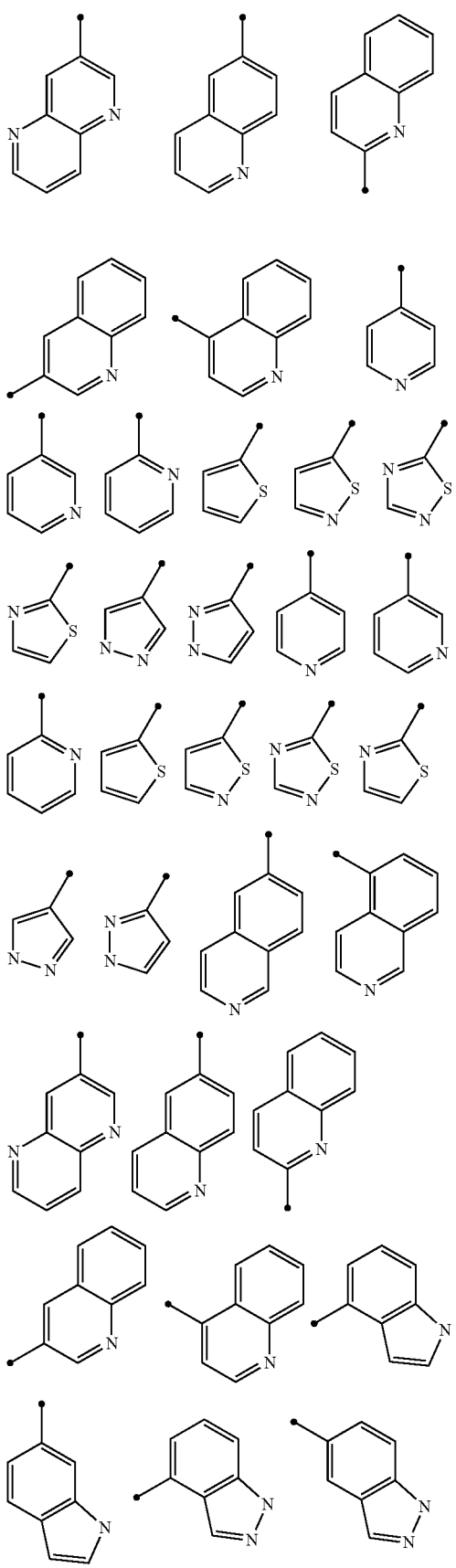

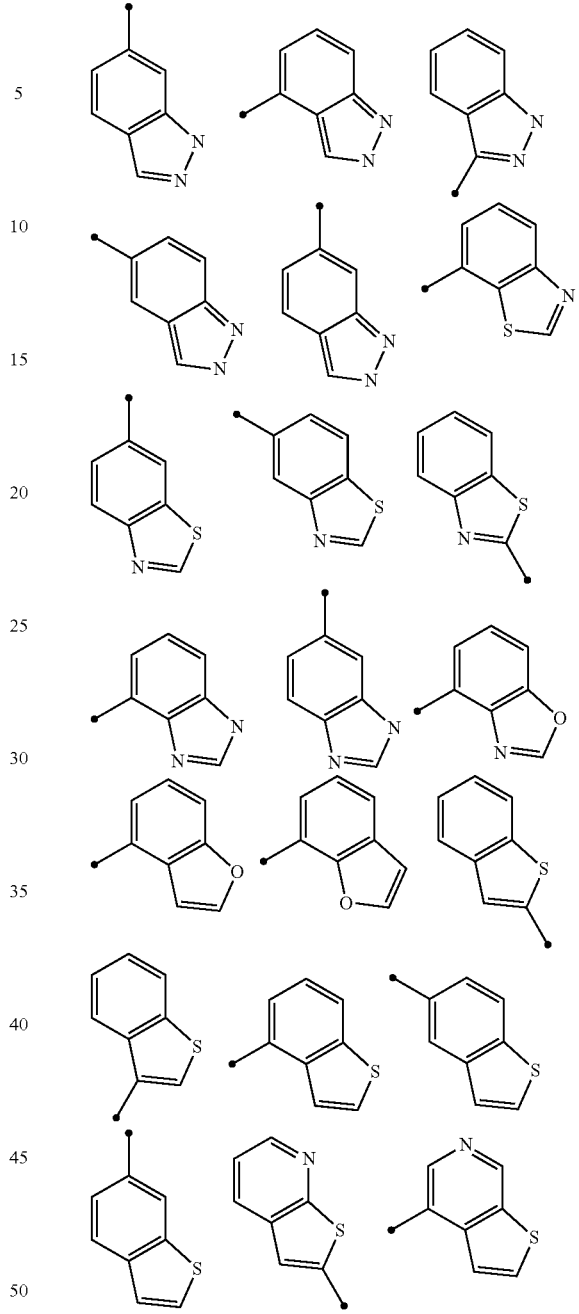

The compound of the present invention is preferably a compound represented by the general formula (I) wherein $R_1$ is a hydrogen atom or a $C_1$-$C_6$ alkyl group, A is a $C_1$-$C_8$ alkyl group optionally substituted by 1 to 5 identical or different $R_a$, a $C_3$-$C_{10}$ cycloalkyl group optionally substituted by 1 to 3 identical or different $R_b$, or a 4- to 10-membered saturated heterocyclic group optionally substituted by 1 to 3 identical or different $R_b$, or $R_1$ and A form a 4- to 10-membered unsaturated heterocyclic ring or a 4- to 10-membered saturated heterocyclic ring together with the nitrogen atom bonded thereto (wherein the 4- to 10-membered unsaturated heterocyclic ring and the 4- to 10-membered saturated heterocyclic ring are each optionally substituted by $R_b$), $R_2$ is a hydrogen atom, and B is a 5- or 6-membered monocyclic fully unsaturated or partially saturated heterocyclic group having 1 to 3 heteroatoms selected from N, S, and O or a 9- or 10-membered bicyclic fully unsaturated or partially saturated heterocyclic group (except for a 3,4-methylenedioxyphenyl group) having 1 to 3 heteroatoms selected from N, S, and O, wherein the heterocyclic group is optionally substituted by 1 to 5 identical or different substituents selected from the group consisting of a halogen atom, a cyano group, an oxide group, a $C_1$-$C_6$ alkyl group, —C(=O)$R_x$, —C(=O)O$R_x$, —C(=O)N($R_x$)($R_y$), a $C_3$-$C_{10}$ cycloalkyl group, a $C_6$-$C_{14}$ aromatic hydrocarbon group, a 4- to 10-membered unsaturated heterocyclic group, and a 4- to 10-membered saturated heterocyclic group (wherein the $C_1$-$C_6$ alkyl group is optionally substituted by $R_d$, and the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of $R_d$, an oxo group, an oxide group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group);

more preferably a compound represented by the general formula (I) wherein $R_1$ is a hydrogen atom or a $C_1$-$C_6$ alkyl group, A is a $C_1$-$C_8$ alkyl group optionally substituted by 1 to 5 identical or different substituents selected from the group consisting of a halogen atom, an amino group, a $C_1$-$C_6$ alkylamino group, a hydroxyl group, a $C_1$-$C_6$ alkoxy group, a $C_3$-$C_{10}$ cycloalkyl group, or a $C_6$-$C_{14}$ aromatic hydrocarbon group (wherein the $C_3$-$C_{10}$ cycloalkyl group and the 4- to 10-membered saturated heterocyclic group are each optionally substituted by an amino group); a $C_3$-$C_{10}$ cycloalkyl group optionally substituted by 1 to 3 identical or different substituents selected from the group consisting of a hydroxyl group, an amino group, and a $C_1$-$C_6$ alkylamino group; or a 4- to 10-membered saturated heterocyclic group optionally substituted by 1 to 3 identical or different substituents selected from a $C_1$-$C_6$ alkyl group, a hydroxyl group, and an amino group, or $R_1$ and A form a 4- to 10-membered saturated heterocyclic ring together with the nitrogen atom bonded thereto (wherein the 4- to 10-membered saturated heterocyclic ring is optionally substituted by 1 to 3 identical or different substituents selected from the group consisting of an amino group and a hydroxyl group), $R_2$ is a hydrogen atom, and B is a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzoxazolyl group, a benzothiazolyl group, a benzothienyl group, a benzofuranyl group, a quinolyl group, or a naphthyridinyl group optionally substituted by 1 to 5 identical or different substituents selected from the group consisting of: a halogen atom; a cyano group; an oxide group; a $C_1$-$C_6$ alkyl group optionally substituted by 1 to 5 identical or different substituents selected from the group consisting of a heavy hydrogen atom, a halogen atom, a hydroxyl group, a $C_1$-$C_6$alkoxy group, a $C_6$-$C_{14}$ aromatic hydrocarbon group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a hydroxyl group and a $C_1$-$C_6$ alkyl group; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a $C_2$-$C_7$alkanoyl group; and a 4- to 10-membered saturated heterocyclic group optionally substituted by an oxo group;

further preferably a compound represented by the general formula (I) wherein $R_1$ is a hydrogen atom or a $C_1$-$C_6$ alkyl group, A is a $C_1$-$C_8$ alkyl group optionally substituted by 1 to 5 identical or different substituents selected from the group consisting of a halogen atom, an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by 1 to 3 identical or different substituents selected from a hydroxyl group and an amino group, or $R_1$ and A form a 4- to 10-membered saturated heterocyclic ring together with the nitrogen atom bonded thereto, $R_2$ is a hydrogen atom, and B is a thienyl group, a thiazolyl group, an isothiazolyl group, a thiadiazolyl group, a pyrazolyl group, a pyridyl group, an indolyl group, an indazolyl group, an imidazopyridyl group, a thienopyridyl group, a benzimidazolyl group, a benzothiazolyl group, a benzothienyl group, a benzofuranyl group, or a quinolyl group optionally substituted by 1 to 5 identical or different substituents selected from the group consisting of: a halogen atom; a cyano group; a $C_1$-$C_6$ alkyl group optionally substituted by 1 to 5 identical or different substituents selected from the group consisting of a heavy hydrogen atom, a halogen atom, a hydroxyl group, a $C_1$-$C_6$ alkoxy group, a $C_6$-$C_{14}$ aromatic hydrocarbon group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a hydroxyl group and a $C_1$-$C_6$ alkyl group; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a $C_2$-$C_7$alkanoyl group; and a 4- to 10-membered saturated heterocyclic group optionally substituted by an oxo group;

still further preferably a compound represented by the general formula (I) wherein $R_1$ is a hydrogen atom, A is a $C_1$-$C_8$ alkyl group optionally substituted by 1 to 5 identical or different substituents selected from the group consisting of an amino group, a $C_1$-$C_6$ alkoxy group, a $C_3$-$C_{10}$ cycloalkyl group, and a $C_6$-$C_{14}$ aromatic hydrocarbon group (wherein the $C_3$-$C_{10}$ cycloalkyl group is optionally substituted by an amino group); a $C_3$-$C_{10}$ cycloalkyl group optionally substituted by an amino group; or a 4- to 10-membered saturated heterocyclic group optionally substituted by an amino group, $R_2$ is a hydrogen atom, and B is a thienyl group, a thiazolyl group, an isothiazolyl group, a pyrazolyl group, a pyridyl group, an indolyl group, an indazolyl group, a thienopyridyl group, a benzimidazolyl group, a benzothiazolyl group, a benzothienyl group, a benzofuranyl group, or a quinolyl group optionally substituted by 1 to 5 identical or different substituents selected from the group consisting of: a halogen atom; a cyano group; a $C_1$-$C_6$ alkyl group optionally substituted by 1 to 5 identical or different substituents selected from the group consisting of a heavy hydrogen atom, a halogen atom, a hydroxyl group, a $C_1$-$C_6$ alkoxy group, and a 4- to 10-membered unsaturated heterocyclic group; —C(=O)$R_x$; —C(=O)O$R_x$; —C(=O)N($R_x$)($R_y$); —O$R_x$; a $C_3$-$C_{10}$ cycloalkyl group optionally substituted by 1 to 3 identical or different substituents selected from the group consisting of a hydroxyl group and a $C_1$-$C_6$ alkyl group; a $C_6$-$C_{14}$ aromatic hydrocarbon group; a 4- to 10-membered unsaturated heterocyclic group optionally substituted by 1 to 3 identical or different substituents selected from the group consisting of a $C_1$-$C_6$ alkyl group, a $C_1$-$C_6$ alkoxy group, and a C₂-C₇alkanoyl group; and a 4- to 10-membered saturated heterocyclic group optionally substituted by an oxo group;

particularly preferably a compound represented by the general formula (I) wherein R₁ is a hydrogen atom, A is a C₁-C₈ alkyl group optionally substituted by 1 to 5 identical or different substituents selected from the group consisting of an amino group and a C₁-C₆ alkoxy group; a C₃-C₁₀ cycloalkyl group optionally substituted by an amino group; or a 4- to 10-membered saturated heterocyclic group optionally substituted by an amino group, R₂ is a hydrogen atom, and B is a thienyl group, an indolyl group, an indazolyl group, a benzothienyl group, or a quinolyl group optionally substituted by 1 to 5 identical or different substituents selected from the group consisting of: a halogen atom; a C₁-C₆ alkyl group optionally substituted by 1 to 5 identical or different substituents selected from the group consisting of a heavy hydrogen atom, a halogen atom, and a hydroxyl group; a C₃-C₁₀cycloalkyl group optionally substituted by 1 to 3 hydroxyl groups; a C₆-C₁₄ aromatic hydrocarbon group; a 4- to 10-membered unsaturated heterocyclic group optionally substituted by 1 to 3 C₁-C₆ alkyl groups; and a 4- to 10-membered saturated heterocyclic group.

Specific examples of the preferred compound of the present invention can include the following:
(1) 3-((1R,2S)-2-aminocyclohexylamino)-5-(2-cyclobutyl-2H-indazol-5-ylamino)-1,2,4-triazine-6-carboxamide (compound of Example 11)
(2) 3-(((3R,4R)-3-aminotetrahydro-2H-pyran-4-yl)amino)-5-((2-(tert-butyl)-7-methyl-2H-indazol-5-yl)amino)-1,2,4-triazine-6-carboxamide (compound of Example 61)
(3) 3-(((1R,2S)-2-aminocyclohexyl)amino)-5-((2-(difluoromethyl)-7-methyl-2H-indazol-5-yl)amino)-1,2,4-triazine-6-carboxamide (compound of Example 62)
(4) 3-(((1R,2S)-2-aminocyclohexyl)amino)-5-((1-(1-methyl-1H-pyrazol-4-yl)-1H-indol-4-yl)amino)-1,2,4-triazine-6-carboxamide (compound of Example 67)
(5) 3-(((1R,2S)-2-aminocyclohexyl)amino)-5-((4-(pyrimidin-2-yl)thiophen-2-yl)amino)-1,2,4-triazine-6-carboxamide (compound of Example 76
(6) 3-((1R,2S)-2-aminocyclohexyl)amino)-5-((1-(trans-4-hydroxycyclohexyl)-6-methyl-1H-indol-4-yl)amino)-1,2,4-triazine-6-carboxamide (compound of Example 78)
(7) 3-(((1R,2S)-2-aminocyclohexyl)amino)-5-((1-(2-hydroxyethyl)-1H-indol-4-yl)amino)-1,2,4-triazine-6-carboxamide (compound of Example 93)
(8) 3-(((1R,2S)-2-aminocyclohexyl)amino)-5-((1-ethyl-4-methyl-1H-indazol-6-yl)amino)-1,2,4-triazine-6-carboxamide (compound of Example 97)
(9) 3-(((3R,4R)-3-aminotetrahydro-2H-pyran-4-yl)amino)-5-((2-(tert-butyl)-7-chloro-2H-indazol-5-yl)amino)-1,2,4-triazine-6-carboxamide (compound of Example 100)
(10) 3-(((2R,3R)-3-amino-4-methoxybutan-2-yl)amino)-5-((1,6-dimethyl-1H-indol-4-yl)amino)-1,2,4-triazine-6-carboxamide (compound of Example 256)
(11) 3-(((3R,4R)-3-aminotetrahydro-2H-pyran-4-yl)amino)-5-((2-methyl-7-phenyl-2H-indazol-5-yl)amino)-1,2,4-triazine-6-carboxamide (compound of Example 257)
(12) 3-(((1R,2S)-2-aminocyclohexyl)amino)-5-((8-methylquinolin-6-yl)amino)-1,2,4-triazine-6-carboxamide (compound of Example 259)
(13) 3-(((1R,2S)-2-aminocyclohexyl)amino)-5-((2-(difluoromethyl)-4-methyl-2H-indazol-6-yl)amino)-1,2,4-triazine-6-carboxamide (compound of Example 265)
(14) 3-(((2R,3R)-3-amino-4-methoxybutan-2-yl)amino)-5-((1-ethyl-7-methyl-1H-indazol-5-yl)amino)-1,2,4-triazine-6-carboxamide (compound of Example 311)
(15) 3-(((1R,2S)-2-aminocycloheptyl)amino)-5-((2-ethyl-2H-indazol-6-yl)amino)-1,2,4-triazine-6-carboxamide (compound of Example 316); and
(16) 3-(((3R,4R)-3-aminotetrahydro-2H-pyran-4-yl)amino)-5-((7-methylbenzo[b]thiophen-5-yl)amino)-1,2,4-triazine-6-carboxamide dihydrochloride (compound of Example 359).

Next, a method for producing the compound according to the present invention will be described.

The compound (I) of the present invention can be produced by, for example, production schemes shown below or methods shown in Examples. However, the method for producing the compound (I) of the present invention is not limited by these reaction examples.

Production Scheme 1

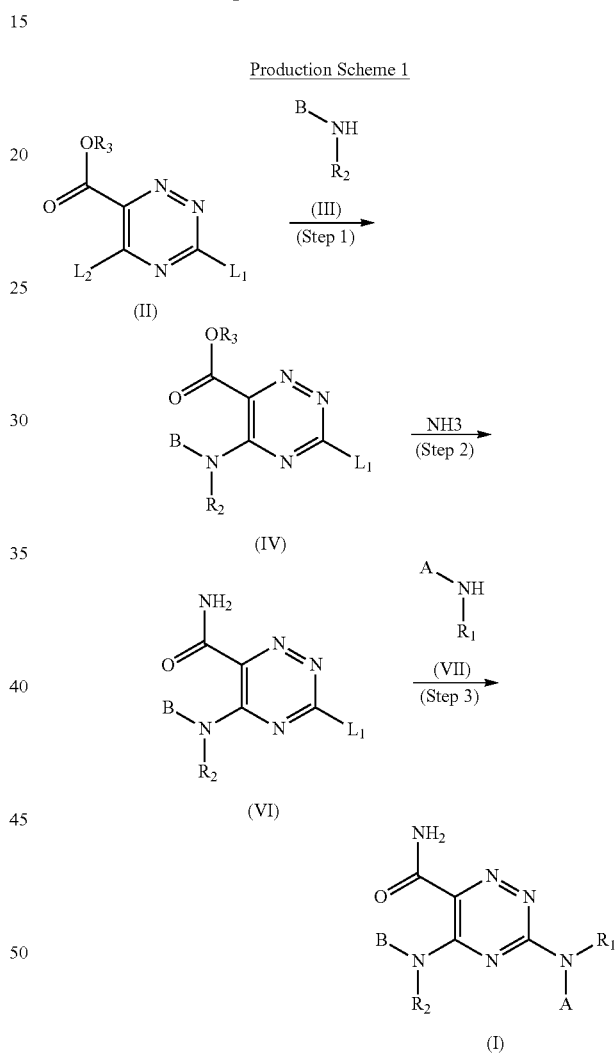

wherein L₁ and L₂ each independently represent a leaving group; R₃ represents hydrogen or a protective group; and A, B, R₁, and R₂ are as defined above.

(Step 1)

This step is the step of reacting a compound represented by the general formula (II) with a compound represented by the general formula (III) or a salt thereof to produce a compound represented by the general formula (IV). The removal or conversion of the protective group and the conversion of the leaving groups L₁ and L₂ can be appropriately performed.

Examples of the leaving groups represented by L₁ and L₂ include: halogen atoms such as a chlorine atom, a bromine atom, and an iodine atom; a methylsulfinyl group; organic sulfonyl groups such as a methylsulfonyl group, an ethylsulfonyl group, and a phenylsulfonyl group; organic sulfonyloxy groups such as a methylsulfonyloxy group, a trifluoromethylsulfonyloxy group, and a p-tolylsulfonyloxy group; organic thio groups such as a methylthio group, an ethylthio group, a phenylthio group, and a benzylthio group; and 1H-benzotriazol-1-yloxy. Among them, for example, a chlorine atom, a methylthio group, a methylsulfinyl group, and a methylsulfonyl group are preferred.

This step is usually performed using 0.5 moles to excess mole, preferably 1 to 3 moles of the compound represented by the general formula (III) with respect to 1 mole of the compound represented by the general formula (II).

The reaction solvent is not particularly limited as long as the solvent does not hinder the reaction. The reaction solvent is preferably, for example, isopropanol, tert-butyl alcohol, toluene, benzene, methylene chloride, chloroform, tetrahydrofuran, dioxane, dimethylformamide, N-methylpyrrolidinone, dimethyl sulfoxide, or a mixed solvent thereof.

Also, the reaction can be performed, if necessary, using a base or an acid. For example, an organic base such as triethylamine, diisopropylethylamine, pyridine, or 4-dimethylaminopyridine or an inorganic base such as sodium bicarbonate, sodium carbonate, potassium carbonate, cesium carbonate, sodium hydroxide, sodium hydride, or potassium tert-butyrate can be used as the base. For example, hydrochloric acid, p-toluenesulfonic acid, trifluoroacetic acid, acetic acid, phosphoric acid, or phenol can be used as the acid.

The amount of the base used is usually 0.1 moles to excess mole, preferably 1 to 3 moles, with respect to 1 mole of the compound represented by the general formula (II).

The amount of the acid used is usually 0.01 moles to excess mole, preferably 0.1 to 3 moles, with respect to 1 mole of the compound represented by the general formula (II).

The reaction temperature is usually 0° C. to 200° C., preferably 0° C. to 150° C.

The reaction time is usually 1 minute to 7 days, preferably 5 minutes to 24 hours.

The compound (IV) thus obtained may be isolated and purified by separation and purification means known in the art, for example, concentration, concentration under reduced pressure, crystallization, solvent extraction, reprecipitation, or chromatography or may be subjected to the next step without being isolated or purified.

(Step 2)

This step is the step of reacting the compound represented by the general formula (IV) with ammonia or a salt thereof to produce a compound represented by the general formula (VI).

The amount of the ammonia or the salt thereof used in this step is usually equal mole to excess mole with respect to 1 mole of the compound represented by the general formula (IV). The reaction solvent is not particularly limited as long as the solvent does not hinder the reaction. The reaction solvent is preferably, for example, water, methanol, ethanol, isopropanol, tert-butyl alcohol, tetrahydrofuran, dioxane, dimethylformamide, N-methylpyrrolidone, dimethyl sulfoxide, or a mixed solvent thereof.

The reaction temperature is usually 0° C. to 200° C., preferably room temperature to 150° C.

The reaction time is usually 5 minutes to 7 days, preferably 1 minute to 24 hours.

The compound (VI) thus obtained may be isolated and purified by separation and purification means known in the art, for example, concentration, concentration under reduced pressure, crystallization, solvent extraction, reprecipitation, or chromatography or may be subjected to the next step without being isolated or purified.

(Step 3)

This step is the step of reacting the compound represented by the general formula (VI) with a compound represented by the general formula (VII) or a salt thereof to produce the compound represented by the general formula (I).

This step is usually performed using 0.5 moles to excess mole, preferably 1 to 3 moles of the compound represented by the general formula (VII) with respect to 1 mole of the compound represented by the general formula (VI).

The reaction solvent is not particularly limited as long as the solvent does not hinder the reaction. The reaction solvent is preferably, for example, isopropanol, tert-butyl alcohol, toluene, benzene, methylene chloride, chloroform, tetrahydrofuran, dioxane, dimethylformamide, N-methylpyrrolidinone, dimethyl sulfoxide, or a mixed solvent thereof.

Also, the reaction can be performed, if necessary, using a base. For example, an organic base such as triethylamine, diisopropylethylamine, pyridine, or 4-dimethylaminopyridine or an inorganic base such as sodium bicarbonate, sodium carbonate, potassium carbonate, cesium carbonate, sodium hydroxide, sodium hydride, or potassium tert-butyrate can be used as the base.

The amount of the base used is usually 0.1 moles to excess mole, preferably 1 to 3 moles, with respect to 1 mole of the compound represented by the general formula (VI).

The reaction temperature is usually 0° C. to 200° C., preferably 0° C. to 100° C.

The reaction time is usually 1 minute to 7 days, preferably 5 minutes to 24 hours.

When the leaving group in the compound represented by the general formula (IV) or (VI) is an organic thio group, this organic thio group can be converted to an organic sulfinyl group or an organic sulfonyl group through oxidation by a method known in the art and then used in the reaction. This conversion can be performed using, for example, 0.5 moles to excess mole, preferably equal mole to 2 moles of an oxidizing agent such as m-chloroperbenzoic acid or oxon with respect to 1 mole of the compound represented by the general formula (IV) or (VI), for example, in an inert solvent such as benzene, toluene, methylene chloride, chloroform, tetrahydrofuran, acetonitrile, dimethylformamide, or N-methylpyrrolidone. Also, a desiccant such as anhydrous sodium sulfate, anhydrous magnesium sulfate, calcium sulfate, or molecular sieves or an inorganic base such as sodium bicarbonate or sodium carbonate may be added thereto as an additive.

Alternatively, when the leaving group in the compound represented by the general formula (IV) or (VI) is an organic thio group, this organic thio group can be halogenated by a method known in the art and then used in the reaction. This halogenation can be performed using, for example, 0.5 moles to excess mole, preferably 3 moles to 10 moles of a chlorinating agent such as sulfuryl chloride with respect to 1 mole of the compound represented by the general formula (IV) or (VI), for example, without a solvent or in an inert solvent such as benzene, toluene, methylene chloride, chloroform, tetrahydrofuran, acetonitrile, dimethylformamide, or N-methylpyrrolidone.

The thus-obtained compound having the organic sulfinyl group, the organic sulfonyl group, or the halogenated group may be isolated and purified by separation and purification means known in the art, for example, concentration, concentration under reduced pressure, crystallization, solvent extraction, reprecipitation, or chromatography or may be subjected to the next step without being isolated or purified.

The compound represented by the general formula (II) can be produced by methods described in literatures [see e.g., JP-A-2009-007341; and European Journal of Medicinal Chemistry, Vol. 15 (No. 3), p. 269-273] or methods equivalent thereto. The compounds represented by the general formulas (III) and (V) may be, for example, commercially available products or may be produced by methods described in literatures or methods equivalent thereto, or by an appropriate combination of methods shown below and methods described in Examples and Production Examples, etc., according to the need.

The compound (I) thus obtained can be isolated and purified by separation and purification means known in the art, for example, concentration, concentration under reduced pressure, crystallization, solvent extraction, reprecipitation, or chromatography.

Production Scheme 2

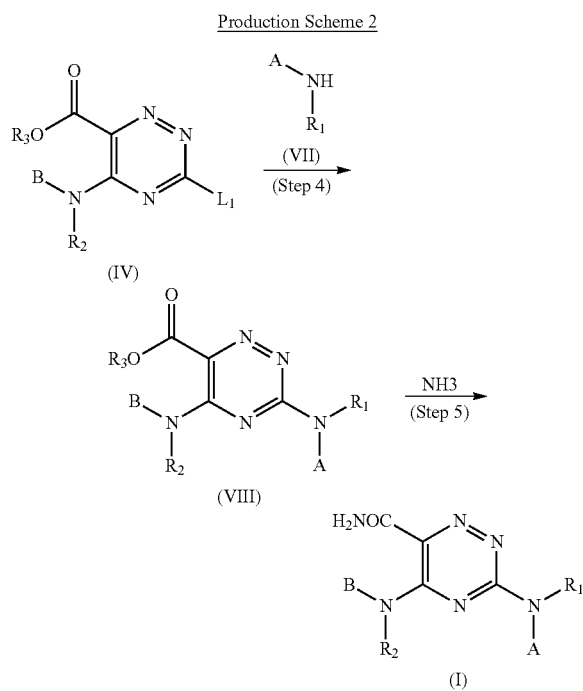

wherein A, B, $L_1$, $R_1$, $R_2$, and $R_3$ are as defined above.

(Step 4)

This step is the step of reacting the compound represented by the general formula (IV) with the compound represented by the general formula (VII) or a salt thereof to produce a compound represented by the general formula (VIII).

This step can be performed by the same method as in above Step 3 or a method equivalent thereto, or by a combination of any of these methods with a routine method.

This step is usually performed using 0.5 moles to excess mole, preferably equal mole to 3 moles of the compound (VII) with respect to 1 mole of the compound (IV).

The reaction solvent is not particularly limited as long as the solvent does not hinder the reaction. The reaction solvent is preferably, for example, methanol, ethanol, isopropanol, tert-butyl alcohol, toluene, benzene, methylene chloride, chloroform, tetrahydrofuran, dioxane, dimethylformamide, acetonitrile, N-methylpyrrolidone, dimethyl sulfoxide, or a mixed solvent thereof.

Also, the reaction can be performed, if necessary, using a base. For example, an organic base such as triethylamine, diisopropylethylamine, pyridine, or 4-dimethylaminopyridine or an inorganic base such as sodium bicarbonate, sodium carbonate, potassium carbonate, cesium carbonate, sodium hydroxide, sodium hydride, or potassium tert-butyrate can be used as the base.

The amount of the base used is usually equal mole to excess mol, preferably 1 to 3 moles, with respect to 1 mole of the compound represented by the general formula (IV).

The reaction temperature is usually 0° C. to 200° C., preferably room temperature to 130° C.

The reaction time is usually 1 minute to 7 days, preferably 5 minutes to 24 hours.

The thus-obtained compound represented by the general formula (VIII) may be isolated and purified by separation and purification means known in the art, for example, concentration, concentration under reduced pressure, crystallization, solvent extraction, reprecipitation, or chromatography or may be subjected to the next step without being isolated or purified.

(Step 5)

This step is the step of reacting the compound represented by the general formula (VIII) with ammonia or a salt thereof to produce the compound represented by the general formula (I).

This step can be performed by the same method as in above Step 2 or a method equivalent thereto, or by a combination of any of these methods with a routine method.

The amount of the ammonia or the salt thereof is usually equal mole to excess mole, preferably excess mole, with respect to 1 mole of the compound represented by the general formula (VIII).

The reaction solvent is not particularly limited as long as the solvent does not hinder the reaction. The reaction solvent is preferably, for example, methanol, ethanol, isopropanol, tert-butyl alcohol, toluene, benzene, methylene chloride, chloroform, tetrahydrofuran, dioxane, dimethylformamide, acetonitrile, N-methylpyrrolidinone, dimethyl sulfoxide, or a mixed solvent thereof.

The reaction temperature is usually 0° C. to 200° C., preferably room temperature to 160° C.

The reaction time is usually 10 minutes to 12 hours, preferably 5 minutes to 2 hours.

The compound (I) thus obtained can be isolated and purified by separation and purification means known in the art, for example, concentration, concentration under reduced pressure, crystallization, solvent extraction, reprecipitation, or chromatography.

In above Reaction Schemes 1 and 2, for example, an amino group, an imino group, a hydroxy group, a carboxyl group, a carbonyl group, and an amide group, and functional groups having active proton, such as indole can be subjected to the introduction of a protective group in an appropriate step of each production scheme using a protected reagent or according to a routine method, and the protective group can then be removed.

The "protective group for an amino group or an imino group" is not particularly limited as long as the protective group has the desired functions. Examples thereof include: aralkyl groups such as a benzyl group, a p-methoxybenzyl group, a 3,4-dimethoxybenzyl group, a o-nitrobenzyl group, a p-nitrobenzyl group, a benzhydryl group, a trityl group, and a cumyl group; lower alkanoyl groups such as a formyl group, an acetyl group, a propionyl group, a butyryl group, a pivaloyl group, a trifluoroacetyl group, and a trichloroacetyl group; a benzoyl group; arylalkanoyl groups such as a phenylacetyl group and a phenoxyacetyl group; lower alkoxycarbonyl groups such as a methoxycarbonyl group, an ethoxycarbonyl group, a propyloxycarbonyl group, and a tert-butoxycarbonyl group; aralkyloxycarbonyl groups such as a p-nitrobenzyloxycarbonyl group and a phenethyloxycarbonyl group; lower alkylsilyl groups such as a trimethylsilyl group and a tert-butyldimethylsilyl group; a tetrahydropyranyl group; a trimethylsilylethoxymethyl group; lower alkylsulfonyl groups such as a methylsulfonyl group, an ethylsulfonyl group, and a tert-butylsulfonyl group; lower alkylsulfinyl groups such as a tert-butylsulfinyl group; arylsulfonyl groups such as a benzenesulfonyl group and a toluenesulfonyl group; and imide groups such as a phthalimide group. Particularly, for example, a trifluoroacetyl group, an acetyl group, a tert-butoxycarbonyl group, a benzyloxycarbonyl group, a trimethylsilylethoxymethyl group, and a cumyl group are preferred.

The "protective group for a hydroxy group" is not particularly limited as long as the protective group has the desired functions. Examples thereof include: lower alkyl groups such as a methyl group, an ethyl group, a propyl group, an isopropyl group, and a tert-butyl group; lower alkylsilyl groups such as a trimethylsilyl group and a tert-butyldimethylsilyl group; lower alkoxymethyl groups such as a methoxymethyl group and a 2-methoxyethoxymethyl group; a tetrahydropyranyl group; a trimethylsilylethoxymethyl group; aralkyl groups such as a benzyl group, a p-methoxybenzyl group, a 2,3-dimethoxybenzyl group, a o-nitrobenzyl group, a p-nitrobenzyl group, and a trityl group; and acyl groups such as a formyl group, an acetyl group, and a trifluoroacetyl group. Particularly, for example, a methyl group, a methoxymethyl group, a tetrahydropyranyl group, a trimethylsilylethoxymethyl group, a tert-butyldimethylsilyl group, and an acetyl group are preferred.

The "protective group for a carboxyl group" is not particularly limited as long as the protective group has the desired functions. Examples thereof include: lower alkyl groups such as a methyl group, an ethyl group, a propyl group, an isopropyl group, and a tert-butyl group; halo-lower alkyl groups such as a 2,2,2-trichloroethyl group; lower alkenyl groups such as an allyl group; a trimethylsilylethoxymethyl group; and aralkyl groups such as a benzyl group, a p-methoxybenzyl group, a p-nitrobenzyl group, a benzhydryl group, and a trityl group. Particularly, for example, a methyl group, an ethyl group, a tert-butyl group, an allyl group, a benzyl group, a p-methoxybenzyl group, and a trimethylsilylethoxymethyl group are preferred.

The "protective group for a carbonyl group" is not particularly limited as long as the protective group has the desired functions. Examples thereof include acetals and ketals such as ethylene ketal, trimethylene ketal, and dimethyl ketal.

Methods for removing these protective groups differ depending on the types of the protective groups and the stability of the compound (I) of interest, etc. The protective groups can be removed, for example, according to methods described in literatures [see Protective Groups in Organic Synthesis, the 3rd edition, T. W. Greene, John Wiley & Sons, Inc. (1999)] or methods equivalent thereto, for example, by solvolysis using an acid or a base, i.e., a method which involves allowing, for example, 0.01 moles to a large excess of an acid, preferably trifluoroacetic acid, formic acid, or hydrochloric acid, or equal mole to a large excess of a base, preferably potassium hydroxide or calcium hydroxide to act or by chemical reduction using, for example, a metal hydride complex or by catalytic reduction using, for example, a palladium-carbon catalyst, a Raney nickel catalyst.

The compound of the present invention can be easily isolated and purified by usual separation means. Examples of such means can include solvent extraction, recrystallization, preparative reverse-phase high-performance liquid chromatography, column chromatography, and preparative thin-layer chromatography.

The compound of the present invention may have isomers such as optical isomers, stereoisomers, positional isomers, or rotational isomers. In such a case, all of these isomers and mixtures thereof are encompassed by the compound of the present invention. For example, when the compound of the present invention has optical isomers, optical isomers resolved from a racemate are also encompassed by the compound of the present invention. These isomers can each be prepared into single compounds by synthesis approaches and separation approaches (concentration, solvent extraction, column chromatography, recrystallization, etc.) known per se in the art. Also, the compound of the present invention wherein each of $R_1$ and $R_2$ is hydrogen has tautomers shown below. All of these isomers are also encompassed by the compound of the present invention.

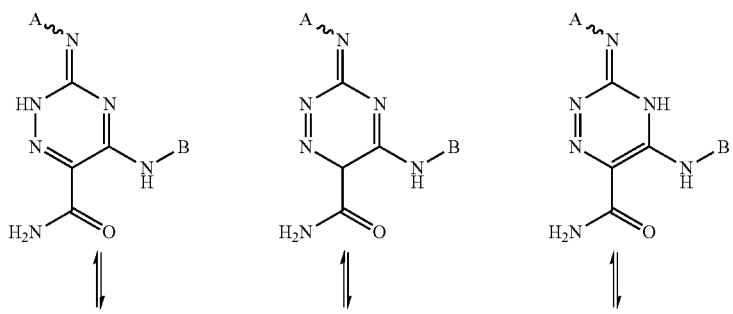

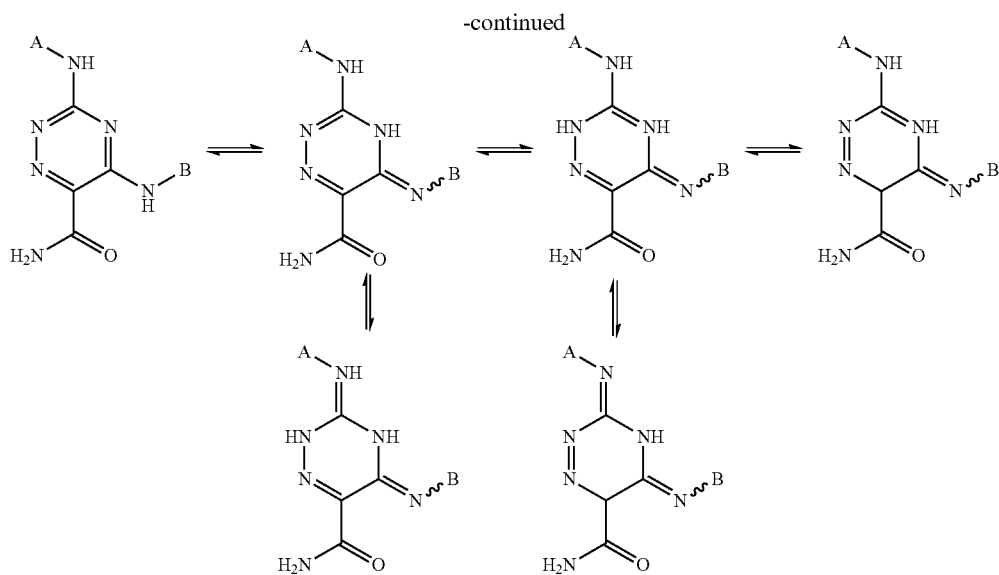

-continued

The compound of the present invention or the salt thereof may be crystals. Single crystal forms and polymorphic mixtures are both encompassed by the compound of the present invention or the salt thereof. The crystals can be produced by crystallizing the compound of the present invention or the salt thereof by the application of a crystallization method known per se in the art. The compound of the present invention or the salt thereof may be a solvate (e.g., a hydrate) or may be a non-solvate. Both of these forms are encompassed by the compound of the present invention or the salt thereof. Compounds labeled with, for example, isotopes (e.g., 3H, 14C, 35S, and 125I) are also encompassed by the compound of the present invention or the salt thereof.

A prodrug of the compound of the present invention or the salt thereof refers to a compound which is converted to the compound of the present invention or the salt thereof through reaction with, for example, an enzyme, and gastric acid under physiological conditions in vivo, i.e., a compound which is converted to the compound of the present invention or the salt thereof through enzymatic oxidation, reduction, hydrolysis, etc., or a compound which is converted to the compound of the present invention or the salt thereof through hydrolysis, etc. caused by, for example, gastric acid. Alternatively, the prodrug of the compound of the present invention or the salt thereof may be a compound which is converted to the compound of the present invention or the salt thereof under physiological conditions as described in Hirokawa Shoten Co., Ltd., "Development of Medicines" published in 1990, Vol. 7, Molecular Design, p. 163-198.

The salt of the compound of the present invention means a salt routinely used in the field of organic chemistry. Examples thereof can include a base-addition salt to a carboxyl group when the compound has the carboxyl group, and an acid-addition salt to an amino group or a basic heterocyclic group when the compound has the amino group or the basic heterocyclic group.

Examples of the base-addition salt include: alkali metal salts such as sodium salt and potassium salt; alkaline-earth metal salts such as calcium salt and magnesium salt; ammonium salts; and organic amine salts such as trimethylamine salt, triethylamine salt, dicyclohexylamine salt, ethanolamine salt, diethanolamine salt, triethanolamine salt, procaine salt, and N,N'-dibenzylethylenediamine salt.

Examples of the acid-addition salt include: inorganic acid salts such as hydrochloride, sulfate, nitrate, phosphate, and perchlorate; organic acid salts such as acetate, formate, maleate, fumarate, tartrate, citrate, ascorbate, and trifluoroacetate; and sulfonates such as methanesulfonate, isethionate, benzenesulfonate, and p-toluenesulfonate.

The compound of the present invention or the salt thereof has excellent Syk inhibitory activity and is useful as an antitumor agent. The compound of the present invention or the salt thereof also advantageously has few adverse effects attributed to other kinases, by virtue of its excellent selectivity for Syk. Examples of the targeted cancer include, but not particularly limited to, head and neck cancer, esophageal cancer, gastric cancer, colon cancer, rectal cancer, liver cancer, gallbladder or bile duct cancer, biliary cancer, pancreatic cancer, lung cancer, breast cancer, ovary cancer, uterine cervix cancer, uterine body cancer, kidney cancer, bladder cancer, prostate cancer, testicular tumor, osteosarcoma, soft tissue sarcoma, blood cancer, multiple myeloma, skin cancer, brain tumor, and mesothelioma. The cancer is preferably blood cancer such as B cell lymphoma, chronic lymphatic leukemia, peripheral T cell lymphoma, myelodysplastic syndrome, acute myeloid leukemia, or acute lymphatic leukemia.

For use in a pharmaceutical agent, the compound of the present invention or the salt thereof can be mixed, if necessary, with a pharmaceutically acceptable carrier. Various dosage forms can be adopted according to preventive or therapeutic purposes. The forms may be any of, for example, oral preparations, injections, suppositories, ointments, and adhesive agents. Preferably, an oral preparation is adopted. These dosage forms can each be produced by a routine formulation method generally known to those skilled in the art.

Various organic or inorganic carrier substances routinely used as pharmaceutical materials can be used as the pharmaceutically acceptable carrier. Solid preparations can be formulated using, for example, an excipient, a binder, a disintegrant, a lubricant, and/or a colorant. Liquid preparations can be formulated using, for example, a solvent, a solubilizer, a suspending agent, a tonicity agent, a buffer, and/or a soothing agent. If necessary, pharmaceutical additives such as antiseptics, antioxidants, colorants, sweeteners, and stabilizers may be used.

For preparing oral solid preparations, the compound of the present invention can be supplemented with an excipient, if necessary, an excipient, a binder, a disintegrant, a lubricant, a colorant, a corrigent etc., and then prepared into, for example, tablets, coated tablets, granules, powders, or capsules by a routine method.

For preparing injections, the compound of the present invention can be supplemented with, for example, a pH adjuster, a buffer, a stabilizer, a tonicity agent, a local anesthetic, and prepared into subcutaneous, intramuscular, or intravenous injections by a routine method.

The amount of the compound of the present invention to be contained in each of these unit dosage forms varies depending on the symptoms of a patient to receive this pharmaceutical agent or depending on the dosage form thereof, etc. In general, the amount of the compound of the present invention is desirably approximately 0.05 to 1000 mg for oral preparations, approximately 0.01 to 500 mg for injections, and approximately 1 to 1000 mg for suppositories, per unit dosage form.

The daily dose of a drug having any of these dosage forms differs depending on the symptoms, body weight, age, sex, etc. of a patient and cannot be generalized. The daily dose in an adult (body weight: 50 kg) can be usually approximately 0.05 to 5000 mg, preferably 0.1 to 1000 mg, in terms of the amount of the compound of the present invention. This daily dose is preferably administered once a day or at approximately two or three divided doses.

EXAMPLES

Hereinafter, the present invention will be described more specifically with reference to Examples. However, the present invention is not limited by these examples by any means.

Various reagents used in Examples were commercially available products unless otherwise specified. Purif-Pack® SI manufactured by Moritex Corp., SNAP KP-Sil® Silica prepacked column manufactured by Biotage AB, SNAP HP-Sil® Silica prepacked column manufactured by Biotage AB, or SNAP Ultra® Silica prepacked column manufactured by Biotage AB were used in silica gel column chromatography. Purif-Pack® NH manufactured by Moritex Corp. or SNAP KP-NH® prepacked column manufactured by Biotage AB were used in basic silica gel column chromatography. Kieselgel™ 60 F254, Art. 5744 manufactured by Merck KGaA was used in preparative thin-layer chromatography. NMR spectra were measured using AL400 (400 MHz; JEOL Ltd.) or Mercury 400 (400 MHz; Varian, Inc.) spectrometer and tetramethylsilane as an internal standard (when a deuterated solvent contained tetramethylsilane) or NMR solvent as an internal standard (in other cases). Total δ values were indicated by ppm. Microwave reaction was performed using Initiator® manufactured by Biotage AB.

LCMS spectra were measured using SQD manufactured by Waters Corp. under the following conditions:
Column: Acquity HSS-T3, 2.1×30 mm, 1.8 μm
MS detection: ESI positive
UV detection: 254 and 210 nm
Column flow rate: 0.5 mL/min
Mobile phase: water/acetonitrile (0.1% formic acid)
Injection quantity: 1 μL Method A

| | Gradient | |
|---|---|---|
| Time (min) | Water | Acetonitrile |
| 0 | 95 | 5 |
| 0.1 | 95 | 5 |
| 1.1 | 5 | 95 |
| 2.0 | STOP | |

Method B

| | Gradient | |
|---|---|---|
| Time (min) | Water | Acetonitrile |
| 0 | 95 | 5 |
| 0.1 | 95 | 5 |
| 2.1 | 5 | 95 |
| 3.0 | STOP | |

Reverse-phase preparative HPLC purification was carried out under the following conditions:
Column: YMC-Actus Triart C18, 30×50 mm, 5 m manufactured by YMC Co., Ltd.
UV detection: 254 nm
Column flow rate: 40 mL/min
Mobile phase: water/acetonitrile (0.1% formic acid)
Injection quantity: 1.0 mL
Gradient: water/acetonitrile 10%→60% (7 min.)

Abbreviations are defined as follows:
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple double doublet
m: multiplet
br: broad
DMSO-d6: deuterated dimethyl sulfoxide
CDCl3: deuterated chloroform
CD3OD: deuterated methanol
THF: tetrahydrofuran
DMF: N,N-dimethylformamide
NMP: N-methyl-pyrrolidinone
DMSO: dimethyl sulfoxide
TFA: trifluoroacetic acid
WSC: 1-(3-dimethylaminopropyl)-3-ethylcarbodiimide hydrochloride
HOBt: 1-hydroxybenzotriazole monohydrate
HATU: O-(7-azabenzotriazol-1-yl)-N,N,N',N'-tetramethyluronium hexafluorophosphate
m-CPBA: 3-chloroperbenzoic acid

Example 1

3-((1R,2S)-2-aminocyclohexylamino)-5-(quinolin-6-ylamino)-1,2,4-triazine-6-carboxamide (Step 1)

Diisopropylethylamine (0.53 ml) was added to a solution of ethyl 5-chloro-3-(methylthio)-1,2,4-triazine-6-carboxylate (234 mg) and 6-aminoquinoline (173 mg) in acetonitrile (3 ml), and the reaction solution was stirred in a microwave reactor at 100° C. for 1 hour. The solvent was evaporated under vacuum, and then the residue was purified by column chromatography on silica gel (developing solvent:hexane/ethyl acetate) to obtain ethyl 3-(methylthio)-5-(quinolin-6-ylamino)-1,2,4-triazine-6-carboxylate as a white solid.

(Step 2)

A 2 M ammonia-methanol solution (3 ml) was added to a solution of ethyl 3-(methylthio)-5-(quinolin-6-ylamino)-1,2,4-triazine-6-carboxylate obtained in the above-described Step 1 (150 mg) in THF (0.5 ml), and then the reaction solution was stirred in a microwave reactor at 130° C. for 30 minutes. The precipitate was filtrated to obtain 3-(methylthio)-5-(quinolin-6-ylamino)-1,2,4-triazine-6-carboxamide as a crude white solid.

(Step 3)

A solution of m-CPBA (55 mg) in THF (0.5 ml) was added to a solution of 3-(methylthio)-5-(quinolin-6-ylamino)-1,2,4-triazine-6-carboxamide obtained in the above-described Step 2 (45 mg) in DMF (1.5 ml), and the reaction solution was stirred at room temperature for 20 minutes. A solution of m-CPBA (55 mg) in THF (0.5 ml) was further added to the reaction solution, and the reaction solution was stirred at room temperature for 20 minutes. Thereafter, tert-butyl((1S,2R)-2-aminocyclohexyl)carbamate (60 mg) and diisopropylethylamine (0.20 ml) were added, and then the reaction solution was heated in a microwave reactor at 100° C. for 10 minutes. The solvent was evaporated under vacuum, and then the residue was purified by column chromatography on silica gel (developing solvent:hexane/ethyl acetate) to obtain tert-butyl(1S,2R)-2-(6-carbamoyl-5-(quinolin-6-ylamino)-1,2,4-triazin-3-ylamino)cyclohexyl carbamate as a white solid.

(Step 4)

Trifluoroacetic acid (0.6 mL) was added to tert-butyl(1S,2R)-2-(6-carbamoyl-5-(quinolin-6-ylamino)-1,2,4-triazin-3-ylamino)cyclohexyl carbamate obtained in the above-described Step 3 (40 mg), and then the reaction solution was stirred at room temperature for 5 minutes. The solvent was evaporated under vacuum, and the resultant residue was purified by column chromatography on basic silica gel (developing solvent:hexane/ethyl acetate) to obtain the titled compound as a white solid.

Example 2

3-((1R,2S)-2-aminocyclohexylamino)-5-(benzo[b]thiophen-4-ylamino)-1,2,4-triazine-6-carboxamide (Step 1)

Diisopropylethylamine (0.10 ml) was added to a solution of ethyl 5-chloro-3-(methylthio)-1,2,4-triazine-6-carboxylate (70 mg) and benzo[b]thiophen-4-amine (70 mg) in THF (1 ml), and the reaction solution was stirred at room temperature for 35 minutes. The solvent was evaporated under vacuum, and then the resultant residue was purified by column chromatography on silica gel (developing solvent:hexane/ethyl acetate) to obtain ethyl 5-(benzo[b]thiophen-4-ylamino)-3-(methylthio)-1,2,4-triazine-6-carboxylate as a white solid.

(Step 2)

A solution of m-CPBA (65 mg) in chloroform (1.5 ml) was added to a solution of ethyl 5-(benzo[b]thiophen-4-ylamino)-3-(methylthio)-1,2,4-triazine-6-carboxylate obtained in the above-described Step 1 (33 mg) in chloroform (1.5 ml), the reaction solution was stirred at room temperature for 10 minutes. Thereafter, tert-butyl((1S,2R)-2-aminocyclohexyl)carbamate (60 mg) and diisopropylethylamine (0.10 ml) were added, and then the reaction solution was stirred at room temperature for 3 hours. The reaction solution was diluted with ethyl acetate and then washed successively with an aqueous sodium bicarbonate solution and a saturated saline solution. After drying over anhydrous sodium sulfate, the solvent was evaporated under vacuum, and then the resultant residue was purified by column chromatography on silica gel (developing solvent:hexane/ethyl acetate) to obtain ethyl 5-(benzo[b]thiophen-4-ylamino)-3-((1R,2S)-2-(tert-butoxycarbonylamino)cyclohexylamino)-1,2,4-triazine-6-carboxylate.

(Step 3)

A 7 M ammonia-methanol solution (2 ml) was added to ethyl 5-(benzo[b]thiophen-4-ylamino)-3-((1R,2S)-2-(tert-butoxycarbonylamino)cyclohexylamino)-1,2,4-triazine-6-carboxylate obtained in the above-described Step 2 (71.8 mg), and then the reaction solution was allowed to react in a microwave reactor at 130° C. for 1 hour. The solvent was evaporated under vacuum, then trifluoroacetic acid (0.5 ml) was added to the resultant residue, and the reaction solution was stirred at room temperature for 5 minutes. The solvent was evaporated under vacuum, and then the resultant residue was purified by column chromatography on basic silica gel (developing solvent:hexane/ethyl acetate) to obtain the titled compound as a white solid.

Example 3

3-((1R,2S)-2-aminocyclohexylamino)-5-(1-methyl-H-indol-4-ylamino)-1,2,4-triazine-6-carboxamide (Step 1)

Sulfuryl chloride (500 µl) was added to ethyl 5-chloro-3-(methylthio)-1,2,4-triazine-6-carboxylate (466 mg), and then the reaction solution was stirred at 70° C. for 2 hours. Thereafter, sulfuryl chloride (150 µl) was added, and the reaction solution was further stirred for 30 minutes. The reaction solution was diluted with THF, and then the solvent was concentrated under vacuum. The resultant residue was dissolved in THF (10 ml), then 1-methyl-1H-indol-4-amine (470 mg) and diisopropylethylamine (0.85 ml) were successively added, and then the reaction solution was stirred at room temperature for 15 minutes. The reaction solution was diluted with ethyl acetate, washed successively with an aqueous sodium bicarbonate solution and a saturated saline solution, and then dried over anhydrous sodium sulfate. The solvent was evaporated under vacuum, and the resultant residue was purified by column chromatography on silica gel (developing solvent:hexane/ethyl acetate) to obtain ethyl 3-chloro-5-(1-methyl-1H-indol-4-ylamino)-1,2,4-triazine-6-carboxylate as a white solid.

(Step 2)

Tert-butyl((1S,2R)-2-aminocyclohexyl)carbamate (302 mg) and diisopropylethylamine (0.40 ml) were added successively to a solution of ethyl 3-chloro-5-(1-methyl-1H-indol-4-ylamino)-1,2,4-triazine-6-carboxylate (390 mg) obtained in the above-described Step 1 in THF (10 ml), and the reaction solution was allowed to react at 70° C. for 2 hours. The reaction solution was diluted with ethyl acetate, washed successively with an aqueous sodium bicarbonate solution and a saturated saline solution, and then dried over anhydrous sodium sulfate. The solvent was evaporated under vacuum, and the resultant residue was purified by column chromatography on silica gel (developing solvent:hexane/ethyl acetate) to obtain ethyl 3-((1R,2S)-2-(tert-butoxycarbonylamino)cyclohexylamino)-5-(1-methyl-1H-indol-4-ylamino)-1,2,4-triazine-6-carboxylate as a yellow solid.
(Step 3)
A 7 M ammonia-methanol solution (10 ml) was added to ethyl 3-((1R,2S)-2-(tert-butoxycarbonylamino)cyclohexylamino)-5-(1-methyl-1H-indol-4-ylamino)-1,2,4-triazine-6-carboxylate obtained in the above-described Step 2 (596 mg), and the reaction solution was allowed to react in a microwave reactor at 130° C. for 90 minutes. The solvent was evaporated under vacuum, and ethanol was added to the resultant residue. The deposited precipitate was filtrated to obtain tert-butyl(1S,2R)-2-(6-carbamoyl-5-(1-methyl-1H-indol-4-ylamino)-1,2,4-triazin-3-ylamino)cyclohexyl carbamate as a yellow solid.
(Step 4)
Concentrated hydrochloric acid (3 ml) was added to a solution of tert-butyl(1S,2R)-2-(6-carbamoyl-5-(1-methyl-1H-indol-4-ylamino)-1,2,4-triazin-3-ylamino)cyclohexyl carbamate obtained in the above-described Step 3 (575 mg) in ethanol (3 ml). Thereafter, the reaction solution was stirred at room temperature for 30 minutes. The reaction solution was diluted with water, a 5 N aqueous sodium hydroxide solution was added for basification, and then the resultant was extracted with chloroform. After drying over anhydrous sodium sulfate, the solvent was evaporated under vacuum. Ethanol was added to the resultant residue, and the deposited precipitate was filtrated to obtain the titled compound as a white solid.

Example 4

3-((1R,2S)-2-aminocyclohexylamino)-5-(2-(ethyl-d5)-2H-indazol-5-ylamino)-1,2,4-triazine-6-carboxamide (Step 1)
60% Sodium hydride (including 40% liquid paraffin as an additive) (60 mg) was added to a solution of 5-nitro-1H-indazole (210 mg) and ethyl bromide-d5 (170 mg) in DMF (4.2 ml), and the reaction solution was stirred at room temperature overnight. Water was added to the reaction solution, the deposited precipitate was filtrated, and then the resultant crude product was purified by column chromatography on silica gel (developing solvent:hexane/ethyl acetate) to obtain 5-nitro-1-(ethyl-d5)-1H-indazole and 5-nitro-2-(ethyl-d5)-2H-indazole as a white solid, respectively.
(Step 2)
5-Nitro-2-(ethyl-d5)-2H-indazole obtained in the above-described Step 1 (65 mg) was dissolved in methanol (3 ml), developed Raney nickel (20 mg) and hydrazine monohydrate (0.15 ml) were added, and the reaction solution was stirred at room temperature for 15 minutes. The insolubles were filtrated through celite, and the solvent was evaporated under vacuum to obtain 2-(ethyl-d5)-2H-indazol-5-amine as a yellow solid.
(Step 3)
In accordance with Example 1 (Steps 1 to 4), 2-(ethyl-d5)-2H-indazol-5-amine obtained in the above-described Step 2 was used instead of 6-aminoquinoline to obtain the titled compound as a yellow solid.

Example 5

3-((1R,2S)-2-aminocyclohexylamino)-5-(1-(ethyl-d5)-1H-indazol-5-ylamino)-1,2,4-triazine-6-carboxamide (Step 1)
In accordance with Example 4 (Step 2), 5-nitro-1-(ethyl-d5)-1H-indazole obtained in Example 4 (Step 1) was used instead of 5-nitro-2-(ethyl-d5)-2H-indazole to obtain 1-(ethyl-d5)-1H-indazol-5-amine as a yellow solid.
(Step 2)
1-(Ethyl-d5)-1H-indazol-5-amine obtained in the above-described Step 1 (40 mg) was added to a solution of ethyl 5-chloro-3-(methylthio)-1,2,4-triazine-6-carboxylate (60 mg) in THF (1 ml), and the reaction solution was allowed to react at 50° C. for 15 minutes. The solvent was evaporated under vacuum, then water was added to the residue, and the precipitate was filtrated to obtain ethyl 3-(methylthio)-5-(1-(ethyl-d5)-1H-indazol-5-ylamino)-1,2,4-triazine-6-carboxylate as a yellow solid.
(Step 3)
In accordance with Example 1 (Steps 3 and 4), 3-(methylthio)-5-(1-(ethyl-d5)-1H-indazol-5-ylamino)-1,2,4-triazine-6-carboxamide obtained in the above-described Step 2 was used instead of 3-(methylthio)-5-(quinolin-6-ylamino)-1,2,4-triazine-6-carboxamide to obtain the titled compound as a yellow solid.

Example 6

3-((1R,2S)-2-(dimethylamino)cyclohexylamino)-5-(1-(ethyl-d5)-1H-indazol-5-ylamino)-1,2,4-triazine-6-carboxamide diformate An aqueous 50% formaldehyde solution (0.01 ml) and a 0.3 M Zn(BH$_3$CN)$_2$-methanol solution (0.1 ml) prepared by a known method were added to a solution of 3-((1R,2S)-2-aminocyclohexylamino)-5-(1-(ethyl-d5)-1H-indazol-5-ylamino)-1,2,4-triazine-6-carboxamide obtained in Example 5 (2 mg) in methanol (1 ml), and the reaction solution was stirred at room temperature for 15 minutes. The solvent was evaporated under vacuum, the residue was purified by reverse phase preparative HPLC, and the resultant fraction was concentrated under vacuum to obtain the titled compound.

Example 7

(S)-5-(1-(ethyl-d5)-1H-indazol-5-ylamino)-3-(piperidin-3-ylamino)-1,2,4-triazine-6-carboxamide diformate m-CPBA (3.3 mg) was added to a solution of 3-(methylthio)-5-(1-(ethyl-d5)-1H-indazol-5-ylamino)-1,2,4-triazine-6-carboxamide obtained in Example 5 (Step 2) (4 mg) in THF (0.5 mL), and the reaction solution was stirred at room temperature for 1 hour. (S)-tert-butyl 3-aminopiperidine-1-carboxylate (5 mg) was added, the mixture was allowed to react at 50° C. overnight, and then the solvent was evaporated from the reaction solution. Trifluoroacetic acid (0.2 ml) was added to the residue, and the reaction solution was stirred at room temperature for 10 minutes. Thereafter, the resultant was purified by reverse phase preparative HPLC. The resultant fraction was concentrated under vacuum to obtain the titled compound as white amorphous.

Example 8

3-((3R,4R)-3-aminotetrahydro-2H-pyran-4-ylamino)-5-(benzo[b]thiophen-4-ylamino)-1,2,4-triazine-6-carboxamide (Step 1)

Sulfuryl chloride (0.30 ml) was added to ethyl 5-chloro-3-(methylthio)-1,2,4-triazine-6-carboxylate (234 mg), and the reaction solution was stirred at room temperature for 10 hours. The solvent was evaporated under vacuum, and the resultant residue was dissolved in THF (5 ml). Benzo[b]thiophen-4-amine (179 mg) and diisopropylethylamine (0.51 ml) were added, and the reaction solution was stirred at room temperature for 5 minutes. The reaction solution was diluted with ethyl acetate, and washed successively with an aqueous sodium bicarbonate solution and a saturated saline solution. After drying over anhydrous sodium sulfate, the solvent was evaporated under vacuum. The residue was purified by column chromatography on silica gel (developing solvent:hexane-ethyl acetate) to obtain ethyl 3-chloro-5-(benzo[b]thiophen-4-ylamino)-1,2,4-triazine-6-carboxylate as a white solid.

(Step 2)

Tert-butyl((3R,4R)-4-aminotetrahydro-2H-pyran-3-yl)carbamate (26 mg) and diisopropylethylamine (0.050 ml) were added to a solution of ethyl 3-chloro-5-(benzo[b]thiophen-4-ylamino)-1,2,4-triazine-6-carboxylate obtained in the above-described Step 1 (34 mg) in THF (1 mL), and the reaction solution was stirred at 80° C. for 30 minutes. The solvent was evaporated under vacuum, and the resultant residue was purified by column chromatography on silica gel (developing solvent:hexane-ethyl acetate) to obtain ethyl 5-(benzo[b]thiophen-4-ylamino)-3-((3R,4R)-3-(tert-butoxycarbonylamino)tetrahydro-2H-pyran-4-ylamino)-1,2,4-triazine-6-carboxylate.

(Step 3)

A 7 M ammonia-methanol solution (2 mL) was added to ethyl 5-(benzo[b]thiophen-4-ylamino)-3-((3R,4R)-3-(tert-butoxycarbonylamino)tetrahydro-2H-pyran-4-ylamino)-1,2,4-triazine-6-carboxylate obtained in the above-described Step 2 (50 mg), and the reaction solution was stirred in a microwave reactor at 130° C. for 1 hour. The reaction solution was cooled to room temperature, and then the deposited precipitate was filtrated to obtain tert-butyl(3R,4R)-4-(5-(benzo[b]thiophen-4-ylamino)-6-carbamoyl-1,2,4-triazin-3-ylamino)tetrahydro-2H-pyran-3-yl carbamate.

(Step 4)

Trifluoroacetic acid (0.5 mL) was added to tert-butyl(3R,4R)-4-(5-(benzo[b]thiophen-4-ylamino)-6-carbamoyl-1,2,4-triazin-3-ylamino)tetrahydro-2H-pyran-3-yl carbamate obtained in the above-described Step 3 (46 mg), and the reaction solution was stirred at room temperature for 5 minutes. The solvent was evaporated under vacuum, and then the residue was purified by column chromatography on silica gel (developing solvent:hexane-ethyl acetate) to obtain the titled compound as a light yellow solid.

Example 9

3-((1R,2S)-2-aminocyclohexylamino)-5-(1-(ethyl-d5)-1H-indol-4-ylamino)-1,2,4-triazine-6-carboxamide (Step 1)

60% Sodium hydride (including 40% liquid paraffin as an additive) (100 mg) was added to a solution of 4-nitro-1H-indole (320 mg) and ethyl bromide-d5 (250 mg) in DMF (2 ml), and the reaction solution was stirred at room temperature for 10 minutes. The reaction solution was diluted with ethyl acetate, and washed successively with water and a saturated saline solution. After drying over anhydrous sodium sulfate, the solvent was evaporated under vacuum. The resultant residue was purified by column chromatography on silica gel (developing solvent:hexane/ethyl acetate) to obtain 4-nitro-1-(ethyl-d5)-1H-indole as a white solid.

(Step 2)

4-Nitro-1-(ethyl-d5)-1H-indole obtained in the above-described Step 1 (100 mg) was dissolved in methanol (5 ml), then developed Raney nickel (50 mg) and hydrazine monohydrate (0.2 ml) were added, and the reaction solution was stirred at room temperature for 15 minutes. The insolubles were filtrated through celite, and the solvent was evaporated under vacuum to obtain 1-(ethyl-d5)-1H-indol-4-amine as a yellow oily substance.

(Step 3)

1-(Ethyl-d5)-1H-indol-4-amine obtained in the above-described Step 2 (40 mg) was added to a solution of ethyl 5-chloro-3-(methylthio)-1,2,4-triazine-6-carboxylate (60 mg) in THF (2 ml), and the reaction solution was stirred at room temperature for 15 minutes. The solvent was evaporated under vacuum, and the resultant residue was purified by column chromatography on silica gel (developing solvent:hexane/ethyl acetate) to obtain ethyl 5-(1-(ethyl-d5)-1H-indol-4-ylamino)-3-(methylthio)-1,2,4-triazine-6-carboxylate as a yellow solid.

(Step 4)

A 7 M ammonia-methanol solution (1 ml) was added to ethyl 5-(1-(ethyl-d5)-1H-indol-4-ylamino)-3-(methylthio)-1,2,4-triazine-6-carboxylate obtained in the above-described Step 3 (47 mg), and the reaction solution was stirred at 80° C. for 5 minutes. Thereafter, the solvent was evaporated under vacuum. Subsequently, m-CPBA (45 mg) was added to a solution of the resultant residue in THF (2 ml), and the reaction solution was stirred at room temperature for 30 minutes. Thereafter, tert-butyl((1S,2R)-2-aminocyclohexyl)carbamate (50 mg) was added, and the reaction solution was stirred at 50° C. for 2 hours. The solvent was evaporated under vacuum, and then 4 M hydrochloric acid-dioxane (2 ml) was added to the residue. The reaction solution was stirred at room temperature for 10 minutes, and then the solvent was evaporated under vacuum. The residue was purified by reverse phase preparative HPLC, and the resultant fraction was concentrated under vacuum to obtain the titled compound as a white solid.

Example 10

3-((1R,2S)-2-aminocyclohexylamino)-5-(1-cyclopropyl-1H-indol-4-ylamino)-1,2,4-triazine-6-carboxamide (Step 1)

Cyclopropyl boronic acid (1.0 g), sodium bicarbonate (0.99 g), copper acetate (II) (1.1 g), and 2,2'-bipyridine (0.92 g) were added to a solution of 4-nitro-1H-indole (0.96 g) in 1,2-dichloroethane (60 ml). The reaction solution was stirred at room temperature for 7 days, and then further stirred at 60° C. for 2 hours. The insolubles were filtrated through celite, and then the resultant was washed successively with water and a saturated saline solution. After drying over anhydrous sodium sulfate, the solvent was evaporated under vacuum.

The resultant residue was purified by column chromatography on silica gel (developing solvent:hexane/ethyl acetate) to obtain 1-cyclopropyl-4-nitro-1H-indole as a yellow solid.
(Step 2)
1-Cyclopropyl-4-nitro-1H-indole obtained in the above-described Step 1 (190 mg) was dissolved in methanol (5 ml), and developed Raney nickel (100 mg) and hydrazine monohydrate (0.2 ml) were added. Subsequently, the reaction solution was stirred at room temperature for 20 minutes. The insolubles were filtrated through celite, and the solvent was evaporated under vacuum to obtain 1-cyclopropyl-1H-indol-4-amine as a light yellow solid.
(Step 3)
In accordance with Example 9 (Steps 3 and 4), 1-cyclopropyl-1H-indol-4-amine obtained in the above-described Step 2 was used instead of 1-(ethyl-d5)-1H-indol-4-amine to obtain the titled compound as a yellow solid.

Example 11

3-((1R,2S)-2-aminocyclohexylamino)-5-(2-cyclobutyl-2H-indazol-5-ylamino)-1,2,4-triazine-6-carboxamide (Step 1)
Cyclobutanol (260 mg), triphenylphosphine (1.1 g), and diisopropyl azo dicarboxylate (790 mg) were added successively to a solution of 5-nitro-1H-indazole (490 mg) in THF (10 ml) at room temperature, and the reaction solution was stirred at room temperature overnight. The solvent was evaporated under vacuum, and the residue was purified by column chromatography on silica gel (developing solvent: hexane/ethyl acetate) to obtain 5-nitro-1-(cyclobutyl)-1H-indazole and 5-nitro-2-(cyclobutyl)-2H-indazole as a yellow oily substance, respectively.
(Step 2)
In accordance with Example 4 (Steps 2 and 3), 5-nitro-2-(cyclobutyl)-2H-indazole was used instead of 5-nitro-2-(ethyl-d5)-2H-indazole to obtain the titled compound as a yellow solid.

Example 12

6-(3-((1R,2S)-2-aminocyclohexylamino)6-carbamoyl-1,2,4-triazin-5-ylamino)quinoline 1-oxide In accordance with Example 1 (Steps 3 and 4), an excessive quantity of m-CPBA was used to obtain the titled compound as a white solid.

Example 13

3-((1R,2S)-2-aminocyclohexylamino)-5-(1-methyl-6-(1-methyl-1H-pyrazol-4-yl)-1H-indazol-4-ylamino)-1,2,4-triazine-6-carboxamide (Step 1)
60% Sodium hydride (including 40% liquid paraffin as an additive) (213 mg) was added to a solution of 6-bromo-4-nitro-1H-indazole (901 mg) in DMF (19 ml) in an ice bath. Subsequently, the reaction solution was stirred at 0° C. for 15 minutes, then methyl iodide (0.35 ml) was added, and the reaction solution was allowed to react at room temperature for 11 hours. The reaction solution was poured into water, and the deposited precipitate was filtrated to obtain a crude product. The crude product was purified by column chromatography on silica gel (developing solvent:hexane/ethyl acetate) to obtain 6-bromo-1-methyl-4-nitro-1H-indazole and 6-bromo-2-methyl-4-nitro-2H-indazole as a yellow solid, respectively.
(Step 2)
2-Dicyclohexylphosphino-2',4',6'-triisopropyl biphenyl (4.9 mg), chloro(2-dicyclohexylphosphino-2',4',6'-triisopropyl-1,1'-biphenyl)[2-(2-aminoethyl)phenyl)]palladium(II) (10 mg), a 2 M aqueous sodium carbonate solution (0.2 ml), and dioxane (0.8 ml) were added to 6-bromo-1-methyl-4-nitro-1H-indazole obtained in the above-described Step 1 (51.0 mg) and 1-methyl-4-(4,4,5,5-tetramethyl-1,3,2-dioxaborolan-2-yl)-1H-pyrazole (65 mg). Subsequently, the reaction solution was allowed to react in a microwave reactor at 110° C. for 1.5 hours. The solvent was evaporated under vacuum, and the residue was purified by column chromatography on silica gel (developing solvent:hexane/ethyl acetate) to obtain 1-methyl-6-(1-methyl-1H-pyrazol-4-yl)-4-nitro-1H-indazole as a yellow solid.
(Step 3)
1-Methyl-6-(1-methyl-1H-pyrazol-4-yl)-4-nitro-1H-indazole obtained in the above-described Step 2 (46 mg) was dissolved in a methanol-ethyl acetate mixed solvent (1:2, 13.5 ml). Subsequently, 20% palladium hydroxide-carbon (10 mg) was added, and the reaction solution was allowed to react under hydrogen atmosphere at room temperature for 5 hours. The insolubles were filtrated through celite, and the solvent was evaporated under vacuum to obtain 1-methyl-6-(1-methyl-1H-pyrazol-4-yl)-1H-indazol-4-amine as a yellow oily substance.
(Step 4)
In accordance with Example 2 (Steps 1 to 3), 1-methyl-6-(1-methyl-1H-pyrazol-4-yl)-1H-indazol-4-amine obtained in the above-described Step 3 was used instead of benzo[b]thiophen-4-amine to obtain the titled compound as a yellow solid.

Example 14

5-(5-Acetyl-2,3'-bithiophen-5'-ylamino)-3-((1R,2S)-2-aminocyclohexylamino)-1,2,4-triazine-6-carboxamide In accordance with Example 13 (Steps 2 to 4), tert-butyl 4-bromothiophen-2-yl carbamate was used instead of 6-bromo-1-methyl-4-nitro-1H-indazole, and 5-acetylthiophen-2-yl boronic acid was used instead of 1-methyl-4-(4,4,5,5-tetramethyl-1,3,2-dioxaborolan-2-yl)-1H-pyrazole to obtain the titled compound as a light yellow solid.

Example 15

5-(5-(5-Acetylthiophen-2-yl)pyridin-3-ylamino)-3-((1R,2S)-2-aminocyclohexylamino)-1,2,4-triazine-6-carboxamide In accordance with Example 13 (Steps 2 to 4), 5-bromopyridin-3-amine was used instead of 6-bromo-1-methyl-4-nitro-1H-indazole, and 5-acetylthiophen-2-yl boronic acid was used instead of 1-methyl-4-(4,4,5,5-tetramethyl-1,3,2-dioxaborolan-2-yl)-1H-pyrazole to obtain the titled compound as a yellow solid.

Example 16

3-((1R,2S)-2-aminocyclohexylamino)-5-(5-cyclopropylpyridin-3-ylamino)-1,2,4-triazine-6-carboxamide (Step 1)
A solution of cyclopropyl boronic acid (497 mg), palladium acetate (II) (65 mg), tricyclohexylphosphine (162 mg), and potassium phosphate (2.5 g) in toluene (9 mL) and water (0.45 mL) was added to 5-bromopyridin-3-amine (500 mg), and the mixture was stirred at 100° C. for 11 hours. Ethyl acetate and water were added, the organic layer was separated, and the resultant was washed with a saturated saline solution. After drying over anhydrous sodium sulfate, the solvent was evaporated under vacuum. The resultant residue was purified by column chromatography on silica gel (developing solvent:hexane/ethyl acetate) to obtain 3-amino-5-cyclopropylpyridine.

(Step 2)
3-Amino-5-cyclopropylpyridine obtained in the above-described Step 1 (67 mg) and p-toluenesulfonic acid monohydrate (10 mg) were added to a solution of ethyl 5-chloro-3-(methylthio)-1,2,4-triazine-6-carboxylate (70 mg) in DMF (1 ml), and the reaction solution was stirred in a microwave reactor at 100° C. for 30 minutes. The reaction solution was diluted with ethyl acetate, and washed successively with an aqueous sodium bicarbonate solution, water, and a saturated saline solution. After drying over anhydrous sodium sulfate, the solvent was evaporated under vacuum. The resultant residue was purified by column chromatography on silica gel (developing solvent:hexane/ethyl acetate) to obtain ethyl 5-(5-cyclopropylpyridin-3-ylamino)-3-(methylthio)-1,2,4-triazine-6-carboxylate as a white solid.

(Step 3)
In accordance with Example 2 (Steps 3 and 4), ethyl 5-(5-cyclopropylpyridin-3-ylamino)-3-(methylthio)-1,2,4-triazine-6-carboxylate was used instead of ethyl 5-(benzo[b]thiophen-4-ylamino)-3-(methylthio)-1,2,4-triazine-6-carboxylate to obtain the titled compound as a white solid.

Example 17

3-((1R,2S)-2-aminocyclohexylamino)-5-(1-ethyl-1H-indol-4-ylamino)-1,2,4-triazine-6-carboxamide In accordance with Example 9 (Steps 1 to 4), ethyl bromide was used instead of ethyl bromide-d5 to obtain the titled compound as a white solid.

Example 18

3-((1R,2S)-2-aminocyclohexylamino)-5-(6-(cyclopropylcarbamoyl)pyridin-3-ylamino)-1,2,4-triazine-6-carboxamide (Step 1)
5-Aminopicolinate (44 mg) was added to a solution of ethyl 5-chloro-3-(methylthio)-1,2,4-triazine-6-carboxylate (70 mg) in dimethylsulfoxide (1.5 ml), and the reaction solution was stirred at room temperature for 10 minutes. Thereafter, cyclopropylamine (0.017 ml), diisopropylethylamine (0.079 ml), and HATU (125 mg) were successively added, and the reaction solution was stirred at room temperature overnight. The reaction solution was diluted with ethyl acetate, and washed successively with an aqueous sodium bicarbonate solution and a saturated saline solution. After drying over anhydrous sodium sulfate, the solvent was evaporated under vacuum. The resultant residue was purified by column chromatography on silica gel (developing solvent: hexane/ethyl acetate) to obtain ethyl 5-(6-(cyclopropylcarbamoyl)pyridin-3-ylamino)-3-(methylthio)-1,2,4-triazine-6-carboxylate.

(Step 2)
In accordance with Example 2 (Steps 2 and 3), ethyl 5-(6-(cyclopropylcarbamoyl)pyridin-3-ylamino)-3-(methylthio)-1,2,4-triazine-6-carboxylate obtained in the above-described Step 1 was used instead of ethyl 5-(benzo[b]thiophen-4-ylamino)-3-(methylthio)-1,2,4-triazine-6-carboxylate to obtain the titled compound as a light yellow solid.

Example 19

3-((1R,2S)-2-aminocyclohexylamino)-5-(6-(methylcarbamoyl)pyridin-3-ylamino)-1,2,4-triazine-6-carboxamide In accordance with Example 18 (Steps 1 and 2), methylamine was used instead of cyclopropylamine to obtain the titled compound as a white solid.

Example 20

3-((1R,2S)-2-aminocyclohexylamino)-5-(2-methyl-6-(1-methyl-1H-pyrazol-4-yl)-2H-indazol-4-ylamino)-1,2,4-triazine-6-carboxamide In accordance with Example 13 (Steps 2 to 4), 6-bromo-2-methyl-4-nitro-2H-indazole obtained in Example 13 (Step 1) was used instead of 6-bromo-1-methyl-4-nitro-1H-indazole to obtain the titled compound as a yellow solid.

Example 21

3-((1R,2S)-2-aminocyclohexylamino)-5-(6-methylbenzo[b]thiophen-4-ylamino)-1,2,4-triazine-6-carboxamide (Step 1)
Methyl thioglycolate (0.060 ml) and potassium carbonate (190 mg) were added to a solution of 2,6-dibromo-4-methylbenzaldehyde (153 mg) in dimethylsulfoxide (1.7 mL), and the reaction solution was stirred at 120° C. for 7 hours. The reaction solution was neutralized with 2 M hydrochloric acid, extracted with ethyl acetate, and washed with a saturated saline solution. After drying over anhydrous sodium sulfate, the solvent was evaporated under vacuum. A 5 M aqueous sodium hydroxide solution (0.8 ml) was added to a solution of the resultant residue in a mixture of THF-methanol (1:1) (3.2 ml), and the reaction solution was stirred at room temperature for 2 hours. The reaction solution was diluted with ethyl acetate, and washed successively with 2 M hydrochloric acid and a saturated saline solution. After drying over anhydrous sodium sulfate, the solvent was evaporated under vacuum. Silver carbonate (30 mg) and acetic acid (0.005 ml) were added to a solution of the resultant residue in dimethylsulfoxide (1.1 mL), and the reaction solution was stirred at 120° C. for 6 hours. The reaction solution was diluted with ethyl acetate, and washed successively with an aqueous sodium bicarbonate solution and a saturated saline solution. After drying over anhydrous sodium sulfate, the solvent was evaporated under vacuum. The resultant residue was purified by column chromatography on silica gel (developing solvent: hexane-ethyl acetate) to obtain 4-bromo-6-methylbenzo[b]thiophene.

(Step 2)

Tert-butyl carbamate (109 mg), cesium carbonate (456 mg), palladium acetate (5.0 mg), and 2-dicyclohexylphosphino-2',4',6'-triisopropyl biphenyl (22 mg) were added to a solution of 4-bromo-6-methylbenzo[b]thiophene obtained in the above-described Step 1 (106 mg) in 1,4-dioxane (2.3 mL), and the reaction solution was stirred at 100° C. for 2 hours. The reaction solution was diluted with ethyl acetate, and washed successively with water and a saturated saline solution. After drying over anhydrous sodium sulfate, the solvent was evaporated under vacuum. The residue was purified by column chromatography on silica gel (developing solvent: hexane-ethyl acetate) to obtain tert-butyl 6-methylbenzo[b]thiophen-4-yl carbamate.

(Step 3)

Trifluoroacetic acid (2.0 mL) was added to tert-butyl 6-methylbenzo[b]thiophen-4-yl carbamate obtained in the above-described Step 2 (100 mg), and the reaction solution was stirred at room temperature for 30 minutes. The solvent was evaporated under vacuum, and then the residue was purified by column chromatography on basic silica gel (developing solvent:hexane-ethyl acetate) to obtain 6-methylbenzo[b]thiophen-4-amine.

(Step 4)

In accordance with Example 3 (Steps 1 to 4), 6-methylbenzo[b]thiophen-4-amine obtained in the above-described Step 3 was used instead of 1-methyl-1H-indol-4-amine to obtain the titled compound as a light yellow solid.

Example 22

Ethyl 4-(3-((1R,2S)-2-aminocyclohexylamino)-6-carbamoyl-1,2,4-triazin-5-ylamino)benzo[b]thiophene-6-carboxylate (Step 1)

Potassium carbonate (400 mg) was added to a solution of ethyl 4-acetoxybenzo[b]thiophene-6-carboxylate (760 mg) synthesized according to the method described in WO 2005/007635 in ethanol (6 ml), and the reaction solution was stirred at room temperature for 1 hour. The insolubles were filtrated, then the solvent was evaporated under vacuum, and the residue was purified by column chromatography on silica gel (developing solvent:hexane-ethyl acetate) to obtain ethyl 4-hydroxybenzo[b]thiophene-6-carboxylate as a white solid.

(Step 2)

Anhydrous trifluoromethanesulfonic acid (0.091 ml) was added to a solution of ethyl 4-hydroxy benzo[b]thiophene-6-carboxylate obtained in the above-described Step 1 (100 mg) and triethylamine (0.160 ml) in methylene chloride (2.3 ml) in an ice bath, and the reaction solution was stirred at 0° C. for 2 hours. The reaction solution was diluted with ethyl acetate, and washed successively with a saturated aqueous sodium bicarbonate solution and a saturated saline solution. After drying over anhydrous sodium sulfate, the solvent was evaporated under vacuum. The residue was purified by column chromatography on silica gel (developing solvent:hexane-ethyl acetate) to obtain ethyl 4-(trifluoromethylsulfonyloxy)benzo[b]thiophene-6-carboxylate.

(Step 3)

Tert-butyl carbamate (81 mg), palladium acetate (4 mg), 2-dicyclohexylphosphino-2',4',6'-triisopropyl biphenyl (17 mg), and cesium carbonate (340 mg) were added to a solution of ethyl 4-(trifluoromethylsulfonyloxy)benzo[b]thiophene-6-carboxylate obtained in the above-described Step 2 (120 mg) in dioxane (2 ml), and the reaction solution was stirred at 100° C. for 3 hours. The reaction solution was diluted with ethyl acetate, and washed successively with a saturated aqueous sodium bicarbonate solution and a saturated saline solution. After drying over anhydrous sodium sulfate, the solvent was evaporated under vacuum. The residue was purified by column chromatography on silica gel (developing solvent: hexane-ethyl acetate) to obtain ethyl 4-(tert-butoxycarbonylamino)benzo[b]thiophene-6-carboxylate.

(Step 4)

In accordance with Example 21 (Steps 3 and 4), ethyl 4-(tert-butoxycarbonylamino)benzo[b]thiophene-6-carboxylate obtained in the above-described Step 3 was used instead of tert-butyl 6-methylbenzo[b]thiophen-4-yl carbamate to obtain the titled compound as a light yellow solid.

Example 23

3-((1R,2S)-2-aminocyclohexylamino)-5-(6-(methylcarbamoyl)benzo[b]thiophen-4-ylamino)-1,2,4-triazine-6-carboxamide (Step 1)

A 40% methylamine-methanol solution (3 ml) was added to ethyl 4-(tert-butoxycarbonylamino)benzo[b]thiophene-6-carboxylate obtained in Example 22 (Step 3) (110 mg), and the reaction solution was stirred at 90° C. overnight. Trifluoroacetic acid (0.5 ml) was added to the resultant residue, and the reaction solution was stirred at room temperature for 15 minutes. Thereafter, the solvent was evaporated under vacuum, and the residue was purified by column chromatography on silica gel (developing solvent:hexane-ethyl acetate) to obtain 4-amino-N-methylbenzo[b]thiophene-6-carboxamide.

(Step 2)

In accordance with Example 3 (Steps 1 to 4), 4-amino-N-methylbenzo[b]thiophene-6-carboxamide obtained in the above-described Step 1 was used instead of 1-methyl-1H-indol-4-amine to obtain the titled compound as a light yellow solid.

Example 24

3-((1R,2S)-2-aminocyclohexylamino)-5-(2-(difluoromethyl)-2H-indazol-6-ylamino)-1,2,4-triazine-6-carboxamide (Step 1)

60% Sodium hydride (including 40% liquid paraffin as an additive) (1.2 g) was added to a solution of 6-nitro-1H-indazole (5.90 g) and sodium chlorodifluoroacetate (9.15 g) in N-methylpyrrolidinone (100 ml). Thereafter, the reaction solution was stirred at room temperature for 15 minutes, and further stirred at 100° C. for 30 minutes. The reaction solution was diluted with ethyl acetate, and washed successively with water and a saturated saline solution. After drying over anhydrous sodium sulfate, the solvent was evaporated under vacuum. The residue was purified by column chromatography on silica gel (developing solvent:hexane-ethyl acetate) to obtain 1-(difluoromethyl)-6-nitro-1H-indazole and 2-(difluoromethyl)-6-nitro-2H-indazole as a mixture.

(Step 2)

10% Palladium-carbon (4.0 g) was added to a solution of a mixture (7.05 g) of 1-(difluoromethyl)-6-nitro-1H-indazole obtained in the above-described Step 1 and 2-(difluoromethyl)-6-nitro-2H-indazole in ethyl acetate (60 ml) under nitrogen airflow, and the reaction solution was stirred under hydrogen atmosphere at room temperature overnight. The insolubles were filtrated with celite, and then the solvent was evaporated under vacuum. The resultant residue was purified by column chromatography on silica gel (developing solvent: hexane-ethyl acetate) to obtain 1-(difluoromethyl)-1H-indazol-6-amine and 2-(difluoromethyl)-2H-indazol-6-amine as a white solid, respectively.
(Step 3)
In accordance with Example 8 (Steps 1 to 4), 2-(difluoromethyl)-2H-indazol-6-amine obtained in the above-described Step 2 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 25

3-((1R,2S)-2-aminocyclohexylamino)-5-(1-(1-methyl-1H-pyrazol-3-yl)-1H-indol-4-ylamino)-1,2,4-triazine-6-carboxamide (Step 1)
Trans-N,N'-dimethylcyclohexane-1,2-diamine (a racemate) (0.643 ml) and toluene (10 ml) were added to a mixture of 4-nitro-1H-indole (660 mg), 3-iodine-1-methyl-1H-pyrazole (853 mg), tripotassium phosphate (864 mg), and copper iodide (I) (775 mg), and the reaction solution was stirred at 100° C. for 8 hours. The reaction solution was returned to room temperature, then diluted with ethyl acetate, and washed successively with 28% aqueous ammonia and a saturated saline solution. After drying over anhydrous sodium sulfate, the solvent was evaporated under vacuum. The residue was purified by column chromatography on silica gel (developing solvent:hexane-ethyl acetate) to obtain 1-(1-methyl-1H-pyrazol-3-yl)-4-nitro-1H-indole.
(Step 2)
10% Palladium-carbon (500 mg) was added to a solution of 1-(1-methyl-1H-pyrazol-3-yl)-4-nitro-1H-indole obtained in the above-described Step 1 (625 mg) in ethyl acetate (20 ml) under nitrogen airflow. Then the reaction solution was stirred under hydrogen atmosphere at room temperature for 2 hours and a half. The insolubles were filtrated with celite, and then the solvent was evaporated under vacuum. The resultant residue was purified by column chromatography on silica gel (developing solvent:hexane-ethyl acetate) to obtain 1-(1-methyl-1H-pyrazol-3-yl)-1H-indol-4-amine.
(Step 3)
In accordance with Example 3 (Steps 1 to 4), 1-(1-methyl-1H-pyrazol-3-yl)-1H-indol-4-amine obtained in the above-described Step 2 was used instead of 1-methyl-1H-indol-4-amine to obtain the titled compound as a white solid.

Example 26

3-((1R,2S)-2-aminocyclohexylamino)-5-(1-(difluoromethyl)-1H-indol-4-ylamino)-1,2,4-triazine-6-carboxamide In accordance with Example 24 (Steps 1 to 3), 4-nitro-1H-indole was used instead of 6-nitro-1H-indazole to obtain the titled compound as a white solid.

Example 27

3-((1R,2S)-2-aminocyclohexylamino)-5-(1-cyclobutyl-H-indazol-5-ylamino)-1,2,4-triazine-6-carboxamide In accordance with Example 4 (Steps 2 and 3), 5-nitro-1-(cyclobutyl)-1H-indazole obtained in Example 11 (Step 1) was used instead of 5-nitro-2-(ethyl-d5)-2H-indazole to obtain the titled compound as a yellow solid.

Example 28

3-((1R,2S)-2-aminocyclohexylamino)-5-(2-ethyl-2H-indazol-4-ylamino)-1,2,4-triazine-6-carboxamide (Step 1)
In accordance with Example 4 (Steps 1 and 2), 4-nitro-1H-indazole was used instead of 5-nitro-1H-indazole, and 2-iodoethane was used instead of ethyl bromide-d5 to obtain 2-ethyl-2H-indazol-4-amine.
(Step 2)
In accordance with Example 1 (Steps 1 to 4), 2-ethyl-2H-indazol-4-amine obtained in the above-described Step 1 was used instead of 6-aminoquinoline to obtain 3-((1R,2S)-2-aminocyclohexylamino)-5-(2-ethyl-2H-indazol-4-ylamino)-1,2,4-triazine-6-carboxamide as a yellow solid.

Example 29

3-(5-Acetylthiophen-2-yl)-5-(3-((1R,2S)-2-aminocyclohexylamino)-6-carbamoyl-1,2,4-triazin-5 ylamino)pyridine 1-oxide An excessive quantity of m-CPBA was used, and a method similar to that in Example 1 (Step 3) and (Step 4), a method according to these methods, or a combination of them with routine procedures was used for 3-(methylthio)-5-(5-(5-acetylthiophen-2-yl)pyridin-3-ylamino)-1,2,4-triazine-6-carboxamide obtained in Example 15 to obtain the titled compound as a white solid.

Example 30

3-((1R,2S)-2-aminocyclohexylamino)-5-(1-ethyl-H-indol-6-ylamino)-1,2,4-triazine-6-carboxamide In accordance with Example 9 (Steps 1 to 4), 6-nitro-1H-indole was used instead of 4-nitro-1H-indole, and ethyl bromide was used instead of ethyl bromide-d5 to obtain the titled compound.

Example 31

3-((1R,2S)-2-aminocyclohexylamino)-5-(1-cyclopropyl-H-indazol-4-ylamino)-1,2,4-triazine-6-carboxamide In accordance with Example 10 (Steps 1 to 3), 4-nitro-1H-indazole was used instead of 4-nitro-1H-indole to obtain the titled compound.

Example 32

3-((1R,2S)-2-aminocyclohexylamino)-5-(1-ethyl-2-methyl-1H-indol-4-ylamino)-1,2,4-triazine-6-carboxamide (Step 1)
Acetone (1.0 mL) and tert-butoxy potassium (2.7 g) were added to a solution of 3-nitroaniline (1.38 g) in dimethylsulfoxide (20 ml), and the reaction solution was stirred at room temperature for 3 hours. The reaction solution was diluted with ethyl acetate, and washed successively with an aqueous ammonium chloride solution and a saturated saline solution.

After drying over anhydrous sodium sulfate, the solvent was evaporated under vacuum. The residue was purified by column chromatography on silica gel (developing solvent:hexane-ethyl acetate) to obtain 2-methyl-4-nitro-1H-indole.
(Step 2)
In accordance with Example 9 (Steps 1 to 4), 2-methyl-4-nitro-1H-indole obtained in the above-described Step 1 was used instead of 4-nitro-1H-indole, and ethyl bromide was used instead of ethyl bromide-d5 to obtain the titled compound.

Example 33

3-((1R,2S)-2-aminocyclohexylamino)-5-(1-cyclopropyl-2-methyl-H-indol-4-ylamino)-1,2,4-triazine-6-carboxamide In accordance with Example 10 (Steps 1 to 3), 2-methyl-4-nitro-1H-indole obtained in Example 32 (Step 1) was used instead of 4-nitro-1H-indole to obtain the titled compound.

Example 34

3-((1R,2S)-2-aminocyclohexylamino)-5-(1-(oxetan-3-yl)-H-indol-4-ylamino)-1,2,4-triazine-6-carboxamide (Step 1)
In accordance with Example 9 (Steps 1 and 2), 3-oxetane bromide was used instead of ethyl bromide-d5 to obtain 1-(oxetan-3-yl)-1H-indol-4-amine.
(Step 2)
In accordance with Example 3 (Steps 1 to 4), 1-(oxetan-3-yl)-1H-indol-4-amine obtained in the above-described Step 1 was used instead of 1-methyl-1H-indol-4-amine to obtain the titled compound.

Example 35

3-((1R,2S)-2-aminocyclohexylamino)-5-(1-(2-fluoroethyl)-1H-indol-4-ylamino)-1,2,4-triazine-6-carboxamide In accordance with Example 34 (Steps 1 and 2), 1-iodine-2-fluoroethane was used instead of 3-oxetane bromide to obtain the titled compound.

Example 36

3-((1R,2S)-2-aminocyclohexylamino)-5-(1-(pyridin-2-yl)-1H-indol-4-ylamino)-1,2,4-triazine-6-carboxamide In accordance with Example 25 (Steps 1 to 3), 2-bromopyridine was used instead of 3-iodine-1-methyl-1H-pyrazole to obtain the titled compound.

Example 37

3-((1R,2S)-2-aminocyclohexylamino)-5-(1-phenyl-H-indol-4-ylamino)-1,2,4-triazine-6-carboxamide In accordance with Example 25 (Steps 1 and 2), iodobenzene was used instead of 3-iodine-1-methyl-1H-pyrazole to obtain the titled compound.

Example 38

3-((1R,2S)-2-aminocyclohexylamino)-5-(1-(difluoromethyl)-1H-indazol-4-ylamino)-1,2,4-triazine-6-carboxamide (Step 1)
In accordance with Example 24 (Steps 1 and 2), 4-nitro-1H-indazole was used instead of 6-nitro-1H-indazole to obtain 1-(difluoromethyl)-1H-indazol-4-amine and 2-(difluoromethyl)-2H-indazol-4-amine, respectively.
(Step 2)
In accordance with Example 3 (Steps 1 to 4), 1-(difluoromethyl)-1H-indazol-4-amine obtained in the above-described Step 1 was used instead of 1-methyl-1H-indol-4-amine to obtain the titled compound.

Example 39

3-((1R,2S)-2-aminocyclohexylamino)-5-(1-(2-hydroxy-2-methylpropyl)-1H-indol-4-ylamino)-1,2,4-triazine-6-carboxamide In accordance with Example 34 (Steps 1 and 2), 1-iodine-2-methyl propan-2-ol was used instead of 3-oxetane bromide to obtain the titled compound.

Example 40

3-((1R,2S)-2-aminocyclohexylamino)-5-(1-(2,2-difluoroethyl)-1H-indol-4-ylamino)-1,2,4-triazine-6-carboxamide In accordance with Example 34 (Steps 1 and 2), 1,1-difluoro-2-iodoethane was used instead of 3-oxetane bromide to obtain the titled compound.

Example 41

3-((1R,2S)-2-aminocyclohexylamino)-5-(1-(1,1-difluoro-2-hydroxyethyl)-1H-indol-4-ylamino)-1,2,4-triazine-6-carboxamide In accordance with Example 34 (Steps 1 and 2), 2,2-difluoro-iodoethanol was used instead of 3-oxetane bromide to obtain the titled compound.

Example 42

3-((1R,2S)-2-aminocyclohexylamino)-5-(1-(methyl-d3)-1H-indol-4-ylamino)-1,2,4-triazine-6-carboxamide In accordance with Example 34 (Steps 1 and 2), methyl iodide-d3 was used instead of 3-oxetane bromide to obtain the titled compound as a white solid.

Example 43

3-((1R,2S)-2-aminocyclohexylamino)-5-(thieno[2,3-c]pyridin-4-ylamino)-1,2,4-triazine-6-carboxamide (Step 1)
Methyl thioglycolate (0.653 ml) and potassium carbonate (2.1 g) were added to a solution of 3,5-dibromo-4-pyridinecarboxaldehyde (1.6 g) in DMF (12 ml), and the reaction solution was stirred at 120° C. for 2 hours. 2 M hydrochloric acid was added to the reaction solution to be weakly-acidic, then the reaction solution was extracted with ethyl acetate, and the organic layer was washed with a saturated saline solution. After drying over anhydrous sodium sulfate, the solvent was evaporated under vacuum to obtain a crude product. A 5 M aqueous sodium hydroxide solution (2.4 ml) was added to a solution of the resultant crude product in a THF-methanol mixture (1:1) (24 ml), and the reaction solution was stirred at room temperature for 4 hours. The solvent was evaporated under vacuum, and then 2 M hydrochloric acid was added. The deposited precipitate was filtrated to obtain 4-bromothieno[2,3-c]pyridine-2-carboxylate.
(Step 2)
Silver carbonate (28 mg) and acetic acid (0.006 ml) were added to a solution of 4-bromothieno[2,3-c]pyridine-2-carboxylate obtained in the above-described Step 1 (258 mg) in DMF (2.0 ml), and the reaction solution was stirred at 120° C. for 24 hours. The reaction solution was diluted with ethyl acetate and washed successively with an aqueous sodium bicarbonate solution and a saturated saline solution. After drying over anhydrous sodium sulfate, the solvent was evaporated under vacuum. The resultant residue was purified by column chromatography on silica gel (developing solvent: hexane-ethyl acetate) to obtain 4-bromothieno[2,3-c]pyridine.
(Step 3)
In accordance with Example 21 (Steps 2 to 4), 4-bromothieno[2,3-c]pyridine obtained in the above-described Step 2 was used instead of 4-bromo-6-methylbenzo[b]thiophene to obtain the titled compound.

Example 44

3-((1R,2S)-2-aminocyclohexylamino)-5-(1-propyl-1H-indol-4-ylamino)-1,2,4-triazine-6-carboxamide In accordance with Example 34 (Steps 1 and 2), 1-iodopropane was used instead of 3-oxetane bromide to obtain the titled compound.

Example 45

3-((1R,2S)-2-aminocyclohexylamino)-5-(1-isopropyl-1H-indol-4-ylamino)-1,2,4-triazine-6-carboxamide In accordance with Example 34 (Steps 1 and 2), 2-iodopropane was used instead of 3-oxetane bromide to obtain the titled compound.

Example 46

3-((1R,2S)-2-aminocyclohexylamino)-5-(1-(2-methoxyethyl)-1H-indol-4-ylamino)-1,2,4-triazine-6-carboxamide In accordance with Example 34 (Steps 1 and 2), 1-bromo-2-methoxyethane was used instead of 3-oxetane bromide to obtain the titled compound.

Example 47

3-((1R,2S)-2-aminocyclohexylamino)-5-(1-cyclobutyl-1H-indol-4-ylamino)-1,2,4-triazine-6-carboxamide In accordance with Example 34 (Steps 1 and 2), cyclobutane bromide was used instead of 3-oxetane bromide to obtain the titled compound.

Example 48

3-((1R,2S)-2-aminocyclohexylamino)-5-(5-methoxy-3-methylbenzo[b]thiophen-2-ylamino)-1,2,4-triazine-6-carboxamide (Step 1)
Methyl boronic acid (120 mg), potassium phosphate (849 mg), water (0.30 ml), palladium acetate (22 mg), and 2-dicyclohexylphosphino-2',4',6'-triisopropyl biphenyl (95 mg) were added to a solution of methyl 3-chloro-5-methoxy-1-benzothiophene-2-carboxylate (257 mg) in 1,4-dioxane (3.0 ml), and the reaction solution was stirred at 100° C. for 12 hours. The reaction solution was diluted with ethyl acetate and washed successively with an aqueous ammonium chloride solution, an aqueous sodium bicarbonate solution, and a saturated saline solution. After drying over anhydrous sodium sulfate, the solvent was evaporated under vacuum. The resultant residue was purified by column chromatography on silica gel (developing solvent:hexane-ethyl acetate) to obtain methyl 5-methoxy-3-methylbenzo[b]thiophene-2-carboxylate.
(Step 2)
A 5 M aqueous sodium hydroxide solution (1.5 ml) was added to a solution (6.0 ml) of methyl 5-methoxy-3-methylbenzo[b]thiophene-2-carboxylate obtained in the above-described Step 1 (250 mg) in a THF-methanol mixture (1:1), and the reaction solution was stirred at room temperature for 2 hours. The reaction solution was neutralized with 2 N hydrochloric acid, then extracted with ethyl acetate, and washed with a saturated saline solution. After drying over anhydrous sodium sulfate, the solvent was evaporated under vacuum. N,N-diisopropylethylamine (0.184 ml) and diphenylphosphoryl azide (0.248 ml) were added to a solution of the resultant residue in tert-butanol (2.0 ml), and the reaction solution was stirred at 100° C. for 5 hours. The solvent was evaporated under vacuum, and the resultant residue was purified by column chromatography on silica gel (developing solvent:hexane-ethyl acetate) to obtain tert-butyl 5-methoxy-3-methylbenzo[b]thiophen-2-yl carbamate.
(Step 3)
A 4 M hydrochloric acid-1,4-dioxane solution was added to tert-butyl 5-methoxy-3-methylbenzo[b]thiophen-2-yl carbamate obtained in the above-described Step 2 (210 mg), and the reaction solution was stirred at room temperature for 3 hours. Diethyl ether was added to the reaction solution and the deposited precipitate was filtrated to obtain 5-methoxy-3-methylbenzo[b]thiophen-2-amine monohydrochloride.
(Step 4)
In accordance with Example 3 (Steps 1 to 4), 5-methoxy-3-methylbenzo[b]thiophen-2-amine hydrochloride obtained in the above-described Step 3 was used instead of 1-methyl-1H-indol-4-amine to obtain the titled compound.

Example 49

3-((1R,2S)-2-aminocyclohexylamino)-5-(1-methyl-6-phenyl-1H-indol-4-ylamino)-1,2,4-triazine-6-carboxamide In accordance with Example 13 (Steps 1 to 4), 6-bromo-4-nitro-1H-indole was used instead of 6-bromo-4-nitro-1H-indazole, and phenylboronic acid was used instead of 1-methyl-4-(4,4,5,5-tetramethyl-1,3,2-dioxaborolan-2-yl)-1H-pyrazole to obtain the titled compound.

Example 50

3-((1R,2S)-2-aminocyclohexylamino)-5-(1-ethyl-3-methyl-1H-indazol-6-ylamino)-1,2,4-triazine-6-carboxamide In accordance with Example 4 (Steps 1 to 3), 6-nitro-3-methyl-1H-indazole was used instead of 5-nitro-1H-indazole, and iodoethane was used instead of ethyl bromide-d5 to obtain the titled compound.

Example 51

3-((1R,2S)-2-aminocyclohexylamino)-5-(1,3-dimethyl-1H-indol-4-ylamino)-1,2,4-triazine-6-carboxamide In accordance with Example 34 (Steps 1 and 2), 3-methyl-4-nitro-1H-indole was used instead of 4-nitro-1H-indole, and methyl iodide was used instead of 3-oxetane bromide to obtain the titled compound.

Example 52

3-((1R,2S)-2-aminocyclohexylamino)-5-(1-isopropyl-1H-indazol-6-ylamino)-1,2,4-triazine-6-carboxamide In accordance with Example 4 (Steps 1 to 3), 6-nitro-1H-indazole was used instead of 5-nitro-1H-indazole, and 2-iodopropane was used instead of ethyl bromide-d5 to obtain the titled compound as a yellow solid.

Example 53

3-((1R,2S)-2-aminocyclohexylamino)-5-(2-isopropyl-2H-indazol-6-ylamino)-1,2,4-triazine-6-carboxamide In accordance with Example 4 (Steps 2 and 3), 6-nitro-2-isopropyl-2H-indazole obtained in Example 52 as a byproduct was used instead of 5-nitro-2-(ethyl-d5)-1H-indazole to obtain the titled compound as a yellow solid.

Example 54

3-((1R,2S)-2-aminocyclohexylamino)-5-(1-(2,2-difluoroethyl)-1H-indazol-6-ylamino)-1,2,4-triazine-6-carboxamide In accordance with Example 4 (Steps 1 to 3), 6-nitro-1H-indazole was used instead of 5-nitro-1H-indazole, and 1,1-difluoro-2-iodoethane was used instead of ethyl bromide-d5 to obtain the titled compound as a yellow solid.

Example 55

3-((1R,2S)-2-aminocyclohexylamino)-5-(1-(2-fluoroethyl)-1H-indazol-6-ylamino)-1,2,4-triazine-6-carboxamide In accordance with Example 4 (Steps 1 to 3), 6-nitro-1H-indazole was used instead of 5-nitro-1H-indazole, and 1-fluoro-2-iodoethane was used instead of ethyl bromide-d5 to obtain the titled compound as a yellow solid.

Example 56

3-((1R,2S)-2-aminocyclohexylamino)-5-(1-ethyl-3-methyl-1H-indazol-5-ylamino)-1,2,4-triazine-6-carboxamide In accordance with Example 4 (Steps 1 to 3), 5-nitro-3-methyl-1H-indazole was used instead of 5-nitro-1H-indazole, and iodoethane was used instead of ethyl bromide-d5 to obtain the titled compound as a yellow solid.

Example 57

3-((1R,2S)-2-aminocyclohexylamino)-5-(2-(difluoromethyl)-2H-indazol-5-ylamino)-1,2,4-triazine-6-carboxamide In accordance with Example 24 (Steps 1 to 3), 5-nitro-1H-indazole was used instead of 6-nitro-1H-indazole to obtain the titled compound as a yellow solid.

Example 58

5-(2-(2H-1,2,3-triazol-2-yl)pyridin-4-ylamino)-3-((1R,2S)-2-aminocyclohexylamino)-1,2,4-triazine-6-carboxamide (Step 1)

A solution of 1H-1,2,3-triazole (518 mg), 2-fluoro-4-iodopyridine (892 mg), and cesium carbonate (1.63 mg) in NMP (10 mL) was stirred at 100° C. for 4 hours. The reaction solution was poured into water, and extracted with diethyl ether. The organic layer was washed with water and a saturated saline solution, and dried over sodium sulfate. After concentration, the resultant was purified by column chromatography on silica gel (developing solvent:hexane/ethyl acetate) to obtain 4-iodine-2-(2H-1,2,3-triazol-2-yl)pyridine as a white solid.

(Step 2)

A mixed solution of a concentrated aqueous ammonia solution (2 mL) and NMP (2 mL) was added to 4-iodine-2-(2H-1,2,3-triazol-2-yl)pyridine obtained in the above-described Step 1 (394 mg) and copper oxide (I) (40 mg). The reaction solution was allowed to react in a microwave reactor at 100° C. for 12 hours. The reaction solution was poured into water, and extracted with ethyl acetate. The organic layer was washed with water and a saturated saline solution, and dried over sodium sulfate. After concentration, the resultant was purified by column chromatography on silica gel (developing solvent:hexane/ethyl acetate) to obtain 2-(2H-1,2,3-triazol-2-yl)pyridin-4-amine as a white solid.

(Step 3)

In accordance with Example 3 (Steps 1 to 4), 2-(2H-1,2,3-triazol-2-yl)pyridin-4-amine was used instead of 1-methyl-1H-indol-4-amine to obtain the titled compound as a white solid.

Example 59

3-((1R,2S)-2-aminocyclohexylamino)-5-(2-(difluoromethyl)-3-methyl-2H-indazol-5-ylamino)-1,2,4-triazine-6-carboxamide In accordance with Example 24 (Steps 1 to 3), 3-methyl-5-nitro-1H-indazole was used instead of 6-nitro-1H-indazole to obtain the titled compound as a light yellow solid.

Example 60

3-(((1R,2S)-2-aminocyclohexyl)amino)-5-((1,6-dimethyl-1H-indol-4-yl)amino)-1,2,4-triazine-6-carboxamide (Step 1)
In accordance with Example 9 (Steps 1 and 2), 6-methyl-4-nitro-1H-indole was used instead of 4-nitro-1H-indole, and methyl iodide was used instead of ethyl bromide-d5 to obtain 1,6-dimethyl-1H-indol-4-amine.
(Step 2)
In accordance with Example 3 (Steps 1 to 4), 1,6-dimethyl-1H-indol-4-amine obtained in the above-described Step 1 was used instead of 1-methyl-1H-indol-4-amine to obtain the titled compound as a light grayish brown solid.

Example 61

3-(((3R,4R)-3-aminotetrahydro-2H-pyran-4-yl)amino)-5-((2-(tert-butyl)-7-methyl-2H-indazol-5-yl)amino)-1,2,4-triazine-6-carboxamide (Step 1)
Toluene (150 mL), acetic acid tert-butyl ester (360 mL), and methanesulfonic acid (22 mL) were added to 5-bromo-7-methyl-1H-indazole (35.9 g), and the reaction solution was stirred at 80° C. for 28 hours. The reaction solution was cooled to room temperature, water (500 mL) was added, and extracted with toluene (500 mL) and 200 mL toluene. After separation, the organic layer was washed with water twice. After drying over anhydrous sodium sulfate, the solvent was evaporated under vacuum. Hexane was added to the resultant residue and the insolubles were separated by filtration. The solvent was evaporated from the filtrate under vacuum. The resultant residue was purified by column chromatography on silica gel (developing solvent:hexane/ethyl acetate) to obtain 5-bromo-2-(tert-butyl)-7-methyl-2H-indazole as a light red oily substance.
(Step 2)
Copper oxide (I) (2.7 g), NMP (150 mL), and concentrated aqueous ammonia (150 mL) were added to 5-bromo-2-(tert-butyl)-7-methyl-2H-indazole obtained in the above-described Step 1 (40.3 g). The reaction solution was stirred in a portable reactor at 95° C. for 10 hours. The reaction solution was cooled to room temperature, and ethyl acetate (500 mL), hexane (200 mL), and water (300 mL) were added. After separation, the organic layer was washed successively with water four times and then with a saturated saline solution. After drying over anhydrous sodium sulfate, the solvent was evaporated under vacuum to obtain 2-(tert-butyl)-7-methyl-2H-indazol-5-amine as a purple solid.
(Step 3)
In accordance with Example 8 (Steps 1 to 4), 2-(tert-butyl)-7-methyl-2H-indazol-5-amine obtained in the above-described Step was used instead of benzo[b]thiophen-4-amine to obtain the titled compound as a light yellow solid.

Example 62

3-(((1R,2S)-2-aminocyclohexyl)amino)-5-((2-(difluoromethyl)-7-methyl-2H-indazol-5-yl)amino)-1,2,4-triazine-6-carboxamide (Step 1)
Potassium carbonate (2.76 g) and 2,2-difluoro-2-(fluorosulfonyl)acetic acid (2.06 mL) were added to a solution of 5-bromo-7-methyl-1H-indazole (2.11 g) in ethyl acetate (50 mL), and the reaction solution was stirred at room temperature for 3 hours. An aqueous sodium bicarbonate solution was added, the organic layer was separated, and then washed with a saturated saline solution. After drying over anhydrous sodium sulfate, the solvent was evaporated under vacuum. The resultant residue was purified by column chromatography on silica gel (developing solvent: hexane/ethyl acetate). Copper oxide (I) (143 mg), NMP (6 mL), and concentrated aqueous ammonia (6 mL) were added to the resultant product, and the reaction solution was allowed to react in a microwave reactor at 100° C. for 5 hours. Ethyl acetate (500 mL) and water (300 mL) were added, and the organic layer was separated. Thereafter, the organic layer was washed successively with water four times and then with a saturated saline solution. After drying over anhydrous sodium sulfate, the solvent was evaporated under vacuum, and the resultant was purified by column chromatography on silica gel (developing solvent: hexane/ethyl acetate) to obtain 2-(difluoromethyl)-7-methyl-2H-indazol-5-amine as a white solid.
(Step 2)
In accordance with Example 8 (Steps 1 to 4), 2-(difluoromethyl)-7-methyl-2H-indazol-5-amine obtained in the above-described Step 1 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 63

3-(((2R,3R)-3-amino-4-ethoxybutan-2-yl)amino)-5-((2-(difluoromethyl)-7-methyl-2H-indazol-5-yl)amino)-1,2,4-triazine-6-carboxamide (Step 1)
Iodoethane (0.80 mL) was added to a solution of (4S,5S)-tert-butyl 4-(hydroxymethyl)-2,2,5-trimethyloxazolidine-3-carboxylate (1.23 g), which can be synthesized by a method described in Bioorganic Chemistry 36 (2008) 4-15, in DMF (10 mL). Sodium hydride (60% in oil, 300 mg) was added under ice-cooling. Thereafter, the ice bath was removed, and the reaction solution was stirred at room temperature for 1 hour. Water and ethyl acetate were added to the reaction solution. After separation, the organic layer was washed with water twice. After drying over anhydrous sodium sulfate, the solvent was evaporated under vacuum. The resultant residue was purified by column chromatography on silica gel (developing solvent:hexane/ethyl acetate) to obtain (4S,5S)-tert-butyl 4-(ethoxymethyl)-2,2,5-trimethyloxazolidine-3-carboxylate as light yellow amorphous.
(Step 2)
Methanol (130 mL) and p-toluenesulfonic acid monohydrate (134 mg) were added to (4S,5S)-tert-butyl 4-(ethoxymethyl)-2,2,5-trimethyloxazolidine-3-carboxylate obtained in the above-described Step 1 (1.34 g), and the reaction solution was stirred at room temperature overnight. An aqueous sodium bicarbonate solution was added to the reaction solution, and methanol was evaporated under vacuum. Water and ethyl acetate were added, the organic layer was separated, and then washed with a saturated saline solution. After drying over anhydrous sodium sulfate, the solvent was evaporated under vacuum. The resultant residue was purified by column chromatography on silica gel (developing solvent:hexane/ ethyl acetate) to obtain tert-butyl((2S,3S)-1-ethoxy-3-hydroxybutan-2-yl)carbamate as colorless amorphous.

(Step 3)

Triethylamine (1.25 mL) and methanesulfonyl chloride (0.457 mL) were added to a solution of tert-butyl((2S,3S)-1-ethoxy-3-hydroxybutan-2-yl)carbamate obtained in the above-described Step 2 (1.06 g) in THF (20 mL), and the reaction solution was stirred at room temperature for 20 minutes. 10% Aqueous phosphoric acid solution was added to the reaction solution. Thereafter, the reaction solution was extracted with ethyl acetate and washed successively with a saturated aqueous sodium bicarbonate solution and a saturated saline solution. After drying over anhydrous sodium sulfate, the solvent was evaporated under vacuum. DMF (10 mL) and tetrabutylammonium azide (2 g) were added to the resultant residue, and the reaction solution was stirred at 70° C. for 2 hours. The reaction solution was returned to room temperature, then diluted with diethyl ether, and washed with water and a saturated saline solution. After drying over anhydrous sodium sulfate, the solvent was evaporated under vacuum. The resultant residue was purified by column chromatography on silica gel (developing solvent:hexane/ethyl acetate), and the solvent was evaporated under vacuum. THF (5 mL) and ethanol (5 mL) were added to the resultant residue, and 10% palladium on carbon (600 mg) was added under nitrogen atmosphere. The reaction solution was stirred under hydrogen atmosphere at room temperature overnight. The insolubles were filtrated, and the solvent was evaporated under vacuum to obtain tert-butyl((2R,3R)-3-amino-1-ethoxybutan-2-yl)carbamate as a colorless oily substance.
(Step 4)

In accordance with Example 8 (Steps 1 to 4), 2-(difluoromethyl)-7-methyl-2H-indazol-5-amine obtained in Example 62 (Step 1) was used instead of benzo[b]thiophen-4-amine, and tert-butyl((2R,3R)-3-amino-1-ethoxybutan-2-yl)carbamate obtained in the above-described Step 3 was used instead of tert-butyl((3R,4R)-4-aminotetrahydro-2H-pyran-3-yl)carbamate to obtain the titled compound as a light yellow solid.

Example 64

3-(((2R,3R)-3-amino-4-methoxybutan-2-yl)amino)-5-((1-isopropyl-1H-indol-4-yl)amino)-1,2,4-triazine-6-carboxamide (Step 1)
In accordance with Example 63 (Steps 1 to 3), iodomethane was used instead of iodoethane of Example 63 (Step 1) to obtain tert-butyl((2R,3R)-3-amino-1-methoxybutan-2-yl)carbamate as white amorphous.
(Step 2)
In accordance with Example 3 (Steps 1 to 4), 1-isopropyl-1H-indol-4-amine obtained in Example 45 was used instead of 1-methyl-1H-indol-4-amine, and tert-butyl((2R,3R)-3-amino-1-methoxybutan-2-yl)carbamate obtained in the above-described Step 1 was used instead of tert-butyl((1S,2R)-2-aminocyclohexyl)carbamate to obtain the titled compound as a light yellow solid.

Example 65

3-(((1R,2S)-2-aminocyclohexyl)amino)-5-((2-methyl-7-phenyl-2H-indazol-5-yl)amino)-1,2,4-triazine-6-carboxamide (Step 1)
Trimethyloxonium tetrafluoroborate (1.5 g) was added to a solution of 7-bromo-5-nitro-1H-indazole (1.21 g) in ethyl acetate (12 mL), and the reaction solution was stirred at room temperature for 6 hours. After dilution with ethyl acetate, the reaction solution was washed successively with water and a saturated saline solution and then dried over anhydrous sodium sulfate. The solvent was evaporated under vacuum, ethyl acetate and isopropyl ether were added to the resultant residue, and the deposited precipitate was filtrated to obtain 7-bromo-2-methyl-5-nitro-2H-indazole as a light yellow solid.
(Step 2)
Phenylboronic acid (244 mg), [1,1'-bis(diphenylphosphino)ferrocene]dichloropalladium(II) (1:1, 40 mg), dioxane (4 mL), a 2 M aqueous sodium carbonate solution (1 mL), and the reaction solution were added to 7-bromo-2-methyl-5-nitro-2H-indazole obtained in the above-described Step 1 (256 mg). The reaction solution was allowed to react in a microwave reactor at 130° C. for 1 hour. The solvent was evaporated under vacuum, and the resultant residue was purified by column chromatography on silica gel (developing solvent:hexane/ethyl acetate) to obtain 2-methyl-5-nitro-7-phenyl-2H-indazole.
(Step 3)
Ethyl acetate (5 mL) and THF (2 mL) were added to 2-methyl-5-nitro-7-phenyl-2H-indazole obtained in the above-described Step 2 (260 mg). Thereafter, 10% palladium on carbon (300 mg) was added under nitrogen atmosphere, and the reaction solution was stirred under hydrogen atmosphere at room temperature overnight. The insolubles were filtrated, and then the solvent was evaporated under vacuum. Subsequently, the resultant residue was purified by column chromatography on basic silica gel (developing solvent:hexane/ethyl acetate) to obtain 2-methyl-7-phenyl-2H-indazol-5-amine as brown amorphous.
(Step 4)
In accordance with Example 8 (Steps 1 to 4), 2-methyl-7-phenyl-2H-indazol-5-amine obtained in the above-described Step 3 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 66

3-(((1R,2S)-2-aminocyclohexyl)amino)-5-((2-(tert-butyl)-7-(1H-pyrazol-1-yl)-2H-indazol-5-yl)amino)-1,2,4-triazine-6-carboxamide (Step 1)
2-Methyl-2-propanol (5 mL) and concentrated sulfuric acid (0.1 mL) were added to 7-bromo-5-nitro-1H-indazole (484 mg), and the reaction solution was allowed to react in a microwave reactor at 100° C. for 1 hour. After dilution with ethyl acetate, the reaction solution was washed successively with an aqueous sodium bicarbonate solution and a saturated saline solution. After drying over anhydrous sodium sulfate, the solvent was evaporated under vacuum to obtain 7-bromo-2-(tert-butyl)-5-nitro-2H-indazole as a light yellow solid.
(Step 2)
DMF (6 mL) was added to 7-bromo-2-(tert-butyl)-5-nitro-2H-indazole obtained in the above-described Step 1 (438 mg), pyrazole (200 mg), copper oxide (I) (42 mg), and cesium carbonate (960 mg), and the reaction solution was stirred at 120° C. overnight. The reaction solution was cooled to room temperature, water and ethyl acetate were added, and then the insolubles were filtrated. After separation, the organic layer was washed with water and a saturated saline solution and dried over anhydrous sodium sulfate. Thereafter, the solvent was evaporated under vacuum. The resultant residue was purified by column chromatography on silica gel (developing solvent:hexane/ethyl acetate) to obtain 2-(tert-butyl)-5-nitro-7-(1H-pyrazol-1-yl)-2H-indazole as colorless amorphous.

(Step 3)

10% Palladium on carbon (300 mg) was added to a solution of 2-(tert-butyl)-5-nitro-7-(1H-pyrazol-1-yl)-2H-indazole obtained in the above-described Step 2 (255 mg) in ethyl acetate (5 mL), and the reaction solution was stirred under hydrogen atmosphere at room temperature overnight. The insolubles were filtrated, and the solvent was evaporated under vacuum. Thereafter, the resultant residue was purified by column chromatography on basic silica gel (developing solvent:hexane/ethyl acetate) to obtain 2-(tert-butyl)-7-(1H-pyrazol-1-yl)-2H-indazol-5-amine as brown amorphous.

(Step 4)

In accordance with Example 3 (Steps 1 to 4), 2-(tert-butyl)-7-(1H-pyrazol-1-yl)-2H-indazol-5-amine obtained in the above-described Step 3 was used instead of 1-methyl-1H-indol-4-amine to obtain the titled compound as a light yellow solid.

Example 67

3-(((1R,2S)-2-aminocyclohexyl)amino)-5-((1-(1-methyl-1H-pyrazol-4-yl)-1H-indol-4-yl)amino)-1,2,4-triazine-6-carboxamide In accordance with Example 25 (Steps 1 to 3), 4-iodine-1-methyl-1H-pyrazole was used instead of 3-iodine-1-methyl-1H-pyrazole to obtain the titled compound as a light yellow solid.

Example 68

3-(((1R,2S)-2-aminocyclohexyl)amino)-5-((1-((R)-tetrahydrofuran-3-yl)-1H-indol-4-yl)amino)-1,2,4-triazine-6-carboxamide (Step 1)

Triethylamine (2.05 mL) and methanesulfonyl chloride (1.05 mL) were added to a solution of (S)-tetrahydrofuran-3-ol (1.0 g) in toluene (10 mL), and the reaction solution was stirred at room temperature for 2 hours. Water was added to the reaction solution, then the reaction solution was extracted with toluene and washed with a saturated saline solution. After drying over anhydrous sodium sulfate, the solvent was evaporated under vacuum to obtain (S)-tetrahydrofuran-3-yl methanesulfonate as a colorless oily substance.

(Step 2)

Potassium carbonate (2.5 g) and (S)-tetrahydrofuran-3-yl methanesulfonate obtained in the above-described Step (1.01 g) were added to a solution of 4-nitro-1H-indole (980 mg) in DMF (10 mL), and the reaction solution was stirred at 100° C. for 24 hours. Water was added to the reaction solution, the reaction solution was extracted with ethyl acetate twice, and then washed successively with water and a saturated saline solution. After drying over anhydrous sodium sulfate, the solvent was evaporated under vacuum. The resultant residue was purified by column chromatography on silica gel (developing solvent:hexane/ethyl acetate). THF (10 mL) was added to the resultant residue, 10% palladium on carbon (100 mg) was added, and the reaction solution was stirred under hydrogen atmosphere at room temperature for 14 hours. The insolubles were filtrated with celite, and the solvent was evaporated under vacuum. Thereafter, the resultant residue was purified by column chromatography on silica gel (developing solvent:hexane/ethyl acetate) to obtain 1-((R)-tetrahydrofuran-3-yl)-1H-indol-4-amine as a white solid.

(Step 3)

In accordance with Example 3 (Steps 1 to 4), 1-((R)-tetrahydrofuran-3-yl)-1H-indol-4-amine obtained in the above-described Step was used instead of 1-methyl-1H-indol-4-amine to obtain the titled compound as a light yellow solid.

Example 69

3-(((1R,2S)-2-aminocyclohexyl)amino)-5-((1-(2-methylpyridin-4-yl)-1H-indol-4-yl)amino)-1,2,4-triazine-6-carboxamide In accordance with Example 25 (Steps 1 to 3), 4-iodine-2-picoline was used instead of 3-iodine-1-methyl-1H-pyrazole to obtain the titled compound as a light yellow solid.

Example 70

3-(((1R,2S)-2-aminocyclohexyl)amino)-5-((2-ethyl-7-methyl-2H-indazol-5-yl)amino)-1,2,4-triazine-6-carboxamide (Step 1)

Sodium hydride (60% in oil, 240 mg) and iodoethane (0.64 mL) were added to a solution of 5-bromo-7-methyl-1H-indazole (844 mg) in DMF (10 mL), and the reaction solution was stirred at room temperature for 15 minutes. Water was added to the reaction solution, and then the reaction solution was extracted with ethyl acetate. The organic layer was washed successively with water and a saturated saline solution. After drying over anhydrous sodium sulfate, the solvent was evaporated under vacuum. The resultant residue was purified by column chromatography on silica gel (developing solvent: hexane/ethyl acetate) to obtain 5-bromo-1-ethyl-7-methyl-1H-indazole and 5-bromo-2-ethyl-7-methyl-2H-indazole.

(Step 2)

Copper oxide (I) (60 mg), NMP (2 mL), and concentrated aqueous ammonia (2 mL) were added to 5-bromo-2-ethyl-7-methyl-2H-indazole obtained in the above-described Step 1 (446 mg), and the reaction solution was stirred in a microwave reactor at 100° C. for 10 hours. The reaction solution was cooled to room temperature, and diluted with ethyl acetate. Thereafter, the reaction solution was washed successively with water four times and then with a saturated saline solution. After drying over anhydrous sodium sulfate, the solvent was evaporated under vacuum. The resultant residue was purified by column chromatography on silica gel (developing solvent:hexane/ethyl acetate) to obtain 2-ethyl-7-methyl-2H-indazol-5-amine.

(Step 3)

In accordance with Example 8 (Steps 1 to 4), 2-ethyl-7-methyl-2H-indazol-5-amine obtained in the above-described Step 2 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 71

3-(((1R,2S)-2-aminocyclohexyl)amino)-5-((1-(6-methylpyridazin-3-yl)-1H-indol-4-yl)amino)-1,2,4-triazine-6-carboxamide In accordance with Example 25 (Steps 1 to 3), 3-chloro-6-methylpyridazine was used instead of 3-iodine-1-methyl-1H-pyrazole to obtain the titled compound as a light yellow solid.

Example 72

3-(((1R,2S)-2-aminocyclohexyl)amino)-5-((1-(pyrimidin-5-yl)-1H-indol-4-yl)amino)-1,2,4-triazine-6-carboxamide In accordance with Example 25 (Steps 1 to 3), 5-bromopyrimidine was used instead of 3-iodine-1-methyl-1H-pyrazole to obtain the titled compound as a light yellow solid.

Example 73

3-(((1R,2S)-2-aminocyclohexyl)amino)-5-((1-(trans-4-hydroxycyclohexyl)-1H-indol-4-yl)amino)-1,2,4-triazine-6-carboxamide In accordance with Example 68 (Steps 2 and 3), 4-{[tert-butyl(dimethyl)silyl]oxy}cyclohexyl methanesulfonate, which can be synthesized according to the method described in WO 2004/050024, was used instead of (S)-tetrahydrofuran-3-yl methanesulfonate to obtain the titled compound as a light yellow solid.

Example 74

3-(((1R,2S)-2-aminocyclohexyl)amino)-5-((2-isopropyl-7-methyl-2H-indazol-5-yl)amino)-1,2,4-triazine-6-carboxamide In accordance with Example 70 (Steps 1 to 3), 2-iodopropane was used instead of iodoethane to obtain the titled compound as a light yellow solid.

Example 75

3-(((1R,2S)-2-aminocyclohexyl)amino)-5-((1-(tetrahydro-2H-pyran-4-yl)-1H-indol-4-yl)amino)-1,2,4-triazine-6-carboxamide In accordance with Example 68 (Steps 1 to 3), tetrahydro-2H-pyran-4-ol was used instead of (S)-tetrahydrofuran-3-ol to obtain the titled compound as a light yellow solid.

Example 76

3-(((1R,2S)-2-aminocyclohexyl)amino)-5-((4-(pyrimidin-2-yl)thiophen-2-yl)amino)-1,2,4-triazine-6-carboxamide (Step 1)
Tert-amyl alcohol (100 mL) was added to tris(dibenzylideneacetone)dipalladium(0) (460 mg), 2-(dicyclohexylphosphino)-2',4',6'-triisopropyl-1,1'-biphenyl (960 mg), 3-thiophene boronic acid (9.60 g), 2-chloropyrimidine (5.72 g), potassium phosphate (21.2 g), and molecular sieve 4 A (12.5 g). The reaction solution was stirred at 100° C. overnight. The insolubles were filtrated, and then the solvent was evaporated under vacuum. The resultant residue was purified by column chromatography on silica gel (developing solvent: hexane/ethyl acetate) to obtain 2-(thiophen-3-yl) pyrimidine as a white solid.

(Step 2)
2-(Thiophen-3-yl)pyrimidine obtained in the above-described Step 1 (6.99 g) was added to concentrated sulfuric acid (35 mL) under ice-cooling. Furthermore, a mixed solution of fuming nitric acid (1.5) (1.81 mL) and concentrated sulfuric acid (35 mL) was slowly added under ice-cooling. Thereafter, the ice bath was removed and the resultant was slowly heated to room temperature. After stirring at room temperature for 1 hour, the reaction solution was poured into ice. The deposited solid was filtrated to obtain 2-(5-nitrothiophen-3-yl)pyrimidine.

(Step 3)
Pearlman's catalyst (Pd 20%; approximately 50% water-wet product) (6.0 g) was added to a solution of 2-(5-nitrothiophen-3-yl)pyrimidine obtained in the above-described Step 2 (7.23 g), di-tert-butyl dicarbonate (9.90 g), and sodium bicarbonate (3.52 g) in THF (100 mL) and ethanol (50 mL), and the reaction solution was stirred under hydrogen atmosphere at room temperature overnight. A solution of di-tert-butyl dicarbonate (5.5 g) in THF (50 mL) was added to the reaction solution. Thereafter, the insolubles were filtrated, and the filtrate was heated to 60° C. and stirred for 30 minutes. The solvent was evaporated under vacuum, and the resultant residue was purified by column chromatography on silica gel (developing solvent:hexane-chloroform (1:1) mixed solvent/ethyl acetate) to obtain tert-butyl(4-(pyrimidin-2-yl)thiophen-2-yl)carbamate.

(Step 4)
A 4 N hydrochloric acid-dioxane solution (20 mL) was added to tert-butyl(4-(pyrimidin-2-yl)thiophen-2-yl)carbamate obtained in the above-described Step 3, and the reaction solution was stirred at room temperature for 2 hours. The solvent was evaporated under vacuum, and then isopropyl ether was added. The deposited precipitate was filtrated to obtain 4-(pyrimidin-2-yl)thiophen-2-amine hydrochloride.

(Step 5)
In accordance with Example 8 (Steps 1 to 4), 4-(pyrimidin-2-yl)thiophen-2-amine hydrochloride obtained in the above-described Step 4 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a brown solid.

Example 77

3-(((1R,2S)-2-aminocyclohexyl)amino)-5-((4-(pyridin-2-yl)thiophen-2-yl)amino)-1,2,4-triazine-6-carboxamide (Step 1)
Reaction solution including a solution of tert-butyl (4-bromothiophen-2-yl)carbamate (5.4 g), bis(pinacolato)diboron (9.86 g), [1,1'-bis(diphenylphosphino)ferrocene]dichloropalladium(II) (1:1; 800 mg), and potassium acetate (3.39 g) in DMF (40 mL) was stirred at 80° C. for 90 minutes. The solvent was evaporated under vacuum, then the reaction solution was diluted with ethyl acetate, and washed successively with water and a saturated saline solution. After drying over anhydrous sodium sulfate, the solvent was evaporated under vacuum. The resultant residue was purified by column chromatography on silica gel (developing solvent:hexane/ethyl acetate) to obtain tert-butyl(4-(4,4,5,5-tetramethyl-1,3,2-dioxaborolan-2-yl)thiophen-2-yl)carbamate.
(Step 2)
2-Bromopyridine (2.26 g), tetrakis(triphenylphosphine)palladium(0) (414 mg), and a 2 M aqueous sodium carbonate solution (7 mL) were added to a solution of tert-butyl(4-(4,4,5,5-tetramethyl-1,3,2-dioxaborolan-2-yl)thiophen-2-yl)carbamate obtained in the above-described Step (2.33 g) in dioxane (30 mL), and the reaction solution was stirred at 100° C. overnight. The reaction solution was cooled to room temperature and diluted with ethyl acetate. Thereafter, the reaction solution was washed successively with water and a saturated saline solution. After drying over anhydrous sodium sulfate, the solvent was evaporated under vacuum. The resultant residue was purified by column chromatography on silica gel (developing solvent:hexane/ethyl acetate). 4 N hydrochloric acid-dioxane (8 mL) was added to the resultant residue, and the reaction solution was allowed to stand at room temperature for 3 hours. The solvent was evaporated under vacuum, and then isopropyl ether was added to the residue. The deposited precipitate was filtrated to obtain 4-(pyridin-2-yl)thiophen-2-amine dihydrochloride.
(Step 3)
In accordance with Example 8 (Steps 1 to 4), 4-(pyridin-2-yl)thiophen-2-amine dihydrochloride obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a yellow solid.

Example 78

3-(((1R,2S)-2-aminocyclohexyl)amino)-5-((1-(trans-4-hydroxycyclohexyl)-6-methyl-1H-indol-4-yl)amino)-1,2,4-triazine-6-carboxamide In accordance with Example 9 (Steps 1 to 4), 6-methyl-4-nitro-1H-indole was used instead of 4-nitro-1H-indole, and 4-{[tert-butyl(dimethyl)silyl]oxy}cyclohexyl methanesulfonate, which can be synthesized according to the method described in WO 2004/050024, was used instead of ethyl bromide-d5 to obtain the titled compound as a light yellow solid.

Example 79

3-(((1R,2S)-2-aminocyclohexyl)amino)-5-((2-ethyl-7-(1H-pyrazol-1-yl)-2H-indazol-5-yl)amino)-1,2,4-triazine-6-carboxamide (Step 1)
In accordance with Example 65 (Step 1), triethyl oxonium tetrafluoroborate was used instead of trimethyl oxonium tetrafluoroborate to obtain 7-bromo-2-ethyl-5-nitro-2H-indazole.
(Step 2)
In accordance with Example 66 (Steps 2 and 3), 7-bromo-2-ethyl-5-nitro-2H-indazole obtained in the above-described Step 1 was used instead of 7-bromo-2-(tert-butyl)-5-nitro-2H-indazole to obtain 2-ethyl-7-(1H-pyrazol-1-yl)-2H-indazol-5-amine.
(Step 3)
In accordance with Example 8 (Steps 1 to 4), 2-ethyl-7-(1H-pyrazol-1-yl)-2H-indazol-5-amine obtained in the above-described Step 2 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 80

5-((1-(1,3,4-thiadiazol-2-yl)-1H-indol-4-yl)amino)-3-(((1R,2S)-2-aminocyclohexyl)amino)-1,2,4-triazine-6-carboxamide In accordance with Example 25 (Steps 1 to 3), 2-bromo-1,3,4-thiadiazole was used instead of 3-iodine-1-methyl-1H-pyrazole to obtain the titled compound as a light yellow solid.

Example 81

3-(((1R,2S)-2-aminocyclohexyl)amino)-5-((7-chloro-2-ethyl-2H-indazol-5-yl)amino)-1,2,4-triazine-6-carboxamide (Step 1)
Triethyl oxonium tetrafluoroborate (2.5 g) was added to a solution of 5-bromo-7-chloro-1H-indazole (1.38 g) in ethyl acetate (15 mL), and the reaction solution was stirred at room temperature overnight. After dilution with ethyl acetate, the reaction solution was washed successively with water and a saturated saline solution, dried over anhydrous sodium sulfate, and the solvent was evaporated under vacuum. The resultant residue was purified by column chromatography on silica gel (developing solvent:hexane/ethyl acetate) to obtain 5-bromo-7-chloro-2-ethyl-2H-indazole.
(Step 2)
Copper oxide (I) (200 mg), NMP (7 mL), and concentrated aqueous ammonia (7 mL) were added to 5-bromo-7-chloro-2-ethyl-2H-indazole obtained in the above-described Step 1 (1.43 g), and the reaction solution was stirred in a microwave reactor at 80° C. for 10 hours. The reaction solution was cooled to room temperature, and diluted with ethyl acetate. Thereafter, the reaction solution was washed successively with water four times and then with a saturated saline solution. After drying over anhydrous sodium sulfate, the solvent was evaporated under vacuum, and the resultant was purified by column chromatography on silica gel (developing solvent: hexane/ethyl acetate) to obtain 7-chloro-2-ethyl-2H-indazol-5-amine.
(Step 3)
In accordance with Example 8 (Steps 1 to 4), 7-chloro-2-ethyl-2H-indazol-5-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 82

3-(((1R,2S)-2-aminocyclohexyl)amino)-5-((2,7-dimethyl-2H-indazol-5-yl)amino)-1,2,4-triazine-6-carboxamide In accordance with Example 81 (Steps 1 to 3), 5-bromo-7-methyl-1H-indazole was used instead of 5-bromo-7-chloro-1H-indazole, and trimethyl oxonium tetrafluoroborate was used instead of triethyl oxonium tetrafluoroborate to obtain the titled compound as a yellow solid.

Example 83

3-(((1R,2S)-2-aminocyclohexyl)amino)-5-((7-methyl-2-(1-methylcyclobutyl)-2H-indazol-5-yl)amino)-1,2,4-triazine-6-carboxamide (Step 1)

1-Methyl-1-cyclobutanol (3 mL) and concentrated sulfuric acid (0.1 mL) were added to 5-bromo-7-methyl-1H-indazole (633 mg). The reaction solution was allowed to react in a microwave reactor at 100° C. for 30 minutes, and then further allowed to react at 120° C. for 30 minutes. An aqueous sodium bicarbonate solution and ethyl acetate were added to the reaction solution. After separation, the organic layer was washed with a saturated saline solution. After drying over anhydrous sodium sulfate, the solvent was evaporated under vacuum, and the resultant was purified by column chromatography on silica gel (developing solvent:hexane/ethyl acetate) to obtain 5-bromo-7-methyl-2-(1-methylcyclobutyl)-2H-indazole.

(Step 2)

Copper oxide (I) (50 mg), NMP (2.5 mL), and concentrated aqueous ammonia (2.5 mL) were added to 5-bromo-7-methyl-2-(1-methylcyclobutyl)-2H-indazole obtained in the above-described Step 1 (536 mg), and the reaction solution was stirred in a microwave reactor at 100° C. for 5 hours. The reaction solution was cooled to room temperature, diluted with ethyl acetate, and then washed successively with water three times and then with a saturated saline solution. After drying over anhydrous sodium sulfate, the solvent was evaporated under vacuum, and the resultant was purified by column chromatography on silica gel (developing solvent:hexane/ethyl acetate) to obtain 7-methyl-2-(1-methylcyclobutyl)-2H-indazol-5-amine.

(Step 3)

In accordance with Example 8 (Steps 1 to 4), 7-methyl-2-(1-methylcyclobutyl)-2H-indazol-5-amine obtained in the above-described Step 2 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 84

3-(((1R,2S)-2-aminocyclohexyl)amino)-5-((1-(pyrazin-2-yl)-1H-indol-4-yl)amino)-1,2,4-triazine-6-carboxamide In accordance with Example 25 (Steps 1 to 3), 2-bromopyrazine was used instead of 3-iodine-1-methyl-1H-pyrazole to obtain the titled compound as a light yellow solid.

Example 85

3-(((1R,2S)-2-aminocyclohexyl)amino)-5-((7-cyclopropyl-2-methyl-2H-indazol-5-yl)amino)-1,2,4-triazine-6-carboxamide (Step 1)

A solution of cyclopropyl boronic acid (347 mg), palladium acetate (II) (31 mg), tricyclohexylphosphine tetrafluoroborate (99 mg), and potassium phosphate (1 g) in toluene (20 mL) and water (1 mL) was added to 7-bromo-2-methyl-5-nitro-2H-indazole obtained in Example 65 (Step 1) (361 mg), and the reaction solution was stirred at 100° C. for 11 hours. After dilution with ethyl acetate, the reaction solution was washed successively with water and a saturated saline solution. After drying over anhydrous sodium sulfate, the solvent was evaporated under vacuum. The resultant residue was purified by column chromatography on silica gel (developing solvent:hexane/ethyl acetate) to obtain 7-cyclopropyl-2-methyl-5-nitro-2H-indazole.

(Step 2)

10% Palladium on carbon (300 mg) was added to a solution of 7-cyclopropyl-2-methyl-5-nitro-2H-indazole obtained in the above-described Step 1 (311 mg) in ethyl acetate (5 mL) under nitrogen atmosphere, and the reaction solution was stirred under hydrogen atmosphere at room temperature overnight. The insolubles were filtrated, then the solvent was evaporated under vacuum, and the resultant residue was purified by column chromatography on silica gel (developing solvent:hexane/ethyl acetate) to obtain 7-cyclopropyl-2-methyl-2H-indazol-5-amine as brown amorphous.

(Step 3)

In accordance with Example 8 (Steps 1 to 4), 7-cyclopropyl-2-methyl-2H-indazol-5-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 86

3-(((1R,2S)-2-aminocyclohexyl)amino)-5-((1-(difluoromethyl)-4-methyl-1H-indazol-6-yl)amino)-1,2,4-triazine-6-carboxamide (Step 1)

In accordance with Example 24 (Steps 1 and 2), 4-methyl-6-nitro-1H-indazole (934 mg) was used instead of 6-nitro-1H-indazole to obtain 1-(difluoromethyl)-4-methyl-1H-indazol-6-amine (112 mg) and 2-(difluoromethyl)-4-methyl-2H-indazol-6-amine.

(Step 2)

In accordance with Example 8 (Steps 1 to 4), 1-(difluoromethyl)-4-methyl-1H-indazol-6-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a white solid.

Example 87

3-(((1R,2S)-2-aminocyclohexyl)amino)-5-((1-(difluoromethyl)-1H-indazol-5-yl)amino)-1,2,4-triazine-6-carboxamide (Step 1)

In accordance with Example 24 (Steps 1 and 2), 5-nitro-1H-indazole was used instead of 6-nitro-1H-indazole to obtain the titled compounds 1-(difluoromethyl)-1H-indazol-5-amine and 2-(difluoromethyl)-4-methyl-2H-indazol-5-amine.

(Step 2)

In accordance with Example 1 (Steps 1 to 4), 1-(difluoromethyl)-1H-indazol-5-amine obtained in the above-described Step was used instead of 6-aminoquinoline to obtain the titled compound as a yellow solid.

Example 88

3-(((1R,2S)-2-aminocyclohexyl)amino)-5-((1-ethyl-7-methyl-1H-indazol-5-yl)amino)-1,2,4-triazine-6-carboxamide (Step 1)

In accordance with Example 70 (Step 2), 5-bromo-1-ethyl-7-methyl-1H-indazole obtained in Example 70 (Step 1) (374 mg) was used instead of 5-bromo-2-ethyl-7-methyl-2H-indazole to obtain 1-ethyl-7-methyl-1H-indazol-5-amine.

(Step 2)

In accordance with Example 8 (Steps 1 to 4), 1-ethyl-7-methyl-1H-indazol-5-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 89

3-(((2S,3R)-2-amino-5-methylhexan-3-yl)amino)-5-((2-cyclobutyl-2H-indazol-5-yl)amino)-1,2,4-triazine-6-carboxamide (Step 1)

Toluene (30 mL) and cyclobutylamine (2.25 mL) were added to methyl 3-formyl-4-nitrobenzoate (5.00 g), and the reaction solution was stirred at room temperature for 5 minutes. The solvent was evaporated under vacuum, then triethyl phosphite (11.3 mL) was added to the residue, and the reaction solution was stirred at 100° C. for 7 hours. The solvent was evaporated under vacuum, the resultant residue was purified by column chromatography on silica gel (developing solvent:hexane/ethyl acetate). Ethanol (2 mL) and a 5 N aqueous sodium hydroxide solution (5.0 mL) were added to the resultant crude product, and the reaction solution was stirred at room temperature for 1 hour. A 10% aqueous phosphoric acid solution was added to acidify the reaction solution. Furthermore, water was added, and the deposited precipitate was filtrated to obtain 2-cyclobutyl-2H-indazole-5-carboxylate as a white solid.

(Step 2)

Diphenylphosphoryl azide (4.15 mL) and triethylamine (3.76 mL) were added to a solution of 2-cyclobutyl-2H-indazole-5-carboxylic acid obtained in the above-described Step 1 (3.26 g) in 1,4-dioxane (50 mL), and the reaction solution was stirred at room temperature for 2 hours and 20 minutes. Thereafter, 1 N hydrochloric acid (100 mL) was added to the reaction solution, and then the reaction solution was stirred at 100° C. for 30 minutes. The reaction solution was cooled to room temperature, and potassium carbonate (14 g) was slowly added. The reaction solution was extracted with ethyl acetate, and then the organic layer was washed with a saturated saline solution. After drying over anhydrous sodium sulfate, the solvent was evaporated under vacuum. The resultant residue was purified by column chromatography on silica gel (developing solvent:hexane/ethyl acetate) to obtain 2-cyclobutyl-2H-indazol-5-amine as a light yellow solid.

(Step 3)

In accordance with Example 8 (Steps 1 to 4), 2-cyclobutyl-2H-indazol-5-amine obtained in the above-described Step was used instead of benzo[b]thiophen-4-amine, and tert-butyl((2S,3R)-3-amino-5-methylhexan-2-yl)carbamate synthesized by the method described in Patent No. WO 2012/002577 was used instead of tert-butyl((3R,4R)-4-aminotetrahydro-2H-pyran-3-yl)carbamate to obtain the titled compound as a light yellow solid.

Example 90

3-(((1R,2S)-2-aminocyclohexyl)amino)-5-((1-(3-methylpyrazin-2-yl)-1H-indol-4-yl)amino)-1,2,4-triazine-6-carboxamide In accordance with Example 25 (Steps 1 to 3), 2-bromo-3-methylpyrazine was used instead of 3-iodine-1-methyl-1H-pyrazole to obtain the titled compound as a light yellow solid.

Example 91

3-(((1R,2S)-2-aminocyclohexyl)amino)-5-((2,4-dimethyl-2H-indazol-6-yl)amino)-1,2,4-triazine-6-carboxamide diformate (Step 1)

In accordance with Example 24 (Steps 1 and 2), 4-methyl-6-nitro-1H-indazole was used instead of 6-nitro-1H-indazole, and iodomethane was used instead of sodium chlorodifluoroacetate to obtain 1,4-dimethyl-1H-indazol-6-amine and 2,4-dimethyl-2H-indazol-6-amine.

(Step 2)

In accordance with Example 1 (Steps 1 to 4), 2,4-dimethyl-2H-indazol-6-amine was used instead of 6-aminoquinoline to obtain the titled compound as a yellow solid.

Example 92

3-(((1R,2S)-2-aminocyclohexyl)amino)-5-((6-methyl-1-(tetrahydro-2H-pyran-4-yl)-1H-indol-4-yl)amino)-1,2,4-triazine-6-carboxamide In accordance with Example 68 (Steps 1 to 3), 6-methyl-4-nitro-1H-indole was used instead of 4-nitro-1H-indole, and tetrahydro-2H-pyran-4-ol was used instead of (S)-tetrahydrofuran-3-ol to obtain the titled compound as a light yellow solid.

Example 93

3-(((1R,2S)-2-aminocyclohexyl)amino)-5-((1-(2-hydroxyethyl)-1H-indol-4-yl)amino)-1,2,4-triazine-6-carboxamide In accordance with Example 68 (Steps 1 to 3), 2-(tert-butyldimethylsiloxy)ethanol was used instead of (S)-tetrahydrofuran-3-ol to obtain the titled compound as a light yellow solid.

Example 94

3-(((1R,2S)-2-aminocycloheptyl)amino)-5-((1-(2-methoxyethyl)-1H-indol-4-yl)amino)-1,2,4-triazine-6-carboxamide (Step 1)

Di-tert-butyl dicarbonate (2.16 g) was added to a solution of (1S,2S)-aminocycloheptanol (1 g) in methanol (20 mL), and the reaction solution was stirred at room temperature for 10 minutes. Thereafter, the solvent was evaporated under vacuum. Hexane was added to the resultant residue, and the precipitate was filtrated to obtain tert-butyl((2S,3S)-(2-hydroxycycloheptyl))carbamate as a white solid.

(Step 2)

In accordance with Example 63 (Step 3), tert-butyl((2S,3S)-(2-hydroxycycloheptyl))carbamate obtained in the above-described Step (1.74 g) was used instead of tert-butyl((2S,3S)-1-ethoxy-3-hydroxybutan-2-yl)carbamate to obtain tert-butyl((1S,2R)-2-aminocycloheptyl)carbamate.

(Step 3)

In accordance with Example 3 (Steps 1 to 4), 1-(2-methoxyethyl)-1H-indol-4-amine obtained in Example 46 was used instead of 1-methyl-1H-indol-4-amine, and tert-butyl ((1S,2R)-2-aminocycloheptyl)carbamate obtained in the above-described Step was used instead of tert-butyl((1S,2R)-2-aminocyclohexyl)carbamate to obtain the titled compound as a light yellow solid.

Example 95

3-(((1R,2S)-2-aminocyclohexyl)amino)-5-((1,7-dimethyl-1H-indazol-5-yl)amino)-1,2,4-triazine-6-carboxamide (Step 1)

In accordance with Example 70 (Step 1), iodomethane was used instead of iodoethane to obtain 5-bromo-2,7-dimethyl-2H-indazole.

(Step 2)

In accordance with Example 88 (Steps 1 and 2), 5-bromo-2,7-dimethyl-2H-indazole obtained in the above-described Step was used instead of 5-bromo-1-ethyl-7-methyl-1H-indazole to obtain the titled compound as a yellow solid.

Example 96

3-(((1R,2S)-2-aminocyclohexyl)amino)-5-((7-methyl-2-(2,2,2-trifluoroethyl)-2H-indazol-5-yl)amino)-1,2,4-triazine-6-carboxamide (Step 1)

In accordance with Example 70 (Step 1), 1-iodine-2,2,2-trifluoroethane was used instead of iodoethane to obtain 5-bromo-7-methyl-1-(2,2,2-trifluoroethyl)-1H-indazole and 5-bromo-7-methyl-2-(2,2,2-trifluoroethyl)-2H-indazole.

(Step 2)

In accordance with Example 70 (Steps 2 and 3), 5-bromo-7-methyl-2-(2,2,2-trifluoroethyl)-2H-indazole obtained in the above-described Step was used instead of 5-bromo-2-ethyl-7-methyl-2H-indazole to obtain the titled compound as a light yellow solid.

Example 97

3-(((1R,2S)-2-aminocyclohexyl)amino)-5-((1-ethyl-4-methyl-1H-indazol-6-yl)amino)-1,2,4-triazine-6-carboxamide (Step 1)

Iodoethane (1.2 mL) and sodium hydride (60% in oil; 600 mg) were added to a solution of 4-methyl-6-nitro-1H-indazole (1.77 g), which can be synthesized by the method described in Patent No. WO 2009/084695, in DMF (17 mL), and the reaction solution was stirred at room temperature for 15 minutes. After dilution with ethyl acetate, the reaction solution was washed with water twice and then with a saturated saline solution. After drying over anhydrous sodium sulfate, the solvent was evaporated under vacuum. The resultant residue was purified by column chromatography on silica gel (developing solvent:hexane/ethyl acetate) to obtain 1-ethyl-4-methyl-6-nitro-1H-indazole and 2-ethyl-4-methyl-6-nitro-2H-indazole as a light yellow solid, respectively.

(Step 2)

10% Palladium on carbon (1.0 g) was added to a solution of 1-ethyl-4-methyl-6-nitro-1H-indazole obtained in the above-described Step 1 (975 mg) in ethyl acetate (10 mL), and the reaction solution was stirred under hydrogen atmosphere at room temperature overnight. The insolubles were filtrated, and the solvent was evaporated under vacuum to obtain 1-ethyl-4-methyl-1H-indazol-6-amine.

(Step 3)

In accordance with Example 8 (Steps 1 to 4), 1-ethyl-4-methyl-1H-indazol-6-amine obtained in the above-described Step 2 was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a yellow solid.

Example 98

3-(((3R,4R)-3-aminotetrahydro-2H-pyran-4-yl)amino)-5-((1-ethyl-6-(2-hydroxypropan-2-yl)-1H-indazol-4-yl)amino)-1,2,4-triazine-6-carboxamide (Step 1)

In accordance with Example 4 (Steps 1 and 2), methyl 4-bromo-1H-indazole-6-carboxylate was used instead of 5-nitro-1H-indazole, and 2-iodoethane was used instead of ethyl bromide-d5 to obtain methyl 4-bromo-1-ethyl-1H-indazole-6-carboxylate.

(Step 2)

Methyl magnesium chloride (a 3 M THF solution; 2.5 ml) was added to a solution of methyl 4-bromo-1-ethyl-1H-indazole-6-carboxylate obtained in the above-described Step 1 (0.70 g) in THF (20 mL), and the reaction solution was stirred at room temperature for 3 hours. A saturated aqueous ammonium chloride solution was added to the reaction solution, and then the reaction solution was extracted with ethyl acetate. The organic layer was washed with a saturated saline solution, and dried over anhydrous sodium sulfate. Thereafter, the solvent was evaporated under vacuum, and the resultant residue was purified by column chromatography on silica gel (developing solvent:hexane/ethyl acetate) to obtain 2-(4-bromo-1H-indazol-6-yl)propan-2-ol.

(Step 3)

In accordance with Example 58 (Step 2), 2-(4-bromo-1H-indazol-6-yl)propan-2-ol obtained in the above-described Step 2 was used instead of 4-iodine-2-(2H-1,2,3-triazol-2-yl)pyridine to obtain 1-ethyl-6-(2-hydroxypropan-2-yl)-1H-indazol-4-amine.

(Step 4)

In accordance with Example 1 (Steps 1 to 4), 1-ethyl-6-(2-hydroxypropan-2-yl)-1H-indazol-4-amine obtained in the above-described Step 3 was used instead of 6-aminoquinoline, and tert-butyl((3R,4R)-4-aminotetrahydro-2H-pyran-3-yl)carbamate was used instead of tert-butyl((1S,2R)-2-aminocyclohexyl)carbamate to obtain the titled compound as a yellow solid.

Example 99

3-(((3R,4R)-3-aminotetrahydro-2H-pyran-4-yl)amino)-5-((2-(1-hydroxy-2-methylpropan-2-yl)-7-methyl-2H-indazol-5-yl)amino)-1,2,4-triazine-6-carboxamide (Step 1)
Cesium carbonate (6.52 g) and ethyl 2-bromo isobutyrate (2.2 mL) were added to a solution of 5-bromo-7-methyl-1H-indazole (2.11 g) in DMF (20 mL), and the reaction solution was stirred at room temperature for 2 hours. Water was added to the reaction solution, and then the reaction solution was extracted with ethyl acetate. The organic layer was washed successively with water and a saturated saline solution. After drying over anhydrous sodium sulfate, the solvent was evaporated under vacuum. The resultant residue was purified by column chromatography on silica gel (developing solvent: hexane/ethyl acetate) to obtain ethyl 2-(5-bromo-7-methyl-2H-indazol-2-yl)-2-methyl propanoate.

(Step 2)
A solution of 0.99 M diisobutylaluminium hydride in toluene (34.4 mL) was added to a solution of ethyl 2-(5-bromo-7-methyl-2H-indazol-2-yl)-2-methyl propanoate obtained in the above-described Step (2.77 g) in THF (30 mL) under ice-cooling. The reaction solution was stirred under ice-cooling for 30 minutes, and then 5 N hydrochloric acid (30 mL) was slowly added to the reaction solution. The reaction solution was diluted with water and then extracted with diethyl ether. The organic layer was washed successively with 2 N hydrochloric acid, an aqueous sodium bicarbonate solution, and a saturated saline solution. After drying over anhydrous sodium sulfate, the solvent was evaporated under vacuum. The resultant residue was purified by column chromatography on silica gel (developing solvent:hexane/ethyl acetate) to obtain 2-(5-bromo-7-methyl-2H-indol-2-yl)-2-methylpropan-1-ol.

(Step 3)
In accordance with Example 61 (Steps 2 and 3), 2-(5-bromo-7-methyl-2H-indol-2-yl)-2-methylpropan-1-ol obtained in the above-described Step 2 was used instead of 5-bromo-2-(tert-butyl)-7-methyl-2H-indazole to obtain the titled compound as a light yellow solid.

Example 100

3-(((3R,4R)-3-aminotetrahydro-2H-pyran-4-yl)amino)-5-((2-(tert-butyl)-7-chloro-2H-indazol-5-yl)amino)-1,2,4-triazine-6-carboxamide (Step 1)
In accordance with Example 83 (Steps 1 and 2), 5-bromo-7-chloro-1H-indazole was used instead of 5-bromo-7-methyl-1H-indazole, and 2-methyl-2-propanol was used instead of 1-methyl-1-cyclobutanol to obtain 2-(tert-butyl)-7-chloro-2H-indazol-5-amine.

(Step 2)
In accordance with Example 8 (Steps 1 to 4), 2-(tert-butyl)-7-chloro-2H-indazol-5-amine obtained in the above-described Step was used instead of benzo[b]thiophen-4-amine to obtain the titled compound as a light yellow solid.

Example 101

3-(((1R,2S)-2-aminocyclohexyl)amino)-5-((2-ethyl-4-methyl-2H-indazol-6-yl)amino)-1,2,4-triazine-6-carboxamide In accordance with Example 97 (Steps 2 and 3), 2-ethyl-4-methyl-6-nitro-2H-indazole obtained in Example 97 (Step 1) was used instead of 1-ethyl-4-methyl-6-nitro-1H-indazole to obtain the titled compound as a yellow solid.

Example 102

3-(((1R,2S)-2-aminocyclohexyl)amino)-5-((4-(4-methyl pyrimidin-2-yl)thiophen-2-yl)amino)-1,2,4-triazine-6-carboxamide In accordance with Example 77 (Steps 2 and 3), 2-chloro-4-methyl pyrimidine was used instead of 2-bromopyridine to obtain the titled compound as a light yellow solid.

Example 103

3-(((1R,2S)-2-aminocyclohexyl)amino)-5-((1-isopropyl-7-methyl-H-indazol-5-yl)amino)-1,2,4-triazine-6-carboxamide (Step 1)
In accordance with Example 70 (Step 1), 2-iodopropane was used instead of iodoethane to obtain 5-bromo-1-isopropyl-7-methyl-1H-indazole (450 mg) and 5-bromo-2-isopropyl-7-methyl-2H-indazole (479 mg).

(Step 2)
In accordance with Example 70 (Steps 2 and 3), 5-bromo-1-isopropyl-7-methyl-1H-indazole was used instead of 5-bromo-2-ethyl-7-methyl-2H-indazole to obtain the titled compound as an orange solid.

Example 104

3-(((1R,2S)-2-aminocyclohexyl)amino)-5-((2-(tert-butyl)-2H-indazol-5-yl)amino)-1,2,4-triazine-6-carboxamide In accordance with Example 89 (Steps 1 to 3), tert-butylamine was used instead of cyclobutylamine, and tert-butyl ((1S,2R)-2-aminocyclohexyl)carbamate was used instead of tert-butyl((2S,3R)-3-amino-5-methylhexan-2-yl)carbamate to obtain the titled compound as a light yellow solid.

Example 105

3-(((1R,2S)-2-aminocyclohexyl)amino)-5-((1-(3-hydroxy-2,2-dimethylpropyl)-1H-indol-4-yl)amino)-1,2,4-triazine-6-carboxamide In accordance with Example 68 (Steps 2 and 3), (3-bromo-2,2-dimethylpropoxy) (tert-butyl)dimethylsilane, which can be synthesized by the method described in Journal of Organic Chemistry, 1988, 53(3), 507-15, was used instead of (S)-tetrahydrofuran-3-yl methanesulfonate to obtain the titled compound as a light yellow solid.

Example 106

3-(((1-aminocyclobutyl)methyl)amino)-5-((1-(1-methyl-1H-pyrazol-3-yl)-1H-indol-4-yl)amino)-1,2,4-triazine-6-carboxamide (Step 1)
In accordance with Example 63 (Step 3), tert-butyl(1-(hydroxymethyl)cyclobutyl)carbamate (2.01 g) was used instead of tert-butyl((2S,3S)-1-ethoxy-3-hydroxybutan-2-yl)carbamate to obtain tert-butyl(1-(aminomethyl)cyclobutyl)carbamate.

(Step 2)

In accordance with Example 3 (Steps 1 to 4), 1-(1-methyl-1H-pyrazol-3-yl)-1H-indol-4-amine obtained in Example 25 (Step 2) was used instead of 1-methyl-1H-indol-4-amine, and tert-butyl(1-(aminomethyl)cyclobutyl)carbamate obtained in the above-described Step was used instead of tert-butyl((1S,2R)-2-aminocyclohexyl)carbamate to obtain the titled compound as a light yellow solid.

Example 107

3-(((1R,2S)-2-aminocyclohexyl)amino)-5-((1-ethyl-1H-indazol-4-yl)amino)-1,2,4-triazine-6-carboxamide (Step 1)

In accordance with Example 68 (Step 2), 4-nitro-1H-indazole was used instead of 4-nitro-1H-indole, and iodoethane was used instead of (S)-tetrahydrofuran-3-yl methanesulfonate to obtain 1-ethyl-1H-indazol-4-amine.

(Step 2)

In accordance with Example 8 (Steps 1 to 4), 1-ethyl-1H-indazol-4-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 108

3-(((1R,2S)-2-aminocyclohexyl)amino)-5-((2-cyclopentyl-2H-indazol-5-yl)amino)-1,2,4-triazine-6-carboxamide In accordance with Example 89 (Steps 1 to 3), cyclopentylamine was used instead of cyclobutylamine, and tert-butyl((1S,2R)-2-aminocyclohexyl)carbamate was used instead of tert-butyl((2S,3R)-3-amino-5-methylhexan-2-yl)carbamate to obtain the titled compound as a light yellow solid.

Example 109

3-(((1R,2S)-2-aminocyclohexyl)amino)-5-((2-ethyl-4-methoxy-2H-indazol-6-yl)amino)-1,2,4-triazine-6-carboxamide (Step 1)

In accordance with Example 70 (Step 1), 6-bromo-4-methoxy-1H-indazole (329 mg) was used instead of 5-bromo-7-methyl-1H-indazole to obtain 6-bromo-1-ethyl-4-methoxy-1H-indazole (210 mg) and 6-bromo-2-ethyl-4-methoxy-2H-indazole.

(Step 2)

In accordance with Example 70 (Steps 2 and 3), 6-bromo-2-ethyl-4-methoxy-2H-indazole obtained in the above-described Step was used instead of 5-bromo-2-ethyl-7-methyl-2H-indazole to obtain the titled compound as a light yellow solid.

Example 110

3-(((1R,2S)-2-aminocyclohexyl)amino)-5-((1-ethyl-4-methoxy-1H-indazol-6-yl)amino)-1,2,4-triazine-6-carboxamide In accordance with Example 70 (Steps 2 and 3), 6-bromo-1-ethyl-4-methoxy-1H-indazole obtained in Example 109 (Step 1) was used instead of 5-bromo-2-ethyl-7-methyl-2H-indazole to obtain the titled compound as a light yellow solid.

Example 111

3-(((1R,2S)-2-aminocyclohexyl)amino)-5-((1-(2,6-dimethoxypyrimidin-4-yl)-1H-indol-4-yl)amino)-1,2,4-triazine-6-carboxamide In accordance with Example 25 (Steps 1 to 3), 4-chloro-2,6-dimethoxypyrimidine was used instead of 3-iodine-1-methyl-1H-pyrazole to obtain the titled compound as a light yellow solid.

Example 112

3-(((1R,2S)-2-aminocyclohexyl)amino)-5-((5-(pyrimidin-2-yl)thiophen-3-yl)amino)-1,2,4-triazine-6-carboxamide (Step 1)

A solution of bromine (4.4 mL) in acetic acid (30 mL) was added to a solution of thiophene-3-carboxylic acid (9.8 g) in acetic acid (40 mL) at room temperature for as long as 30 minutes. The reaction solution was stirred at room temperature for 7 hours, and water (200 mL) was added. The deposited precipitate was filtrated to obtain a mixture of 2-bromothiophene-4-carboxylic acid and 2,5-dibromothiophene-3-carboxylic acid (approximately 5:1).

(Step 2)

Triethylamine (15 mL) and diphenylphosphoryl azide (16.5 mL) were added to a solution of the mixture of 2-bromothiophene-4-carboxylic acid obtained in the above-described Step (14.48 g) in toluene (250 mL) at room temperature. The reaction solution was stirred for 2 hours. 2-Methyl-2-propanol (40 mL) was added to the reaction solution, and then the reaction solution was stirred at 100° C. for 2 hours. The reaction solution was evaporated under vacuum, and the resultant residue was purified by column chromatography on silica gel (developing solvent:hexane/ethyl acetate) to obtain tert-butyl(5-bromothiophen-3-yl)carbamate as a white solid.

(Step 3)

[1,1'-Bis(diphenylphosphino)ferrocene]dichloropalladium(II) (1:1; 204 mg), potassium acetate (3.39 g), and DMF (10 mL) were added to tert-butyl(5-bromothiophen-3-yl)carbamate obtained in the above-described Step (1.4 g) and bis(pinacolato)diboron (2.54 g), and the reaction solution was stirred at 80° C. for 1 hour. Diethyl ether and water were added to the reaction solution, and the insolubles were filtrated. Thereafter, the organic layer was separated and then washed successively with water twice and a saturated saline solution. After drying over anhydrous sodium sulfate, the solvent was evaporated under vacuum. 2-Chloropyrimidine (1 g), tetrakis triphenylphosphine palladium (300 mg), dioxane (50 mL), and a 2 M aqueous sodium carbonate solution (5 mL) were added to the resultant residue. Thereafter, the reaction solution was stirred at 85° C. overnight. Ethyl acetate and water were added to the reaction solution, and then the organic layer was separated and washed with a saturated saline solution. After drying over anhydrous sodium sulfate, the solvent was evaporated under vacuum. The resultant residue was purified by column chromatography on silica gel (developing solvent:hexane/ethyl acetate) to obtain tert-butyl (5-(pyrimidin-2-yl)thiophen-3-yl)carbamate.

(Step 4)

A 4 N hydrochloric acid-dioxane solution (8 mL) was added to tert-butyl(5-(pyrimidin-2-yl)thiophen-3-yl)carbamate obtained in the above-described Step (544 mg), and the reaction solution was stirred at room temperature for 90 minutes. The solvent was evaporated under vacuum to obtain 5-(pyrimidin-2-yl)thiophen-3-amine hydrochloride as a brown solid.

(Step 5)

In accordance with Example 8 (Steps 1 to 4), 5-(pyrimidin-2-yl)thiophen-3-amine hydrochloride obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 113

3-(((3R,4R)-3-aminotetrahydro-2H-pyran-4-yl)amino)-5-((7-methyl-2-(tert-pentyl)-2H-indazol-5-yl)amino)-1,2,4-triazine-6-carboxamide (Step 1)

In accordance with Example 83 (Steps 1 and 2), 2-methylbutan-2-ol was used instead of 1-methyl-1-cyclobutanol to obtain 7-methyl-2-(tert-pentyl)-2H-indazol-5-amine.

(Step 2)

In accordance with Example 8 (Steps 1 to 4), 7-methyl-2-(tert-pentyl)-2H-indazol-5-amine obtained in the above-described Step was used instead of benzo[b]thiophen-4-amine to obtain the titled compound as a light yellow solid.

Example 114

3-(((1R,2S)-2-aminocyclohexyl)amino)-5-((1-(4-methoxy pyrimidin-2-yl)-1H-indol-4-yl)amino)-1,2,4-triazine-6-carboxamide In accordance with Example 25 (Steps 1 to 3), 2-chloro-4-methoxypyrimidine was used instead of 3-iodine-1-methyl-1H-pyrazole to obtain the titled compound as a light yellow solid.

Example 115

3-(((1R,2S)-2-aminocyclohexyl)amino)-5-((2-methyl-4-(trifluoromethyl)-2H-indazol-6-yl)amino)-1,2,4-triazine-6-carboxamide (Step 1)

In accordance with Example 24 (Steps 1 and 2), 4-(trifluoromethyl)-6-nitro-1H-indazole obtained by the method described in Patent No. WO 2009/064695 was used instead of 6-nitro-1H-indazole, and iodomethane was used instead of sodium chlorodifluoroacetate to obtain 1-methyl-4-(trifluoromethyl)-1H-indazol-6-amine and 2-methyl-4-(trifluoromethyl)-2H-indazol-6-amine.

(Step 2)

In accordance with Example 8 (Steps 1 to 4), 2-methyl-4-(trifluoromethyl)-2H-indazol-6-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a white solid.

Example 116

3-(((1R,2S)-2-aminocyclohexyl)amino)-5-((7-methyl-1-(2,2,2-trifluoroethyl)-1H-indazol-5-yl)amino)-1,2,4-triazine-6-carboxamide In accordance with Example 70 (Steps 2 and 3), 5-bromo-7-methyl-1-(2,2,2-trifluoroethyl)-1H-indazole obtained in Example 96 (Step 1) was used instead of 5-bromo-2-ethyl-7-methyl-2H-indazole to obtain the titled compound as a light yellow solid.

Example 117

3-(((1R,2S)-2-aminocyclohexyl)amino)-5-((2-(tetrahydro-2H-pyran-4-yl)-2H-indazol-5-yl)amino)-1,2,4-triazine-6-carboxamide (Step 1)

In accordance with Example 11 (Steps 1 and 2), tetrahydro-2H-pyran-4-ol was used instead of cyclobutanol to obtain 1-(tetrahydro-2H-pyran-4-yl)-1H-indazol-5-amine and 2-(tetrahydro-2H-pyran-4-yl)-2H-indazol-5-amine.

(Step 2)

In accordance with Example 1 (Steps 1 to 4), 2-(tetrahydro-2H-pyran-4-yl)-2H-indazol-5-amine obtained in the above-described Step was used instead of 6-aminoquinoline to obtain the titled compound as a yellow solid.

Example 118

3-(((2R,3R)-3-amino-4-methoxybutan-2-yl)amino)-5-((2-ethyl-4-methyl-2H-indazol-6-yl)amino)-1,2,4-triazine-6-carboxamide In accordance with Example 97 (Steps 2 and 3), 2-ethyl-4-methyl-6-nitro-2H-indazole obtained in Example 97 (Step 1) was used instead of 1-ethyl-4-methyl-6-nitro-1H-indazole, and tert-butyl((2R,3R)-3-amino-1-methoxybutan-2-yl)carbamate obtained in Example 64 (Step 1) was used instead of tert-butyl((1S,2R)-2-aminocyclohexyl)carbamate to obtain the titled compound as a light yellow solid.

Example 119

3-(((1R,2S)-2-aminocyclohexyl)amino)-5-((1-(pyrimidin-2-yl)-1H-indol-4-yl)amino)-1,2,4-triazine-6-carboxamide In accordance with Example 25 (Steps 1 to 3), 2-chloropyrimidine was used instead of 3-iodine-1-methyl-1H-pyrazole to obtain the titled compound as a light yellow solid.

Example 120

3-(((1R,2S)-2-aminocyclohexyl)amino)-5-((2-phenyl-2H-indazol-5-yl)amino)-1,2,4-triazine-6-carboxamide In accordance with Example 89 (Steps 1 to 3), aniline was used instead of cyclobutylamine, and tert-butyl((1S,2R)-2-aminocyclohexyl)carbamate was used instead of tert-butyl ((2S,3R)-3-amino-5-methylhexan-2-yl)carbamate to obtain the titled compound as a light yellow solid.

Example 121

3-(((1R,2S)-2-aminocyclohexyl)amino)-5-((1-(pyridin-3-yl)-1H-indazol-4-yl)amino)-1,2,4-triazine-6-carboxamide In accordance with Example 25 (Steps 1 to 3), 4-nitro-1H-indazole was used instead of 4-nitro-1H-indole, and 3-iodopyridine was used instead of 3-iodine-1-methyl-1H-pyrazole to obtain the titled compound as a light yellow solid.

Example 122

3-(((1R,2S)-2-aminocyclohexyl)amino)-5-((1-(1-methyl-1H-pyrazol-4-yl)-1H-indazol-4-yl)amino)-1,2,4-triazine-6-carboxamide In accordance with Example 25 (Steps 1 to 3), 4-nitro-1H-indazole was used instead of 4-nitro-1H-indole, and 4-iodine-1-methyl-1H-pyrazole was used instead of 3-iodine-1-methyl-1H-pyrazole to obtain the titled compound as a light yellow solid.

Example 123

3-(((1R,2S)-2-aminocyclohexyl)amino)-5-((1-cyclobutyl-4-methyl-1H-indazol-6-yl)amino)-1,2,4-triazine-6-carboxamide dihydrochloride (Step 1)
In accordance with Example 24 (Steps 1 and 2), 4-methyl-6-nitro-1H-indazole was used instead of 6-nitro-1H-indazole, and bromocyclobutane was used instead of chlorodifluoroacetic acid sodium to obtain 1-cyclobutyl-4-methyl-1H-indazol-6-amine and 2-cyclobutyl-4-methyl-2H-indazol-6-amine.
(Step 2)
In accordance with Example 1 (Steps 1 to 4), 1-cyclobutyl-4-methyl-1H-indazol-6-amine obtained in the above-described Step was used instead of 6-aminoquinoline to obtain the titled compound as a yellow solid.

Example 124

3-(((1R,2S)-2-aminocyclohexyl)amino)-5-((1-ethyl-1H-benzo[d]imidazol-5-yl)amino)-1,2,4-triazine-6-carboxamide (Step 1)
In accordance with Example 68 (Step 2), 5-nitrobenzoimidazole was used instead of 4-nitro-1H-indole, and iodoethane was used instead of (S)-tetrahydrofuran-3-yl methanesulfonate to obtain 1-ethyl-1H-benzo[d]imidazol-5-amine (317 mg) and 1-ethyl-1H-benzo[d]imidazol-6-amine.
(Step 2)
In accordance with Example 8 (Steps 1 to 4), 1-ethyl-1H-benzo[d]imidazol-5-amine obtained in the above-described Step was used instead of benzo[b]thiophen-4-amine, and tert-butyl((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 125

3-(((3R,4R)-3-aminotetrahydro-2H-pyran-4-yl)amino)-5-((2-(difluoromethyl)-2H-indazol-5-yl)amino)-1,2,4-triazine-6-carboxamide (Step 1)
In accordance with Example 62 (Step 1), ethyl acetate (20 mL) was added to 2-(difluoromethyl)-5-nitro-2H-indazole (429 mg) obtained by using 5-nitro-1H-indazole instead of 5-bromo-7-methyl-1H-indazole. Thereafter, 10% palladium on carbon (300 mg) was added, and the reaction solution was stirred under hydrogen atmosphere at room temperature for 4 hours. The insolubles were filtrated, and then the solvent was evaporated under vacuum to obtain 2-(difluoromethyl)-2H-indazol-5-amine as a white solid.
(Step 2)
In accordance with Example 1 (Steps 1 to 4), 2-(difluoromethyl)-2H-indazol-5-amine obtained in the above-described Step was used instead of 6-aminoquinoline, and tert-butyl ((3R,4R)-4-aminotetrahydro-2H-pyran-3-yl)carbamate was used instead of tert-butyl((1S,2R)-2-aminocyclohexyl)carbamate to obtain the titled compound as a yellow solid.

Example 126

3-(((1R,2S)-2-aminocyclohexyl)amino)-5-((1-((S)-tetrahydrofuran-3-yl)-1H-indazol-4-yl)amino)-1,2,4-triazine-6-carboxamide In accordance with Example 68 (Steps 1 to 3), 4-nitro-1H-indazole was used instead of 4-nitro-1H-indole to obtain the titled compound as a light yellow solid.

Example 127

3-(((1R,2S)-2-aminocyclohexyl)amino)-5-((1-((S)-tetrahydrofuran-3-yl)-1H-indazol-4-yl)amino)-1,2,4-triazine-6-carboxamide In accordance with Example 68 (Steps 1 to 3), (R)-tetrahydrofuran-3-ol was used instead of (S)-tetrahydrofuran-3-ol, and 4-nitro-1H-indazole was used instead of 4-nitro-1H-indole to obtain the titled compound as a light yellow solid.

Example 128

3-(((3R,4R)-3-aminotetrahydro-2H-pyran-4-yl)amino)-5-((2-(tert-butyl)-7-ethyl-2H-indazol-5-yl)amino)-1,2,4-triazine-6-carboxamide (Step 1)
In accordance with Example 83 (Steps 1 and 2), 5-bromo-7-ethyl-1H-indazole was used instead of 5-bromo-7-methyl-1H-indazole, and 2-methyl-2-propanol was used instead of 1-methyl-1-cyclobutanol to obtain 2-(tert-butyl)-7-ethyl-2H-indazol-5-amine.
(Step 2)
In accordance with Example 8 (Steps 1 to 4), 2-(tert-butyl)-7-ethyl-2H-indazol-5-amine obtained in the above-described Step was used instead of benzo[b]thiophen-4-amine to obtain the titled compound as a light yellow solid.

Example 129

3-(((1R,2S)-2-aminocyclohexyl)amino)-5-((1-(1-methyl-1H-pyrazol-3-yl)-1H-indazol-4-yl)amino)-1,2,4-triazine-6-carboxamide In accordance with Example 25 (Steps 1 to 3), 4-nitro-1H-indazole was used instead of 4-nitro-1H-indole to obtain the titled compound as a light yellow solid.

Example 130

3-(((1R,2S)-2-aminocyclohexyl)amino)-5-((1-(tetrahydro-2H-pyran-4-yl)-1H-indazol-4-yl)amino)-1,2,4-triazine-6-carboxamide In accordance with Example 68 (Steps 1 to 3), tetrahydro-2H-pyran-4-ol was used instead of (S)-tetrahydrofuran-3-ol, and 4-nitro-1H-indazole was used instead of 4-nitro-1H-indole to obtain the titled compound as a light yellow solid.

Example 131

3-(((1R,2S)-2-aminocyclohexyl)amino)-5-((1-isopropyl-1H-indazol-4-yl)amino)-1,2,4-triazine-6-carboxamide In accordance with Example 68 (Steps 1 to 3), 2-iodopropane was used instead of (S)-tetrahydrofuran-3-ol, and 4-nitro-1H-indazole was used instead of 4-nitro-1H-indole to obtain the titled compound as a light yellow solid.

Example 132

3-(((1R,2S)-2-aminocyclohexyl)amino)-5-((1-(pyridin-2-yl)-1H-indazol-4-yl)amino)-1,2,4-triazine-6-carboxamide In accordance with Example 25 (Steps 1 to 3), 4-nitro-1H-indazole was used instead of 4-nitro-1H-indole, and 2-bromopyridine was used instead of 3-iodine-1-methyl-1H-pyrazole to obtain the titled compound as a light yellow solid.

Example 133

3-(((1R,2S)-2-aminocyclohexyl)amino)-5-((2-(tert-butyl)-2H-indazol-6-yl)amino)-1,2,4-triazine-6-carboxamide (Step 1)
Tert-butylamine (2 mL) was added to a solution of 2,4-dinitrobenzaldehyde (1.96 g) in ethanol (10 mL), and the reaction solution was stirred at 40° C. for 30 minutes. The solvent was evaporated under vacuum, then tert-butylamine (1 mL) was added to the resultant residue, and the reaction solution was heated at 50° C. for 30 minutes. The solvent was evaporated under vacuum, then trimethyl phosphite (6 mL) was added, and the reaction solution was stirred at 110° C. for 1 hour. The solvent was evaporated under vacuum, and the resultant residue was purified by column chromatography on silica gel (developing solvent:hexane/ethyl acetate). Thereafter, isopropyl ether was added to the resultant residue, and the precipitate was filtrated to obtain 2-(tert-butyl)-6-nitro-2H-indazole as a white solid.
(Step 2)
10% Palladium on carbon (1 g) was added to a solution of 2-(tert-butyl)-6-nitro-2H-indazole obtained in the above-described Step (1.1 g) in ethyl acetate (12 mL), and the reaction solution was stirred under hydrogen atmosphere at room temperature for 4 hours. The insolubles were filtrated, and the solvent was evaporated under vacuum. Thereafter, the resultant residue was purified by column chromatography on silica gel (developing solvent:hexane/ethyl acetate) to obtain 2-(tert-butyl)-2H-indazol-6-amine as a white solid.
(Step 3)
In accordance with Example 8 (Steps 1 to 4), 2-(tert-butyl)-2H-indazol-6-amine obtained in the above-described Step was used instead of benzo[b]thiophen-4-amine, and tert-butyl ((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 134

3-(((1R,2S)-2-aminocyclohexyl)amino)-5-((1-(pyridin-4-ylmethyl)-1H-indazol-4-yl)amino)-1,2,4-triazine-6-carboxamide In accordance with Example 68 (Steps 2 and 3), 4-nitro-1H-indazole was used instead of 4-nitro-1H-indole, and 4-(chloromethyl)pyridine hydrochloride was used instead of (S)-tetrahydrofuran-3-yl methanesulfonate to obtain the titled compound as a light yellow solid.

Example 135

3-(((1R,2S)-2-aminocyclohexyl)amino)-5-((1-(2-ethoxyethyl)-1H-indazol-4-yl)amino)-1,2,4-triazine-6-carboxamide In accordance with Example 68 (Steps 2 and 3), 4-nitro-1H-indazole was used instead of 4-nitro-1H-indole, and bromoethyl ethyl ether was used instead of (S)-tetrahydrofuran-3-yl methanesulfonate to obtain the titled compound as a light yellow solid.

Example 136

3-(((3R,4R)-3-aminotetrahydro-2H-pyran-4-yl)amino)-5-((2,7-diethyl-3-methyl-2H-indazol-5-yl)amino)-1,2,4-triazine-6-carboxamide In accordance with Example 81 (Steps 1 to 3), 5-bromo-7-ethyl-3-methyl-1H-indazole was used instead of 5-bromo-7-chloro-2-ethyl-2H-indazole to obtain the titled compound as a light yellow solid.

Example 137

3-(((3R,4R)-3-aminotetrahydro-2H-pyran-4-yl)amino)-5-((6-methyl-1-(tetrahydro-2H-pyran-4-yl)-1H-indol-4-yl)amino)-1,2,4-triazine-6-carboxamide (Step 1)
In accordance with Example 68 (Steps 1 and 2), tetrahydro-2H-pyran-4-ol was used instead of (S)-tetrahydrofuran-3-ol, and 6-methyl-4-nitro-1H-indole was used instead of 4-nitro-1H-indole to obtain 6-methyl-1-(tetrahydro-2H-pyran-4-yl)-1H-indol-4-amine.
(Step 2)
In accordance with Example 3 (Steps 1 to 4), 6-methyl-1-(tetrahydro-2H-pyran-4-yl)-1H-indol-4-amine obtained in the above-described Step was used instead of 1-methyl-1H-indol-4-amine, and tert-butyl((3R,4R)-4-aminotetrahydro- 2H-pyran-3-yl)carbamate was used instead of tert-butyl((1S,2R)-2-aminocyclohexyl)carbamate to obtain the titled compound as a light yellow solid.

Example 138

3-(((3R,4R)-3-aminotetrahydro-2H-pyran-4-yl) amino)-5-((2-(tert-butyl)-7-methoxy-2H-indazol-5-yl)amino)-1,2,4-triazine-6-carboxamide In accordance with Example 128 (Steps 1 and 2), 5-bromo-7-methoxy-1H-indazole was used instead of 5-bromo-7-methyl-1H-indazole to obtain the titled compound as a light yellow solid.

Example 139

3-(((3R,4R)-3-aminotetrahydro-2H-pyran-4-yl) amino)-5-((7-chloro-1-isobutyl-1H-indazol-5-yl) amino)-1,2,4-triazine-6-carboxamide (Step 1)
In accordance with Example 70 (Steps 1 and 2), 5-bromo-7-chloro-1H-indazole was used instead of 5-bromo-7-methyl-1H-indazole, and 1-iodine-2-methylpropane was used instead of iodoethane to obtain 7-chloro-1-isobutyl-H-indazol-5-amine.
(Step 2)
In accordance with Example 8 (Steps 1 to 4), 7-chloro-1-isobutyl-1H-indazol-5-amine obtained in the above-described Step was used instead of benzo[b]thiophen-4-amine to obtain the titled compound as a light yellow solid.

Example 140

3-(((3R,4R)-3-aminotetrahydro-2H-pyran-4-yl) amino)-5-((1-(difluoromethyl)-7-methyl-H-indazol-5-yl)amino)-1,2,4-triazine-6-carboxamide (Step 1)
In accordance with Example 70 (Steps 1 and 2), sodium chlorodifluoroacetate was used instead of iodoethane to obtain 1-(difluoromethyl)-7-methyl-1H-indazol-5-amine.
(Step 2)
In accordance with Example 8 (Steps 1 to 4), 1-(difluoromethyl)-7-methyl-1H-indazol-5-amine obtained in the above-described Step was used instead of benzo[b]thiophen-4-amine to obtain the titled compound as a light yellow solid.

Example 141

3-(((1R,2S)-2-aminocyclohexyl)amino)-5-((1-(pyrazin-2-yl)-1H-indazol-4-yl)amino)-1,2,4-triazine-6-carboxamide In accordance with Example 25 (Steps 1 to 3), 4-nitro-1H-indazole was used instead of 4-nitro-1H-indole, and 2-bromo pyrazine was used instead of 3-iodine-1-methyl-1H-pyrazole to obtain the titled compound as a light yellow solid.

Example 142

3-(((1R,2S)-2-aminocyclohexyl)amino)-5-((1-(2-oxotetrahydrofuran-3-yl)-1H-indol-4-yl)amino)-1,2,4-triazine-6-carboxamide dihydrochloride In accordance with Example 68 (Steps 1 to 3), 2-oxotetrahydrofuran-3-ol was used instead of (S)-tetrahydrofuran-3-ol to obtain the titled compound as a light yellow solid.

Example 143

3-((2-Aminoethyl)(methyl)amino)-5-((1-ethyl-d5-1H-indazol-5-yl)amino)-1,2,4-triazine-6-carboxamide (Step 1)
In accordance with Example 4 (Step 2), 5-nitro-1-(ethyl-d5)-1H-indazole obtained in Example 4 (Step 1) was used instead of 5-nitro-2-(ethyl-d5)-2H-indazole to obtain 1-ethyl-d5-1H-indazol-5-amine as a white solid.
(Step 2)
In accordance with Example 1 (Steps 1 to 4), 1-ethyl-d5-1H-indazol-5-amine obtained in the above-described Step was used instead of 6-aminoquinoline, and tert-butyl(2-(methylamino)ethyl)carbamate was used instead of tert-butyl ((1S,2R)-2-aminocyclohexyl)carbamate to obtain the titled compound as a yellow solid.

Example 144

3-(((1R,2S)-2-aminocyclohexyl)amino)-5-((1-(pyridin-3-yl)-1H-indol-4-yl)amino)-1,2,4-triazine-6-carboxamide In accordance with Example 25 (Steps 1 to 3), 3-iodopyridine was used instead of 3-iodine-1-methyl-1H-pyrazole to obtain the titled compound as a light yellow solid.

Example 145

3-(((R,2S)-2-aminocyclohexyl)amino)-5-((1-(thiazol-2-yl)-1H-indol-4-yl)amino)-1,2,4-triazine-6-carboxamide In accordance with Example 25 (Steps 1 to 3), 2-bromothiazole was used instead of 3-iodine-1-methyl-1H-pyrazole to obtain the titled compound as a light yellow solid.

Example 146

3-(((1R,2S)-2-aminocyclohexyl)amino)-5-((1-(thiazol-2-yl)-1H-indazol-4-yl)amino)-1,2,4-triazine-6-carboxamide In accordance with Example 25 (Steps 1 to 3), 4-nitro-1H-indazole was used instead of 4-nitro-1H-indole, and 2-bromothiazole was used instead of 3-iodine-1-methyl-1H-pyrazole to obtain the titled compound as a light yellow solid.

Example 147

3-(((1R,2S)-2-aminocyclohexyl)amino)-5-((2-phenyl-2H-indazol-6-yl)amino)-1,2,4-triazine-6-carboxamide (Step 1)
In accordance with Example 133 (Steps 1 and 2), aniline was used instead of tert-butylamine to obtain 2-phenyl-2H-indazol-6-amine as a white solid.
(Step 2)
In accordance with Example 8 (Steps 1 to 4), 2-phenyl-2H-indazol-6-amine obtained in the above-described Step was used instead of benzo[b]thiophen-4-amine, and tert-butyl ((1S,2R)-2-aminocyclohexyl)carbamate was used instead of tert-butyl((3R,4R)-4-aminotetrahydro-2H-pyran-3-yl)carbamate to obtain the titled compound as a light yellow solid.

Example 148

3-(((1R,2S)-2-aminocyclohexyl)amino)-5-((1-cyclopentyl-1H-indazol-4-yl)amino)-1,2,4-triazine-6-carboxamide In accordance with Example 68 (Steps 2 and 3), 4-nitro-1H-indazole was used instead of 4-nitro-1H-indole, and bromocyclopentane was used instead of (S)-tetrahydrofuran-3-yl methanesulfonate to obtain the titled compound as a light yellow solid.

Example 149

3-(((1R,2S)-2-aminocyclohexyl)amino)-5-((1-cyclohexyl-1H-indazol-4-yl)amino)-1,2,4-triazine-6-carboxamide In accordance with Example 68 (Steps 2 and 3), 4-nitro-1H-indazole was used instead of 4-nitro-1H-indole, and bromocyclohexane was used instead of (S)-tetrahydrofuran-3-yl methanesulfonate to obtain the titled compound as a light yellow solid.

Example 150

3-(((1R,2S)-2-aminocyclohexyl)amino)-5-((1-benzyl-1H-indazol-4-yl)amino)-1,2,4-triazine-6-carboxamide In accordance with Example 68 (Steps 2 and 3), 4-nitro-1H-indazole was used instead of 4-nitro-1H-indole, and benzylbromide was used instead of (S)-tetrahydrofuran-3-yl methanesulfonate to obtain the titled compound as a light yellow solid.

Example 151

3-(((1R,2S)-2-aminocyclohexyl)amino)-5-((1-(pyridin-3-ylmethyl)-1H-indazol-4-yl)amino)-1,2,4-triazine-6-carboxamide In accordance with Example 68 (Steps 2 and 3), 4-nitro-1H-indazole was used instead of 4-nitro-1H-indole, and 3-picolyl chloride hydrochloride was used instead of (S)-tetrahydrofuran-3-yl methanesulfonate to obtain the titled compound as a light yellow solid.

Compounds according to Examples 152 to 414 were produced according to the above-described Examples 1 to 151 or by usually known production methods. With respect to each compound, source materials that were used (including compounds represented by general formula (III) and compounds represented by general formula (VII)) and Examples followed in the production are illustrated in Tables 1 to 11.

TABLE 1

| Example | Corresponding Example | Compound represented by general formula (III) B–NH–R$_2$ | Compound represented by general formula (VII) A–NH–R$_1$ | Form |
|---|---|---|---|---|
| 152 | 2 | 1-ethyl-1H-indazol-5-amine | tert-butyl((1S,2R)-2-aminocyclohexyl)carbamate | |
| 153 | 1 | 6-aminoquinoline | (S)-tert-butyl 3-aminopiperidine-1-carboxylate | Yellow amorphous |
| 154 | 2 | 1-ethyl-1H-indazol-6-amine (WO2007/088478) | tert-butyl((1S,2R)-2-aminocyclohexyl)carbamate | White solid |
| 155 | 1 | 1-ethyl-1H-indazol-6-amine (WO2007/088478) | (S)-tert-butyl 3-aminopiperidine-1-carboxylate | Yellow amorphous |
| 156 | 1 | 1-methyl-1H-indol-4-amine | (R)-tert-butyl 3-aminopiperidine-1-carboxylate | Yellow amorphous |
| 157 | 3 | benzo[b]thiophene-4-amine | (S)-tert-butyl 3-aminopiperidine-1-carboxylate | Light yellow solid |
| 158 | 1 | 1-methyl-1H-indol-4-amine | tert-butyl((3R,4R)-4-aminotetrahydro-2H-pyran-3-yl)carbamate | Yellow amorphous |
| 159 | 1 | 1-cyclopropyl-1H-indol-4-amine (Example 15) | (S)-tert-butyl 3-aminopiperidine-1-carboxylate | Deep orange solid |
| 160 | 1 | 1-cyclopropyl-1H-indol-4-amine (Example 15) | tert-butyl((3R,4R)-4-aminotetrahydro-2H-pyran-3-yl)carbamate | Yellow solid |
| 161 | 3 | benzo[b]thiophene-2-amine | tert-butyl((1S,2R)-2-aminocyclohexyl)carbamate | Yellow solid |
| 162 | 3 | benzo[b]thiophene-2-amine | tert-butyl((3R,4R)-4-aminotetrahydro-2H-pyran-3-yl)carbamate | Yellow solid |
| 163 | 16 | 1,5-naphthyridine-3-amine | tert-butyl((1S,2R)-2-aminocyclohexyl)carbamate | Yellow solid |
| 164 | 2 | 4-phenylthiophene-2-amine | tert-butyl((1S,2R)-2-aminocyclohexyl)carbamate | Yellow solid |
| 165 | 3 | 1-(difluoromethyl)-1H-indazol-6-amine (Example 36) | tert-butyl((1S,2R)-2-aminocyclohexyl)carbamate | White solid |
| 166 | 1 | 1-(difluoromethyl)-1H-indol-4-amine (Example 39) | tert-butyl((3R,4R)-4-aminotetrahydro-2H-pyran-3-yl)carbamate | White solid |
| 167 | 1 | 2-(ethyl-d5)-2H-indazol-5-amine (Example 4) | tert-butyl((3R,4R)-4-aminotetrahydro-2H-pyran-3-yl)carbamate | Yellow amorphous |
| 168 | 2 | 1-ethyl-1H-indazol-6-amine (WO2007/088478) | tert-butyl((3R,4R)-4-aminotetrahydro-2H-pyran-3-yl)carbamate | White solid |

TABLE 1-continued

| Example | Corresponding Example | Compound represented by general formula (III) B\NH\|R$_2$ | Compound represented by general formula (VII) A\NH\|R$_1$ | Form |
|---|---|---|---|---|
| 169 | 1 | 1-(ethyl-d5)-1H-indazol-5-amine (Example 4) | tert-butyl((3R,4R)-4-aminotetrahydro-2H-pyran-3-yl)carbamate | |
| 170 | 3 | 1-(difluoromethyl)-1H-indazol-6-amine (Example 36) | tert-butyl((3R,4R)-4-aminotetrahydro-2H-pyran-3-yl)carbamate | Yellow amorphous |
| 171 | 3 | 1-(1-methyl-1H-pyrazol-3-yl)-1H-indol-4-amine (Example 38) | tert-butyl((3R,4R)-4-aminotetrahydro-2H-pyran-3-yl)carbamate | White solid |
| 172 | 2 | quinolin-3-amine | tert-butyl((1S,2R)-2-aminocyclohexyl)carbamate | |
| 173 | 2 | 1-methyl-1H-indazol-6-amine | tert-butyl((1S,2R)-2-aminocyclohexyl)carbamate | White solid |
| 174 | 2 | 4-methylthiophene-2-amine | tert-butyl((1S,2R)-2-aminocyclohexyl)carbamate | |
| 175 | 2 | 5-methyl-1-phenyl-1H-pyrazol-3-amine | tert-butyl((1S,2R)-2-aminocyclohexyl)carbamate | |

TABLE 2

| Example | Corresponding Example | Compound represented by general formula (III) B\NH\|R$_2$ | Compound represented by general formula (VII) A\NH\|R$_1$ | Form |
|---|---|---|---|---|
| 176 | 2 | 1-phenyl-1H-pyrazol-4-amine | tert-butyl((1S,2R)-2-aminocyclohexyl)carbamate | White solid |
| 177 | 2 | benzo[d]thiazol-6-amine | tert-butyl(1S,2R)-2-aminocyclohexyl)carbamate | |
| 178 | 2 | 2-methyl-2H-indazol-4-amine | tert-butyl((1S,2R)-2-aminocyclohexyl)carbamate | |
| 179 | 2 | 2-methyl-2H-indazol-5-amine | tert-butyl((1S,2R)-2-aminocyclohexyl)carbamate | |
| 180 | 2 | 2-methyl-2H-indazol-6-amine | tert-butyl((1S,2R)-2-aminocyclohexyl)carbamate | |
| 181 | 2 | 2-methylbenzo[d]thiazol-5-amine | tert-butyl((1S,2R)-2-aminocyclohexyl)carbamate | |
| 415 | 3 | 2-cyclobutyl-2H-indazol-5-amine (Example 152) | 3,3,3-trifluoropropane-1,2-diamine | Yellow solid |
| 183 | 2 | 6-bromopyridine-2-amine | tert-butyl((1S,2R)-2-aminocyclohexyl)carbamate | |
| 184 | 2 | 4-phenylthiazol-2-amine | tert-butyl((1S,2R)-2-aminocyclohexyl)carbamate | |
| 185 | 2 | quinolin-5-amine | tert-butyl((1S,2R)-2-aminocyclohexyl)carbamate | |
| 186 | 2 | 2-methylquinolin-4-amine | tert-butyl((1S,2R)-2-aminocyclohexyl)carbamate | |
| 187 | 2 | 1-isopropyl-1H-indazol-5-amine (WO2007/088478) | tert-butyl((1S,2R)-2-aminocyclohexyl)carbamate | |
| 188 | 2 | 3-methylisothiazol-5-amine | tert-butyl((1S,2R)-2-aminocyclohexyl)carbamate | |
| 189 | 2 | quinolin-2-amine | tert-butyl((1S,2R)-2-aminocyclohexyl)carbamate | |
| 190 | 2 | 5-methylthiophene-2-amine | tert-butyl((1S,2R)-2-aminocyclohexyl)carbamate | |
| 191 | 2 | 5-methoxybenzo[d]thiazol-2-amine | tert-butyl((1S,2R)-2-aminocyclohexyl)carbamate | |
| 192 | 2 | 3-phenyl-1,2,4-thiadiazol-5-amine | tert-butyl((1S,2R)-2-aminocyclohexyl)carbamate | |
| 193 | 2 | 4-bromopyridine-2-amine | tert-butyl((1S,2R)-2-aminocyclohexyl)carbamate | |
| 194 | 2 | benzo[d]thiazol-5-amine | tert-butyl((1S,2R)-2-aminocyclohexyl)carbamate | |
| 195 | 1 | 4-methoxy-6-nitroquinoline | tert-butyl((1S,2R)-2-aminocyclohexyl)carbamate | |
| 196 | 2 | 2-ethyl-2H-indazol-6-amine (WO2007/088478) | tert-butyl((1S,2R)-2-aminocyclohexyl)carbamate | |

TABLE 2-continued

| Example | Corresponding Example | Compound represented by general formula (III) B−NH−R₂ | Compound represented by general formula (VII) A−NH−R₁ | Form |
|---|---|---|---|---|
| 197 | 2 | 4-cyclopropylthiophene-2-amine | tert-butyl((1S,2R)-2-aminocyclohexyl)carbamate | |
| 198 | 2 | 1-methyl-1H-indazol-3-amine | tert-butyl((1S,2R)-2-aminocyclohexyl)carbamate | |
| 199 | 2 | 1-methyl-1H-benzo[d]imidazol-4-amine | tert-butyl((1S,2R)-2-aminocyclohexyl)carbamate | |

TABLE 3

| Example | Corresponding Example | Compound represented by general formula (III) B−NH−R₂ | Compound represented by general formula (VII) A−NH−R₁ | Form |
|---|---|---|---|---|
| 200 | 2 | 1-isopropyl-1H-benzo[d]imidazol-4-amine | tert-butyl((1S,2R)-2-aminocyclohexyl)carbamate | |
| 201 | 3 | benzo[d]oxazol-4-amine | tert-butyl((1S,2R)-2-aminocyclohexyl)carbamate | |
| 202 | 3 | benzofuran-7-amine | tert-butyl((1S,2R)-2-aminocyclohexyl)carbamate | |
| 203 | 3 | 2-methylbenzofuran-7-amine | tert-butyl((1S,2R)-2-aminocyclohexyl)carbamate | |
| 204 | 3 | 2-methylbenzo[d]thiazol-7-amine | tert-butyl((1S,2R)-2-aminocyclohexyl)carbamate | |
| 205 | 3 | 1,2-dimethyl-1H-indol-4-amine | tert-butyl((1S,2R)-2-aminocyclohexyl)carbamate | |
| 206 | 3 | benzofuran-4-amine | tert-butyl((1S,2R)-2-aminocyclohexyl)carbamate | |
| 207 | 3 | 1H-indol-4-amine | tert-butyl((1S,2R)-2-aminocyclohexyl)carbamate | |
| 208 | 3 | 4-amino-benzo[b]thiophene-6-carbonitrile | tert-butyl((1S,2R)-2-aminocyclohexyl)carbamate | |
| 209 | 3 | 2-(difluoromethyl)-2H-indazol-4-amine (Example 94) | tert-butyl((1S,2R)-2-aminocyclohexyl)carbamate | |
| 210 | 3 | 2-fluoro-5-phenylpyridine-3-amine | te-butyl((1S,2R)-2-aminocyclohexyl)carbamate | |
| 211 | 3 | thieno[2,3-b]pyridine-2-amine | tert-butyl((1S,2R)-2-aminocyclohexyl)carbamate | |
| 212 | 3 | benzo[b]thiophene-3-amine | tert-butyl((1S,2R)-2-aminocyclohexyl)carbamate | |
| 213 | 3 | 3-methylbenzo[b]thiophene-2-amine | tert-butyl((1S,2R)-2-aminocyclohexyl)carbamate | |
| 214 | 3 | 1-formyl-3-methy1-1H-indol-6-amine | tert-butyl((1S,2R)-2-aminocyclohexyl)carbamate | |
| 215 | 3 | 3-cyclopropylbenzo[b]-thiophene-2-amine | tert-butyl((1S,2R)-2-aminocyclohexyl)carbamate | |
| 216 | 3 | 1,3-dimethyl-1H-indazol-5-amine | tert-butyl((1S,2R)-2-aminocyclohexyl)carbamate | |
| 217 | 3 | 1-chloroisoquinolin-5-amine | tert-butyl((1S,2R)-2-aminocyclohexyl)carbamate | Yellow solid |
| 218 | 3 | 1-methoxyisoquinolin-5-amine | tert-butyl((1S,2R)-2-aminocyclohexyl)carbamate | Yellow solid |
| 219 | 3 | 1-methylisoquinolin-5-amine | tert-butyl((1S,2R)-2-aminocyclohexyl)carbamate | Yellow solid |
| 220 | 3 | benzo[b]thiophene-5-amine | tert-butyl((1S,2R)-2-aminocyclohexyl)carbamate | Yellow solid |
| 221 | 1 | 6-aminoquinoline | (R)-tert-butyl 3-aminopiperidine-1-carboxylate | Yellow solid |
| 222 | 1 | 1-ethyl-1H-indazol-6-amine (WO2007/088478) | (R)-cert-butyl 3-aminopiperidine-1-carboxylate | |
| 223 | 1 | 1-ethyl-1H-indazol-6-amine (WO2007/088478) | ethane-1,2-diamine | |

TABLE 4

| Example | Corresponding Example | Compound represented by general formula (III) B−NH−R₂ | Compound represented by general formula (VII) A−NH−R₁ | Form |
|---|---|---|---|---|
| 224 | 1 | 1-ethyl-1H-indazol-6-amine (WO2007/088478) | tert-butyl((1R,2R)-2-aminocyclohexyl)carbamate | |
| 225 | 1 | 1-ethyl-1H-indazol-6-amine (WO2007/088478) | aminocyclohexane | |
| 226 | 1 | 1-ethyl-1H-indazol-6-amine (WO2007/088478) | (1S,2R)-2-aminocyclohexanol | |
| 227 | 1 | 1H-1-methyl-indol-4-amine | cis-cyclohexane-1,4-diamine | |
| 228 | 1 | 1H-1-methyl-indol-4-amine | N',N'-dimethylethane-1,2-diamine | |
| 229 | 1 | 1H-1-methyl-indol-4-amine | trans-cyclohexane-1,4-diamine | |
| 230 | 1 | 1H-1-methyl-indol-4-amine | cyclohexane-1,3-diamine | |
| 231 | 1 | 1H-1-methyl-indol-4-amine | (S)-tert-butyl 3-aminopiperidine-1-carboxylate | |
| 232 | 1 | 1H-1-methyl-indol-4-amine | tert-butyl 4-aminopiperidine-1-carboxylate | |
| 233 | 1 | 1H-1-methyl-indol-4-amine | (R)-tert-butyl 3-aminopyrrolidine-1-carboxylate | |
| 234 | 1 | 1H-1-methyl-indol-4-amine | (S)-tert-butyl 3-aminopyrrolidine-1-carboxylate | |
| 235 | 1 | 1-(ethyl-d5)-1H-indazol-5-amine | tert-butyl 4-aminopiperidine-1-carboxylate | Yellow amorphous |
| 236 | 1 | 1-(ethyl-d5)-1H-indazol-5-amine | (R)-tert-butyl 3-aminopiperidine-1-carboxylate | Yellow amorphous |
| 237 | 1 | 1-(ethyl-d5)-1H-indazol-5-amine | (S)-tert-butyl 3-aminopyrrolidine-1-carboxylate | Yellow amorphous |
| 238 | 1 | 1-(ethyl-d5)-1H-indazol-5-amine | (R)-tert-butyl 3-aminopyrrolidine-1-carboxylate | Yellow amorphous |
| 239 | 1 | 1-(ethyl-d5)-1H-indazol-5-amine | ethane-1,2-diamine | Yellow amorphous |
| 240 | 1 | 1-(ethyl-d5)-1H-indazol-5-amine | N'-methylethane-1,2-diamine | Yellow amorphous |
| 241 | 1 | 1-(ethyl-d5)-1H-indazol-5-amine | cis-cyclohexane-1,4-diamine | Yellow amorphous |
| 242 | 1 | 1-(ethyl-d5)-1H-indazol-5-amine | 2-(pyrrolidin-1-yl)ethaneamine | Yellow amorphous |
| 243 | 1 | 1-(ethyl-d5)-1H-indazol-5-amine | 1-methylpiperidine-3-amine | Yellow amorphous |
| 244 | 1 | 1-(ethyl-d5)-1H-indazol-5-amine | trans-cyclohexane-1,2-diamine | Yellow amorphous |
| 245 | 2 | benzo[b]thiophen-4-ylamino | (S)-tert-butyl 1-aminobutan-2-ylcarbamate | Yellow amorphous |
| 246 | 2 | benzo[b]thiophen-4-ylamino | (R)-tert-butyl 2-aminopropylcarbamate | Yellow amorphous |
| 247 | 2 | benzo[b]thiophen-4-ylamino | (S)-tert-butyl 1-aminopropan-2-ylcarbamate | Yellow amorphous |

TABLE 5

| Example | Corresponding Example | Compound represented by general formula (III) B−NH−R₂ | Compound represented by general formula (VII) A−NH−R₁ | Form |
|---|---|---|---|---|
| 248 | 2 | benzo[b]thiophen-4-ylamino | (S)-tert-butyl 2-amino-1-phenylethylcarbamate | Yellow amorphous |
| 249 | 2 | benzo[b]thiophen-4-ylamino | (S)-tert-butyl 3-aminopyrrolidine-1-carboxylate | Yellow amorphous |
| 250 | 1 | 2-chloropyridine-4-amine | tert-butyl((1S,2R)-2-aminocyclohexyl)carbamate | Yellow solid |
| 251 | 3 | benzo[b]thiophene-6-amine | tert-butyl((1S,2R)-2-aminocyclohexyl)carbamate | Yellow solid |
| 252 | 3 | 2-phenylpyridine-4-amine | tert-butyl((1S,2R)-2-aminocyclohexyl)carbamate | Light yellow solid |
| 253 | 16 | 3-amino-5-(1H-pyrazol-1-yl)pyridine | tert-butyl((1S,2R)-2-aminocyclohexyl)carbamate | White solid |
| 254 | 3 | 2,3-dimethylimdazo[1,2-a]pyridine-6-amine | tert-butyl((1S,2R)-2-aminocyclohexyl)carbamate | Light yellow solid |

TABLE 5-continued

| Example | Corresponding Example | Compound represented by general formula (III) B−NH−R₂ | Compound represented by general formula (VII) A−NH−R₁ | Form |
|---|---|---|---|---|
| 255 | 3 | 2-(1H-pyrazol-1-yl-)pyridine-4-amine | tert-butyl((1S,2R)-2-aminocyclohexyl)carbamate | White solid |
| 256 | 3 | 1,6-dimethyl-1H-indol-4-amine (Example 163) | tert-butyl((2R,3R)-3-amino-1-methoxybutan-2-yl)carbamate (Example 167) | Light grayish brown solid |
| 257 | 3 | 2-methyl-7-phenyl-2H-indazol-5-amine (Example 168) | tert-butyl((3R,4R)-4-aminotetrahydro-2H-pyran-3-yl)carbamate | Light yellow solid |
| 258 | 3 | 2-methyl-7-phenyl-2H-indazol-5-amine (Example 168) | tert-butyl((2R,3R)-3-amino-1-methoxybutan-2-yl)carbamate (Example 167) | Light yellow solid |
| 259 | 3 | 8-methylquinolin-6-amine | tert-butyl((1S,2R)-2-aminocyclohexyl)carbamate | Light yellow solid |
| 260 | 3 | 2-(tert-butyl)-7-methyl-2H-indazol-5-amine (Example 164) | tert-butyl((1S,2R)-2-aminocyclohexyl)carbamate | Light yellow solid |
| 261 | 3 | 1-cyclobutyl-1H-indol-4-amine (Example 106) | (S)-tert-butyl(1-aminopropan-2-yl)carbamate | Light yellow solid |
| 262 | 3 | 1-cyclobutyl-1H-indol-4-amine (Example 106) | (R)-tert-butyl(1-amino-3-methoxypropan-2-yl)carbamate (WO2009/136995) | Light yellow solid |
| 263 | 3 | 1-(1-methyl-1H-pyrazol-4-yl)-1H-indol-4-amine (Example 169-2) | tert-butyl((3R,4R)-4-aminotetrahydro-2H-pyran-3-yl)carbamate | Light yellow solid |
| 264 | 3 | 1-methyl-1H-indol-4-amine | tert-butyl((2S,3R)-3-amino-5-methylhexan-2-yl)carbamate (WO2012/002577) | Light yellowish green solid |
| 265 | 3 | 2-(difluoromethyl)-4-methyl-2H-indazol-6-amine (Example 179) | tert-butyl((1S,2R)-2-aminocyclohexyl)carbamate | Light yellow solid |
| 266 | 3 | 1-(1-methyl-1H-pyrazol-3-yl)-1H-indol-4-amine (Example 38) | (R)-tert-butyl(1-amino-3-methoxypropan-2-yl)carbamate (WO2009/136995) | Light yellow solid |
| 267 | 3 | 1,6-dimethyl-1H-indol-4-amine (Example 163) | tert-butyl((3R,4R)-4-aminotetrahydro-2H-pyran-3-yl)carbamate | Light yellow solid |
| 268 | 3 | 1-cyclobutyl-1H-indol-4-amine (Example 106) | (R)-tert-butyl(1-amino-3-ethoxypropan-2-yl)carbamate (WO2009/136995) | Light yellow solid |
| 269 | 3 | 1,6-dimethyl-1H-indol-4-amine (Example 163) | tert-butyl((2R,3R)-3-amino-1-ethoxybutan-2-yl)carbamate (Example 166) | Light grayish brown solid |
| 270 | 3 | 2-isopropyl-7-methyl-2H-indazol-5-amine (Example 171-5) | tert-butyl((3R,4R)-4-aminotetrahydro-2H-pyran-3-yl)carbamate | Light grayish brown solid |
| 271 | 3 | 1-(1-methyl-1H-pyrazol-3-yl)-1H-indol-4-amine (Example 38) | tert-butyl(1-(aminomethyl)cyclopropyl)carbamate | Light yellow solid |

TABLE 6

| Example | Corresponding Example | Compound represented by general formula (III) B−NH−R₂ | Compound represented by general formula (VII) A−NH−R₁ | Form |
|---|---|---|---|---|
| 272 | 3 | 7-chloro-2-ethyl-2H-indazol-5-amine (Example 176) | tert-butyl((3R,4R)-4-aminotetrahydro-2H-pyran-3-yl)carbamate | Light yellow solid |
| 273 | 3 | 2-ethyl-1,4-dimethyl-1H-benzo[d]imidazol-6-amine | tert-butyl((1S,2R)-2-aminocyclohexyl)carbamate | Light yellow solid |
| 274 | 3 | (2-(tert-butyl)-7-methyl-2H-indazol-5-amine (Example 164) | tert-butyl((2R,3R)-3-amino-1-methoxybutan-2-yl)carbamate (Example 167) | Light yellow solid |
| 275 | 3 | 8-methylquinolin-6-amine | tert-butyl((2R,3R)-3-amino-1-methoxybutan-2-yl)carbamate (Example 167) | Light yellow solid |
| 276 | 1 | 1,4-dimethyl-1H-indazol-6-amine (Example 183) | tert-butyl((1S,2R)-2-aminocyclohexyl)carbamate | Yellow solid |
| 277 | 3 | 1-cyclobutyl-1H-indol-4-amine (Example 106) | tert-butyl((3R,4R)-4-aminotetrahydro-2H-pyran-3-yl)carbamate | Light yellow solid |
| 278 | 3 | 1-(2-methoxyethyl)-1H-indol-4-amine (Example 105) | tert-butyl(1-(aminomethyl)cyclopropyl)carbamate | Light yellow solid |
| 279 | 3 | 2-cyclobutyl-2H-indazol-5-amine (Example 152) | tert-butyl((2S,3R)-3-amino-5-methylhexan-2-yl)carbamate (WO2012/002577) | Light yellow solid |

TABLE 6-continued

| | | Compound represented by general formula (III) B—NH—R₂ | Compound represented by general formula (VII) A—NH—R₁ | |
|---|---|---|---|---|
| Example | Corresponding Example | | | Form |
| 280 | 3 | 1,4-dimethyl-1H-indazol-6-amine (Example 183) | tert-butyl((3R,4R)-4-aminotetrahydro-2H-pyran-3-yl)carbamate | Yellow solid |
| 281 | 3 | 2-(tert-butyl)-7-methyl-2H-indazol-5-amine (Example 164) | (S)-tert-butyl 3-aminopiperidine-1-carboxylate | Yellow solid |
| 282 | 3 | 8-methylquinolin-6-amine | tert-butyl((2R,3R)-3-amino-1-ethoxybutan-2-yl)carbamate (Example 166) | Light yellow solid |
| 283 | 3 | benzo[b]thiophene-5-amine | tert-butyl((2R,3R)-3-amino-1-methoxybutan-2-yl)carbamate (Example 167) | Light yellow solid |
| 284 | 3 | 1-isopropyl-7-methyl-1H-indazol-5-amine (Example 192) | tert-butyl((2R,3R)-3-amino-1-methoxybutan-2-yl)carbamate (Example 167) | Light reddish brown solid |
| 285 | 3 | benzo[b]thiophene-5-amine | tert-butyl((2S,3R)-3-amino-5-methylhexan-2-yl)carbamate (WO2012/002577) | Light yellow solid |
| 286 | 3 | 2-(tert-butyl)-7-chloro-2H-indazol-5-amine (Example 190) | tert-butyl((2R,3R)-3-amino-1-methoxybutan-2-yl)carbamate (Example 167) | Light yellow solid |
| 287 | 3 | 7-methyl-2-(1-methylcyclobutyl)-2H-indazol-5-amine (Example 177) | tert-butyl((3R,4R)-4-aminotetrahydro-2H-pyran-3-yl)carbamate | Light yellow solid |
| 288 | 3 | 1-cyclobutyl-1H-indol-4-amine (Example 106) | tert-butyl(1-(aminomethyl)cyclopropyl)carbamate | Light yellow solid |
| 289 | 3 | 2-isopropyl-7-methyl-2H-indazol-5-amine (Example 171-5) | tert-butyl((2R,3R)-3-amino-1-methoxybutan-2-yl)carbamate (Example 167) | Light grayish brown solid |
| 290 | 3 | 2-methylquinolin-6-amine | tert-butyl(1-(aminomethyl)cyclopropyl)carbamate | White solid |
| 291 | 3 | 2-isopropyl-7-methyl-2H-indazol-5-amine (Example 171-5) | tert-butyl((2R,3R)-3-amino-1-ethoxybutan-2-yl)carbamate (Example 166) | Light grayish brown solid |
| 292 | 1 | 2-(difluoromethyl)-4-methyl-2H-indazol-6-amine (Example 179) | tert-butyl((3R,4R)-4-aminotetrahydro-2H-pyran-3-yl)carbamate | Yellow solid |
| 293 | 3 | 2-ethyl-2H-indazol-6-amine (WO2007/088478) | tert-butyl((2S,3R)-3-amino-5-methylhexan-2-yl)carbamate (WO2012/002577) | Light yellow solid |
| 294 | 1 | 4-methyl-1H-indazol-6-amine | tert-butyl((1S,2R)-2-aminocyclohexyl)carbamate | Yellow solid |
| 295 | 3 | 1-methyl-1H-indol-4-amine | (R)-tert-butyl(1-amino-3-ethoxypropan-2-yl)carbamate (WO2009/136995) | Light yellow solid |

TABLE 7

| | | Compound represented by general formula (III) B—NH—R₂ | Compound represented by general formula (VII) A—NH—R₁ | |
|---|---|---|---|---|
| Example | Corresponding Example | | | Form |
| 296 | 3 | 4-phenylthiophene-2-amine hydrochloride | tert-butyl((3R,4R)-4-aminotetrahydro-2H-pyran-3-yl)carbamate | Yellow solid |
| 297 | 3 | 2-ethyl-7-methyl-2H-indazol-5-amine (Example 171) | tert-butyl((2R,3R)-3-amino-1-methoxybutan-2-yl)carbamate (Example 167) | Light yellow solid |
| 298 | 3 | 1-methyl-1H-indol-4-amine | tert-butyl(1-(aminomethyl)cyclopropyl)carbamate | Light yellow solid |
| 299 | 3 | 2,7-dimethyl-2H-indazol-5-amine (Example 176-2) | (S)-tert-butyl(2-amino-1-phenylethyl)carbamate | Light yellow solid |
| 300 | 3 | 7-methyl-2-(1-methylcyclobutyl)-2H-indazol-5-amine (Example 177) | tert-butyl((2R,3R)-3-amino-1-ethoxybutan-2-yl)carbamate (Example 166) | Light yellow solid |
| 301 | 3 | 2-cyclobutyl-2H-indazol-5-amine (Example 152) | tert-butyl((2S,3R)-3-amino-5-methylhexan-2-yl)carbamate (WO2012/002577) | Light yellow solid |
| 302 | 3 | 2-(difluoromethyl)-7-methyl-2H-indazol-5-amine (Example 165) | tert-butyl((2R,3R)-3-amino-1-methoxybutan-2-yl)carbamate (Example 167) | Light yellow solid |
| 303 | 3 | 1-ethyl-7-methyl-1H-indazol-5-amine (Example 181) | tert-butyl((2R,3R)-3-amino-1-ethoxybutan-2-yl)carbamate (Example 166) | Light yellow solid |
| 304 | 3 | 2-ethyl-7-methyl-2H-indazol-5-amine (Example 171) | tert-butyl((2R,3R)-3-amino-1-ethoxybutan-2-yl)carbamate (Example 166) | Light yellow solid |
| 305 | 3 | 2-ethyl-7-methyl-2H-indazol-5-amine (Example 171) | tert-butyl((2S,3R)-3-amino-5-methylhexan-2-yl)carbamate (WO2012/002577) | Light yellow solid |
| 306 | 3 | 1-isopropyl-7-methyl-1H-indazol-5-amine (Example 192) | tert-butyl((3R,4R)-4-aminotetrahydro-2H-pyran-3-yl)carbamate | Light reddish brown solid |

TABLE 7-continued

| Example | Corresponding Example | Compound represented by general formula (III) B−NH−R₂ | Compound represented by general formula (VII) A−NH−R₁ | Form |
|---|---|---|---|---|
| 307 | 3 | benzo[b]thiophene-5-amine | tert-butyl(1-(aminomethyl)cyclopropyl)carbamate | Light yellow solid |
| 308 | 3 | 2-isopropyl-7-methyl-2H-indazol-5-amine (Example 171-5) | (R)-tert-butyl(1-amino-3-ethoxypropan-2-yl)carbamate (WO2009/136995) | Light grayish brown solid |
| 309 | 3 | 2-isopropyl-7-methyl-2H-indazol-5-amine (Example 171-5) | (R)-tert-butyl(1-amino-3-methoxypropan-2-yl)carbamate (WO2009/136995) | Light grayish brown solid |
| 310 | 1 | 1-ethyl-4-methyl-1H-indazol-6-amine (Example 187) | tert-butyl((3R,4R)-4-aminotetrahydro-2H-pyran-3-yl)carbamate | Yellow solid |
| 311 | 3 | 1-ethyl-7-methyl-1H-indazol-5-amine (Example 181) | tert-butyl((2R,3R)-3-amino-1-methoxybutan-2-yl)carbamate (Example 167) | Light yellow solid |
| 312 | 3 | 1-ethyl-4-methyl-1H-indazol-6-amine (Example 187) | tert-butyl((2R,3R)-3-amino-1-methoxybutan-2-yl)carbamate (Example 167) | Light yellow solid |
| 313 | 3 | 2-(tert-butyl)-7-methyl-2H-indazol-5-amine (Example 164) | tert-butyl((2R,3R)-3-amino-1-ethoxybutan-2-yl)carbamate (Example 166) | Light yellow solid |
| 314 | 3 | 2-methyl-2H-indazol-5-amine | (S)-tert-butyl(2-amino-1-phenylethyl)carbamate | Light yellow solid |
| 315 | 3 | 1-methyl-1H-indol-4-amine | tert-butyl((2R,3R)-3-amino-1-methoxybutan-2-yl)carbamate (Example 167) | Yellow solid |
| 316 | 3 | 2-ethyl-2H-indazol-6-amine (WO2007/088478) | tert-butyl((1S,2R)-2-aminocycloheptyl)carbamate (Example 184) | Light yellow solid |
| 317 | 3 | 7-chloro-2-ethyl-2H-indazol-5-amine (Example 176) | tert-butyl((2R,3R)-3-amino-1-methoxybutan-2-yl)carbamate (Example 167) | Light yellow solid |
| 318 | 3 | 1-ethyl-7-methyl-1H-indazol-5-amine (Example 181) | tert-butyl((3R,4R)-4-aminotetrahydro-2H-pyran-3-yl)carbamate | Light yellow solid |
| 319 | 3 | 2-cyclobutyl-2H-indazol-5-amine (Example 152) | tert-butyl((2R,3R)-3-amino-1-methoxy-5-methylhexan-2-yl)carbamate (WO2012/002577) | Light yellow solid |

TABLE 8

| Example | Corresponding Example | Compound represented by general formula (III) B−NH−R₂ | Compound represented by general formula (VII) A−NH−R₁ | Form |
|---|---|---|---|---|
| 320 | 3 | 1-ethyl-7-methyl-1H-indazol-5-amine (Example 181) | tert-butyl((2R,3R)-1-amino-3-methoxybutan-2-yl)carbamate (WO2009/136995) | Light yellow solid |
| 321 | 3 | 2-ethyl-2H-indazol-6-amine (WO2007/088478) | (R)-tert-butyl(2-amino-4-methylpentyl)carbamate (WO2012/002577) | Light yellow solid |
| 322 | 3 | 1-isopropyl-7-methyl-1H-indazol-5-amine (Example 192) | (R)-tert-butyl(1-amino-3-methoxypropan-2-yl)carbamate (WO2009/136995) | Light reddish brown solid |
| 323 | 3 | 2-(tert-butyl)-7-methyl-2H-indazol-5-amine (Example 164) | (R)-tert-butyl(1-amino-3-ethoxypropan-2-yl)carbamate (WO2009/136995) | Light yellow solid |
| 324 | 1 | 1H-indazol-6-amine | tert-butyl((1S,2R)-2-aminocyclohexyl)carbamate | Yellow solid |
| 325 | 3 | benzo[b]thiophene-2-amine hydrochloride | (R)-tert-butyl(1-amino-3-methoxypropan-2-yl)carbamate (WO2009/136995) | Light brown solid |
| 326 | 3 | 7-methyl-2-(2,2,2-trifluoroethyl)-2H-indazol-5-amine (Example 186) | tert-butyl((3R,4R)-4-aminotetrahydro-2H-pyran-3-yl)carbamate | Light yellow solid |
| 327 | 1 | 2-methyl-2H-indazol-5-amine | tert-butyl((1S,2R)-2-aminocyclohexyl)carbamate | Yellow solid |
| 328 | 3 | 2-(difluoromethyl)-7-methyl-2H-indazol-5-amine (Example 165) | tert-butyl((3R,4R)-4-aminotetrahydro-2H-pyran-3-yl)carbamate | Light yellow solid |
| 329 | 3 | 2-chloroquinolin-6-amine | tert-butyl((1S,2R)-2-aminocyclohexyl)carbamate | White solid |
| 330 | 1 | 1-(difluoromethyl)-1H-indazol-5-amine (Example 180) | tert-butyl((3R,4R)-4-aminotetrahydro-2H-pyran-3-yl)carbamate | Light yellow solid |
| 331 | 3 | 7-methyl-2-(1-methylcyclobutyl)-2H-indazol-5-amine (Example 177) | tert-butyl((1S,2R)-2-aminocyclopentyl)carbamate | Light yellow solid |
| 332 | 3 | 2-methylquinolin-6-amine | (R)-tert-butyl(1-amino-3-methoxypropan-2-yl)carbamate (WO2009/136995) | White solid |
| 333 | 1 | thieno[2,3-b]pyridine-2-amine hydrochloride | tert-butyl((3R, 4R)-4-aminotetrahydro-2H-pyran-3-yl)carbamate | Yellow solid |

TABLE 8-continued

| Example | Corresponding Example | Compound represented by general formula (III) B—NH—R₂ | Compound represented by general formula (VII) A—NH—R₁ | Form |
|---|---|---|---|---|
| 334 | 3 | benzo[b]thiophene-5-amine | (R)-tert-butyl(2-amino-2-phenylethyl)carbamate | Light yellow solid |
| 335 | 3 | 2-cyclopentyl-2H-indazol-5-amine (Example 194-2) | tert-butyl((2R,3R)-3-amino-1-methoxybutan-2-yl)carbamate (Example 167) | Light yellow solid |
| 336 | 3 | 2-cyclobutyl-2H-indazol-5-amine (Example 152) | tert-butyl((2S,3S)-3-amino-5-methylhexan-2-yl)carbamate (WO2012/002577) | Yellow solid |
| 337 | 3 | 2-(tert-butyl)-7-methyl-2H-indazol-5-amine (Example 164) | (R)-tert-butyl(1-amino-3-methoxypropan-2-yl)carbamate (WO2009/136995) | Light yellow solid |
| 338 | 3 | 4-phenylthiophene-2-amine hydrochloride | (R)-tert-butyl(1-amino-3-methoxypropan-2-yl)carbamate (WO2009/136995) | Yellow solid |
| 339 | 3 | 1-methyl-4-(trifluoromethyl)-1H-indazol-6-amine (Example 198) | tert-butyl((1S,2R)-2-aminocyclohexyl)carbamate | White solid |
| 340 | 1 | benzo[b]thiophene-5-amine | tert-butyl((3R,4R)-4-aminotetrahydro-2H-pyran-3-yl)carbamate | Yellow solid |
| 341 | 3 | 1-isopropyl-7-methyl-1H-indazol-5-amine (Example 192) | tert-butyl((2R,3R)-3-amino-1-ethoxybutan-2-yl)carbamate (Example 166) | Light reddish brown solid |
| 342 | 3 | benzofuran-5-amine | tert-butyl((1S,2R)-2-aminocyclohexyl)carbamate | Light yellow solid |
| 343 | 3 | 1-ethyl-7-methyl-1H-indazol-5-amine (Example 181) | (R)-tert-butyl(1-amino-3-ethoxypropan-2-yl)carbamate (WO2009/136995) | Light yellow solid |

TABLE 9

| Example | Corresponding Example | Compound represented by general formula (III) B—NH—R₂ | Compound represented by general formula (VII) A—NH—R₁ | Form |
|---|---|---|---|---|
| 344 | 1 | 2,4-dimethyl-2H-indazol-6-amine (Example 183) | tert-butyl((3R,4R)-4-aminotetrahydro-2H-pyran-3-yl)carbamate | Yellow solid |
| 345 | 3 | 2-ethyl-7-methyl-2H-indazol-5-amine (Example 171) | (R)-tert-butyl(1-amino-3-ethoxypropan-2-yl)carbamate (WO2009/136995) | Light yellow solid |
| 346 | 3 | 1-methyl-1H-indazol-4-amine | tert-butyl((1S,2R)-2-aminocyclohexyl)carbamate | Light yellow solid |
| 347 | 3 | 1-isopropyl-7-methyl-1H-indazol-5-amine (Example 192) | (R)-tert-butyl(1-amino-3-ethoxypropan-2-yl)carbamate (WO2009/136995) | Light reddish brown solid |
| 348 | 1 | 1-(tetrahydro-2H-pyran-4-yl)-1H-indazol-5-amine (Example 199) | tert-butyl((1S,2R)-2-aminocyclohexyl)carbamate | Yellow solid |
| 349 | 3 | 2-(difluoromethyl)-7-methyl-2H-indazol-5-amine (Example 165) | (R)-tert-butyl(1-amino-3-ethoxypropan-2-yl)carbamate (WO2009/136995) | Light yellow solid |
| 350 | 1 | 2-cyclobutyl-2H-indazol-5-amine (Example 152) | tert-butyl((3R,4R)-4-aminotetrahydro-2H-pyran-3-yl)carbamate | Light yellow solid |
| 351 | 3 | 3-methylbenzo[b]thiophene-5-amine | tert-butyl((1S,2R)-2-aminocyclohexyl)carbamate | Light yellow solid |
| 352 | 3 | 1-ethyl-7-methyl-1H-indazol-5-amine (Example 181) | tert-butyl((2S,3S)-2-amino-3-methoxybutyl)carbamate (WO2012/002577) | Light grayish brown solid |
| 353 | 3 | 2-methylquinolin-6-amine | (R)-tert-butyl(1-amino-3-ethoxypropan-2-yl)carbamate (WO2009/136995) | White solid |
| 354 | 1 | benzo[b]thiophene-3-amine hydrochloride | tert-butyl((3R,4R)-4-aminotetrahydro-2H-pyran-3-yl)carbamate | Yellow solid |
| 355 | 16 | isoquinolin-4-amine hydrochloride | tert-butyl((1S,2R)-2-aminocyclohexyl)carbamate | Yellow solid |
| 356 | 1 | 1-cyclobutyl-4-methyl-1H-indazol-6-amine (Example 201) | tert-butyl((3R,4R)-4-aminotetrahydro-2H-pyran-3-yl)carbamate | Yellow solid |
| 357 | 1 | 2-cyclobutyl-4-methyl-2H-indazol-6-amine (Example 201) | tert-butyl((1S,2R)-2-aminocyclohexyl)carbamate | Yellow solid |
| 358 | 1 | 1H-indazol-5-amine | tert-butyl((1S,2R)-2-aminocyclohexyl)carbamate | Yellow solid |
| 359 | 1 | 7-methylbenzo[b]thiophene-5-amine | tert-butyl((3R,4R)-4-aminotetrahydro-2H-pyran-3-yl)carbamate | Yellow solid |

TABLE 9-continued

| Example | Corresponding Example | Compound represented by general formula (III) B–NH–R$_2$ | Compound represented by general formula (VII) A–NH–R$_1$ | Form |
|---|---|---|---|---|
| 360 | 3 | 7-methyl-1-(2,2,2-trifluoroethyl)-1H-indazol-5-amine (Example 198-2) | tert-butyl((3R,4R)-4-aminotetrahydro-2H-pyran-3-yl)carbamate | Light yellow solid |
| 361 | 3 | 1-ethyl-1H-benzo[d]imidazol-6-amine (Example 202) | tert-butyl((1S,2R)-2-aminocyclohexyl)carbamate | Light yellow solid |
| 362 | 3 | benzo[b]thiophene-5-amine | (R)-tert-butyl(2-amino-4-methylpentyl)carbamate (WO2012/002577) | Light yellow solid |
| 363 | 1 | 2-cyclobutyl-2H-indazol-6-amine (Example 152) | tert-butyl((1S,2R)-2-aminocyclohexyl)carbamate | Yellow solid |
| 364 | 3 | 2-ethyl-2H-indazol-6-amine (WO2007/088478) | tert-butyl((2R,3R)-3-amino-1-methoxy-5-methylhexan-2-yl)carbamate (WO2012/002577) | Light yellow solid |
| 365 | 3 | 1-(difluoromethyl)-1H-indazol-6-amine (Example 36) | tert-butyl((2R,3R)-3-amino-1-methoxy-5-methylhexan-2-yl)carbamate (WO2012/002577) | Yellow solid |
| 366 | 1 | 2-(difluoromethyl)-2H-indazol-6-amine (Example 36) | tert-butyl((3R,4R)-4-aminotetrahydro-2H-pyran-3-yl)carbamate | Yellow solid |
| 367 | 1 | benzo[b]thiophene-5-amine | tert-butyl((1R,2R)-2-aminocyclohexyl)carbamate | Yellow solid |

TABLE 10

| Example | Corresponding Example | Compound represented by general formula (III) B–NH–R$_2$ | Compound represented by general formula (VII) A–NH–R$_1$ | Form |
|---|---|---|---|---|
| 368 | 3 | 1-(tetrahydro-2H-pyran-4-yl)-1H-indazol-4-amine (Example 204-3) | (R)-tert-butyl(1-amino-3-ethoxypropan-2-yl)carbamate (WO2009/136995) | Light yellow solid |
| 369 | 1 | 4-methyl-1H-indazol-6-amine | tert-butyl((3R,4R)-4-aminotetrahydro-2H-pyran-3-yl)carbamate | Yellow solid |
| 370 | 3 | benzo[b]biophene-5-amine | tert-butyl((2S,3S)-3-amino-5-methylhexan-2-yl)carbamate (WO2012/002577) | Light yellow solid |
| 371 | 3 | 2-(difluoromethyl)-2H-indazol-6-amine (Example 36) | (S)-tert-butyl(2-amino-1-phenylethyl)carbamate | White solid |
| 372 | 1 | 2-ethyl-4-methyl-2H-indazol-6-amine (Example 191) | tert-butyl((3R,4R)-4-aminotetrahydro-2H-pyran-3-yl)carbamate | Yellow solid |
| 373 | 1 | 1-(tetrahydro-2H-pyran-4-yl)-1H-indazol-5-amine (Example 199) | tert-butyl((3R,4R)-4-aminotetrahydro-2H-pyran-3-yl)carbamate | Yellow solid |
| 374 | 1 | 2-(tetrahydro-2H-pyran-4-yl)-2H-indazol-5-amine (Example 199) | tert-butyl((3R,4R)-4-aminotetrahydro-2H-pyran-3-yl)carbamate | Yellow solid |
| 375 | 3 | 2-(tert-butyl)-7-methyl-2H-indazol-5-amine (Example 164) | azetidine hydrochloride | Light yellow solid |
| 376 | 3 | 2-(tert-butyl)-7-methyl-2H-indazol-5-amine (Example 164) | tert-butyl 3-aminoazetidine-1-carboxylate | Light yellow solid |
| 377 | 1 | 7-methyl-1H-indazol-6-amine | tert-butyl((1S,2R)-2-aminocyclohexyl)carbamate | Yellow solid |
| 378 | 1 | 1H-indazol-5-amine | tert-butyl((3R,4R)-4-aminotetrahydro-2H-pyran-3-yl)carbamate | Yellow solid |
| 379 | 12 | 6-aminoquinoline | (S)-tert-butyl 3-aminopiperidine-1-carboxylate | Yellow solid |
| 380 | 12 | 6-aminoquinoline | (R)-tert-butyl 3-aminopiperidine-1-carboxylate | Yellow solid |
| 381 | 1 | 2-(ethyl-d5)-2H-indazol-5-amine (Example 4) | tert-butyl(cis-4-aminocyclohexyl)carbamate | Yellow solid |
| 382 | 1 | 2-(ethyl-d5)-2H-indazol-5-amine (Example 4) | tert-butyl((1R,2R)-2-aminocyclohexyl)carbamate | Yellow solid |
| 383 | 1 | benzo[b]thiophene-5-amine | tert-butyl((1R,2R)-2-aminocyclohexyl)carbamate | Yellow solid |
| 384 | 1 | 2-(difluoromethyl)-2H-indazol-5-amine (Example 203) | tert-butyl((3R,4R)-4-aminotetrahydro-2H-pyran-3-yl)carbamate | Yellow solid |

TABLE 10-continued

| Example | Corresponding Example | Compound represented by general formula (III) B-NH-R₂ | Compound represented by general formula (VII) A-NH-R₁ | Form |
|---|---|---|---|---|
| 385 | 1 | 1-(difluoromethyl)-1H-indazol-6-amine (Example 36) | (S)-tert-butyl 3-aminopiperidine-1-carboxylate | Yellow solid |
| 386 | 1 | 1-(difluoromethyl)-1H-indazol-5-amine (Example 180) | (S)-tert-butyl 3-aminopiperidine-1-carboxylate | Yellow solid |
| 387 | 1 | 2-(difluoromethyl)-2H-indazol-5-amine (Example 203) | (S)-tert-butyl 3-aminopiperidine-1-carboxylate | Yellow solid |
| 388 | 1 | 2-(tetrahydro-2H-pyran-4-yl)-2H-indazol-5-amine (Example 199) | (3R,4S)-tetrahydrofuran-3,4-diamine | Yellow solid |
| 389 | 1 | 2-cyclobutyl-2H-indazol-5-amine (Example 152) | methylamine | Yellow solid |
| 390 | 1 | 2-cyclobutyl-2H-indazol-5-amine (Example 152) | 2-aminopropane-1,3-diol | Yellow solid |
| 391 | 1 | 2-cyclobutyl-2H-indazol-5-amine (Example 152) | 2-amino-1-phenylethanol | Yellow solid |

TABLE 11

| Example | Corresponding Example | Compound represented by general formula (III) B-NH-R₂ | Compound represented by general formula (VII) A-NH-R₁ | Form |
|---|---|---|---|---|
| 392 | 16 | isoquinolin-4-amine hydrochloride | tert-butyl((3R,4R)-4-aminotetrahydro-2H-pyran-3-yl)carbamate | Yellow solid |
| 393 | 3 | 1-cyclopropyl-1H-indol-4-amine (Example 15) | tert-butyl((2S,3S)-3-amino-5-methylhexan-2-yl)carbamate (WO2012/002577) | Yellow solid |
| 394 | 1 | 2-cyclobutyl-2H-indazol-5-amine (Example 152) | 1,3-diaminopropane-2-ol | Yellow solid |
| 395 | 1 | 2-cyclobutyl-2H-indazol-5-amine (Example 152) | 2,2-dimethylpropane-1,3-diamine | Yellow solid |
| 396 | 1 | 2-cyclobutyl-2H-indazol-5-amine (Example 152) | tert-butyl(2-aminoethyl)(2-hydroxyethyl)carbamate | Yellow solid |
| 397 | 3 | 2-cyclobutyl-2H-indazol-5-amine (Example 152) | 3,3-difluoropropane-1,2-diamine | |
| 398 | 1 | 2-(tert-butyl)-7-methyl-2H-indazol-5-amine (Example 164) | (R)-tert-butyl 3-aminopiperidine-1-carboxylate | Yellow solid |
| 399 | 1 | 6-fluoro-1H-indazol-5-amine | tert-butyl((1S,2R)-2-aminocyclohexyl)carbamate | Light yellow solid |
| 400 | 3 | 1-(difluoromethyl)-1H-indazol-6-amine (Example 36) | (R)-tert-butyl(1-amino-3-methoxypropan-2-yl)carbamate (WO2009/136995) | White solid |
| 401 | 3 | 4-phenylthiophene-2-amine hydrochloride | (S)-tert-butyl 3-aminopiperidine-1-carboxylate | Yellow solid |
| 402 | 3 | benzo[b]thiophene-5-amine | tert-butyl(1-(aminomethyl)cyclobutyl)carbamate (Example 193) | Light yellow solid |
| 403 | 3 | 2-(difluoromethyl)-2H-indazol-6-amine (Example 36) | tert-butyl(1-(aminomethyl)cyclopropyl)carbamate | White solid |
| 404 | 3 | benzo[b]thiophene-5-amine | (R)-2-aminobutan-1-ol | Light yellow solid |
| 405 | 3 | benzo[b]thiophene-5-amine | (3S,4S)-tert-butyl 3-amino-4-hydroxypyrrolidine-1-carboxylate | Light yellow solid |
| 406 | 3 | 1-methyl-1H-indol-4-amine | (R)-tert-butyl(2-amino-2-phenylethyl)carbamate | Light yellow solid |
| 407 | 3 | 1-((R)-tetrahydrofuran-3-yl)-1H-indol-4-amine (Example 170) | 40% methylamine methanol solution | Light yellow solid |
| 408 | 3 | 1-((R)-tetrahydrofuran-3-yl)-1H-indol-4-amine (Example 170) | dimethylamine hydrochloride | Light yellow solid |
| 409 | 3 | 2-(tert-butyl)-7-methyl-2H-indazol-5-amine (Example 164) | 40% methylamine methanol solution | Light yellow solid |
| 410 | 3 | 2-(tert-butyl)-7-methyl-2H-indazol-5-amine (Example 164) | dimethylamine hydrochloride | Light yellow solid |
| 411 | 3 | 2-(tert-butyl)-7-methyl-2H-indazol-5-amine (Example 164) | azetidin-3-ol | Light yellow solid |

TABLE 11-continued

| Example | Corresponding Example | Compound represented by general formula (III) B\NH\R₂ | Compound represented by general formula (VII) A\NH\R₁ | Form |
|---|---|---|---|---|
| 412 | 3 | 2-(tert-butyl)-7-methyl-2H-indazol-5-amine (Example 164) | tert-butyl azetidin-3-yl carbamate | Light yellow solid |
| 413 | 3 | 7-bromo-2-(tert-butyl)-2H-indazol-5-amine | tert-butyl((1S,2R)-2-aminocyclohexyl)carbamate | Light yellow solid |
| 414 | 3 | 2-cyclobutyl-2H-indazol-5-amine (Example 152) | 3-(aminomethyl)oxetane-3-amine | Yellow solid |

The chemical structural formula and physical properties of the compounds of Examples 1 to 414 are illustrated in Tables 12 to 94.

TABLE 12

| Example No. | Structural formula | Physical property |
|---|---|---|
| 1 | (structure) | ¹H-NMR (CD₃OD/CDCl₃(2/1)) δ: 8.84-8.72 (0H, m), 8.76 (1H, d, J = 2.7 Hz), 8.57-8.43 (1H, m), 8.41-8.26 (1H, m), 8.01 (1H, d, J = 9.0 Hz), 7.94 (1H, dd, J = 9.0, 2.4 Hz), 7.53 (1H, dd, J = 8.3, 4.4 Hz), 4.20-4.08 (1H, m), 3.26-3.22 (1H, m), 1.90-1.81 (1H, m), 1.78-1.62 (5H, m), 1.54-1.44 (2H, m). LC/MS (a) Rt = 0.63 min; m/z [M + H]⁺ 379. |
| 2 | (structure) | ¹H-NMR (CD₃OD/CDCl₃(1/1)) δ: 8.32-8.13 (1H, m), 7.65 (2H, d, J = 5.9 Hz), 7.53 (1H, d, J = 5.5 Hz), 7.49 (1H, d, J = 5.5 Hz), 7.32 (1H, t, J = 7.9 Hz), 4.28-3.90 (1H, m), 1.80-1.38 (8H, m). LC/MS (a) Rt = 0.82 min; m/z [M + H]⁺ 384. |
| 3 | (structure) | ¹H-NMR (DMSO-d₆) δ: 11.92 (1H, s), 8.37 (1H, s), 8.16-8.09 (1H, m), 7.37 (1H, d, J = 2.8 Hz), 7.26-7.10 (2H, m), 6.48 (1H, d, J = 2.8 Hz), 3.80 (3H, s), 1.83-1.45 (6H, m), 1.44-1.25 (2H, m). LC/MS (a) Rt = 0.79 min; m/z [M + H]⁺ 381. |

TABLE 12-continued

| Example No. | Structural formula | Physical property |
|---|---|---|
| 4 | (structure) | LC/MS (a) Rt = 0.69 min; m/z [M + H]+ 401. |
| 5 | (structure) | LC/MS (a) Rt = 0.73 min; m/z [M+ H]+ 401. |

TABLE 13

| Example No. | Structural formula | Physical property |
|---|---|---|
| 6 | (structure) | LC/MS (a) Rt = 0.75 min; m/z [M + H]+ 429. |

TABLE 13-continued

| Example No. | Structural formula | Physical property |
|---|---|---|
| 7 | | LC/MS (a) Rt = 0.71 min; m/z [M + H]+ 387. |
| 8 | | ¹H-NMR (CD₃OD/CDCl₃(3/1)) δ: 8.49-8.04 (1H, m), 7.72 (1H, d, J = 8.8 Hz), 7.61 (1H, d, J = 5.5 Hz), 7.53 (1H, s), 7.37 (1H, t, J = 7.9 Hz), 4.37-3.93 (2H, m), 3.87-3.76 (1H, m), 3.62-3.39 (2H, m), 3.22-3.03 (1H, m), 2.02-1.87 (1H, m), 1.86-1.69 (1H, m). LC/MS (a) Rt = 0.76 min; m/z [M + H]+ 386. |
| 9 | | LC/MS (a) Rt = 0.83 min; m/z [M + H]+ 400. |
| 10 | | LC/MS (a) Rt = 0.96 min; m/z [M + H]+ 407. |

TABLE 14

| Example No. | Structural formula | Physical property |
|---|---|---|
| 11 | | LC/MS (a) Rt = 0.76 min; m/z [M + H]+ 422. |
| 12 | | LC/MS (a) Rt = 0.63 min; m/z [M + H]+ 395. |
| 13 | | LC/MS (a) Rt = 0.73 min; m/z [M + H]+ 462. |
| 14 | | 1H-NMR (DMSO-d6) δ: 8.40 (1H, s), 7.97-7.87 (2H, m), 7.76 (1H, s), 7.62 (1H, s), 7.50 (1H, d, J = 3.9 Hz), 7.40 (1H, d, J = 1.2 Hz), 4.01 (1H, s), 3.18 (1H, s), 2.51 (3H, s), 1.80-1.53 (6H, m), 1.43-1.30 (2H, m).<br>LC/MS (a) Rt = 0.86 min; m/z [M + H]+ 458. |

TABLE 14-continued

| Example No. | Structural formula | Physical property |
|---|---|---|
| 15 | | LC/MS (a) Rt = 0.77 min; m/z [M + H]+ 453. |

TABLE 15

| Example No. | Structural formula | Physical property |
|---|---|---|
| 16 | | $^1$H-NMR (CD$_3$OD/CDCl$_3$(3/1)) δ: 8.98-8.66 (1H, m), 8.11 (1H, br s), 7.83 (1H, br s), 4.31-3.99 (1H, m), 3.17 (1H, br s), 2.05-1.93 (1H, m), 1.88-1.44 (8H, m), 1.16-1.03 (2H, m), 0.86-0.76 (2H, m). LC/MS (a) Rt = 0.79 min; m/z [M + H]+ 381. |
| 17 | | $^1$H-NMR (CD$_3$OD) δ: 8.12-8.00 (1H, m), 7.27 (1H, d, J = 3.2 Hz), 7.23 (1H, d, J = 8.4 Hz), 7.17 (1H, dd, J = 8.4, 7.6 Hz), 6.58 (1H, d, J = 3.2 Hz), 4.23 (2H, q, J = 7.2 Hz), 1.85-1.59 (6H, m), 1.54-1.41 (5H, m). LC/MS (a) Rt = 0.83 min; m/z [M + H]+ 395. |
| 18 | | LC/MS (a) Rt = 0.82 min; m/z [M + H]+ 411. |

TABLE 15-continued

| Example No. | Structural formula | Physical property |
|---|---|---|
| 19 | | ¹H-NMR (DMSO-d₆) δ: 11.69 (1H, s), 8.85 (1H, s), 8.69-8.56 (2H, m), 8.40 (2H, s), 8.00 (1H, d, J = 8.3 Hz), 7.83-7.72 (1H, m), 3.76 (1H, s), 3.09 (1H, s), 2.80 (3H, d, J = 4.9 Hz), 1.77-1.49 (6H, m), 1.38-1.26 (2H, m).<br>LC/MS (a) Rt = 0.67 min; m/z [M + H]⁺ 385. |
| 20 | | LC/MS (a) Rt = 0.70 min; m/z [M + H]⁺ 462. |

TABLE 16

| Example No. | Structural formula | Physical property |
|---|---|---|
| 21 | | ¹H-NMR (DMSO-d₆) δ: 12.18 (1H, s), 8.45 (1H, s), 8.26 (1H, s), 7.85-7.71 (3H, m), 7.56 (1H, s), 7.43 (1H, d, J = 5.6 Hz), 3.80 (1H, s), 3.13 (1H, s), 2.46 (3H, s), 1.88-1.48 (6H, m), 1.38-1.24 (2H, m).<br>LC/MS (a) Rt = 0.88 min; m/z [M + H]⁺ 398. |
| 22 | | LC/MS (a) Rt = 1.04 min; m/z [M + H]⁺ 456. |

TABLE 16-continued

| Example No. | Structural formula | Physical property |
|---|---|---|
| 23 | | LC/MS (a) Rt = 0.84 min; m/z [M + H]⁺ 440. |
| 24 | | ¹H-NMR (CD₃OD/CDCl₃(1/1)) δ: 8.67-8.41 (1H, m), 8.47 (1H, s), 7.73 (1H, d, J = 9.2 Hz), 7.62 (1H, t, J = 59.8 Hz), 7.18-7.07 (1H, m), 4.36-4.13 (1H, m), 3.29-3.22 (1H, m), 1.93-1.45 (8H, m). LC/MS (a) Rt = 0.87 min; m/z [M + H]⁺ 418. |
| 25 | | ¹H-NMR (CD₃OD/CDCl₃(1/1)) δ: 8.09 (1H, d, J = 7.7 Hz), 7.69 (1H, d, J = 8.4 Hz), 7.60 (1H, d, J = 2.2 Hz), 7.54 (1H, d, J = 3.3 Hz), 7.28 (1H, t, J = 8.1 Hz), 6.81 (1H, d, J = 2.9 Hz), 6.43 (1H, d, J = 2.6 Hz), 4.19-4.04 (1H, m), 3.97 (3H, s), 3.26-3.20 (1H, m), 1.60 (8H, d, J = 76.6 Hz). LC/MS (a) Rt = 0.79 min; m/z [M+H]⁺ 447. |

TABLE 17

| Example No. | Structural formula | Physical property |
|---|---|---|
| 26 | | $^1$H-NMR (CD$_3$OD) δ: 8.36-8.05 (1H, m), 7.66 (1H, t, J = 59.9 Hz), 7.50 (1H, d, J = 3.7 Hz), 7.45 (1H, d, J = 8.1 Hz), 7.30 (1H, t, J = 8.1 Hz), 6.77 (1H, d, J = 3.7 Hz), 4.47-3.99 (1H, m), 3.37-3.32 (1H, m), 1.91-1.59 (6H, m), 1.59-1.44 (2H, m).<br>LC/MS (a) Rt = 0.94 min; m/z [M + H]$^+$ 417. |
| 27 | | LC/MS (a) Rt = 0.82 min; m/z [M + H]$^+$ 422. |
| 28 | | LC/MS (a) Rt = 0.74 min; m/z [M + H]$^+$ 396. |
| 29 | | LC/MS (a) Rt = 0.72 min; m/z [M + H]$^+$ 469. |

TABLE 17-continued

| Example No. | Structural formula | Physical property |
|---|---|---|
| 30 | | LC/MS (a) Rt = 0.83 min; m/z [M + H]+ 395. |

TABLE 18

| Example No. | Structural formula | Physical property |
|---|---|---|
| 31 | | LC/MS (a) Rt = 0.80 min; m/z[M + H]+408. |
| 32 | | LC/MS (a) Rt = 0.97 min; m/z[M + H]+409. |
| 33 | | LC/MS (a) Rt = 0.99 min; m/z[M + H]+421. |

TABLE 18-continued

| Example No. | Structural formula | Physical property |
|---|---|---|
| 34 | 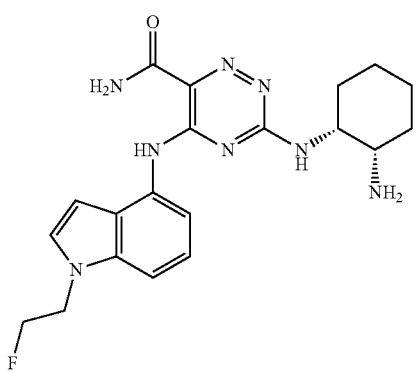 [SMILES: NC(=O)c1nnc(N[C@@H]2CCCC[C@@H]2N)nc1Nc1cccc2c1ccn2CCF] | ¹H-NMR (CD₃OD/CDCl₃(2/1)) δ: 8.06 (1H, d = 7.3 Hz), 7.52 (1H, d, J = 3.3 Hz), 7.33 (1H, d, J = 8.1 Hz), 7.26 (1H, t, J = 7.9 Hz), 6.77 (1H, d, J = 2.6 Hz), 5.66 (1H, tt, J = 7.3, 6.8 Hz), 5.23 (2H, t, J = 7.3 Hz), 5.12 (2H, t, J = 6.8 Hz), 4.23-3.98 (1H, m), 3.30-3.20 (1H, m), 1.86-1.35 (8H, m). LC/MS (a) Rt = 0.75 min; m/z[M + H]⁺423. |
| 35 |  | ¹H-NMR (CD₃OD/CDCl₃(5/1)) δ: 8.06 (1H, s), 7.28 (1H, d, J = 3.2 Hz), 7.27-7.17 (3H, m), 6.64 (1H, d, J = 3.2 Hz), 4.78 (1H, t, J = 4.8 Hz), 4.66 (1H, t, J = 4.8 Hz), 4.53 (1H, t, J = 4.8 Hz), 4.46 (1H, t, J = 4.6 Hz), 4.33-4.05 (1H, m), 3.27-3.22 (1H, m), 1.87-1.44 (8H, m). LC/MS (a) Rt = 0.89 min; m/z[M + H]⁺413. |

TABLE 19

| Example No. | Structural formula | Physical property |
|---|---|---|
| 36 |  | ¹H-NMR (CD₃OD/CDCl₃(1/1)) δ: 8.57 (1H, d, J = 3.7 Hz), 8.13 (1H, d, J = 7.7 Hz), 7.99-7.93 (2H, m), 7.78 (1H, d, J = 3.3 Hz), 7.63 (1H, d, J = 8.4 Hz), 7.35-7.28 (2H, m), 6.90 (1H, d, J = 3.3 Hz), 4.35-4.04 (1H, m), 3.28-3.22 (1H, m), 1.85-1.43 (8H, m). LC/MS (a) Rt = 0.85 min; m/z [M + H]⁺ 444. |

TABLE 19-continued

| Example No. | Structural formula | Physical property |
| --- | --- | --- |
| 37 | | $^1$H-NMR (CD$_3$OD/CDCl$_3$(5/1)) δ: 8.09 (1H, d, J = 7.7 Hz), 7.59-7.52 (4H, m), 7.44-7.36 (3H, m), 7.24 (1H, t, J = 8.1 Hz), 6.85 (1H, d, J = 2.9 Hz), 4.35-4.06 (1H, m), 3.27-3.21 (1H, m), 1.91-1.45 (8H, m). LC/MS (a) Rt = 0.89 min; m/z [M + H]$^+$ 443. |
| 38 | | $^1$H-NMR (CD$_3$OD/CDCl$_3$(1/1)) δ: 8.65 (1H, s), 8.21-7.97 (1H, m), 7.68 (1H, t, J = 59.9 Hz), 7.48 (1H, d, J = 9.0 Hz), 7.41 (1H, t, J = 7.9 Hz), 4.35-3.99 (1H, m), 3.27-3.20 (1H, m), 1.84-1.43 (8H, m). LC/MS (a) Rt = 0.77 min; m/z [M + H]$^+$ 418. |
| 39 | | $^1$H-NMR (CD$_3$OD/CDCl$_3$(1/1)) δ: 8.02 (1H, d, J = 7.3 Hz), 7.28 (1H, d, J = 2.9 Hz), 7.26 (1H, d, J = 8.6 Hz), 7.20 (1H, dd, J = 8.6, 7.3 Hz), 6.66 (1H, d, J = 2.9 Hz), 4.16-4.06 (1H, m), 4.13 (2H, s), 3.25-3.19 (1H, m), 1.81-1.45 (8H, m), 1.24 (6H, s). LC/MS (a) Rt = 0.76 min; m/z [M + H]$^+$ 439. |
| 40 | | $^1$H-NMR (CD$_3$OD/CDCl$_3$(1/1)) δ: 8.10-8.05 (1H, m), 7.28 (2H, d, J = 4.4 Hz), 7.25 (1H, d, J = 3.3 Hz), 6.73 (1H, d, J = 3.3 Hz), 6.11 (1H, tt, J = 55.2, 3.8 Hz), 4.57 (2H, td, J = 14.6, 3.8 Hz), 4.35-4.06 (1H, m), 3.28-3.23 (1H, m), 1.82-1.47 (8H, m). LC/MS (a) Rt = 0.79 min; m/z [M + H]$^+$ 431. |

TABLE 20

| Example No. | Structural formula | Physical property |
|---|---|---|
| 41 | | $^1$H-NMR (CD$_3$OD/CDCl$_3$(1/1)) δ: 8.10 (1H, s), 7.46 (2H, d, J = 3.7 Hz), 7.27 (1H, t, J = 8.1 Hz), 6.75 (1H, d, J = 3.7 Hz), 4.24 (2H, t, J = 11.0 Hz), 4.27-3.98 (1H, m), 3.24-3.18 (1H, m), 1.84-1.41 (8H, m). LC/MS (a) Rt = 0.78 min; m/z [M + H]$^+$ 447. |
| 42 | | $^1$H-NMR (CD$_3$OD/CDCl$_3$=(1/1)) δ: 8.03 (1H, d, J = 7.3 Hz), 7.26-7.18 (2H, m), 7.15 (1H, d, J = 3.3 Hz), 6.62 (1H, d, J = 3.3 Hz), 4.29-4.07 (1H, m), 3.25-3.20 (1H, m), 1.83-1.44 (8H, m). LC/MS (a) Rt = 0.77 min; m/z [M + H]$^+$ 384. |
| 43 | | $^1$H-NMR (DMSO-d$_6$) δ: 12.03 (1H, s), 9.30 (1H, s), 9.04 (1H, s), 8.46 (1H, s), 8.19 (1H, d, J = 5.4 Hz), 7.91-7.77 (2H, m), 7.50 (1H, s), 3.71 (1H, s), 3.09 (1H, s), 1.78-1.42 (6H, m), 1.37-1.26 (2H, m). LC/MS (a) Rt = 0.62 min; m/z [M + H]$^+$ 385. |
| 44 | | $^1$H-NMR (CD$_3$OD/CDCl$_3$ = (1/1)) δ: 8.02 (1H, dd, J = 5.3, 3.5 Hz), 7.22-7.19 (3H, m), 6.63 (1H, d, J = 2.9 Hz), 4.20-4.06 (1H, m), 4.15 (2H, t, J = 7.0 Hz), 3.25-3.20 (1H, m), 1.94-1.85 (2H, m), 1.80-1.45 (8H, m), 0.94 (3H, t, J = 7.3 Hz). LC/MS (a) Rt = 0.88 min; m/z [M + H]$^+$ 409. |

TABLE 20-continued

| Example No. | Structural formula | Physical property |
| --- | --- | --- |
| 45 | (structure) | $^1$H-NMR (CD$_3$OD/CDCl$_3$ = (1/1)) δ: 8.01 (1H, d, J = 7.3 Hz), 7.32 (1H, d, J = 3.3 Hz), 7.27-7.18 (2H, m), 6.66 (1H, d, J = 2.6 Hz), 4.74 (1H, septet, J = 6.6 Hz), 4.33-4.05 (1H, m), 3.26-3.17 (1H, m), 1.82-1.45 (8H, m), 1.56 (6H, d, J = 6.6 Hz). LC/MS (a) Rt = 0.84 min; m/z [M + H]$^+$ 409. |

TABLE 21

| Example No. | Structural formula | Physical property |
| --- | --- | --- |
| 46 | (structure) | $^1$H-NMR (CD$_3$OD/CDCl$_3$(1/1)) δ: 8.03 (1H, dd, J = 5.9, 2.6 Hz), 7.25-7.22 (3H, m), 6.64 (1H, d, J = 2.9 Hz), 4.35 (2H, t, J = 5.5 Hz), 4.19-4.06 (1H, m), 3.76 (2H, t, J = 5.3 Hz), 3.32 (3H, s), 3.26-3.20 (1H, m), 1.84-1.44 (8H, m). LC/MS (a) Rt = 0.78 min; m/z [M + H]$^+$ 425. |
| 47 | (structure) | $^1$H-NMR (CD$_3$OD/CDCl$_3$(1/1)) δ: 8.01 (1H, d, J = 7.0 Hz), 7.36 (1H, d, J = 3.3 Hz), 7.24-7.17 (2H, m), 6.66 (1H, d, J = 2.6 Hz), 4.97-4.86 (1H, m), 4.16-4.05 (1H, m), 3.25-3.19 (1H, m), 2.67-2.57 (2H, m), 2.57-2.44 (2H, m), 2.02-1.93 (2H, m), 1.81-1.44 (8H, m). LC/MS (a) Rt = 0.89 min; m/z [M + H]$^+$ 421. |

TABLE 21-continued

| Example No. | Structural formula | Physical property |
|---|---|---|
| 48 | | ¹H-NMR (DMSO-d₆) δ: 12.31 (1H, s), 8.43 (1H, s), 7.90 (1H, s), 7.78 (1H, s), 7.67 (1H, d, J = 8.3 Hz), 7.16 (1H, s), 6.88 (1H, dd, J = 8.5, 1.5 Hz), 4.04 (1H, s), 3.83 (3H, s), 3.21 (1H, s), 2.34 (3H, s), 1.82-1.54 (6H, m), 1.48-1.34 (2H, m). LC/MS (a) Rt = 0.89 min; m/z [M + H]⁺ 428. |
| 49 | | ¹H-NMR (DMSO-d₆) δ: 12.64 (1H, s), 8.77-8.59 (1H, m), 8.37 (1H, s), 8.21-7.98 (3H, m), 7.75 (2H, d, J = 7.6 Hz), 7.63 (1H, s), 7.53-7.45 (2H, m), 7.36 (1H, t, J = 7.2 Hz), 6.52 (1H, d, J = 2.9 Hz), 4.30 (1H, s), 3.88 (3H, s), 3.46 (1H, s), 1.93-1.82 (1H, m), 1.76-1.44 (5H, m), 1.40-1.16 (2H, m). LC/MS (a) Rt = 0.94 min; m/z [M + H]⁺ 457. |
| 50 | | ¹H-NMR (CD₃OD/CDCl₃(1/1)) δ: 8.03 (1H, s), 7.64 (1H, d, J = 8.4 Hz), 7.24 (1H, d, J = 8.4 Hz), 4.37 (2H, q, J = 7.1 Hz), 4.25-4.10 (1H, m), 3.17 (1H, br s), 2.56 (3H, s), 1.91-1.61 (6H,m), 1.55-1.48 (2H, m), 1.49 (3H, t, J = 7.1 Hz). LC/MS (a) Rt = 0.77 min; m/z [M + H]⁺ 410. |

TABLE 22

| Example No. | Structural formula | Physical property |
|---|---|---|
| 51 | 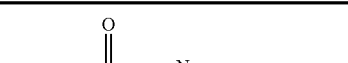 | ¹H-NMR (CD₃OD/CDCl₃(1/1)) δ: 7.56-7.37 (1H, m), 7.24-7.15 (2H, m), 6.86 (1H, s), 3.90-3.80 (1H, m), 3.76 (3H, br s), 3.15-3.00 (1H, m), 2.42 (3H, s), 1.76-1.35 (8H, m). LC/MS (a) Rt = 0.79 min; m/z [M + H]⁺ 395. |

TABLE 22-continued

| Example No. | Structural formula | Physical property |
|---|---|---|
| 52 | | $^1$H-NMR (CD$_3$OD/CDCl$_3$(1/1)) δ: 8.13 (1H, br s), 8.00-7.96 (1H, m), 7.74-7.69 (1H, m), 7.32-7.24 (1H, m), 4.95-4.79 (1H, m), 4.24-4.10 (1H, m), 3.23-3.10 (2H, m), 1.92-1.37 (14H, m).<br>LC/MS (a) Rt = 0.80 min; m/z [M + H]$^+$ 410. |
| 53 | | $^1$H-NMR (CD$_3$OD/CDCl$_3$(1/1)) δ: 8.59-8.18 (1H, m), 7.67 (1H, d, J = 8.8 Hz), 7.60-7.54 (1H, m), 7.23-6.98 (1H, m), 4.87-4.74 (1H, m), 4.44-4.14 (1H, m), 3.24-3.16 (1H, m), 1.87-1.45 (8H, m), 1.67 (6H, d, J = 6.6 Hz).<br>LC/MS (a) Rt = 0.76 min; m/z [M + H]$^+$ 410. |
| 54 | | $^1$H-NMR (CD$_3$OD/CDCl$_3$(1/1)) δ: 8.28 (1H, s), 8.04 (1H, s), 7.74 (1H, d, J = 8.4 Hz), 7.28 (1H, d, J = 8.8 Hz), 6.22 (1H, t, J = 55.4 Hz), 4.85-4.73 (2H, m), 4.31-4.22 (1H, m), 3.20-3.08 (1H, m), 1.97-1.43 (8H, m).<br>LC/MS (a) Rt = 0.77 min; m/z [M + H]$^+$ 432. |
| 55 | | $^1$H-NMR (CD$_3$OD/CDCl$_3$(2/1)) δ: 8.18 (1H, s), 8.01 (1H, s), 7.72 (1H, d, J = 8.8 Hz), 7.27 (1H, d, J = 8.8 Hz), 4.92 (1H, t, J = 4.8 Hz), 4.81 (1H, t, J = 4.8 Hz), 4.73 (1H, br s), 4.66 (1H, br s), 4.30-4.17 (1H, m), 3.22-3.09 (1H, m), 1.94-1.41 (8H, m).<br>LC/MS (a) Rt = 0.73 min; m/z [M + H]$^+$ 414. |

TABLE 23

| Example No. | Structural formula | Physical property |
|---|---|---|
| 56 | (structure) | $^1$H-NMR (CD$_3$OD/CDCl$_3$(2/1)) δ: 8.22-8.08 (1H, m), 7.54-7.50 (1H, m), 7.40 (1H, d, J = 8.8 Hz), 4.40-4.34 (2H, m), 4.13-3.94 (1H, m), 3.22-3.11 (1H, m), 2.58 (3H, s), 1.86-1.56 (6H, m), 1.53-1.42 (2H, m), 1.49 (3H, t, J = 7.1 Hz).<br>LC/MS (a) Rt = 0.75 min; m/z [M + H]$^+$ 410. |
| 57 | (structure) | $^1$H-NMR (CD$_3$OD/CDCl$_3$(1/1)) δ: 8.55-8.24 (2H, m), 7.71 (1H, d, J = 8.8 Hz), 7.64 (1H, t, J = 60.0 Hz), 7.45 (1H, br s), 4.34-4.00 (1H, m), 3.27-3.22 (1H, m), 1.83-1.44 (8H, m).<br>LC/MS (a) Rt = 0.75 min; m/z [M + H]$^+$ 418. |
| 58 | (structure) | 1H-NMR (CD$_3$OD/CDCl$_3$(1/1)) δ: 9.14-8.55 (1H, m), 8.42 (1H, d, J = 5.5 Hz), 7.99 (2H, s), 7.35 (1H, s), 4.43-4.34 (1H, m), 3.32-3.21 (1H, m), 1.88-1.50 (8H, m).<br>LC/MS (a) Rt = 0.69 min; m/z [M + H]$^+$ 396. |
| 59 | (structure) | $^1$H-NMR (CD$_3$OD/CDCl$_3$(1/1)) δ: 8.18 (1H, s), 7.62 (1H, t, J = 58.7 Hz), 7.61 (1H, d, J = 9.5 Hz), 7.43 (1H, dd, J = 9.5, 1.8 Hz), 4.30-4.04 (1H, m), 3.25-3.15 (1H, m), 2.83 (3H, s), 1.90-1.42 (8H, m).<br>LC/MS (a) Rt = 0.76 min; m/z [M + H]$^+$ 432. |

TABLE 23-continued

| Example No. | Structural formula | Physical property |
|---|---|---|
| 60 | | ¹H-NMR (CD₃OD/CDCl₃(1/1)) δ: 8.00-7.90 (1H, m), 7.08 (1H, d, J = 3.2 Hz), 7.05-7.00 (1H, m), 6.61-6.53 (1H, m), 4.35-4.08 (1H, m), 3.82 (3H, s), 3.30-3.20 (1H, m), 2.56 (3H, s), 1.85-1.45 (8H, m). LC/MS (b) Rt = 1.14 min; m/z [M + H]⁺ 395. |

TABLE 24

| Example No. | Structural formula | Physical property |
|---|---|---|
| 61 | | ¹H-NMR (CD₃OD/CDCl₃(1/1)) δ: 8.20-7.84 (1H, m), 8.11 (1H, s), 7.23-7.03 (1H, m), 4.30-4.07 (1H, m), 4.01 (1H, d, J = 11.0 Hz), 3.87 (1H, d, J = 12.1 Hz), 3.64 (1H, q, J = 7.0 Hz), 3.58-3.47 (1H, m), 3.16 (1H, s), 2.63 (3H, s), 1.98-1.88 (1H, m), 1.87-1.81 (1H, m), 1.77 (9H, s). LC/MS (a) Rt = 0.78 min; m/z [M + H]⁺ 440. |
| 62 | | ¹H-NMR (CD₃OD/CDCl₃(1/1)) δ: 8.49-8.06 (1H, m), 8.41 (1H, s), 7.62 (1H, t, J = 60.1 Hz), 7.28-7.03 (1H, m), 4.34-4.00 (1H, m), 3.27-3.23 (1H, m), 2.62 (3H, s), 1.87-1.43 (8H, m). LC/MS (a) Rt = 0.77 min; m/z[M + H]⁺ 432. |

TABLE 24-continued
| Example No. | Structural formula | Physical property |
|---|---|---|
| 63 | 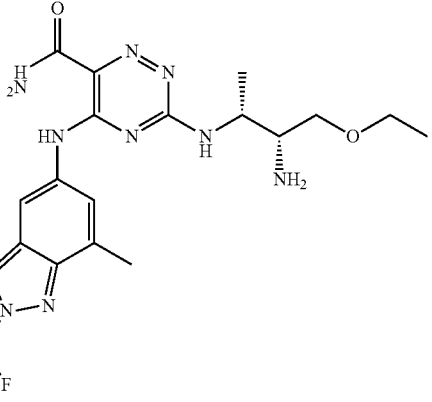 | ¹H-NMR (CD₃OD/CDCl₃(1/1)) δ: 8.54-8.40 (1H, m), 8.35-8.18 (1H, m), 7.61 (1H, t, J = 60.1 Hz), 7.22-7.11 (1H, m), 4.36-4.14 (1H, m), 3.61-3.47 (4H, m), 3.16-3.10 (1H, m), 2.61 (3H, s), 1.32 (3H, d, J = 6.6 Hz), 1.28-1.15 (3H, m). LC/MS (a) Rt = 0.77 min; m/z [M + H]⁺ 450. |
| 64 | 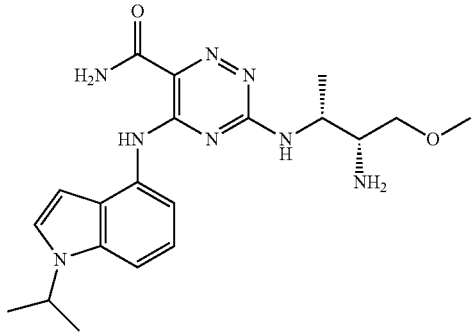 [SMILES: COC[C@H](N)[C@@H](C)Nc1nnc(C(N)=O)c(Nc2cccc3c2ccn3C(C)C)n1] | ¹H-NMR (CD₃OD/CDCl₃(1/1)) δ: 8.05 (1H, d, J = 7.0 Hz), 7.31 (1H, d, J = 3.3 Hz), 7.27-7.20 (2H, m), 6.68 (1H, s), 4.78-4.71 (1H, m), 4.31-4.18 (1H, m), 3.54-3.48 (2H, m), 3.40 (3H, s), 3.17-3.13 (1H, m), 1.56 (6H, d, J = 6.6 Hz), 1.30 (3H, d, J = 6.6 Hz). LC/MS (a) Rt = 0.83 min; m/z [M + H]⁺ 413. |
| 65 | 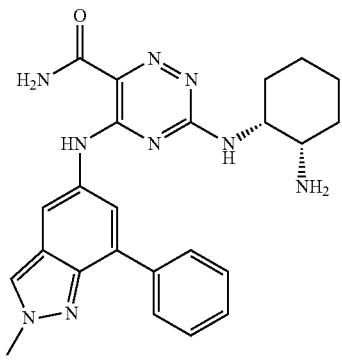 [SMILES: Cn1cc2cc(Nc3nc(N[C@@H]4CCCC[C@@H]4N)nnc3C(N)=O)cc(-c3ccccc3)c2n1] | ¹H-NMR (CD₃OD/CDCl₃(1/1)) δ: 8.10 (1H, s), 8.05-7.61 (1H, m), 7.92 (2H, d, J = 7.7 Hz), 7.50 (2H, t, J = 7.5 Hz), 7.41 (1H, t, J = 7.3 Hz), 4.27-3.95 (1H, m), 4.24 (3H, s), 3.21-3.14 (1H, m), 1.78-1.25 (8H, m). LC/MS (a) Rt = 0.81 min; m/z [M + H]⁺ 458. |

TABLE 25

| Example No. | Structural formula | Physical property |
|---|---|---|
| 66 | | $^1$H-NMR (CD$_3$OD/CDCl$_3$(1/1)) δ: 9.30 (1H, d, J = 2.2 Hz), 8.56-7.76 (1H, m), 8.25 (1H, s), 7.88-7.69 (2H, m), 6.57 (1H, s), 4.35-4.19 (1H, m), 3.24-3.08 (1H, m), 1.88-1.37 (8H, m), 1.81 (9H, s).<br>LC/MS (a) Rt = 0.92 min; m/z [M + H]$^+$ 490. |
| 67 | | $^1$H-NMR (DMSO-d$_6$) δ: 12.03-11.90 (1H, m), 8.44-8.38 (1H, m), 8.23 (1H, s), 8.17 (1H, d, J = 6.6 Hz), 7.82 (1H, s), 7.78-7.71 (1H, m), 7.58 (1H, d, J = 2.7 Hz), 7.28-7.18 (2H, m), 6.70-6.64 (1H, m), 4.16-3.75 (1H, m), 3.92 (3H, s), 3.18-3.11 (1H, m), 1.81-1.48 (8H, m), 1.39-1.27 (2H, m).<br>LC/MS (b) Rt = 1.03 min; m/z [M + H]$^+$ 447. |
| 68 | | $^1$H-NMR (CD$_3$OD/CDCl$_3$(1/1)) δ: 8.12-8.05 (1H, m), 7.80-7.73 (1H, m), 7.28-7.20 (2H, m), 6.74-6.69 (1H, m), 5.14-5.06 (1H, m), 4.21-3.92 (5H, m), 3.26-3.20 (1H, m), 2.58-2.47 (1H, m), 2.28-2.16 (1H, m), 1.88-1.27 (8H, m).<br>LC/MS (a) Rt = 0.79 min; m/z [M + H]$^+$ 437. |
| 69 | | $^1$H-NMR (CD$_3$OD/CDCl$_3$(1/1)) δ: 8.57 (1H, d, J = 5.6 Hz), 8.14 (1H, d, J = 8.0 Hz), 7.53-7.28 (5H, m), 6.95-6.90 (1H, m), 4.38-3.98 (1H, m), 3.26-3.18 (1H, m), 2.66 (3H, s), 1.84-1.39 (8H, m).<br>LC/MS (a) Rt = 0.67 min; m/z [M + H]$^+$ 458. |

TABLE 25-continued

| Example No. | Structural formula | Physical property |
| --- | --- | --- |
| 70 | | ¹H-NMR (CD₃OD/CDCl₃(1/1)) δ: 8.26-7.91 (2H, m), 7.25-7.00 (1H, m), 4.51 (2H, q, J = 7.2 Hz), 4.31-3.96 (1H, m), 2.62 (3H, s), 1.95-1.46 (8H, m), 1.65 (3H, t, J = 7.3 Hz). LC/MS (a) Rt = 0.71 min; m/z [M + H]⁺ 410. |

TABLE 26

| Example No. | Structural formula | Physical property |
| --- | --- | --- |
| 71 | | ¹H-NMR (DMSO-d₆) δ: 12.11-11.94 (1H, m), 8.49-8.23 (2H, m), 8.14-8.10 (2H, m), 8.08 (1H, d, J = 9.3 Hz), 7.83-7.72 (2H, m), 7.79 (1H, d, J = 9.3 Hz), 7.31 (1H, t, J = 8.2 Hz), 6.84 (1H, d, J = 3.4 Hz), 4.18-3.76 (1H, m), 3.18-3.12 (1H, m), 2.67 (4H, s), 1.81-1.49 (8H, m), 1.38-1.26 (2H, m). LC/MS (b) Rt = 1.02 min; m/z [M + H]⁺ 459. |
| 72 | | ¹H-NMR (DMSO-d₆) δ: 12.10-11.96 (1H, m), 9.23 (1H, s), 9.18 (2H, s), 8.47-8.21 (1H, m), 8.44 (1H, s), 7.91-7.74 (1H, m), 7.87 (1H, d, J = 3.4 Hz), 7.38 (1H, d, J = 8.3 Hz), 7.25 (1H, t, J = 8.0 Hz), 6.82 (1H, d, J = 3.7 Hz), 4.17-3.78 (1H, m), 3.18-3.10 (1H, m), 1.79-1.47 (8H, m), 1.38-1.28 (2H, m). LC/MS (b) Rt = 0.98 min; m/z [M + H]⁺ 445. |

TABLE 26-continued
| Example No. | Structural formula | Physical property |
|---|---|---|
| 73 | 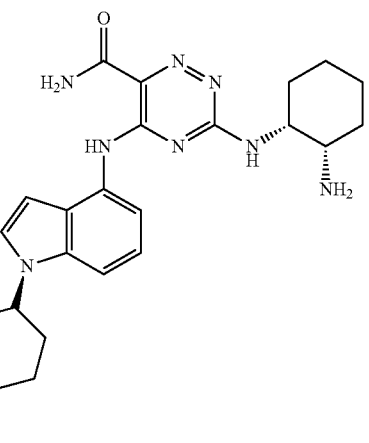 | 1H-NMR (CD₃OD/CDCl₃(1/1)) δ: 8.12-8.03 (1H, m), 7.81-7.74 (1H, m), 7.21-7.15 (2H, m), 6.74-6.66 (1H, m), 4.32-4.21 (1H, m), 3.85-3.74 (1H, m), 3.26-3.20 (1H, m), 2.25-1.33 (17H, m). LC/MS (a) Rt = 0.75 min; m/z [M + H]⁺ 465. |
| 74 | 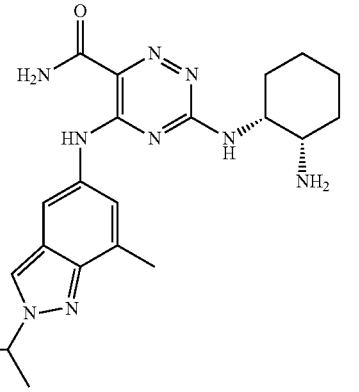 | ¹H-NMR (CD₃OD/CDCl₃(1/1)) δ: 8.18-7.95 (2H, m), 7.22-7.03 (1H, m), 4.91-4.78 (1H, m), 4.32-4.00 (1H, m), 3.26-3.20 (1H, m), 2.62 (3H, s), 1.87-1.58 (6H, m), 1.68 (12H, d, J = 6.6 Hz), 1.56-1.44 (6H, m). LC/MS (a) Rt = 0.71 min; m/z [M + H]⁺ 424. |
| 75 | 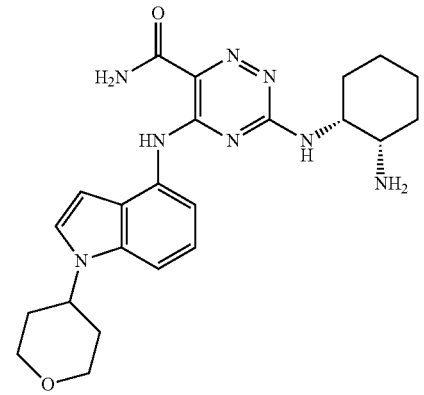 | ¹H-NMR (CD₃OD/CDCl₃(1/1)) δ: 8.06-7.98 (1H, m), 7.31-7.20 (3H, m), 6.74-6.67 (1H, m), 4.54-4.44 (1H, m), 4.21-4.02 (3H, m), 3.69-3.60 (2H, m), 3.28-3.22 (1H, m), 2.19-2.03 (4H, m), 1.82-1.39 (8H, m). LC/MS (a) Rt = 0.8 min; m/z [M + H]⁺ 451. |

TABLE 27

| Example No. | Structural formula | Physical property |
|---|---|---|
| 76 | | $^1$H-NMR (CD$_3$OD/CDCl$_3$(1/1)) δ: 8.77 (2H, d, J = 5.1 Hz), 7.97 (1H, d, J = 1.8 Hz), 7.63-7.60 (1H, m), 7.28 (1H, t, J = 4.9 Hz), 4.36-4.31 (1H, m), 3.37-3.29 (1H, m), 1.87-1.50 (8H, m).<br>LC/MS (a) Rt = 0.74 min; m/z [M + H]$^+$ 412. |
| 77 | | $^1$H-NMR (CD$_3$OD/CDCl$_3$(1/1)) δ: 8.55 (1H, d, J = 4.0 Hz), 7.83 (1H, td, J = 7.8, 1.7 Hz), 7.72 (1H, d, J = 8.1 Hz), 7.59 (1H, d, J = 1.5 Hz), 7.39 (1H, s), 7.28 (1H, dd, J = 6.4, 4.9 Hz), 4.36-4.30 (1H, m), 3.33-3.29 (1H, m), 1.87-1.49 (8H, m).<br>LC/MS (a) Rt = 0.69 min; m/z [M + H]$^+$ 411. |
| 78 | | $^1$H-NMR (CD$_3$OD/CDCl$_3$(1/1)) δ: 7.97-7.88 (1H, m), 7.15-7.12 (1H, m), 7.01-6.97 (1H, m), 6.64-6.57 (1H, m), 4.27-4.16 (1H, m), 3.80-3.69 (1H, m), 3.42-3.36 (1H, m), 3.27-3.19 (1H, m), 2.55-2.52 (3H, m), 2.20-2.11 (4H, m), 1.89-1.37 (12H, m).<br>LC/MS (a) Rt = 0.78 min; m/z [M + H]$^+$ 479. |
| 79 | | $^1$H-NMR (CD$_3$OD/CDCl$_3$(1/1)) δ: 9.13 (1H, s), 8.49-8.26 (1H, m), 8.18 (1H, s), 7.84-7.76 (1H, m), 7.78 (1H, s), 6.58 (1H, s), 4.56 (2H, q, J = 7.3 Hz), 4.34-4.18 (1H, m), 3.27-3.15 (1H, m), 1.83-1.40 (8H, m), 1.69 (3H, t, J = 7.3 Hz).<br>LC/MS (a) Rt = 0.82 min; m/z [M + H]$^+$ 462. |

TABLE 27-continued

| Example No. | Structural formula | Physical property |
|---|---|---|
| 80 | | ¹H-NMR (DMSO-d₆) δ: 12.12-12.00 (1H, m), 9.43 (1H, s), 8.57-8.43 (1H, m), 8.46-8.28 (1H, m), 8.08 (1H, s), 8.00 (1H, d, J = 3.7 Hz), 7.89-7.70 (1H, m), 7.41 (1H, t, J = 8.2 Hz), 6.87 (1H, d, J = 3.7 Hz), 4.17-3.76 (1H, m), 3.17-3.10 (1H, m), 1.80-1.47 (8H, m), 1.39-1.23 (2H, m).<br>LC/MS (b) Rt = 1.03 min; m/z [M + H]⁺ 451. |

TABLE 28

| Example No. | Structural formula | Physical property |
|---|---|---|
| 81 | | ¹H-NMR (CD₃OD/CDCl₃(1/1)) δ: 8.21-7.84 (1H, m), 8.15 (1H, s), 7.81-7.49 (1H, m), 4.53 (2H, q, J = 7.3 Hz), 4.37-3.96 (1H, m), 3.25-3.20 (1H, m), 1.80-1.43 (8H, m), 1.66 (3H, t, J = 7.3 Hz).<br>LC/MS (a) Rt = 0.74 min; m/z [M + H]⁺ 430. |
| 82 | | ¹H-NMR (CD₃OD/CDCl₃(1/1)) δ: 8.21-7.97 (2H, m), 7.22-7.03 (1H, m), 4.24 (3H, s), 4.16-3.98 (1H, m), 3.28-3.19 (1H, m), 2.60 (3H, s), 1.83-1.45 (8H, m).<br>LC/MS (a) Rt = 0.68 min; m/z [M + H]⁺ 396. |

TABLE 28-continued

| Example No. | Structural formula | Physical property |
| --- | --- | --- |
| 83 | | ¹H-NMR (CD₃OD/CDCl₃(1/1)) δ: 8.17-7.93 (2H, m), 7.25-7.03 (1H, m), 4.28-3.99 (1H, m), 3.25-3.20 (1H, m), 2.86 (2H, dd, J = 21.8, 9.7 Hz), 2.63 (3H, s), 2.44 (2H, t, J = 9.2 Hz), 2.16-1.96 (2H, m), 1.86-1.56 (6H, m), 1.83 (3H, s), 1.55-1.43 (2H, m). LC/MS (a) Rt = 0.83 min; m/z [M + H]⁺ 450. |
| 84 | | ¹H-NMR (DMSO-d₆) δ: 12.10-11.94 (1H, m), 9.19 (1H, d, J = 1.2 Hz), 8.63 (1H, s), 8.56 (1H, d, J = 2.7 Hz), 8.43 (1H, s), 8.24 (2H, d, J = 3.4 Hz), 8.16 (1H, d, J = 8.5 Hz), 7.85-7.71 (2H, m), 7.30 (1H, t, J = 8.0 Hz), 6.84 (1H, d, J = 3.7 Hz), 4.16-3.76 (2H, m), 3.16-3.10 (1H, m), 1.83-1.48 (9H, m), 1.40-1.27 (2H, m). LC/MS (b) Rt = 1.08 min; m/z [M + H]⁺ 445. |
| 85 | | ¹H-NMR (CD₃OD/CDCl₃(1/1)) δ: 8.21-7.95 (1H, m), 8.01 (1H, s), 6.87 (1H, brs), 4.25 (3H, s), 4.15-3.98 (1H, m), 3.27-3.17 (1H, m), 2.52-2.39 (1H, m), 1.83-1.44 (8H, m), 1.16-1.08 (2H, m), 0.96-0.86 (2H, m). LC/MS (a) Rt = 0.72 min; m/z [M + H]⁺ 422. |

TABLE 29

| Example No. | Structural formula | Physical property |
|---|---|---|
| 86 | | ¹H-NMR (CD₃OD/CDCl₃(1/1)) δ: 8.55 (1H, br s), 8.13 (1H, s), 7.60 (1H, t, J = 60.1 Hz), 7.06 (1H, br s), 4.32-4.25 (1H, m), 3.16-3.08 (1H, m), 2.63 (3H, s), 1.92-1.43 (8H, m). LC/MS (a) Rt = 0.8 min; m/z [M + H]⁺ 432. |
| 87 | | LC/MS (a) Rt = 0.78 min; m/z [M + H]⁺ 418. |
| 88 | | ¹H-NMR (CD₃OD/CDCl₃(1/1)) δ: 8.32-8.07 (1H, m), 7.97-7.91 (1H, m), 7.28-7.13 (1H, m), 4.66 (2H, q, J = 7.3 Hz), 4.32-3.97 (1H, m), 3.29-3.25 (1H, m), 2.76 (3H, s), 1.81-1.46 (8H, m), 1.49 (3H, t, J = 7.3 Hz). LC/MS (a) Rt = 0.75 min; m/z [M + H]⁺ 410. |
| 89 | | ¹H-NMR (CD₃OD/CDCl₃(1/1)) δ: 8.36-8.11 (2H, m), 7.67 (1H, d, J = 9.2 Hz), 7.39 (1H, dd, J = 9.2, 2.0 Hz), 5.15-5.06 (1H, m), 4.45-4.05 (1H, m), 3.15-3.05 (1H, m), 2.80-2.60 (4H, m), 2.08-1.98 (2H, m), 1.80-1.70 (1H, m), 1.58-1.50 (1H, m), 1.40-1.25 (1H, m), 1.18-1.12 (3H, m), 0.99 (3H, d, J = 6.8 Hz), 1.00-0.99 (3H, m). LC/MS (b) Rt = 1.13 min; m/z [M + H]⁺ 438. |

TABLE 29-continued

| Example No. | Structural formula | Physical property |
|---|---|---|
| 90 | (structure) | ¹H-NMR (CD₃OD/CDCl₃(1/1)) δ: 8.59 (1H, d, J = 2.2 Hz), 8.49-8.46 (1H, m), 8.13 (1H, d, J = 7.8 Hz), 7.41 (1H, d, J = 3.7 Hz), 7.32-7.24 (1H, m), 7.10 (1H, d, J = 8.3 Hz), 6.95-6.93 (1H, m), 4.38-3.95 (1H, m), 3.25-3.18 (1H, m), 2.54 (3H, s), 1.84-1.38 (8H, m). LC/MS (a) Rt = 0.79 min; m/z [M + H]⁺ 459. |

TABLE 30

| Example No. | Structural formula | Physical property |
|---|---|---|
| 91 | (structure) | LC/MS (a) Rt = 0.74 min; m/z [M + H]⁺ 396. |
| 92 | (structure) | ¹H-NMR (CD₃OD/CDCl₃(1/1)) δ: 7.99-7.91 (1H, m), 7.19-7.16 (1H, m), 7.03-7.00 (1H, m), 6.68-6.61 (1H, m), 4.49-4.38 (1H, m), 4.21-4.13 (2H, m), 4.09-4.00 (1H, m), 3.69-3.60 (2H, m), 3.28-3.20 (1H, m), 2.55-2.51 (3H, m), 1.96-1.43 (12H, m). LC/MS (a) Rt = 0.84 min; m/z [M + H]⁺ 465. |

TABLE 30-continued
| Example No. | Structural formula | Physical property |
|---|---|---|
| 93 | 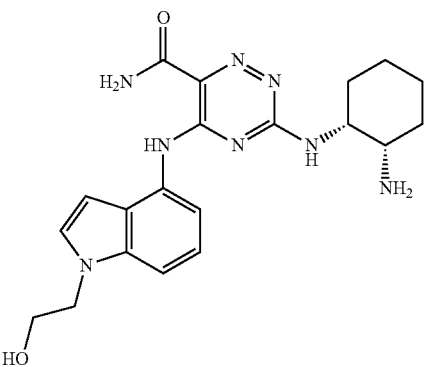 [SMILES: NC(=O)c1nnc(N[C@@H]2CCCC[C@@H]2N)nc1Nc1cccc2c1ccn2CCO] | ¹H-NMR (CD₃OD/CDCl₃(1/1)) δ: 7.89-7.81 (1H, m), 7.30-7.19 (3H, m), 6.59-6.53 (1H, m), 4.34-4.21 (2H, m), 3.97-3.87 (2H, m), 3.78-3.72 (1H, m), 3.41-3.35 (1H, m), 1.78-1.36 (8H, m).<br>LC/MS (a) Rt = 0.72 min; m/z [M + H]⁺ 411. |
| 94 | 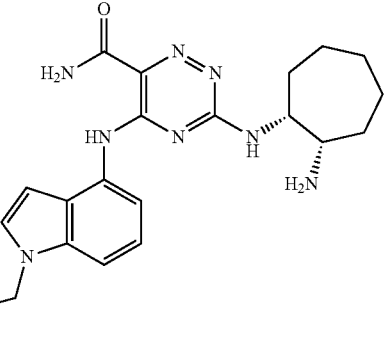 | ¹H-NMR (CD₃OD/CDCl₃(1/1)) δ: 8.05 (1H, dd, J = 6.8, 1.7 Hz), 7.27-7.16 (3H, m), 6.66-6.60 (1H, m), 4.35 (2H, t, J = 5.4 Hz), 4.34-4.14 (1H, m), 3.76 (2H, t, J = 5.4 Hz), 3.32 (3H, s), 3.32-3.30 (1H, m), 1.95-1.50 (10H, m).<br>LC/MS (a) Rt = 0.81 min; m/z [M + H]⁺ 439. |
| 95 | 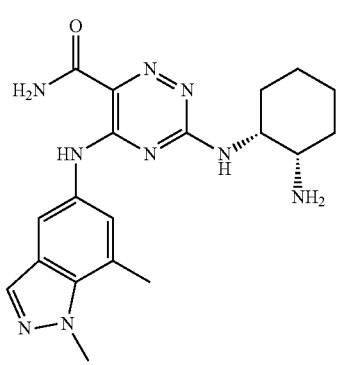 [SMILES: Cc1cc(Nc2nc(N[C@@H]3CCCC[C@@H]3N)nnc2C(N)=O)cc2cnn(C)c12] | ¹H-NMR (CD₃OD/CDCl₃(1/1)) δ: 8.22-8.05 (1H, m), 7.91-7.86 (1H, m), 7.27-7.16 (1H, m), 4.33 (3H, s), 4.28-3.97 (1H, m), 3.27-3.19 (1H, m), 2.80 (3H, s), 1.85-1.42 (8H, m).<br>LC/MS (a) Rt = 0.72 min; m/z [M + H]⁺ 396. |

TABLE 31
| Example No. | Structural formula | Physical property |
|---|---|---|
| 96 | 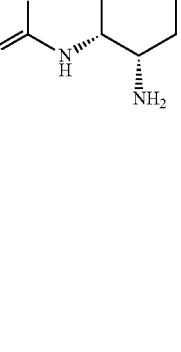 | ¹H-NMR (CD₃OD) δ: 8.27 (1H, s), 8.20-7.98 (1H, br), 7.20-6.90 (1H, br), 5.33-5.20 (2H, m), 4.40-3.90 (1H, m), 3.30-3.15 (1H, m), 2.57 (3H, s), 1.95-1.30 (8H, m). LC/MS (a) Rt = 0.79 min; m/z [M + H]⁺ 464. |
| 97 | 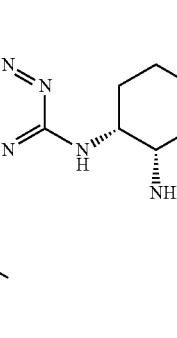 | LC/MS (a) Rt = 0.76 min; m/z [M + H]⁺ 410. |
| 98 | 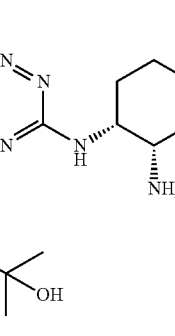 | LC/MS (a) Rt = 0.71 min; m/z [M + H]⁺ 456. |
| 99 | 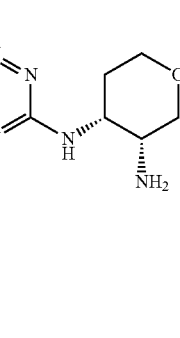 | ¹H-NMR (DMSO-d₆) δ: 11.14-11.40 (m, 1H), 8.22-8.39 (m, 2H), 7.97 (br. s., 1H), 7.09 (br. s., 1H), 6.82-7.86 (m, 2H), 5.02 (t, J = 5.5 Hz, 1H), 3.86-4.29 (m, 1H), 3.75-3.86 (m, 1H), 3.70 (d, J = 5.9 Hz, 2H), 3.63-3.69 (m, 1H), 3.51 (d, J = 11.0 Hz, 1H), 3.35-3.46 (m, 1H), 2.97 (br. s., 1H), 1.85 (d, J = 9.9 Hz, 1H), 1.68 (d, J = 9.5 Hz, 1H), 1.59 (s, 6H) J = 11.0 Hz, 1H), 3.35-3.46 LC/MS (a) Rt = 0.69 min; m/z [M + H]⁺ 456. |

TABLE 31-continued
| Example No. | Structural formula | Physical property |
|---|---|---|
| 100 | 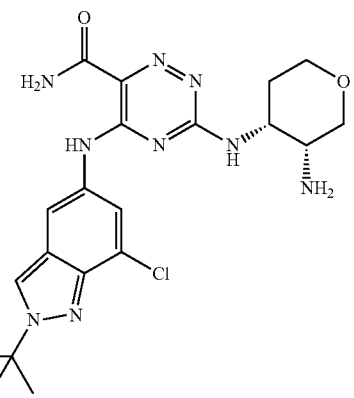 | $^1$H-NMR (CD$_3$OD/CDCl$_3$(1/1)) δ: 8.24 (1H, s), 8.17-7.83 (1H, m), 7.69-7.48 (1H, m), 4.40-4.08 (1H, m), 4.05-3.97 (1H, m), 3.91-3.85 (1H, m), 3.73-3.65 (1H, m), 3.61-3.52 (1H, m), 3.18-3.12 (1H, m), 2.00-1.88 (1H, m), 1.85-1.81 (1H, m), 1.79 (9H, s). LC/MS (a) Rt = 0.79 min; m/z [M + H]$^+$ 460. |
TABLE 32
| Example No. | Structural formula | Physical property |
|---|---|---|
| 101 | 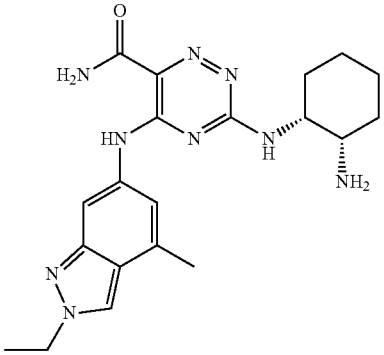 [SMILES: CCn1cc2c(C)cc(Nc3nc(N[C@@H]4CCCC[C@@H]4N)nnc3C(N)=O)cc2n1] | LC/MS (a) Rt = 0.77 min; m/z [M + H]$^+$ 410. |
| 102 | 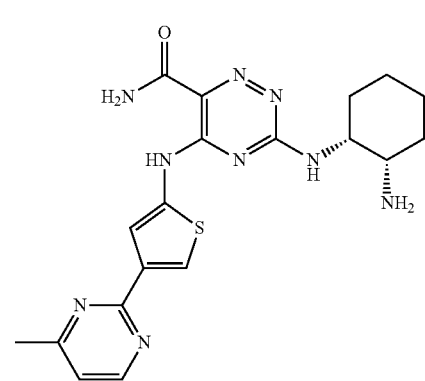 [SMILES: Cc1ccnc(-c2csc(Nc3nc(N[C@@H]4CCCC[C@@H]4N)nnc3C(N)=O)c2)n1] | $^1$H-NMR (CD$_3$OD/CDCl$_3$(1/1)) δ: 8.59 (1H, d, J = 5.1 Hz), 7.96 (1H, d, J = 1.5 Hz), 7.60 (1H, s), 7.14 (1H, d, J = 5.1 Hz), 4.36-4.29 (1H, m), 3.33-3.27 (1H, m), 2.59 (3H, s), 1.86-1.49 (8H, m). LC/MS (a) Rt = 0.76 min; m/z [M + H]$^+$ 426. |

TABLE 32-continued
| Example No. | Structural formula | Physical property |
|---|---|---|
| 103 | 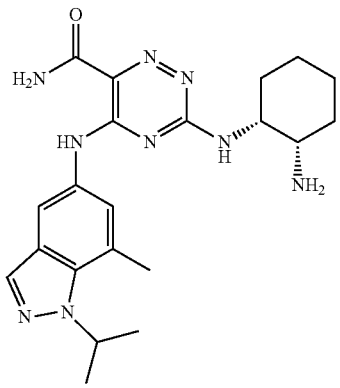 [SMILES: Cc1cc(Nc2nc(N[C@@H]3CCCC[C@@H]3N)nnc2C(N)=O)cc2cnn(C(C)C)c12] | $^1$H-NMR (CD$_3$OD/CDCl$_3$(1/1)) δ: 8.25-8.08 (1H, m), 8.03-7.95 (1H, m), 7.29-7.09 (1H, m), 5.29-5.19 (1H, m), 4.33-3.97 (1H, m), 3.28-3.18 (1H, m), 2.77 (3H, s), 1.84-1.58 (6H, m), 1.60 (6H, d, J = 6.6 Hz), 1.57-1.43 (2H, m).<br>LC/MS (a) Rt = 0.8 min; m/z [M + H]$^+$ 424. |
| 104 | 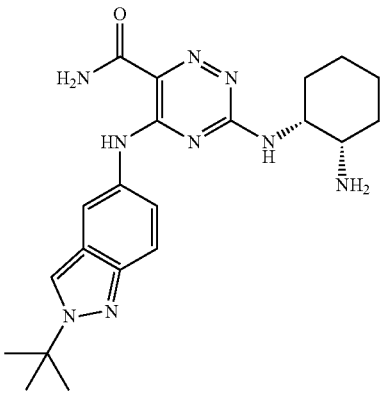 | $^1$H-NMR (CD$_3$OD/CDCl$_3$(1/1)) δ: 8.14 (2H, s), 7.67 (1H, d, J = 9.2 Hz), 7.43-7.35 (1H, m), 4.30-4.01 (1H, m), 3.24-3.17 (1H, m), 1.84-1.59 (6H, m), 1.77 (9H, s), 1.54-1.45 (2H, m).<br>LC/MS (a) Rt = 0.75 min; m/z [M + H]$^+$ 424. |
| 105 | 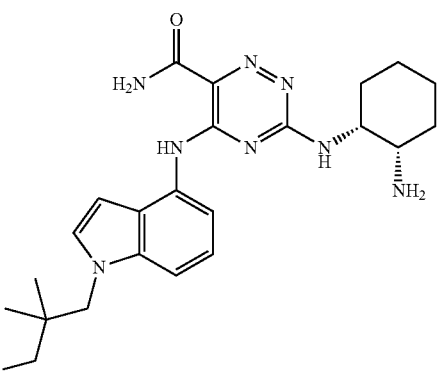 | $^1$H-NMR (CD$_3$OD/CDCl$_3$(1/1)) δ: 8.00-7.93 (1H, m), 7.35-7.16 (3H, m), 6.67-6.62 (1H, m), 4.07 (2H, s), 3.39-3.37 (1H, m), 3.33 (2H, s), 3.23-3.17 (1H, m), 1.80-1.39 (8H, m), 0.95 (6H, s).<br>LC/MS (a) Rt = 0.81 min; m/z [M + H]$^+$ 453. |

TABLE 33

| Example No. | Structural formula | Physical property |
|---|---|---|
| 106 | | ¹H-NMR (CD$_3$OD/CDCl$_3$(1/1)) δ: 8.20-8.09 (1H, m), 7.69 (1H, d, J = 8.4 Hz), 7.59 (1H, d, J = 2.6 Hz), 7.53 (1H, d, J = 3.3 Hz), 7.29 (1H, t, J = 8.1 Hz), 6.81 (1H, d, J = 3.3 Hz), 6.43 (1H, d, J = 2.2 Hz), 3.97 (3H, s), 3.76-3.61 (2H, m), 2.18-2.07 (2H, m), 1.99-1.69 (4H, m).<br>LC/MS (a) Rt = 0.76 min; m/z [M + H]⁺ 433. |
| 107 | | ¹H-NMR (CD$_3$OD/CDCl$_3$(1/1)) δ: 8.14 (1H, s), 8.01 (1H, d, J = 7.1 Hz), 7.39 (1H, dd, J = 8.3, 7.1 Hz), 7.21 (1H, d, J = 8.3 Hz), 4.45 (2H, q, J = 7.2 Hz), 4.53-3.86 (2H, m), 1.83-1.41 (8H, m), 1.52 (3H, t, J = 7.2 Hz).<br>LC/MS (a) Rt = 0.78 min; m/z [M + H]⁺ 396. |
| 108 | | ¹H-NMR (CD$_3$OD/CDCl$_3$(1/1)) δ: 8.26-8.15 (1H, m), 8.13-8.08 (1H, m), 7.67-7.62 (1H, m), 7.42-7.34 (1H, m), 5.02-4.93 (1H, m), 4.11-4.01 (1H, m), 3.26-3.19 (1H, m), 2.38-2.30 (2H, m), 2.23-2.13 (2H, m), 2.05-1.94 (2H, m), 1.89-1.58 (8H, m), 1.55-1.44 (2H, m).<br>LC/MS (a) Rt = 0.78 min; m/z [M + H]⁺ 436. |
| 109 | | ¹H-NMR (CD$_3$OD/CDCl$_3$(1/1)) δ: 8.23-8.07 (1H, m), 7.93-7.83 (1H, m), 6.48-6.22 (1H, m), 4.44 (2H, q, J = 7.3 Hz), 4.33-4.20 (1H, m), 3.97 (3H, s), 3.24-3.16 (1H, m), 1.88-1.46 (8H, m), 1.62 (3H, t, J = 7.3 Hz).<br>LC/MS (a) Rt = 0.75 min; m/z [M + H]⁺ 426. |

TABLE 33-continued
| Example No. | Structural formula | Physical property |
|---|---|---|
| 110 | 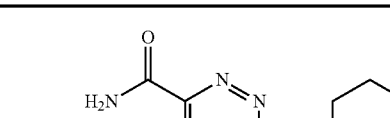 | ¹H-NMR (CD₃OD/CDCl₃(1/1)) δ: 7.98 (1H, s), 7.74 (1H, s), 6.58 (1H, br s), 4.46-4.35 (2H, m), 4.27-4.17 (1H, m), 3.99 (3H, s), 3.23-3.14 (1H, m), 1.94-1.62 (6H, m), 1.54-1.49 (2H, m), 1.51 (3H, t, J = 7.1 Hz). LC/MS (a) Rt = 0.77 min; m/z [M + H]⁺ 426. |
TABLE 34
| Example No. | Structural formula | Physical property |
|---|---|---|
| 111 | 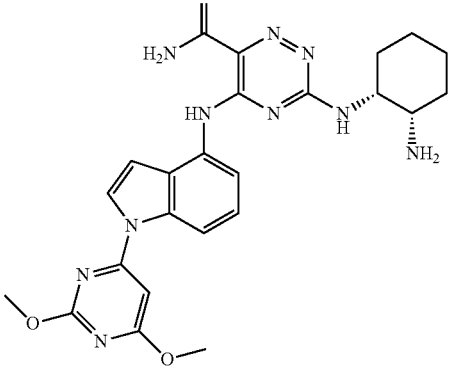 | ¹H-NMR (DMSO-d₆) δ: 12.11-11.94 (1H, m), 8.49-8.23 (2H, m), 8.14-8.10 (2H, m), 8.08 (1H, d, J = 9.3 Hz), 7.83-7.72 (2H, m), 7.79 (1H, d, J = 9.3 Hz), 7.31 (1H, t, J = 8.2 Hz), 6.84 (1H, d, J = 3.4 Hz), 4.18-3.76 (1H, m), 3.18-3.12 (1H, m), 2.67 (4H, s), 1.81-1.49 (8H, m), 1.38-1.26 (2H, m). LC/MS (b) Rt = 1.29 min; m/z [M + H]⁺ 505. |
| 112 | 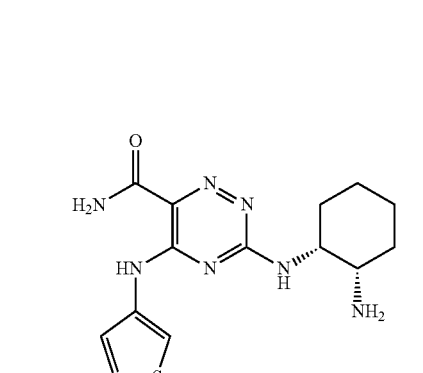 | ¹H-NMR (CD₃OD/CDCl₃(1/1)) δ: 8.74 (2H, d, J = 4.8 Hz), 8.36-8.24 (1H, m), 7.96-7.68 (1H, m), 7.27 (1H, t, J = 4.8 Hz), 4.36-4.11 (1H, m), 3.28-3.24 (1H, m), 1.89-1.47 (8H, m). LC/MS (a) Rt = 0.76 min; m/z [M + H]⁺ 412. |

| Example No. | Structural formula | Physical property |
|---|---|---|
| 113 | 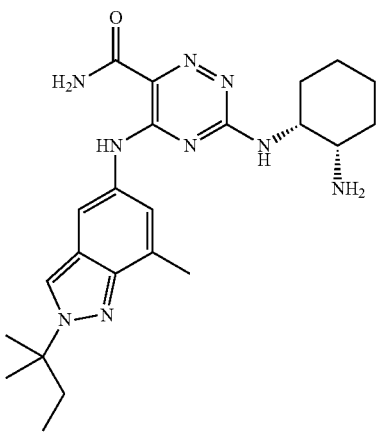 [SMILES: CCC(C)(C)n1cc2cc(Nc3nc(N[C@@H]4CCCC[C@@H]4N)nnc3C(N)=O)cc(C)c2n1] | ¹H-NMR (CD₃OD/CDCl₃(1/1)) δ: 8.21-7.79 (2H, m), 8.08 (2H, s), 7.25-6.98 (1H, m), 4.39-4.07 (1H, m), 4.01 (1H, d, J = 11.0 Hz), 3.87 (1H, d, J = 12.1 Hz), 3.71-3.60 (1H, m), 3.58-3.48 (1H, m), 3.17 (1H, s), 2.63 (3H, s), 2.09 (2H, q, J = 7.4 Hz), 2.00-1.88 (2H, m), 1.88-1.80 (2H, m), 1.75 (6H, s), 0.71 (3H, t, J = 7.4 Hz). LC/MS (a) Rt = 0.82 min; m/z [M + H]⁺ 454. |
| 114 | 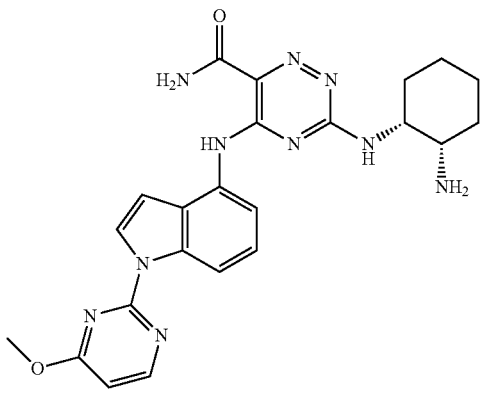 [SMILES: COc1ccnc(-n2ccc3c(Nc4nc(N[C@@H]5CCCC[C@@H]5N)nnc4C(N)=O)cccc32)n1] | ¹H-NMR (DMSO-d₆) δ: 12.05-11.94 (1H, m), 8.55 (1H, d, J = 5.9 Hz), 8.48 (1H, d, J = 8.5 Hz), 8.42 (1H, s), 8.34 (1H, d, J = 3.7 Hz), 8.27-8.22 (1H, m), 7.82-7.72 (2H, m), 7.36-7.29 (1H, m), 6.81-6.77 (2H, m), 4.12-3.76 (4H, m), 4.09 (4H, s), 3.16-3.11 (1H, m), 1.81-1.46 (8H, m), 1.38-1.26 (2H, m). LC/MS (b) Rt = 1.29 min; m/z [M + H]⁺ 475. |
| 115 | 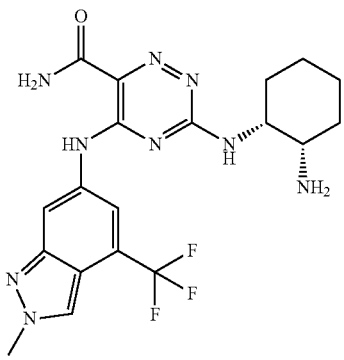 [SMILES: Cn1cc2c(C(F)(F)F)cc(Nc3nc(N[C@@H]4CCCC[C@@H]4N)nnc3C(N)=O)cc2n1] | ¹H-NMR (CD₃OD/CDCl₃(1/1)) δ: 8.82-7.77 (1H, m), 8.20 (1H, s), 4.31-4.07 (1H, m), 4.27 (3H, s), 3.27-3.14 (1H, m), 1.86-1.47 (8H, m). LC/MS (a) Rt = 0.8 min; m/z [M + H]⁺ 450. |

TABLE 35

| Example No. | Structural formula | Physical property |
|---|---|---|
| 116 | | ¹H-NMR (CD₃OD) δ: 8.53-8.22 (1H, br), 8.09 (1H, s), 7.44-7.20 (1H, m), 5.42-5.18 (2H, m), 4.50-3.95 (1H, m), 3.47-3.25 (1H, m), 2.72 (3H, s), 1.98-1.35 (8H, m). LC/MS (a) Rt = 0.79 min; m/z [M + H]⁺ 464. |
| 117 | | LC/MS (a) Rt = 0.70 min; m/z [M + H]⁺ 452. |
| 118 | | ¹H-NMR (CD₃OD/CDCl₃(1/1)) δ: 8.40-8.18 (1H, m), 8.07 (1H, s), 6.91-6.72 (1H, m), 4.47 (2H, q, J = 7.3 Hz), 4.40-4.27 (1H, m), 3.61-3.49 (2H, m), 3.30 (3H, s), 3.14-3.05 (1H, m), 2.54 (3H, s), 1.64 (3H, t, J = 7.3 Hz), 1.35 (3H, d, J = 5.9 Hz). LC/MS (a) Rt = 0.73 min; m/z [M + H]⁺ 414. |

TABLE 35-continued

| Example No. | Structural formula | Physical property |
|---|---|---|
| 119 | | ¹H-NMR (DMSO-d₆) δ: 12.09-11.93 (1H, m), 8.89 (2H, d, J = 4.9 Hz), 8.49 (1H, d, J = 8.5 Hz), 8.44-8.40 (1H, m), 8.34 (1H, d, J = 3.7 Hz), 8.28-8.23 (1H, m), 7.82-7.71 (2H, m), 7.38 (1H, t, J = 4.8 Hz), 7.33 (1H, t, J = 8.2 Hz), 6.82 (1H, d, J = 3.7 Hz), 4.15-3.78 (1H, m), 3.17-3.12 (1H, m), 1.78-1.49 (8H, m), 1.39-1.27 (2H, m). LC/MS (b) Rt = 1.18 min; m/z [M + H]⁺ 445. |
| 120 | | ¹H-NMR (CD₃OD/CDCl₃(1/1)) δ: 8.63-8.54 (1H, m), 8.46-8.20 (1H, m), 7.91 (2H, d, J = 7.7 Hz), 7.74 (1H, d, J = 9.2 Hz), 7.58 (2H, t, J = 7.9 Hz), 7.50-7.41 (1H, m), 7.47 (1H, t, J = 7.5 Hz), 4.38-4.01 (1H, m), 3.31-3.23 (1H, m), 1.87-1.58 (6H, m), 1.57-1.44 (2H, m). LC/MS (a) Rt = 0.83 min; m/z [M + H]⁺ 444. |

TABLE 36

| Example No. | Structural formula | Physical property |
|---|---|---|
| 121 | 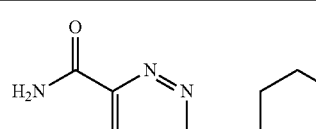 | ¹H-NMR (DMSO-d₆) δ: 12.36-12.17 (1H, m), 9.04 (1H, d, J = 2.4 Hz), 8.63 (1H, d, J = 4.6 Hz), 8.48 (1H, s), 8.33 (1H, s), 8.23 (1H, d, J = 8.0 Hz), 8.15 (1H, d, J = 7.6 Hz), 7.94-7.78 (2H, m), 7.65 (1H, dd, J = 8.3, 4.6 Hz), 7.62-7.57 (1H, m), 7.51 (1H, t, J = 8.0 Hz), 4.18-3.72 (1H, m), 3.16-3.08 (1H, m), 1.83-1.46 (8H, m), 1.37-1.23 (2H, m). LC/MS (b) Rt = 0.99 min; m/z [M + H]⁺ 445. |

TABLE 36-continued

| Example No. | Structural formula | Physical property |
|---|---|---|
| 122 | | $^1$H-NMR (DMSO-d$_6$) δ: 12.27-12.16 (1H, m), 8.48 (1H, s), 8.34 (1H, s), 8.19-8.08 (1H, m), 8.17 (1H, s), 7.93-7.78 (2H, m), 7.91 (1H, s), 7.50-7.30 (2H, m), 4.17-3.73 (1H, m), 3.93 (3H, s) 3.15-3.08 (1H, m), 1.78-1.44 (8H, m), 1.37-1.24 (2H, m). <br> LC/MS (b) Rt = 0.98 min; m/z [M + H]$^+$ 448. |
| 123 | | LC/MS (a) Rt = 0.87 min; m/z [M + H]$^+$ 436. |
| 124 | | $^1$H-NMR (CD$_3$OD/CDCl$_3$(1\1)) δ: 8.52-8.18 (1H, m), 8.10-8.07 (1H, m), 7.53-7.47 (2H, m), 4.32 (2H, q, J = 7.3 Hz), 4.23-4.08 (1H, m), 3.23-3.16 (1H, m), 1.84-1.62 (6H, m), 1.58 (3H, t, J = 7.3 Hz), 1.55-1.45 (2H, m). <br> LC/MS (a) Rt = 0.59 min; m/z [M + H]$^+$ 396. |
| 125 | | LC/MS (a) Rt = 0.68 min; m/z [M + H]$^+$ 420. |

TABLE 37

| Example No. | Structural formula | Physical property |
|---|---|---|
| 126 | | $^1$H-NMR (CD$_3$OD/CDCl$_3$(1/1)) δ: 8.17-8.14 (1H, m), 8.05-8.00 (1H, m), 7.44-7.36 (1H, m), 7.30-7.26 (1H, m), 5.36-5.28 (1H, m), 4.33-3.94 (6H, m), 1.89-1.37 (10H, m). <br> LC/MS (a) Rt = 0.76 min; m/z [M + H]$^+$ 438. |
| 127 | | $^1$H-NMR (CD$_3$OD/CDCl$_3$(1/1)) δ: 8.18-8.11 (1H, m), 8.04-7.97 (1H, m), 7.42-7.23 (2H, m), 5.33-5.26 (1H, m), 4.33-4.14 (3H, m), 4.07-3.92 (2H, m), 3.25-3.15 (1H, m), 1.96-1.19 (10H, m). <br> LC/MS (a) Rt = 0.77 min; m/z [M + H]$^+$ 438. |
| 128 | | $^1$H-NMR (CD$_3$OD/CDCl$_3$(1/1)) δ: 8.18-7.85 (1H, m), 8.10 (1H, s), 7.19-7.06 (1H, m), 4.40-4.09 (1H, m), 4.04-3.97 (1H, m), 3.90-3.83 (1H, m), 3.68-3.49 (3H, m), 3.18-3.13 (1H, m), 3.06 (2H, q, J = 7.6 Hz), 1.98-1.80 (2H, m), 1.77 (8H, s), 1.42 (3H, t, J = 7.5 Hz). <br> LC/MS (a) Rt = 0.83 min; m/z [M + H]$^+$ 454. |
| 129 | | $^1$H-NMR (DMSO-d$_6$) δ: 12.28-12.13 (1H, m), 8.48 (1H, br s), 8.36-8.10 (1H, m), 8.20 (1H, s), 7.99 (1H, d, J = 8.5 Hz), 7.87-7.79 (2H, m), 7.84 (1H, d, J = 2.4 Hz), 7.51 (1H, t, J = 8.2 Hz), 6.54 (1H, d, J = 2.2 Hz), 4.15-3.72 (1H, m), 3.93 (3H, s), 3.15-3.07 (1H, m), 1.78-1.45 (8H, m), 1.35-1.25 (2H, m). <br> LC/MS (b) Rt = 1.07 min; m/z [M + H]$^+$ 448. |

TABLE 37-continued

| Example No. | Structural formula | Physical property |
| --- | --- | --- |
| 130 | | $^1$H-NMR (CD$_3$OD/CDCl$_3$(1/1)) δ: 8.19-8.15 (1H, m), 8.04-7.99 (1H, m), 7.43-7.23 (2H, m), 4.72-4.62 (1H, m), 4.24-4.15 (2H, m), 4.04-3.95 (1H, m), 3.70-3.60 (2H, m), 3.26-3.17 (1H, m), 2.49-2.37 (2H, m), 2.06-1.97 (2H, m), 1.86-1.38 (8H, m). LC/MS (a) Rt = 0.78 min; m/z [M + H]$^+$ 452. |

TABLE 38

| Example No. | Structural formula | Physical property |
| --- | --- | --- |
| 131 | | $^1$H-NMR (CD$_3$OD/CDCl$_3$(1/1)) δ: 8.15 (1H, s), 7.99 (1H, d, J = 7.1 Hz), 7.38 (1H, dd, J = 8.5, 7.1 Hz), 7.24 (1H, d, J = 8.5 Hz), 4.91-4.82 (1H, m), 3.43-3.39 (1H, m), 3.26-3.16 (1H, m), 1.85-1.37 (14H, m). LC/MS (a) Rt = 0.83 min; m/z [M + H]$^+$ 410. |
| 132 | | $^1$H-NMR (DMSO-d$_6$) δ: 12.29-12.14 (1H, m), 8.58 (1H, d, J = 4.9 Hz), 8.52-8.43 (2H, m), 8.32 (1H, s), 8.15 (1H, d, J = 7.6 Hz), 8.06-7.98 (2H, m), 7.92-7.80 (2H, m), 7.55 (1H, t, J = 8.0 Hz), 7.38-7.30 (1H, m), 4.16-3.73 (1H, m), 3.16-3.08 (1H, m), 1.79-1.43 (8H, m), 1.36-1.23 (2H, m). LC/MS (b) Rt = 1.22 min; m/z [M + H]$^+$ 445. |

TABLE 38-continued
| Example No. | Structural formula | Physical property |
|---|---|---|
| 133 | 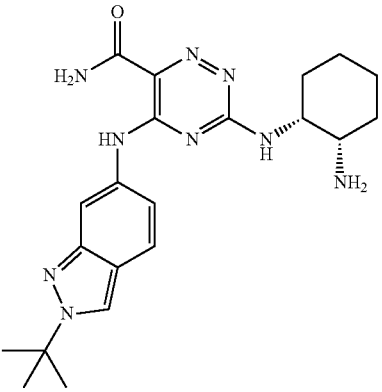 [SMILES: CC(C)(C)n1cc2ccc(Nc3nc(N[C@@H]4CCCC[C@@H]4N)nnc3C(N)=O)cc2n1] | ¹H-NMR (CD₃OD/CDCl₃(1/1)) δ: 8.57-8.23 (1H, m), 8.17 (1H, s), 7.67 (1H, d, J = 8.8 Hz), 7.21-6.95 (1H, m), 4.37-4.15 (1H, m), 3.27-3.20 (1H, m), 1.97-1.76 (4H, m), 1.76 (9H, s), 1.73-1.43 (4H, m). LC/MS (a) Rt = 0.77 min; m/z [M + H]⁺ 424. |
| 134 | 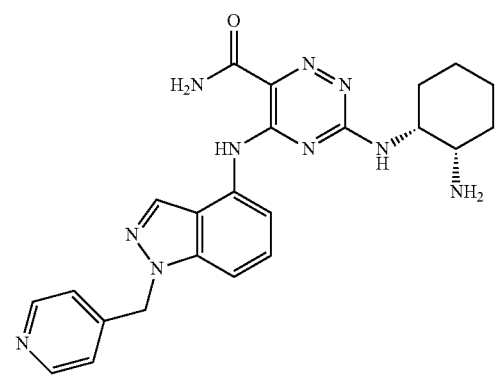 [SMILES: NC(=O)c1nnc(N[C@@H]2CCCC[C@@H]2N)nc1Nc1cccc2c1cnn2Cc1ccncc1] | ¹H-NMR (CD₃OD/CDCl₃(1/1)) δ: 8.53-8.48 (2H, m), 8.26 (1H, s), 8.10-8.03 (1H, m), 7.40-7.34 (1H, m), 7.08-7.02 (3H, m), 5.63 (2H, s), 4.04-3.91 (1H, m), 3.27-3.18 (1H, m), 1.89-1.32 (8H, m). LC/MS (a) Rt = 0.66 min; m/z [M + H]⁺ 459. |
| 135 | 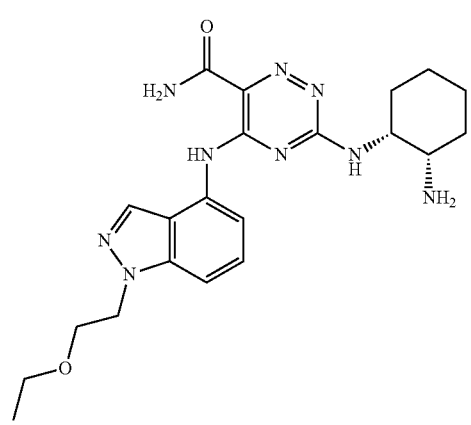 [SMILES: CCOCCn1ncc2c(Nc3nc(N[C@@H]4CCCC[C@@H]4N)nnc3C(N)=O)cccc21] | ¹H-NMR (CD₃OD/CDCl₃(1/1)) δ: 8.16 (1H, s), 8.01 (1H, d, J = 7.6 Hz), 7.42-7.35 (1H, m), 7.31-7.27 (1H, m), 4.59-4.54 (2H, m), 3.90-3.85 (2H, m), 3.46-3.38 (3H, m), 3.26-3.18 (1H, m), 1.85-1.40 (8H, m), 1.12-1.07 (3H, m). LC/MS (a) Rt = 0.8 min; m/z [M + H]⁺ 440. |

TABLE 39
| Example No. | Structural formula | Physical property |
|---|---|---|
| 136 | 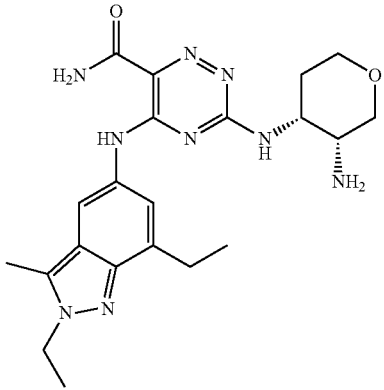 [SMILES: CCc1cc(Nc2nc(N[C@@H]3CCOC[C@@H]3N)nnc2C(N)=O)cc2c(C)n(CC)nc12] | ¹H-NMR (CD₃OD/CDCl₃(1/1)) δ: 7.86 (1H, br s), 7.13 (1H, br s), 4.45 (2H, q, J = 7.2 Hz), 4.32-4.11 (1H, m), 3.99 (1H, d, J = 12.8 Hz), 3.85 (1H, d, J = 9.9 Hz), 3.69-3.43 (2H, m), 3.20-3.09 (1H, m), 3.01 (2H, q, J = 7.6 Hz), 2.66 (3H, s), 1.99-1.89 (1H, m), 1.87-1.79 (1H, m), 1.54 (3H, t, J = 7.3 Hz), 1.40 (3H, t, J = 7.5 Hz). LC/MS (a) Rt = 0.69 min; m/z [M + H]⁺ 440. |
| 137 | 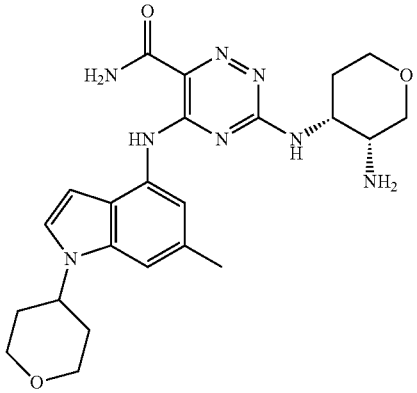 [SMILES: Cc1cc(Nc2nc(N[C@@H]3CCOC[C@@H]3N)nnc2C(N)=O)c2ccn(C3CCOCC3)c2c1] | ¹H-NMR (CD₃OD/CDCl₃(1/1)) δ: 7.90-7.82 (1H, m), 7.21-7.17 (1H, m), 7.05-7.01 (1H, m), 6.67-6.60 (1H, m), 4.50-4.39 (1H, m), 4.21-4.11 (2H, m), 4.06-3.97 (1H, m), 3.92-3.84 (1H, m), 3.71-3.11 (6H, m), 2.55-2.51 (3H, m), 2.19-1.82 (6H, m). LC/MS (a) Rt = 0.79 min; m/z [M + H]⁺ 467. |
| 138 | 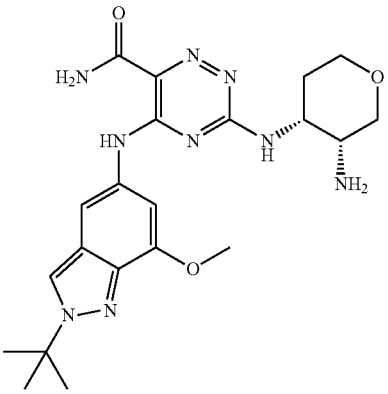 [SMILES: COc1cc(Nc2nc(N[C@@H]3CCOC[C@@H]3N)nnc2C(N)=O)cc2cn(C(C)(C)C)nc12] | ¹H-NMR (CD₃OD/CDCl₃(1/1)) δ: 8.09 (1H, s), 7.95-7.69 (1H, m), 6.61 (1H, s), 4.37-4.11 (1H, m), 4.04 (3H, s), 4.00 (1H, d, J = 11.4 Hz), 3.86 (1H, d, J = 11.7 Hz), 3.68-3.49 (2H, m), 3.18-3.13 (1H, m), 2.00-1.81 (2H, m), 1.76 (9H, s). LC/MS (a) Rt = 0.73 min; m/z [M + H]⁺ 456. |

TABLE 39-continued

| Example No. | Structural formula | Physical property |
|---|---|---|
| 139 | 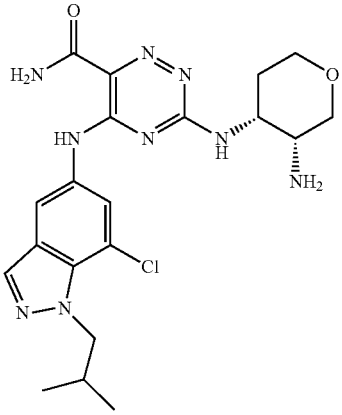 [SMILES: CC(C)Cn1ncc2cc(Nc3nc(N[C@@H]4CCOC[C@@H]4N)nnc3C(N)=O)cc(Cl)c21] | ¹H-NMR (CD₃OD/CDCl₃(1/1)) δ: 8.01 (1H, s), 7.99-7.81 (1H, m), 7.93-7.61 (1H, m), 4.56 (2H, d, J = 7.7 Hz), 4.40-4.06 (1H, m), 4.04-3.98 (1H, m), 3.93-3.85 (1H, m), 3.72-3.65 (1H, m), 3.60-3.52 (1H, m), 3.20-3.11 (1H, m), 2.37-2.26 (1H, m), 2.03-1.89 (1H, m), 1.87-1.80 (1H, m), 0.94 (6H, d, J = 6.6 Hz). LC/MS (a) Rt = 0.84 min; m/z [M + H]⁺ 460. |
| 140 | 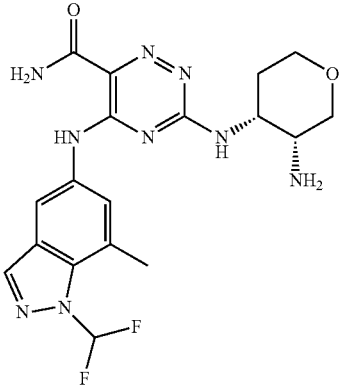 [SMILES: Cc1cc(Nc2nc(N[C@@H]3CCOC[C@@H]3N)nnc2C(N)=O)cc2cnn(C(F)F)c12] | ¹H-NMR (CD₃OD/CDCl₃(1/1)) δ: 8.46-8.05 (1H, m), 8.12 (1H, s), 7.68 (1H, t, J = 60.0 Hz), 7.52-7.36 (1H, m), 4.29-4.09 (1H, m), 4.05-3.99 (1H, m), 3.91-3.87 (1H, m), 3.70-3.59 (1H, m), 3.57-3.49 (1H, m), 3.19-3.12 (1H, m), 2.71 (3H, s), 2.01-1.89 (1H, m), 1.87-1.80 (1H, m). LC/MS (a) Rt = 0.76 min; m/z [M + H]⁺ 434. |

TABLE 40

| Example No. | Structural formula | Physical property |
|---|---|---|
| 141 | 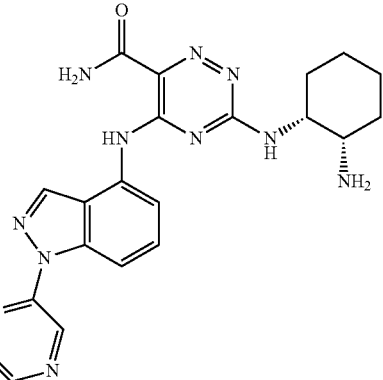 | ¹H-NMR (DMSO-d₆) δ: 12.26-12.18 (1H, m), 9.31 (1H, s), 8.63-8.61 (1H, m), 8.57 (1H, d, J = 2.4 Hz), 8.48 (1H, s), 8.38 (1H, s), 8.35 (1H, d, J = 8.5 Hz), 8.18-8.14 (1H, m), 7.89-7.82 (2H, m), 7.58 (1H, t, J = 8.0 Hz), 4.16-3.69 (1H, m), 3.17-3.07 (1H, m), 1.78-1.42 (8H, m), 1.37-1.21 (2H, m). LC/MS (b) Rt = 1.11 min; m/z [M + H]⁺ 446. |

TABLE 40-continued
| Example No. | Structural formula | Physical property |
|---|---|---|
| 142 | 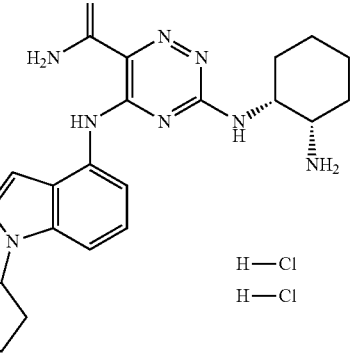 | LC/MS (a) Rt = 0.76 min; m/z [M + H]⁺ 451. |
| 143 | 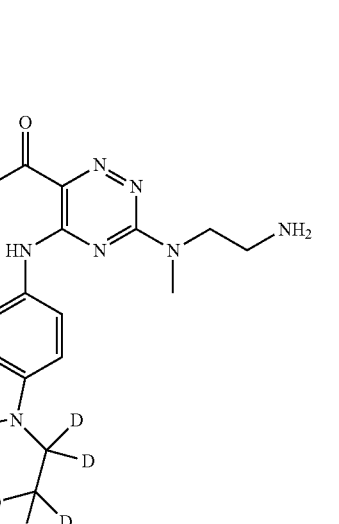 | LC/MS (a) Rt = 0.64 min; m/z [M + H]⁺ 361. |
| 144 | 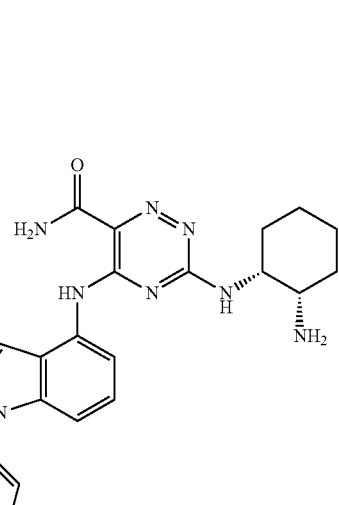 | $^1$H-NMR (DMSO-$d_6$) δ: 12.08-11.96 (1H, m), 8.86 (1H, d, J = 2.7 Hz), 8.63 (1H, dd, J = 4.6, 1.0 Hz), 8.43 (1H, br s), 8.21 (1H, d, J = 7.3 Hz), 8.11-8.07 (1H, m), 7.84-7.72 (2H, m), 7.80 (1H, d, J = 3.2 Hz), 7.63 (1H, dd, J = 8.2, 4.8 Hz), 7.31 (1H, d, J = 8.3 Hz), 7.23 (1H, t, J = 8.0 Hz), 6.78 (1H, d, J = 3.4 Hz), 4.15-3.78 (2H, m), 3.17-3.11 (1H, m), 1.79-1.51 (8H, m), 1.38-1.26 (2H, m). LC/MS (b) Rt = 1.02 min; m/z [M + H]⁺ 444. |

TABLE 40-continued

| Example No. | Structural formula | Physical property |
| --- | --- | --- |
| 145 | 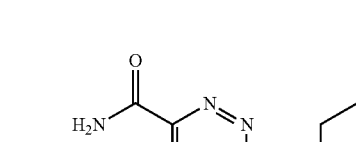 | ¹H-NMR (DMSO-d₆) δ: 12.11-11.96 (1H, m), 8.49-8.40 (1H, m), 8.31-8.22 (1H, m), 8.09-8.03 (1H, m), 7.98 (1H, d, J = 3.7 Hz), 7.85-7.74 (2H, m), 7.71 (1H, t, J = 2.1 Hz), 7.57 (1H, dd, J = 3.5, 0.6 Hz), 7.37 (1H, t, J = 8.2 Hz), 6.81 (1H, d, J = 3.7 Hz), 4.16-3.76 (1H, m), 3.17-3.11 (1H, m), 1.82-1.47 (8H, m), 1.38-1.26 (2H, m).<br>LC/MS (b) Rt = 1.19 min; m/z [M + H]⁺ 450. |

TABLE 41

| Example No. | Structural formula | Physical property |
| --- | --- | --- |
| 146 | | ¹H-NMR (DMSO-d₆) δ: 12.26-12.16 (1H, m), 8.48 (1H, s), 8.35 (1H, s), 8.23 (1H, d, J = 7.8 Hz), 8.16-8.10 (1H, m), 7.92-7.80 (2H, m), 7.73 (1H, d, J = 3.4 Hz), 7.63 (1H, t, J = 8.2 Hz), 7.52 (1H, d, J = 3.4 Hz), 4.17-3.67 (1H, m), 3.16-3.06 (1H, m), 1.85-1.43 (8H, m), 1.36-1.19 (2H, m).<br>LC/MS ( ) Rt = 1.22 min; m/z [M + H]⁺ 451. |
| 147 | | ¹H-NMR (CD₃OD/CDCl₃(1/1)) δ: 8.72-8.39 (1H, m), 8.58 (1H, s), 7.91 (2H, d, J = 8.1 Hz), 7.75 (1H, d, J = 9.2 Hz), 7.57 (2H, d, J = 8.1 Hz), 7.46 (1H, t, J = 7.7 Hz), 7.13 (1H, br s), 4.37-4.19 (1H, m), 3.30-3.25 (1H, m), 1.89-1.45 (8H, m).<br>LC/MS (a) Rt = 0.84 min; m/z [M + H]⁺ 444. |

TABLE 41-continued
| Example No. | Structural formula | Physical property |
|---|---|---|
| 148 | 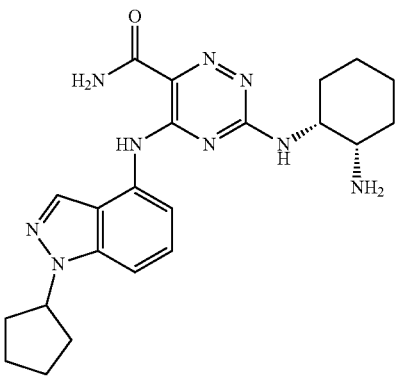 [SMILES: NC(=O)c1nnc(N[C@@H]2CCCC[C@@H]2N)nc1Nc1cccc2c1cnn2C1CCCC1] | ¹H-NMR (CD₃OD/CDCl₃(1/1)) δ: 8.13 (1H, s), 7.98 (1H, d, J = 7.6 Hz), 7.37 (1H, dd, J = 8.3, 7.6 Hz), 7.25 (1H, d, J = 8.3 Hz), 5.05-4.96 (1H, m), 4.06-3.93 (1H, m), 3.25-3.16 (1H, m), 2.23-1.93 (7H, m), 1.84-1.38 (9H, m). LC/MS (a) Rt = 0.9 min; m/z [M + H]⁺ 436. |
| 149 | 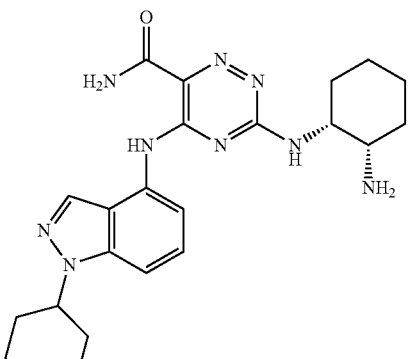 | ¹H-NMR (CD₃OD/CDCl₃(1/1)) δ: 8.14 (1H, s), 7.98 (1H, d, J = 7.3 Hz), 7.37 (1H, dd, J = 8.5, 7.3 Hz), 7.25 (1H, d, J = 8.5 Hz), 4.47-4.37 (1H, m), 4.06-3.94 (1H, m), 3.26-3.17 (1H, m), 2.12-1.32 (18H, m). LC/MS (a) Rt = 0.94 min; m/z [M + H]⁺ 450. |
| 150 | 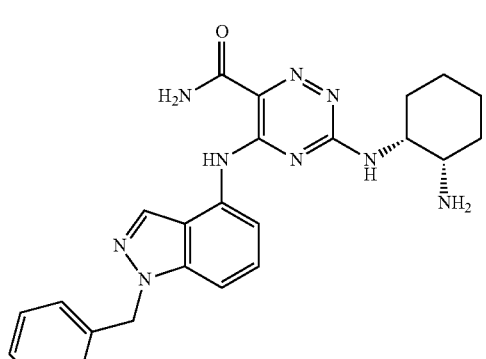 | ¹H-NMR (CD₃OD/CDCl₃(1/1)) δ: 8.20 (1H, s), 8.05-7.94 (1H, m), 7.38-7.10 (7H, m), 5.62 (2H, s), 4.01-3.90 (1H, m), 3.26-3.14 (1H, m), 2.03-1.34 (8H, m). LC/MS (a) Rt = 0.88 min; m/z [M + H]⁺ 458. |

TABLE 42

| Example No. | Structural formula | Physical property |
|---|---|---|
| 151 | (structure) | ¹H-NMR (CD₃OD/CDCl₃(1/1)) δ: 8.54 (1H, d, J = 2.2 Hz), 8.49 (1H, dd, J = 4.9, 1.5 Hz), 8.22 (1H, s), 8.09-8.00 (1H, m), 7.54-7.49 (1H, m), 7.42-7.35 (1H, m), 7.29-7.24 (1H, m), 7.14 (1H, d, J = 8.3 Hz), 5.63 (2H, s), 4.03-3.92 (1H, m), 3.26-3.15 (1H, m), 1.86-1.35 (8H, m).<br>LC/MS (a) Rt = 0.69 min; m/z [M + H]⁺ 459. |
| 152 | (structure) | ¹H-NMR (DMSO-d₆) δ: 11.43 (1H, s), 8.42-8.27 (2H, m), 7.96 (1H, s), 7.75-7.61 (2H, m), 7.48 (1H, br d, J = 8.4 Hz), 4.43 (2H, q, J = 7.2 Hz), 3.79-3.69 (1H, m), 3.15-3.09 (1H, m), 1.84-1.45 (6H, m), 1.43-1.24 (5H, m).<br>LC/MS (a) Rt = 0.74 min; m/z [M + H]⁺ 396. |
| 153 | (structure) | LC/MS (a) Rt = 0.59 min; m/z [M + H]⁺ 365. |
| 154 | (structure) | ¹H-NMR (CD₃OD) δ: 8.23 (1H, s), 7.96 (1H, br s), 7.72 (1H, d, J = 8.8 Hz), 7.23 (1H, br d, J = 8.8 Hz), 4.46 (2H, br q, J = 7.2 Hz), 4.29-4.16 (1H, m), 3.24-3.11 (1H, m), 1.75-1.61 (6H, m), 1.55-1.42 (5H, m).<br>LC/MS (a) Rt = 0.76 min; m/z [M + H]⁺ 396. |

TABLE 42-continued

| Example No. | Structural formula | Physical property |
|---|---|---|
| 155 | (structure) | LC/MS (a) Rt = 0.69 min; m/z [M + H]⁺ 382. |

TABLE 43

| Example No. | Structural formula | Physical property |
|---|---|---|
| 156 | (structure) | LC/MS (a) Rt = 0.71 min; m/z [M + H]⁺ 367. |
| 157 | (structure) | $^1$H-NMR (CD$_3$OD/CDCl$_3$(1/1)) δ: 8.36-8.21 (1H, m), 7.70 (1H, d, J = 8.1 Hz), 7.59-7.54 (2H, m), 7.45-7.36 (1H, m), 4.15-3.81 (1H, m), 3.20 (1H, d, J = 10.6 Hz), 2.93 (1H, d, J = 12.8 Hz), 2.70-2.57 (2H, m), 2.14-2.04 (1H, m), 1.86-1.75 (1H, m), 1.69-1.53 (2H, m). LC/MS (a) Rt = 0.74 min; m/z [M + H]⁺ 370. |
| 158 | (structure) | LC/MS (a) Rt = 0.73 min; m/z [M + H]⁺ 383. |

TABLE 43-continued
| Example No. | Structural formula | Physical property |
| --- | --- | --- |
| 159 | 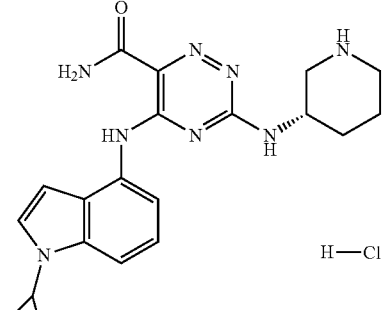 | LC/MS (a) Rt = 0.78 min; m/z [M + H]⁺ 393. |
| 160 | | LC/MS (a) Rt = 0.80 min; m/z [M + H]⁺ 409. |
TABLE 44
| Example No. | Structural formula | Physical property |
| --- | --- | --- |
| 161 | 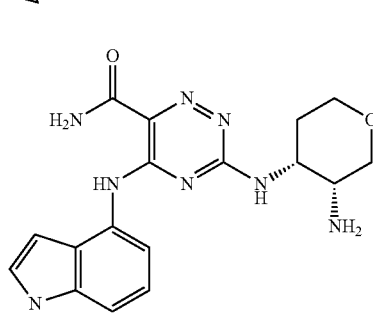 | LC/MS (a) Rt = 0.98 min; m/z [M + H]⁺ 384. |
| 162 | | LC/MS (a) Rt = 0.81 min; m/z [M + H]⁺ 386. |

TABLE 44-continued

| Example No. | Structural formula | Physical property |
|---|---|---|
| 163 | | LC/MS (a) Rt = 0.68 min; m/z [M + H]⁺ 379. |
| 164 | | ¹H-NMR (CD₃OD) δ: 7.63 (2H, d, J = 7.3 Hz), 7.37 (2H, t, J = 7.7 Hz), 7.28-7.22 (3H, m), 4.33-4.27 (1H, m), 3.29-3.26 (1H, m), 1.87-1.46 (8H, m). LC/MS (a) Rt = 0.88 min; m/z [M + H]⁺ 410. |
| 165 | | ¹H-NMR (CD₃OD/CDCl₃(1/1)) δ: 8.75 (1H, s), 8.11 (1H, s), 7.78 (1H, d, J = 8.8 Hz), 7.61 (1H, t, J = 58.7 Hz), 7.29-7.22 (1H, m), 4.33-4.25 (1H, m), 3.25-3.09 (1H, m), 1.92-1.43 (8H, m). LC/MS (a) Rt = 0.89 min; m/z [M + H]⁺ 418. |

TABLE 45

| Example No. | Structural formula | Physical property |
|---|---|---|
| 166 | | ¹H-NMR (CD₃OD/CDCl₃(1/1)) δ: 8.25-7.99 (1H, m), 7.51 (1H, t, J = 60.1 Hz), 7.45 (1H, d, J = 8.1 Hz), 7.42 (1H, d, J = 3.7 Hz), 7.30 (1H, t, J = 8.2 Hz), 6.78 (1H, d, J = 3.7 Hz), 4.28-4.06 (1H, m), 4.00 (1H, d, J = 11.0 Hz), 3.86 (1H, d, J = 10.3 Hz), 3.68-3.48 (2H, m), 3.18-3.09 (1H, m), 1.86-1.79 (1H, m). LC/MS (a) Rt = 0.76 min; m/z [M + H]⁺ 419. |

TABLE 45-continued

| Example No. | Structural formula | Physical property |
|---|---|---|
| 167 | | LC/MS (a) Rt = 0.65 min; m/z [M + H]+ 403. |
| 168 | | LC/MS (a) Rt = 0.80 min; m/z [M + H]+ 434. |
| 169 | | LC/MS (a) Rt = 0.68 min; m/z [M + H]+ 403. |
| 170 | | LC/MS (a) Rt = 0.73 min; m/z [M + H]+ 420. |

TABLE 46

| Example No. | Structural formula | Physical property |
|---|---|---|
| 171 | | LC/MS (a) Rt = 0.76 min; m/z [M + H]+ 449. |
| 172 | | ¹H-NMR (CD₃OD) δ: 9.25-8.81 (2H, m), 8.02 (1H, d, J = 8.8 Hz), 7.98-7.88 (1H, m), 7.72 (1H, t, J = 7.7 Hz), 7.64 (1H, t, J = 7.1 Hz), 4.38-4.06 (1H, m), 3.28-3.22 (1H, m), 1.94-1.81 (1H, m), 1.81-1.64 (5H, m), 1.56-1.47 (2H, m).<br>LC/MS (a) Rt = 0.74 min; m/z [M + H]+ 379. |
| 173 | | ¹H-NMR (CD₃OD/CDCl₃(3/1)) δ: 8.22 (1H, br s), 7.95 (1H, s), 7.72 (1H, d, J = 8.8 Hz), 7.23 (1H, d, J = 8.4 Hz), 4.25-4.14 (1H, m), 4.09 (3H, s), 3.25-3.16 (1H, m), 1.98-1.80 (1H, m), 1.78-1.61 (5H, m), 1.55-1.44 (2H, m).<br>LC/MS (a) Rt = 0.73 min; m/z [M + H]+ 382. |
| 174 | | ¹H-NMR (CD₃OD) δ: 6.68 (1H, s), 6.63 (1H, s), 4.30-4.25 (1H, m), 3.14-3.05 (1H, m), 2.21 (3H, s), 1.77-1.61 (6H, m), 1.53-1.46 (2H, m).<br>LC/MS (a) Rt = 0.79 min; m/z [M + H]+ 348. |

TABLE 46-continued

| Example No. | Structural formula | Physical property |
|---|---|---|
| 175 | | ¹H-NMR (CD₃OD/CDCl₃(1/1) δ: 7.54-7.49 (2H, m), 7.47-7.41 (3H, m), 6.88-6.75 (1H, m), 4.21-4.02 (0H, m), 3.30-3.19 (1H, m), 2.38 (3H, s), 1.90-1.42 (0H, m) LC/MS (a) Rt = 0.82 min; m/z [M + H]⁺ 408. |

TABLE 47

| Example No. | Structural formula | Physical property |
|---|---|---|
| 176 | | ¹H-NMR (CD₃OD/CDCl₃(3/1)) δ: 8.86 (0.4H, br s), 8.56 (0.6H, br s), 7.97 (1H, br s), 7.72 (2H, br s), 7.50 (2H, t, J = 7.9 Hz), 7.33 (1H, t, J = 7.5 Hz), 4.32-4.08 (1H, m), 3.27-3.21 (1H, m), 1.91-1.59 (6H, m), 1.54-1.45 (2H, m). LC/MS (a) Rt = 0.79 min; m/z [M + H]⁺ 394. |
| 177 | | ¹H-NMR (CD₃OD) δ: 9.17 (1H, s), 8.38 (1H, br s), 8.01 (1H, d, J = 8.8 Hz), 7.61 (1H, br d, J = 8.8 Hz), 3.87-3.60 (1H, m), 2.00-1.52 (8H, m). LC/MS (a) Rt = 0.72 min; m/z [M + H]⁺ 385. |
| 178 | | ¹H-NMR (DMSO-d₆) δ: 11.92 (1H, s), 8.44 (1H, br s), 8.29 (1H, s), 7.85-7.72 (2H, m), 7.32 (1H, d, J = 8.4 Hz), 7.21 (1H, br t, J = 8.0 Hz), 4.19 (3H, s), 3.81-3.70 (1H, m), 3.15-3.08 (1H, m), 1.84-1.43 (6H, m), 1.38-1.20 (2H, m). LC/MS (a) Rt = 0.70 min; m/z [M + H]⁺ 382. |

TABLE 47-continued

| Example No. | Structural formula | Physical property |
|---|---|---|
| 179 | (structure) | $^1$H-NMR (DMSO-$d_6$) δ: 11.41 (1H, s), 8.35-8.21 (4H, m), 7.58 (1H, d, J = 8.8 Hz), 7.25 (1H, br d, J = 8.8 Hz), 4.15 (3H, s), 1.88-1.50 (6H, m), 1.45-1.28 (2H, m). LC/MS (a) Rt = 0.66 min; m/z [M + H]$^+$ 382. |
| 180 | (structure) | $^1$H-NMR (DMSO-$d_6$) δ: 11.53 (1H, s), 8.39-8.30 (3H, m), 8.26 (1H, s), 7.66 (1H, d, J= 8.8 Hz), 7.03-6.93 (1H, m), 4.12 (3H, s), 1.88-1.50 (6H, m), 1.46-1.29 (2H, m). LC/MS (a) Rt = 0.69 min; m/z [M + H]$^+$ 382. |

TABLE 48

| Example No. | Structural formula | Physical property |
|---|---|---|
| 181 | (structure) | $^1$H-NMR (DMSO-$d_6$) δ: 11.59 (1H, s), 8.40-8.30 (3H, m), 7.97 (1H, d, J = 8.8 Hz), 7.59-7.48 (1H, m), 2.78 (3H, s), 1.88-1.51 (6H, m), 1.44-1.29 (2H, m). LC/MS (a) Rt = 0.77 min; m/z [M + H]$^+$ 399. |

TABLE 48-continued

| Example No. | Structural formula | Physical property |
|---|---|---|
| 182 | 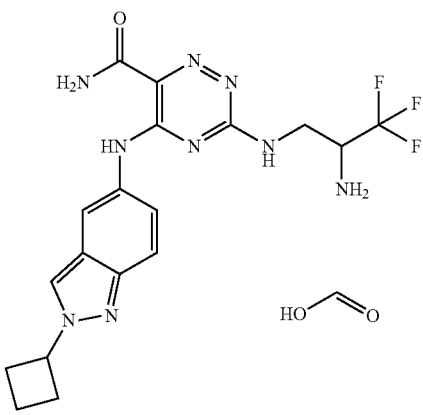 [SMILES: NC(=O)c1nnc(NCC(N)C(F)(F)F)nc1Nc1ccc2nn(C3CCC3)cc2c1 ; O=CO] | $^1$H-NMR (CD$_3$OD) δ: 8.19 (1H, br s), 8.12 (1H, s), 7.62 (1H, d, J = 8.8 Hz), 7.37 (1H, dd, J = 9.0, 2.0 Hz), 5.13 (1H, quin, J = 8.3 Hz), 3.90 (1H, dd, J = 13.9, 4.0 Hz), 3.69 (1H, br s), 2.79-2.52 (4H, m), 2.08-1.92 (2H, m) LC/MS (a) Rt = 0.79 min; m/z [M + H]$^+$ 436. |
| 183 | 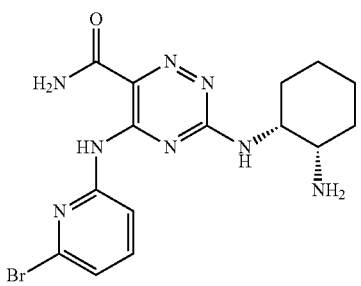 [SMILES: NC(=O)c1nnc(N[C@@H]2CCCC[C@@H]2N)nc1Nc1cccc(Br)n1] | $^1$H-NMR (CD$_3$OD/CDCl$_3$(5/1)) δ: 8.69-8.29 (1H, m), 7.67 (1H, t, J = 8.1 Hz), 7.27 (1H, d, J = 7.7 Hz), 4.36-4.03 (1H, br m), 3.23 (1H, q, J = 4.4 Hz), 1.89-1.61 (6H, m), 1.55-1.45 (2H, m). LC/MS (a) Rt = 0.68 min; m/z [M + H]$^+$ 369. |
| 184 | 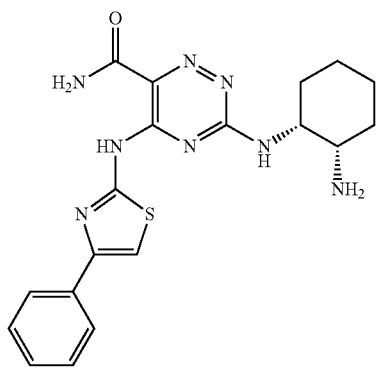 [SMILES: NC(=O)c1nnc(N[C@@H]2CCCC[C@@H]2N)nc1Nc1nc(-c2ccccc2)cs1] | $^1$H-NMR (CDCl$_3$) δ: 7.90 (2H, d, J = 7.3 Hz), 7.69 (1H, s), 7.43 (2H, t, J = 7.5 Hz), 7.33 (1H, t, J = 7.0 Hz), 7.23 (1H, s), 6.75 (1H, d, J = 7.0 Hz), 6.20 (0H, s), 5.64 (1H, s), 4.32-4.13 (1H, m), 3.29-3.23 (1H, m), 1.98-1.43 (8H, m). LC/MS (a) Rt = 0.86 min; m/z [M + H]$^+$ 412. |
| 185 | 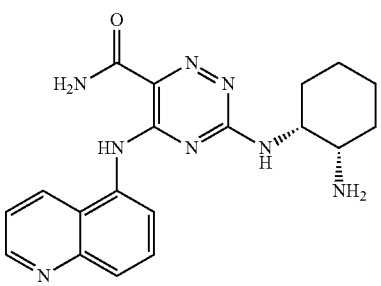 [SMILES: NC(=O)c1nnc(N[C@@H]2CCCC[C@@H]2N)nc1Nc1cccc2ncccc12] | $^1$H-NMR (DMSO-d$_6$) δ: 12.08 (1H, s), 8.95 (1H, dd, J = 3.9, 1.2 Hz), 8.56-8.31 (3H, m), 7.91-7.71 (4H, m), 7.64 (1H, dd, J = 8.8, 3.9 Hz), 3.58 (1H, s), 3.02 (1H, s), 1.75-1.24 (8H, m). LC/MS (a) Rt = 0.74 min; m/z [M + H]$^+$ 385. |

TABLE 49

| Example No. | Structural formula | Physical property |
| --- | --- | --- |
| 186 | | LC/MS (a) Rt = 0.70 min; m/z [M + H]+ 382. |
| 187 | | ¹H-NMR (DMSO-d₆) δ: 11.41 (1H, s), 8.39 (2H, br s), 8.32 (1H, s), 7.98 (1H, s), 7.73-7.62 (1H, m), 7.52-7.41 (1H, m), 5.04-4.90 (1H, m), 1.83-1.52 (6H, m), 1.47 (6H, d, J = 6.8 Hz), 1.41-1.25 (2H, m).<br>LC/MS (a) Rt = 0.78 min; m/z [M + H]+ 410. |
| 188 | | ¹H-NMR (CDCl₃) δ: 11.75 (1H, br s), 7.69 (1H, s), 6.83-6.72 (2H, m), 5.56 (1H, s), 4.32-4.15 (1H, m), 2.44 (3H, s), 1.99-1.89 (1H, m), 1.89-1.67 (3H, m), 1.67-1.43 (4H, m).<br>LC/MS (a) Rt = 0.83 min; m/z [M + H]+ 395. |
| 189 | | ¹H-NMR (DMSO-d₆) δ: 11.97 (1H, s), 8.60 (1H, d, J = 8.0 Hz), 8.46-8.35 (2H, m), 8.03-7.91 (2H, m), 7.86-7.77 (2H, m), 7.71 (1H, t, J = 7.7 Hz), 7.49 (1H, t, J = 7.4 Hz), 3.88 (1H, s), 3.24 (1H, s), 1.75-1.52 (6H, m), 1.37 (2H, s).<br>LC/MS (a) Rt = 0.76 min; m/z [M + H]+ 396. |

TABLE 49-continued

| Example No. | Structural formula | Physical property |
|---|---|---|
| 190 | (structure) | ¹H-NMR (CD₃OD) δ: 6.62 (1H, s), 6.58 (1H, s), 4.42-4.32 (1H, m), 3.28-3.22 (1H, m), 2.43 (3H, s), 1.92-1.53 (8H, m).<br>LC/MS (a) Rt = 0.76 min; m/z [M + H]⁺ 348. |

TABLE 50

| Example No. | Structural formula | Physical property |
|---|---|---|
| 191 | (structure) | ¹H-NMR (DMSO-d₆) δ: 8.63 (1H, s), 8.06 (1H, s), 7.67 (1H, d, J = 9.2 Hz), 7.20 (1H, s), 7.05 (1H, dd, J = 9.3, 3.1 Hz), 4.48-4.41 (2H, m), 4.25-4.13 (1H, m), 3.82 (3H, s), 3.26-3.22 (1H, m), 1.91-1.42 (8H, m).<br>LC/MS (a) Rt = 0.80 min; m/z [M + H]⁺ 415. |
| 192 | (structure) | ¹H-NMR(CD₃OD/CDCl₃(1/1)) δ: 8.22-8.17 (2H, m), 7.50-7.44 (3H, m), 4.55-4.48 (1H, m), 3.48-3.45 (1H, m), 2.00-1.55 (8H, m).<br>LC/MS (a) Rt = 0.86 min; m/z [M + H]⁺ 412. |
| 193 | (structure) | LC/MS (a) Rt = 0.79 min; m/z [M + H]⁺ 407, 409. |

TABLE 50-continued

| Example No. | Structural formula | Physical property |
|---|---|---|
| 194 | 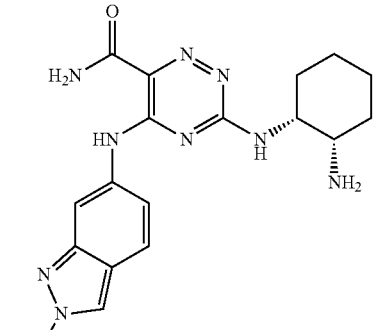 | ¹H-NMR (DMSO-d₆) δ: 11.65 (1H, s), 9.40 (1H, s), 8.81 (1H, d, J = 8.8 Hz), 8.35 (1H, s), 8.12 (1H, d, J = 8.8 Hz), 7.81-7.49 (3H, m), 4.17-4.03 (1H, m), 3.88-3.75 (1H, m), 1.83-1.45 (6H, m), 1.45-1.26 (2H, m). LC/MS (a) Rt = 0.74 min; m/z [M + H]⁺ 385. |
| 195 | | ¹H-NMR (DMSO-d₆) δ: 11.66 (1H, s), 8.78 (1H, s), 8.36 (1H, s), 7.92 (1H, d, J = 7.6 Hz), 7.88 (1H, d, J = 8.5 Hz), 7.78-7.63 (3H, m), 6.02 (1H, d, J = 7.6 Hz), 4.05 (1H, s), 3.81 (3H, s), 3.11 (1H, s), 1.77-1.41 (8H, m). LC/MS (a) Rt = 0.76 min; m/z [M + H]⁺ 396. |

TABLE 51

| Example No. | Structural formula | Physical property |
|---|---|---|
| 196 | 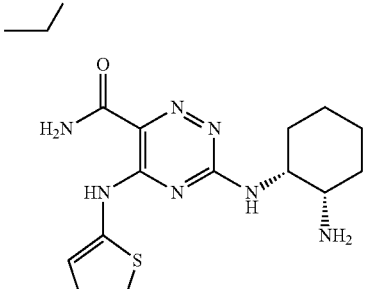 | ¹H-NMR (CD₃OD) δ: 8.33 (1H, br s), 8.19 (1H, s), 7.67 (1H, d, J = 8.8 Hz), 7.06 (1H, br d, J = 8.8 Hz), 4.47 (2H, q, J = 7.2 Hz), 4.30-4.16 (1H, m), 3.26-3.20 (1H, m), 1.94-1.62 (6H, m), 1.59 (3H, 5, J = 7.2 Hz), 1.56-1.40 (2H, m). LC/MS (a) Rt = 0.72 min; m/z [M + H]⁺ 396. |
| 197 | | ¹H-NMR (CD₃OD) δ: 6.59 (2H, s), 4.29-4.23 (1H, m), 3.27-3.22 (1H, m), 1.89-1.59 (7H, m), 1.55-1.43 (2H, m), 0.89-0.84 (2H, m), 0.63-0.59 (2H, m). LC/MS (a) Rt = 0.83 min; m/z [M + H]⁺ 374. |

TABLE 51-continued

| Example No. | Structural formula | Physical property |
|---|---|---|
| 198 | | ¹H-NMR (CD₃OD) δ: 7.66 (1H, d, J = 8.4 Hz), 7.49 (1H, d, J = 8.4 Hz), 7.42 (1H, t, J = 7.7 Hz), 7.12 (1H, t, J = 7.3 Hz), 4.34-3.67 (1H, m), 4.00 (3H, s), 3.14-2.80 (1H, m), 1.76-1.08 (8H, m).<br>LC/MS (a) Rt = 0.78 min; m/z [M + H]⁺ 382. |
| 199 | | ¹H-NMR (DMSO-d₆) δ: 12.08 (1H, s), 8.37 (1H, d, J = 7.8 Hz), 8.26 (1H, s), 8.19 (1H, s), 7.73 (1H, d, J = 6.1 Hz), 7.58 (1H, s), 7.29-7.22 (2H, m), 3.85 (3H, s), 3.17 (1H, s), 1.84-1.51 (6H, m), 1.41-1.27 (2H, m).<br>LC/MS (a) Rt = 0.66 min; m/z [M + H]⁺ 382. |
| 200 | | ¹H-NMR (DMSO-d₆) δ: 12.07 (1H, s), 8.38-8.30 (2H, m), 8.26 (1H, s), 7.72 (1H, d, J = 7.8 Hz), 7.58 (1H, s), 7.35 (1H, d, J = 8.3 Hz), 7.21 (1H, t, J = 8.0 Hz), 4.78-4.71 (1H, m), 3.83 (1H, s), 3.16 (1H, s), 1.79-1.56 (6H, m), 1.54 (6H, d, J = 6.6 Hz), 1.34 (2H, s).<br>LC/MS (a) Rt = 0.73 min; m/z [M + H]⁺ 410. |

TABLE 52

| Example No. | Structural formula | Physical property |
|---|---|---|
| 201 | 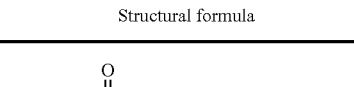 | ¹H-NMR (CD₃OD) δ: 8.64-8.37 (1H, m), 7.47-7.36 (2H, m), 4.36-4.03 (1H, m), 3.30-3.23 (1H, m), 1.86-1.44 (8H, m).<br>LC/MS (a) Rt = 0.75 min; m/z [M + H]⁺ 369. |

TABLE 52-continued

| Example No. | Structural formula | Physical property |
| --- | --- | --- |
| 202 | | ¹H-NMR (CD₃OD) δ: 8.49-8.11 (0H, m), 7.77 (1H, d, J = 2.2 Hz), 7.33 (1H, d, J = 7.7 Hz), 7.16 (1H, t, J = 7.9 Hz), 6.84 (1H, d, J = 2.2 Hz), 4.31-3.87 (0H, m), 3.24-3.13 (0H, m), 1.88-1.35 (8H, m). LC/MS (a) Rt = 0.79 min; m/z [M + H]⁺ 368. |
| 203 | | ¹H-NMR (CD₃OD) δ: 8.35-8.00 (1H, m), 7.19 (1H, d, J = 7.7 Hz), 7.10 (1H, t, J = 7.9 Hz), 6.43 (1H, s), 4.28-3.84 (1H, m), 3.21-3.13 (1H, m), 2.45 (3H, s), 1.83-1.37 (8H, m). LC/MS (a) Rt = 0.83 min; m/z [M + H]⁺ 382. |
| 204 | | ¹H-NMR (DMSO-d₆) δ: 11.67 (1H, s), 8.42 (1H, s), 8.16 (1H, d, J = 7.3 Hz), 7.87-7.67 (3H, m), 7.49 (1H, t, J = 7.9 Hz), 3.67 (1H, s), 3.05 (1H, s), 2.82 (3H, s), 1.77-1.37 (7H, m), 1.30 (1H, s). LC/MS (a) Rt = 0.74 min; m/z [M + H]⁺ 399. |
| 205 | | ¹H-NMR (DMSO-d₆) δ: 11.82 (1H, s), 8.38 (1H, s), 8.06 (1H, d, J = 7.3 Hz), 7.68 (1H, s), 7.41-7.25 (1H, m), 7.15 (1H, d, J = 8.0 Hz), 7.05 (1H, t, J = 7.7 Hz), 6.28 (1H, s), 3.81 (1H, s), 3.66 (3H, s), 3.14 (1H, s), 2.43 (3H, s), 1.81-1.43 (6H, m), 1.39-1.20 (2H, m). LC/MS (a) Rt = 0.83 min; m/z [M + H]⁺ 395. |

TABLE 53

| Example No. | Structural formula | Physical property |
| --- | --- | --- |
| 206 | | LC/MS (a) Rt = 0.90 min; m/z [M + H]⁺ 368. |

TABLE 53-continued

| Example No. | Structural formula | Physical property |
| --- | --- | --- |
| 207 | | LC/MS (a) Rt = 0.81 min; m/z [M + H]⁺ 367. |
| 208 | | ¹H-NMR (DMSO-d₆) δ: 12.47 (1H, s), 8.72 (1H, s), 8.53 (1H, s), 8.39 (1H, s), 8.22 (1H, d, J = 5.6 Hz), 7.97 (1H, s), 7.87 (1H, s), 7.59 (1H, d, J = 5.4 Hz), 3.81 (1H, s), 3.18 (1H, s), 1.80-1.52 (6H, m), 1.39-1.30 (2H, m). LC/MS (a) Rt = 0.84 min; m/z [M + H]⁺ 409. |
| 209 | | ¹H-NMR (CD₃OD/CDCl₃(1/1)) δ: 8.34-8.10 (1H, m), 8.28 (1H, s), 7.64 (1H, t, J = 59.0 Hz), 7.57-7.53 (2H, m), 4.44-3.95 (1H, m), 3.25-3.19 (1H, m), 1.86-1.39 (8H, m). LC/MS (a) Rt = 0.78 min; m/z [M + H]⁺ 418. |
| 210 | | ¹H-NMR (CD₃OD/CDCl₃(1/1)) δ: 9.18 (1H, d, J = 9.5 Hz), 8.06 (1H, s), 7.60 (1H, s), 7.55-7.42 (4H, m), 4.36-3.92 (1H, m), 3.14-3.03 (1H, m), 1.83-1.25 (8H, m). LC/MS (a) Rt = 0.85 min; m/z [M + H]⁺ 423. |

TABLE 54

| Example No. | Structural formula | Physical property |
| --- | --- | --- |
| 211 | | LC/MS (a) Rt = 0.76 min; m/z [M + H]⁺ 385. |
| 212 | | ¹H-NMR (CD₃OD/CDCl₃(1/1)) δ: 8.42-7.98 (1H, m), 7.92-7.84 (2H, m), 7.52-7.40 (2H, m), 4.40-4.03 (1H, m), 3.28-3.18 (1H, m), 1.98-1.45 (8H, m). LC/MS (a) Rt = 0.84 min; m/z [M + H]⁺ 384. |
| 213 | | ¹H-NMR (DMSO-d₆) δ: 12.32 (1H, s), 8.44 (1H, s), 8.00-7.75 (3H, m), 7.67 (1H, d, J = 7.8 Hz), 7.37 (1H, t, J = 7.4 Hz), 7.26 (1H, t, J = 7.6 Hz), 4.04 (1H, s), 3.22 (1H, s), 2.36 (3H, s), 1.82-1.54 (6H, m), 1.49-1.34 (2H, m). LC/MS (a) Rt = 0.90 min; m/z [M + H]⁺ 398. |
| 214 | | ¹H-NMR (CD₃OD/CDCl₃(1/1)) δ: 9.46-9.22 (1H, m), 9.11 (1H, s), 7.55-7.26 (1H, m), 7.51 (1H, d, J = 8.1 Hz), 7.27 (1H, s), 4.61-4.40 (0H, m), 3.23-3.15 (1H, m), 2.31 (3H, d, J = 1.1 Hz), 1.84-1.41 (8H, m). LC/MS (a) Rt = 0.80 min; m/z [M + H]⁺ 409. |

TABLE 54-continued

| Example No. | Structural formula | Physical property |
|---|---|---|
| 215 | (structure) | ¹H-NMR (DMSO-d₆) δ: 12.46 (1H, s), 8.38 (1H, s), 8.04-7.88 (1H, m), 7.85-7.73 (3H, m), 7.37 (1H, t, J = 7.6 Hz), 7.25 (1H, t, J = 7.6 Hz), 4.07 (1H, s), 3.23 (1H, s), 1.84-1.37 (8H, m), 1.22 (1H, s), 1.15 (2H, d, J = 8.0 Hz), 0.63 (2H, d, J = 4.6 Hz). LC/MS (a) Rt = 0.95 min; m/z [M + H]⁺ 424. |

TABLE 55

| Example No. | Structural formula | Physical property |
|---|---|---|
| 216 | (structure) | ¹H-NMR (CD₃OD/CDCl₃(9/1)) δ: 8.22-8.15 (1H, m), 7.58-7.50 (1H, m), 7.47 (1H, d, J = 8.8 Hz), 4.25-4.05 (1H, m), 3.99 (3H, s), 3.22-3.12 (1H, m), 2.56 (3H, s), 1.91-1.40 (8H, m). LC/MS (a) Rt = 0.70 min; m/z [M + H]⁺ 396. |
| 217 | (structure) | ¹H-NMR(CD₃OD/CDCl₃(1/1)) δ: 8.79-8.54 (1H, m), 8.30 (1H, d, J = 5.9 Hz), 8.23 (1H, d, J = 8.4 Hz), 7.95 (1H, d, J = 5.9 Hz), 7.79 (1H, t, J = 8.2 Hz), 4.37-3.79 (1H, m), 3.24-3.07 (1H, m), 1.83-1.32 (8H, m). LC/MS (a) Rt = 0.81 min; m/z [M + H]⁺ 413415. |
| 218 | (structure) | ¹H-NMR (CD₃OD/CDCl₃(1/1)) δ: 8.59-8.43 (1H, m), 8.13 (1H, d, J = 8.1 Hz), 8.03 (1H, d, J = 6.2 Hz), 7.60 (1H, t, J = 8.1 Hz), 7.48 (1H, d, J = 6.2 Hz), 4.35-3.84 (1H, m), 4.15 (3H, s), 3.24-3.07 (1H, m), 1.86-1.34 (0H, m). LC/MS (a) Rt = 0.78 min; m/z [M + H]⁺ 409. |

TABLE 55-continued
| Example No. | Structural formula | Physical property |
|---|---|---|
| 219 | 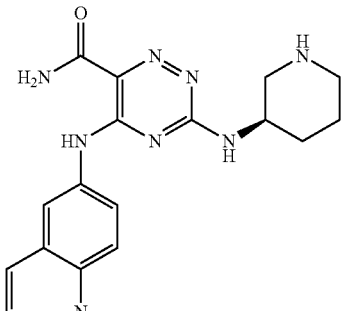 | ¹H-NMR (CD₃OD/CDCl₃(1/1)) δ: 8.68-8.48 (1H, m), 8.36 (1H, d, J = 6.2 Hz), 8.06 (1H, d, J = 8.4 Hz), 7.85 (1H, d, J = 5.9 Hz), 7.71 (1H, t, J = 8.1 Hz), 4.35-3.81 (1H, m), 3.23-3.09 (1H, m), 3.00 (3H, s), 1.86-1.33 (8H, m). LC/MS (a) Rt = 0.59 min; m/z [M + H]⁺ 393. |
| 220 | | ¹H-NMR (CD₃OD/CDCl₃(1/1)) δ: 8.35 (1H, d, J = 1.8 Hz), 7.86 (1H, d, J = 8.8 Hz), 7.56 (1H, d, J = 5.5 Hz), 7.52 (1H, dd, J = 8.6, 2.0 Hz), 7.34 (1H, br s), 4.35-4.00 (1H, m), 3.27-3.20 (1H, m), 1.82-1.43 (8H, m). LC/MS (a) Rt = 0.82 min; m/z [M + H]⁺ 384. |
TABLE 56
| Example No. | Structural formula | Physical property |
|---|---|---|
| 221 | 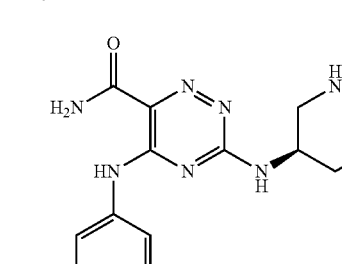 | LC/MS (a) Rt = 0.59 min; m/z [M + H]⁺ 365. |
| 222 | | LC/MS (a) Rt = 0.69 min; m/z [M + H]⁺ 382. |

TABLE 56-continued
| Example No. | Structural formula | Physical property |
|---|---|---|
| 223 | 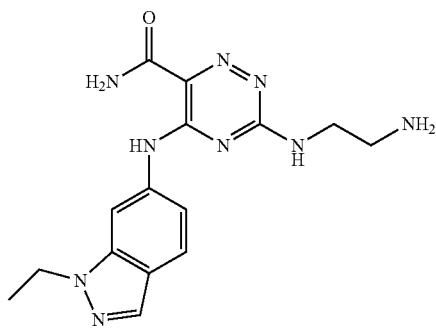 [SMILES: CCn1ncc2ccc(Nc3nc(NCCN)nnc3C(N)=O)cc21] | LC/MS (a) Rt = 0.67 min; m/z [M + H]+ 342. |
| 224 | 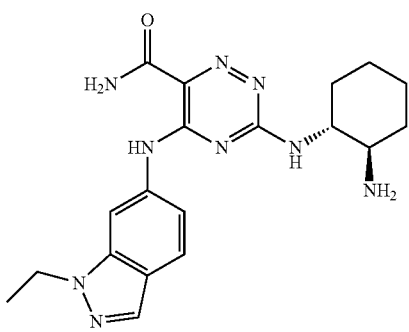 [SMILES: CCn1ncc2ccc(Nc3nc(N[C@@H]4CCCC[C@H]4N)nnc3C(N)=O)cc21] | LC/MS (a) Rt = 0.76 min; m/z [M + H]+ 396. |
| 225 | 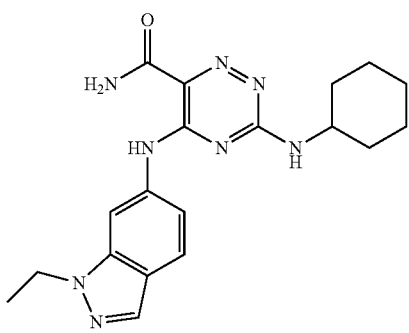 [SMILES: CCn1ncc2ccc(Nc3nc(NC4CCCCC4)nnc3C(N)=O)cc21] | LC/MS (a) Rt = 0.76 min; m/z [M + H]+ 381. |
TABLE 57
| Example No. | Structural formula | Physical property |
|---|---|---|
| 226 | 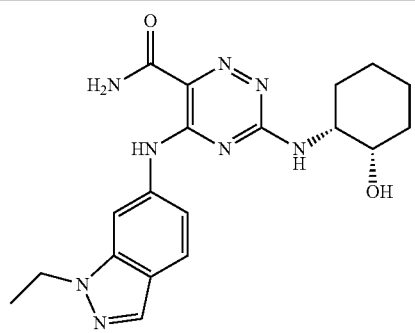 [SMILES: CCn1ncc2ccc(Nc3nc(N[C@@H]4CCCC[C@@H]4O)nnc3C(N)=O)cc21] | LC/MS (a) Rt = 0.87 min; m/z [M + H]+ 397. |

TABLE 57-continued

| Example No. | Structural formula | Physical property |
| --- | --- | --- |
| 227 | | LC/MS (a) Rt = 0.72 min; m/z [M + H]+ 381. |
| 228 | | LC/MS (a) Rt = 0.70 min; m/z [M + H]+ 355. |
| 229 | | LC/MS (a) Rt = 0.67 min; m/z [M + H]+ 381. |
| 230 | | LC/MS (a) Rt = 0.72 min; m/z [M + H]+ 381. |

TABLE 58

| Example No. | Structural formula | Physical property |
|---|---|---|
| 231 | (structure shown) · HCl | LC/MS (a) Rt = 0.71 min; m/z [M + H]⁺ 367. |
| 232 | (structure shown) | LC/MS (a) Rt = 0.71 min; m/z [M + H]⁺ 367. |
| 233 | (structure shown) | LC/MS (a) Rt = 0.70 min; m/z [M + H]⁺ 353. |
| 234 | (structure shown) | LC/MS (a) Rt = 0.70 min; m/z [M + H]⁺ 353. |

TABLE 58-continued
| Example No. | Structural formula | Physical property |
|---|---|---|
| 235 | 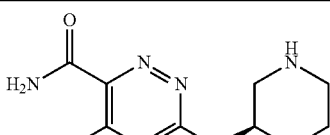 | LC/MS (a) Rt = 0.66 min; m/z [M + H]⁺ 387. |
TABLE 59
| Example No. | Structural formula | Physical property |
|---|---|---|
| 236 | | LC/MS (a) Rt = 0.71 min; m/z [M + H]⁺ 387. |
| 237 | 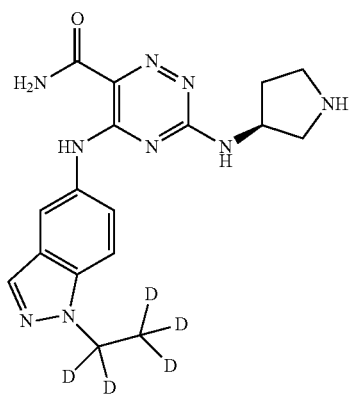 [SMILES: [2H]C([2H])([2H])C([2H])([2H])n1ncc2cc(Nc3nc(N[C@H]4CCNC4)nnc3C(N)=O)ccc21] | LC/MS (a) Rt = 0.65 min; m/z [M + H]⁺ 373. |

TABLE 59-continued
| Example No. | Structural formula | Physical property |
| --- | --- | --- |
| 238 | 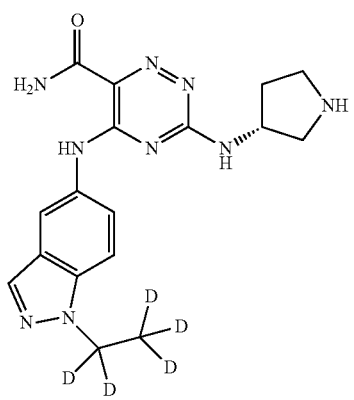 [SMILES: [2H]C([2H])([2H])C([2H])([2H])n1ncc2cc(Nc3nc(N[C@@H]4CCNC4)nnc3C(N)=O)ccc21] | LC/MS (a) Rt = 0.65 min; m/z [M + H]$^+$ 373. |
| 239 | 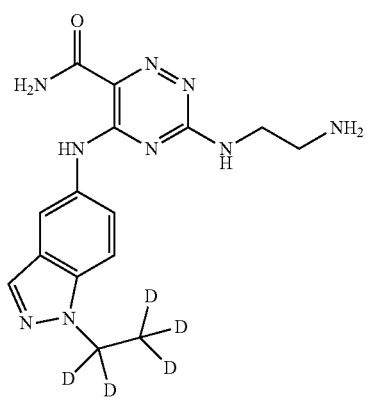 [SMILES: [2H]C([2H])([2H])C([2H])([2H])n1ncc2cc(Nc3nc(NCCN)nnc3C(N)=O)ccc21] | LC/MS (a) Rt = 0.63 min; m/z [M + H]$^+$ 347. |
| 240 | 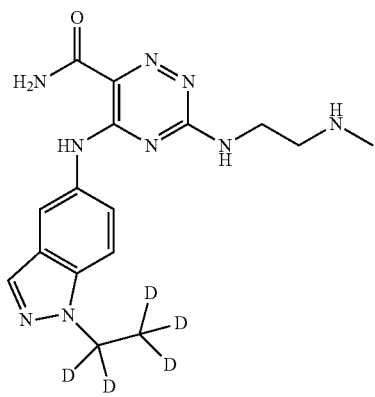 [SMILES: [2H]C([2H])([2H])C([2H])([2H])n1ncc2cc(Nc3nc(NCCNC)nnc3C(N)=O)ccc21] | LC/MS (a) Rt = 0.61 min; m/z [M + H]$^+$ 361. |

TABLE 60

| Example No. | Structural formula | Physical property |
|---|---|---|
| 241 | | LC/MS (a) Rt = 0.66 min; m/z [M + H]+ 401. |
| 242 | | LC/MS (a) Rt = 0.66 min; m/z [M + H]+ 401. |
| 243 | | LC/MS (a) Rt = 0.68 min; m/z [M + H]+ 491. |
| 244 | | LC/MS (a) Rt = 0.73 min; m/z [M + H]+ 491. |

TABLE 60-continued

| Example No. | Structural formula | Physical property |
|---|---|---|
| 245 | (structure) | ¹H-NMR (CD₃OD/CDCl₃(3/1)) δ: 8.48-8.18 (1H, m), 7.69 (1H, d, J = 7.7 Hz), 7.60 (1H, d, J = 5.5 Hz), 7.53 (1H, d, J = 5.5 Hz), 7.36 (1H, t, J = 8.1 Hz), 3.63-3.49 (1H, m), 3.19-3.08 (1H, m), 3.01-2.87 (1H, m), 1.65-1.31 (2H, m), 1.10-0.90 (3H, m). LC/MS (a) Rt = 0.78 min; m/z [M + H]⁺ 358. |

TABLE 61

| Example No. | Structural formula | Physical property |
|---|---|---|
| 246 | (structure) | ¹H-NMR (CD₃OD/CDCl₃(3/1)) δ: 8.47-8.23 (1H, m), 7.69 (1H, d, J = 8.1 Hz), 7.60 (1H, d, J = 5.9 Hz), 7.55 (1H, t, J = 3.1 Hz), 7.38 (1H, t, J = 7.9 Hz), 4.32-3.98 (1H, m), 2.83-2.74 (2H, m), 1.27 (3H, d, J = 6.6 Hz). LC/MS (a) Rt = 0.76 min; m/z [M + H]⁺ 344. |
| 247 | (structure) | ¹H-NMR (CD₃OD/CDCl₃(3/1)) δ: 8.43-8.23 (1H, m), 7.71 (1H, d, J = 8.1 Hz), 7.61 (1H, d, J = 5.5 Hz), 7.55 (1H, d, J = 5.5 Hz), 7.38 (1H, t, J = 7.9 Hz), 3.55-3.30 (2H, m), 3.24-3.14 (1H, m), 1.19-1.08 (3H, m). LC/MS (a) Rt = 0.74 min; m/z [M + H]⁺ 344. |
| 248 | (structure) | ¹H-NMR(CD₃OD/CDCl₃(5/1)) δ: 8.43-8.14(1H, m), 7.78-7.68 (1H, m), 7.63 (1H, d, J = 5.5 Hz), 7.54 (1H, d, J = 5.5 Hz), 7.45-7.21 (5H, m). 7.36 (1H, t, J = 7.7 Hz), 4.25-4.07 (1H, m), 3.74-3.65 (1H, m), 3.45-3.38 (1H, m). LC/MS (a) Rt = 0.95 min; m/z [M + H]⁺ 406. |
| 249 | (structure) | ¹H-NMR(CD₃OD/CDCl₃(1/1)) δ: 8.31-8.24 (1H, m), 7.70 (1H, d, J = 7.7 Hz), 7.59-7.53 (2H, m), 7.38 (1H, t, J = 7.9 Hz), 4.61-4.34 (1H, m), 3.15-3.03 (2H, m), 2.96-2.87 (2H, m), 2.26-2.14 (1H, m), 1.90-1.79 (1H, m). LC/MS (a) Rt = 0.75 min; m/z [M + H]⁺ 356. |

TABLE 61-continued

| Example No. | Structural formula | Physical property |
|---|---|---|
| 250 | (structure) | $^1$H-NMR (CD$_3$OD) δ: 8.27-8.20 (1H, m), 8.22 (1H, d, J = 5.5 Hz), 7.77-7.41 (1H, m), 4.39-4.00 (1H, m), 3.28-3.22 (1H, m), 1.90-1.63 (6H, m), 1.58-1.45 (2H, m). LC/MS (a) Rt = 0.72 min; m/z [M + H]$^+$ 363. |

TABLE 62

| Example No. | Structural formula | Physical property |
|---|---|---|
| 251 | (structure) | $^1$H-NMR (CD$_3$OD/CDCl$_3$(1/1)) δ: 8.62 (1H, s), 7.81 (1H, d, J = 8.8 Hz), 7.46 (1H, d, J = 5.1 Hz), 7.41 (1H, d, J = 8.1 Hz), 7.33 (1H, d, J = 5.5 Hz), 4.33-4.01 (1H, m), 3.32-3.25 (1H, m), 1.85-1.48 (8H, m). LC/MS (a) Rt = 0.84 min; m/z [M + H]$^+$ 384. |
| 252 | (structure) | $^1$H-NMR (CD$_3$OD/CDCl$_3$(1/1)) δ: 8.52 (1H, d, J = 5.5 Hz), 8.34-8.29 (1H, m), 7.88 (2H, d, J = 7.0 Hz), 7.57-7.43 (4H, m), 4.30-4.04 (1H, m), 3.28-3.15 (1H, m), 1.93-1.30 (8H, m). LC/MS (a) Rt = 0.65 min; m/z [M + H]$^+$ 405. |
| 253 | (structure) | $^1$H-NMR (CD$_3$OD/CDCl$_3$(1/1)) δ: 9.12-8.94 (1H, m), 8.68 (1H, d, J = 2.2 Hz), 8.63 (1H, s), 8.36-8.23 (1H, m), 7.87-7.77 (1H, m), 6.66-6.57 (1H, m), 4.39-4.16 (1H, m), 3.30-3.11 (1H, m), 1.89-1.44 (8H, m). LC/MS (a) Rt = 0.72 min; m/z [M + H]$^+$ 395. |

TABLE 62-continued

| Example No. | Structural formula | Physical property |
|---|---|---|
| 254 | | ¹H-NMR (CD₃OD/CDCl₃(1/1)) δ: 8.73 (1H, br s), 7.46 (1H, d, J = 9.2 Hz), 7.27 (1H, d, J = 9.5 Hz), 4.18-4.10 (1H, m), 3.17-3.08 (1H, m), 2.47 (3H, s), 2.41 (3H, s), 1.91-1.42 (8H, m). LC/MS (a) Rt = 0.58 min; m/z [M + H]⁺ 396. |
| 255 | | ¹H-NMR (CD₃OD/CDCl₃(1/1)) δ: 8.98-8.86 (1H, m), 8.65-8.53 (1H, m), 8.29 (1H, d, J = 5.5 Hz), 7.83-7.72 (1H, m), 7.20 (1H, d, J = 4.0 Hz), 6.54 (1H, d, J = 11.7 Hz), 4.42-4.33 (1H, m), 3.32-3.19 (1H, m), 1.88-1.48 (8H, m). LC/MS (a) Rt = 0.78 min; m/z [M + H]⁺ 395. |

TABLE 63

| Example No. | Structural formula | Physical property |
|---|---|---|
| 256 | | ¹H-NMR (CD₃OD/CDCl₃(1/1)) δ: 8.00-7.90 (1H, m), 7.08 (1H, d, J = 3.2 Hz), 7.05-7.00 (1H, m), 6.57 (1H, d, J = 3.2 Hz), 4.32-4.20 (1H, m), 3.82 (3H, s), 3.60-3.46 (2H, m), 3.40 (3H, s), 3.16-3.10 (1H, m), 2.56 (3H, s), 1.33 (3H, d, J = 6.8 Hz). LC/MS (b) Rt = 1.08 min; m/z [M + H]⁺ 399. |
| 257 | | ¹H-NMR (CD₃OD/CDCl₃(1/1)) δ: 8.10 (1H, s), 7.92 (2H, d, J = 7.7 Hz), 7.89-7.83 (1H, m), 7.78-7.71 (1H, m), 7.51 (2H, t, J = 7.5 Hz), 7.41 (1H, t, J = 7.3 Hz), 4.25 (3H, s), 4.05-3.95 (1H, m), 3.88-3.77 (1H, m), 3.65-3.55 (1H, m), 3.35 (3H, s), 3.23-3.12 (2H, m), 3.06-2.97 (1H, m), 1.93-1.79 (1H, m), 1.79-1.65 (1H, m). LC/MS (a) Rt = 0.75 min; m/z [M + H]⁺ 460. |

TABLE 63-continued
| Example No. | Structural formula | Physical property |
|---|---|---|
| 258 | 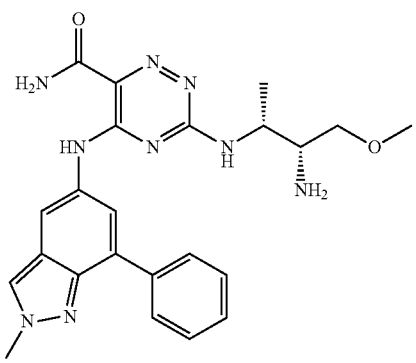 | ¹H-NMR (CD₃OD/CDCl₃(1/1)) δ: 8.14-8.08 (2H, m), 7.92 (2H, d, J = 7.7 Hz), 7.63-7.59 (1H, m), 7.50 (2H, t, J = 7.5 Hz), 7.41 (1H, t, J = 7.3 Hz), 4.24 (3H, s), 4.23-4.14 (3H, m), 3.49-3.39 (2H, m), 3.32 (3H, s), 3.09-3.01 (1H, m), 1.30-1.23 (3H, m).<br>LC/MS (a) Rt = 0.78 min; m/z [M + H]⁺ 462. |
| 259 | 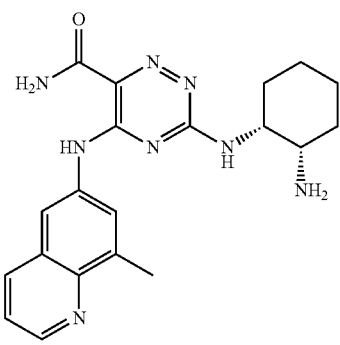 [SMILES: Cc1cc(Nc2nc(N[C@@H]3CCCC[C@@H]3N)nnc2C(N)=O)cc2cccnc12] | ¹H-NMR (CD₃OD/CDCl₃(1/1)) δ: 8.80 (1H, d, J = 3.7 Hz), 8.60-8.27 (1H, m), 8.23-8.13 (1H, m), 7.81-7.69 (1H, m), 7.50 (1H, dd, J = 8.1, 4.4 Hz), 4.35-4.05 (1H, m), 3.31-3.23 (1H, m), 2.80 (3H, s), 1.92-1.69 (5H, m), 1.67-1.46 (3H, m).<br>LC/MS (a) Rt = 0.67 min; m/z [M + H]⁺ 393. |
| 260 | 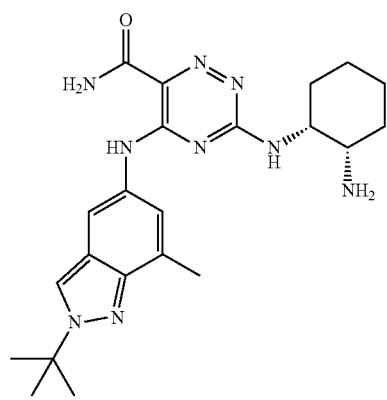 [SMILES: Cc1cc(Nc2nc(N[C@@H]3CCCC[C@@H]3N)nnc2C(N)=O)cc2cn(C(C)(C)C)nc12] | ¹H-NMR (CD₃OD/CDCl₃(1/1)) δ: 8.19-7.93 (2H, m), 7.25-7.02 (1H, m), 4.37-4.00 (1H, m), 3.29-3.21 (1H, m), 1.98-1.61 (6H, m), 1.77 (9H, s), 1.61-1.44 (1H, m).<br>LC/MS (a) Rt = 0.83 min; m/z [M + H]⁺ 438. |

TABLE 64

| Example No. | Structural formula | Physical property |
|---|---|---|
| 261 | | $^1$H-NMR (CD$_3$OD/CDCl$_3$(1/1)) δ: 8.07-8.01 (1H, m), 7.36 (1H, d, J = 3.3 Hz), 7.24-7.16 (2H, m), 6.66 (1H, d, J = 3.3 Hz), 4.97-4.87 (1H, m), 3.57-3.50 (1H, m), 3.27-3.20 (2H, m), 2.66-2.58 (2H, m), 2.56-2.46 (2H, m), 2.02-1.94 (2H, m), 1.18-1.14 (3H, m). LC/MS (a) Rt = 0.81 min; m/z [M + H]$^+$ 381. |
| 262 | | $^1$H-NMR (CD$_3$OD/CDCl$_3$(1/1)) δ: 8.04 (1H, d, J = 6.8 Hz), 7.36 (1H, d, J = 3.4 Hz), 7.24-7.17 (2H, m), 6.66 (1H, d, J = 3.4 Hz), 4.97-4.87 (1H, m), 3.62 (1H, dd, J = 13.9, 5.1 Hz), 3.49-3.43 (1H, m), 3.40-3.36 (2H, m), 3.38 (3H, s), 3.28-3.22 (1H, m), 2.65-2.57 (2H, m), 2.55-2.46 (2H, m), 2.02-1.93 (2H, m). LC/MS (a) Rt = 0.84 min; m/z [M + H]$^+$ 411. |
| 263 | | $^1$H-NMR (DMSO-d$_6$) δ: 12.04-11.93 (1H, m), 8.46-8.42 (1H, m), 8.31-8.23 (1H, m), 8.23-8.09 (1H, m), 7.85-7.75 (2H, m), 7.82 (1H, s), 7.58 (1H, d, J = 3.2 Hz), 7.27-7.19 (2H, m), 6.66 (1H, d, J = 3.4 Hz), 4.32-3.96 (1H, m), 3.92 (3H, s), 3.87-3.80 (1H, m), 3.70 (1H, d, J = 8.5 Hz), 3.53 (1H, d, J = 11.0 Hz), 3.45-3.39 (1H, m), 3.02-2.98 (1H, m), 1.92-1.84 (1H, m), 1.74-1.65 (3H, m). LC/MS (b) Rt = 0.93 min; m/z [M + H]$^+$ 449. |
| 264 | | $^1$H-NMR (CD$_3$OD/CDCl$_3$(1/1)) δ: 8.16-8.02 (1H, m), 7.28-7.20 (2H, m), 7.17 (1H, d, J = 3.2 Hz), 6.63 (1H, d, J = 3.2 Hz), 4.45-4.10 (1H, m), 3.86 (3H, s), 3.15-3.10 (1H, m), 1.80-1.69 (1H, m), 1.60-1.50 (1H, m), 1.40-1.25 (1H, m), 1.20-1.11 (3H, m), 0.99 (3H, d, J = 7.2 Hz), 0.98-0.90 (3H, m). LC/MS (b) Rt = 1.18 min; m/z [M + H]$^+$ 397. |

TABLE 64-continued

| Example No. | Structural formula | Physical property |
|---|---|---|
| 265 | | $^1$H-NMR (CD$_3$OD/CDCl$_3$(1/1)) δ: 8.58-8.19 (1H, m), 8.45 (1H, s), 7.58 (1H, t, J = 60.1 Hz), 6.96-6.76 (1H, m), 4.36-4.14 (1H, m), 3.29-3.23 (1H, m), 2.57 (3H, s), 1.93-1.47 (8H, m).<br>LC/MS (a) Rt = 0.79 min; m/z [M + H]$^+$ 432. |

TABLE 65

| Example No. | Structural formula | Physical property |
|---|---|---|
| 266 | | $^1$H-NMR (CD$_3$OD/CDCl$_3$(1/1)) δ: 8.15-8.07 (1H, m), 7.69 (1H, d, J = 8.4 Hz), 7.61-7.58 (1H, m), 7.54 (1H, d, J = 3.7 Hz), 7.28 (1H, t, J = 8.2 Hz), 6.81 (1H, d, J = 3.3 Hz), 6.43 (1H, d, J = 2.2 Hz), 3.97 (3H, s), 3.63 (1H, dd, J = 13.6, 5.5 Hz), 3.49-3.36 (3H, m), 3.37 (3H, s), 3.29-3.22 (1H, m).<br>LC/MS (a) Rt = 0.74 min; m/z [M + H]$^+$ 437. |
| 267 | | $^1$H-NMR (CD$_3$OD/CDCl$_3$(1/1)) δ: 7.88 (1H, s), 7.07 (1H, d, J = 3.2 Hz), 7.00 (1H, s), 6.56 (1H, d, J = 2.7 Hz), 4.23-4.17 (1H, m), 4.02 (1H, d, J = 11.0 Hz), 3.90 (1H, d, J = 10.7 Hz), 3.80 (3H, s), 3.72-3.50 (2H, m), 3.21-3.16 (1H, m), 2.54 (3H, s), 2.00-1.92 (1H, m), 1.88-1.82 (1H, m).<br>LC/MS (a) Rt = 0.77 min; m/z [M + H]$^+$ 397. |

TABLE 65-continued

| Example No. | Structural formula | Physical property |
|---|---|---|
| 268 | | ¹H-NMR (CD₃OD/CDCl₃(1/1)) δ: 8.12-8.04 (1H, m), 7.38 (1H, d, J = 3.2 Hz), 7.26-7.16 (2H, m), 6.67 (1H, d, J = 3.2 Hz), 5.00-4.90 (1H, m), 3.70-3.40 (6H, m), 3.30-3.21 (1H, m), 2.70-2.45 (4H, m), 2.05-1.92 (2H, m), 1.25-1.19 (3H, m).<br>LC/MS (b) Rt = 1.24 min; m/z [M + H]⁺ 425. |
| 269 | | ¹H-NMR (CD₃OD/CDCl₃(1/1)) δ: 8.00-7.93 (1H, m), 7.08 (1H, d, J = 3.2 Hz), 7.05-7.00 (1H, m), 6.57 (1H, d, J = 3.2 Hz), 4.32-4.20 (1H, m), 3.82 (3H, s), 3.66-3.50 (4H, m), 3.20-3.10 (1H, m), 2.55 (3H, s), 1.34 (3H, d, J = 7.2 Hz), 1.30-1.20 (3H, m).<br>LC/MS (b) Rt = 1.15 min; m/z [M + H]⁺ 413. |
| 270 | | ¹H-NMR (CD₃OD/CDCl₃(1/1)) δ: 8.12-7.90 (2H, m), 7.30-7.05 (1H, m), 4.86 (1H, septet, J = 6.8 Hz), 4.25-4.02 (2H, m), 3.95-3.87 (1H, m), 3.75-3.50 (2H, m), 3.20-3.15 (1H, m), 2.64 (3H, s), 2.00-1.80 (2H, m), 1.69 (6H, d, J = 6.8 Hz).<br>LC/MS (b) Rt = 0.95 min; m/z [M + H]⁺ 426. |

TABLE 66

| Example No. | Structural formula | Physical property |
|---|---|---|
| 271 | | ¹H-NMR (CD₃OD/CDCl₃(1/1)) δ: 8.16-7.97 (1H, m), 7.69 (1H, d, J = 8.4 Hz), 7.54 (1H, t, J = 3.7 Hz), 7.31-7.24 (1H, m), 7.29 (1H, t, J = 8.1 Hz), 6.81 (1H, d, J = 3.3 Hz), 6.43 (1H, d, J = 2.2 Hz), 3.97 (3H, s), 3.57-3.51 (2H, m), 0.69-0.63 (4H, m).<br>LC/MS (a) Rt = 0.73 min; m/z [M + H]⁺ 419. |

TABLE 66-continued

| Example No. | Structural formula | Physical property |
|---|---|---|
| 272 | | ¹H-NMR (CD₃OD/CDCl₃(1/1)) δ: 8.17 (1H, s), 8.01-7.84 (1H, m), 7.76-7.53 (1H, m), 4.54 (2H, q, J = 7.2 Hz), 4.01 (1H, d, J = 9.2 Hz), 3.88 (1H, d, J = 9.9 Hz), 3.68 (1H, d, J = 11.4 Hz), 3.56 (1H, t, J = 10.6 Hz), 3.18-3.12 (1H, m), 2.00-1.89 (1H, m), 1.86-1.80 (1H, m), 1.66 (3H, t, J = 7.3 Hz). LC/MS (a) Rt = 0.68 min; m/z [M + H]⁺ 432. |
| 273 | | ¹H-NMR (CD₃OD/CDCl₃(1/1)) δ: 7.73 (1H, s), 7.25 (1H, s), 4.30-4.07 (1H, m), 3.79 (3H, s), 3.22-3.14 (1H, m), 2.98 (2H, q, J = 7.7 Hz), 2.62 (3H, s), 1.88-1.59 (6H, m), 1.53-1.45 (2H, m), 1.42 (3H, t, J = 7.5 Hz). LC/MS (a) Rt = 0.6 min; m/z [M + H]⁺ 424. |
| 274 | | ¹H-NMR (CD₃OD/CDCl₃(1/1)) δ: 8.15 (1H, s), 8.06 (1H, s), 7.09 (1H, s), 4.25-4.17 (1H, m), 3.54-3.47 (2H, m), 3.37 (3H, s), 3.13 (1H, q, J = 4.8 Hz), 2.63 (3H, s), 1.77 (9H, s), 1.30 (3H, d, J = 7.0 Hz). LC/MS (a) Rt = 0.79 min; m/z [M + H]⁺ 442. |
| 275 | | ¹H-NMR (CD₃OD/CDCl₃(1/1)) δ: 8.80 (1H, d, J = 2.9 Hz), 8.49-8.38 (1H, m), 8.24 (1H, d, J = 8.1 Hz), 7.73-7.67 (1H, m), 7.49 (1H, dd, J = 8.2, 4.2 Hz), 4.44-4.29 (1H, m), 3.59-3.48 (2H, m), 3.38 (3H, br s), 3.19-3.14 (1H, m), 1.35 (3H, d, J = 6.6 Hz). LC/MS (a) Rt = 0.63 min; m/z [M + H]⁺ 397. |

TABLE 67

| Example No. | Structural formula | Physical property |
|---|---|---|
| 276 | (structure) | LC/MS (a) Rt = 0.77 min; m/z [M + H]⁺ 396. |
| 277 | (structure) | ¹H-NMR (CD₃OD/CDCl₃(1/1)) δ: 8.01-7.85 (1H, m), 7.37 (1H, d, J = 3.4 Hz), 7.26-7.16 (2H, m), 6.64 (1H, d, J = 3.2 Hz), 4.97-4.87 (1H, m), 4.38-4.15 (1H, m), 4.03 (1H, d, J = 10.2 Hz), 3.91 (1H, d, J = 11.7 Hz), 3.68-3.60 (1H, m), 3.59-3.51 (1H, m), 3.33-3.27 (1H, m), 2.67-2.58 (2H, m), 2.56-2.44 (2H, m), 2.07-1.93 (3H, m), 1.88-1.80 (1H, m). LC/MS (a) Rt = 0.83 min; m/z [M + H]⁺ 423. |
| 278 | (structure) | ¹H-NMR (CD₃OD/CDCl₃(1/1)) δ: 8.09-7.93 (1H, m), 7.29-7.20 (3H, m), 6.64 (1H, d, J = 2.9 Hz), 4.35 (2H, t, J = 5.3 Hz), 3.76 (2H, t, J = 5.3 Hz), 3.58-3.51 (2H, m), 3.32 (3H, s), 0.71-0.63 (4H, m). LC/MS (a) Rt = 0.71 min; m/z [M + H]⁺ 397. |
| 279 | (structure) | ¹H-NMR (CD₃OD/CDCl₃(1/1)) δ: 8.20-8.08 (1H, m), 8.15 (1H, s), 7.66 (1H, d, J = 9.2 Hz), 7.40-7.35 (1H, m), 5.15-5.06 (1H, m), 3.40-3.25 (2H, m), 2.80-2.60 (4H, m), 2.10-1.98 (2H, m), 1.26 (3H, d, J = 6.0 Hz), 1.10-1.00 (1H, m), 0.78-0.69 (1H, m), 0.59-0.50 (1H, m), 0.50-0.34 (2H, m). LC/MS (b) Rt = 0.99 min; m/z [M + H]⁺ 422. |

TABLE 67-continued

| Example No. | Structural formula | Physical property |
|---|---|---|
| 280 | | LC/MS (a) Rt = 0.71 min; m/z [M + H]⁺ 398. |

TABLE 68

| Example No. | Structural formula | Physical property |
|---|---|---|
| 281 | | LC/MS (a) Rt = 0.77 min; m/z [M + H]⁺ 424. |
| 282 | | $^1$H-NMR (CD$_3$OD/CDCl$_3$(1/1)) δ: 8.82-8.78 (1H, m), 8.50-8.37 (1H, m), 8.23 (1H, d, J = 8.1 Hz), 7.77-7.69 (1H, m), 7.49 (1H, dd, J = 8.2, 4.2 Hz), 4.47-4.24 (1H, m), 3.65-3.50 (4H, m), 3.19-3.13 (1H, m), 2.80 (3H, s), 1.36 (3H, d, J = 6.6 Hz), 1.28-1.16 (3H, m). LC/MS (a) Rt = 0.66 min; m/z [M + H]⁺ 411. |
| 283 | | $^1$H-NMR (CD$_3$OD/CDCl$_3$(1/1)) δ: 8.39-8.30 (1H, m), 7.86 (1H, d, J = 8.8 Hz), 7.57-7.52 (2H, m), 7.35 (1H, d, J = 5.5 Hz), 4.27-4.15 (1H, m), 3.55-3.44 (2H, m), 3.36 (3H, s), 3.17-3.10 (1H, m), 1.30 (3H, d, J = 6.6 Hz). LC/MS (a) Rt = 0.77 min; m/z [M + H]⁺ 388. |

TABLE 68-continued

| Example No. | Structural formula | Physical property |
|---|---|---|
| 284 | (structure) | $^1$H-NMR (CD$_3$OD/CDCl$_3$(1/1)) δ: 8.25-8.10 (1H, m), 8.01 (1H, s), 7.30-7.15 (1H, m), 5.25 (1H, septet, J = 6.8 Hz), 4.30-4.15 (1H, m), 3.60-3.45 (2H, m), 3.39 (3H, s), 3.18-3.12 (1H, m), 2.78 (3H, s), 1.61 (6H, d, J = 6.8 Hz), 1.31 (3H, d, J = 6.8 Hz). LC/MS (b) Rt = 1.06 min; m/z [M + H]$^+$ 428. |
| 285 | (structure) | $^1$H-NMR (CD$_3$OD/CDCl$_3$(1/1)) δ: 8.55-8.26 (1H, m), 7.88 (1H, d, J = 8.8 Hz), 7.59-7.52 (2H, m), 7.44-7.31 (1H, m), 4.35-4.05 (1H, m), 3.08-3.00 (1H, m), 1.80-1.68 (1H, m), 1.62-1.52 (1H, m), 1.43-1.36 (1H, m), 1.25-1.10 (3H, m), 0.97 (3H, d, J = 6.4 Hz), 0.95-0.90 (3H, m). LC/MS (b) Rt = 1.25 min; m/z [M + H]$^+$ 400. |

TABLE 69

| Example No. | Structural formula | Physical property |
|---|---|---|
| 286 | (structure) | $^1$H-NMR (CD$_3$OD/CDCl$_3$(1/1)) δ: 8.30-8.25 (1H, m), 8.13-7.94 (1H, m), 7.66-7.56 (1H, m), 4.43-4.12 (1H, m), 3.54-3.48 (2H, m), 3.36 (3H, s), 3.16-3.07 (1H, m), 1.79 (9H, s), 1.30 (3H, d, J = 6.8 Hz). LC/MS (a) Rt = 0.81 min; m/z [M + H]$^+$ 462. |

TABLE 69-continued

| Example No. | Structural formula | Physical property |
|---|---|---|
| 287 | | ¹H-NMR (CD₃OD/CDCl₃(1/1)) δ: 8.23-7.83 (1H, m), 8.02 (1H, s), 7.28-7.00 (1H, m), 4.34-4.07 (1H, m), 4.01 (1H, d, J = 10.6 Hz), 3.88 (1H, dd, J = 11.5, 2.0 Hz), 3.68-3.60 (1H, m), 3.58-3.50 (1H, m), 3.19-3.15 (1H, m), 2.86 (2H, dq, J = 2.6, 9.9 Hz), 2.63 (3H, s), 2.48-2.41 (2H, m), 2.16-1.90 (3H, m), 1.87-1.85 (1H, m), 1.83 (3H, s).<br>LC/MS (a) Rt = 0.77 min; m/z [M + H]⁺ 452. |
| 288 | | ¹H-NMR (CD₃OD/CDCl₃(1/1)) δ: 8.06-7.91 (1H, m), 7.36 (1H, d, J = 3.4 Hz), 7.27-7.15 (2H, m), 6.65 (1H, d, J = 3.4 Hz), 4.97-4.86 (1H, m), 3.54 (2H, s), 2.66-2.57 (2H, m), 2.55-2.44 (0H, m), 2.02-1.92 (2H, m), 0.70-0.59 (4H, m).<br>LC/MS (a) Rt = 0.84 min; m/z [M + H]⁺ 393. |
| 289 | | ¹H-NMR (CD₃OD/CDCl₃(1/1)) δ: 8.20-8.05 (2H, m), 7.20-7.10 (1H, m), 4.85 (1H, septet, J = 6.8 Hz), 4.30-4.15 (1H, m), 3.58-3.45 (2H, m), 3.38 (3H, s), 3.18-3.10 (1H, m), 2.63 (3H, s), 1.69 (6H, d, J = 6.8 Hz), 1.31 (3H, d, J = 6.8 Hz).<br>LC/MS (b) Rt = 0.97 min; m/z [M + H]⁺ 428. |
| 290 | | ¹H-NMR (CD₃OD/CDCl₃(1/1)) δ: 8.59-8.30 (1H, m), 8.25-8.06 (1H, m), 7.96 (1H, d, J = 9.0 Hz), 7.89 (1H, d, J = 8.0 Hz), 7.40 (1H, d, J = 8.5 Hz), 3.66-3.53 (2H, m), 2.74 (3H, s), 0.74-0.61 (4H, m).<br>LC/MS (a) Rt = 0.56 min; m/z [M + H]⁺ 365. |

TABLE 70

| Example No. | Structural formula | Physical property |
|---|---|---|
| 291 | | ¹H-NMR (CD₃OD/CDCl₃(1/1)) δ: 8.20-8.05 (2H, m), 7.20-7.10 (1H, m), 4.85 (1H, septet, J = 6.8 Hz), 4.30-4.15 (1H, m), 3.61-3.45 (4H, m), 3.17-3.11 (1H, m), 2.63 (3H, s), 1.69 (6H, d, J = 6.8 Hz), 1.33 (3H, d, J = 6.8 Hz), 1.28-1.15 (3H, m). LC/MS (b) Rt = 1.03 min; m/z [M + H]⁺ 442. |
| 292 | | LC/MS (a) Rt = 0.75 min; m/z [M + H]⁺ 434. |
| 293 | | ¹H-NMR (CD₃OD/CDCl₃(1/1)) δ: 8.62-8.25 (1H, m), 8.09 (1H, s), 7.68 (1H, d, J = 8.8 Hz), 7.20-7.00 (1H, m), 4.50 (2H, q, J = 7.2 Hz), 4.45-4.18 (1H, m), 3.20-3.05 (1H, m), 1.80-1.68 (1H, m), 1.66 (3H, t, J = 7.2 Hz), 1.64-1.35 (2H, m), 1.17 (3H, d, J = 6.0 Hz), 1.0-0.89 (6H, m). LC/MS (b) Rt = 1.09 min; m/z [M + H]⁺ 412. |
| 294 | | LC/MS (a) Rt = 0.719 min; m/z [M + H]⁺ 382. |

TABLE 70-continued

| Example No. | Structural formula | Physical property |
|---|---|---|
| 295 | | ¹H-NMR (CD₃OD/CDCl₃(1/1)) δ: 8.10-8.03 (1H, m), 7.27-7.19 (2H, m), 7.15 (1H, d, J = 3.3 Hz), 6.63 (1H, d, J = 2.9 Hz), 3.85 (3H, s), 3.65-3.59 (1H, m), 3.56-3.50 (1H, m), 3.53 (2H, q, J = 7.0 Hz), 3.45-3.39 (2H, m), 3.29-3.23 (1H, m), 1.21 (3H, t, J = 7.0 Hz). LC/MS (a) Rt = 0.75 min; m/z [M + H]⁺ 385. |

TABLE 71

| Example No. | Structural formula | Physical property |
|---|---|---|
| 296 | | ¹H-NMR (CD₃OD/CDCl₃(1/1)) δ: 7.63-7.59 (2H, m), 7.40 (2H, t, J = 7.7 Hz), 7.29 (1H, t, J = 7.3 Hz), 7.19 (2H, s), 4.43-4.37 (1H, m), 4.08-4.02 (1H, m), 3.95-3.90 (1H, m), 3.78-3.73 (1H, m), 3.67-3.59 (1H, m), 3.29-3.23 (1H, m), 2.05-1.87 (2H, m). LC/MS (a) Rt = 0.84 min; m/z [M + H]⁺ 412. |
| 297 | | ¹H-NMR (CD₃OD/CDCl₃(1/1)) δ: 8.25-8.08 (2H, m), 7.20-7.05 (1H, m), 4.52 (2H, q, J = 7.2 Hz), 4.30-4.10 (1H, m), 3.60-3.50 (2H, m), 3.38 (3H, s), 3.20-3.10 (1H, m), 2.63 (3H, s), 1.66 (3H, t, J = 7.2 Hz), 1.32 (3H, d, J = 7.2 Hz). LC/MS (b) Rt = 0.89 min; m/z [M + H]⁺ 414. |
| 298 | | ¹H-NMR (CD₃OD/CDCl₃(1/1)) δ: 8.13-7.95 (1H, m), 7.27-7.18 (2H, m), 7.15 (1H, d, J = 3.3 Hz), 6.62 (1H, d, J = 2.9 Hz), 3.85 (3H, s), 3.61-3.50 (2H, m), 0.73-0.63 (4H, m). LC/MS (a) Rt = 0.7 min; m/z [M + H]⁺ 353. |

TABLE 71-continued

| Example No. | Structural formula | Physical property |
|---|---|---|
| 299 | | ¹H-NMR (CD₃OD/CDCl₃(1/1)) δ: 8.11-8.01 (1H, m), 7.85-7.78 (1H, m), 7.46-7.17 (5H, m), 7.12-7.06 (1H, m), 4.25-4.16 (1H, m), 4.23 (3H, s), 3.79 (1H, dd, J = 13.7, 4.6 Hz), 3.55-3.40 (1H, m), 2.57 (3H, s). LC/MS (a) Rt = 0.68 min; m/z [M + H]⁺ 418. |
| 300 | | ¹H-NMR (CD₃OD/CDCl₃(1/1)) δ: 8.21-7.99 (2H, m), 7.14-7.05 (1H, m), 4.40-4.10 (1H, m), 3.61-3.45 (4H, m), 3.15-3.08 (1H, m), 2.86 (2H, dd, J = 21.8, 10.1 Hz), 2.63 (3H, s), 2.44 (2H, t, J = 9.0 Hz), 2.17-1.95 (2H, m), 1.83 (3H, s), 1.31 (3H, d, J = 6.6 Hz), 1.27-1.15 (3H, m). LC/MS (a) Rt = 0.82 min; m/z [M + H]⁺ 468. |

TABLE 72

| Example No. | Structural formula | Physical property |
|---|---|---|
| 301 | 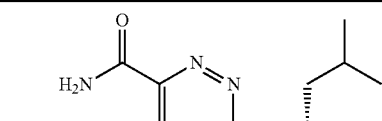 | ¹H-NMR (CD₃OD/CDCl₃(1/1)) δ: 8.35-8.10 (1H, m), 8.12 (1H, s), 7.67 (1H, d, J = 9.2 Hz), 7.42-7.38 (1H, m), 5.15-5.06 (1H, m), 4.32-4.10 (1H, m), 2.92-2.88 (1H, m), 2.80-2.60 (5H, m), 2.08-1.98 (2H, m), 1.82-1.68 (1H, m), 1.60-1.50 (1H, m), 1.45-1.35 (1H, m), 1.01-0.91 (6H, m). LC/MS (b) Rt = 1.11 min; m/z [M + H]⁺ 424. |

TABLE 72-continued

| Example No. | Structural formula | Physical property |
| --- | --- | --- |
| 302 | (structure) | $^1$H-NMR (CD$_3$OD/CDCl$_3$(1/1)) δ: 8.48 (1H, s), 8.34-8.18 (1H, m), 7.61 (1H, t, J = 60.1 Hz), 7.20-7.10 (1H, m), 4.27-4.16 (1H, m), 3.54-3.45 (2H, m), 3.38 (3H, s), 3.14 (1H, q, J = 5.1 Hz), 2.61 (3H, s), 1.31 (3H, d, J = 7.0 Hz).<br>LC/MS (a) Rt = 0.73 min; m/z [M + H]$^+$ 436. |
| 303 | (structure) | $^1$H-NMR (CD$_3$OD/CDCl$_3$(1/1)) δ: 8.32-8.10 (1H, m), 7.97 (1H, s), 7.30-7.12 (1H, m), 4.70-4.61 (2H, m), 4.30-4.15 (1H, m), 3.65-3.45 (4H, m), 3.16-3.10 (1H, m), 2.78 (3H, s), 1.50 (3H, t, J = 7.2 Hz), 1.32 (3H, d, J = 7.2 Hz), 1.30-1.15 (3H, m).<br>LC/MS (b) Rt = 1.03 min; m/z [M + H]$^+$ 428. |
| 304 | (structure) | $^1$H-NMR (CD$_3$OD/CDCl$_3$(1/1)) δ: 8.25-8.05 (2H, m), 7.20-7.05 (1H, m), 4.52 (2H, q, J = 7.2 Hz), 4.30-4.15 (1H, m), 3.65-3.45 (4H, m), 3.15-3.10 (1H, m), 2.63 (3H, s), 1.66 (3H, t, J = 7.2 Hz), 1.32 (3H, d, J = 7.2 Hz), 1.30-1.15 (3H, m).<br>LC/MS (b) Rt = 0.93 min; m/z [M + H]$^+$ 428. |
| 305 | (structure) | $^1$H-NMR (CD$_3$OD/CDCl$_3$(1/1)) δ: 8.25-8.10 (1H, m), 8.08 (1H, s), 7.15-7.05 (1H, m), 4.52 (2H, q, J = 7.2 Hz), 4.35-4.22 (1H, m), 3.55-3.45 (2H, m), 3.33 (3H, s), 3.20-3.04 (1H, m), 2.62 (3H, s), 1.80-1.55 (2H, m), 1.66 (3H, t, J = 7.2 Hz), 1.45-1.35 (1H, m), 1.00-0.85 (6H, m).<br>LC/MS (b) Rt = 1.06 min; m/z [M + H]$^+$ 456. |

TABLE 73

| Example No. | Structural formula | Physical property |
| --- | --- | --- |
| 306 | | ¹H-NMR (CD₃OD/CDCl₃(1/1)) δ: 8.20-7.95 (2H, m), 7.30-7.10 (1H, m), 5.25 (1H, septet, J = 6.8 Hz), 4.30-4.05 (2H, m), 3.95-3.87 (1H, m), 3.70-3.50 (2H, m), 3.25-3.15 (1H, m), 2.78 (3H, s), 2.05-1.80 (2H, m), 1.61 (6H, d, J = 6.8 Hz).<br>LC/MS (b) Rt = 1.03 min; m/z [M + H]⁺ 426. |
| 307 | | ¹H-NMR (CD₃OD/CDCl₃(1/1)) δ: 8.48-8.19 (1H, m), 7.87 (1H, d, J = 8.8 Hz), 7.57-7.52 (2H, m), 7.34 (1H, d, J = 5.1 Hz), 3.63-3.49 (2H, m), 0.80-0.62 (4H, m).<br>LC/MS (a) Rt = 0.75 min; m/z [M + H]⁺ 356. |
| 308 | | ¹H-NMR (CD₃OD/CDCl₃(1/1)) δ: 8.20-8.05 (2H, m), 7.20-7.10 (1H, m), 4.85 (1H, septet, J = 6.8 Hz), 3.70-3.20 (7H, m), 2.64 (3H, s), 1.69 (6H, d, J = 6.8 Hz), 1.28-1.13 (3H, m).<br>LC/MS (b) Rt = 0.99 min; m/z [M + H]⁺ 428. |
| 309 | | ¹H-NMR (CD₃OD/CDCl₃(1/1)) δ: 8.20-8.10 (2H, m), 7.20-7.10 (1H, m), 4.85 (1H, septet, J = 6.8 Hz), 3.72-3.60 (1H, m), 3.60-3.25 (7H, m), 2.64 (3H, s), 1.69 (6H, d, J = 6.8 Hz).<br>LC/MS (b) Rt = 0.92 min; m/z [M + H]⁺ 414. |

TABLE 73-continued

| Example No. | Structural formula | Physical property |
|---|---|---|
| 310 | 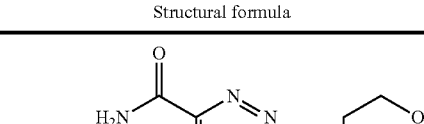 | LC/MS (a) Rt = 0.73 min; m/z [M + H]+ 412. |

TABLE 74

| Example No. | Structural formula | Physical property |
|---|---|---|
| 311 |  | $^{1}$H-NMR (CD$_3$OD/CDCl$_3$(1/1)) δ: 8.30-8.10 (1H, m), 7.98 (1H, s), 7.28-7.10 (1H, m), 4.70-4.60 (2H, m), 4.30-4.15 (1H, m), 3.58-3.45 (2H, m), 3.39 (3H, s), 3.18-3.10 (1H, m), 2.78 (3H, s), 1.50 (3H, t, J = 7.2 Hz), 1.31 (3H, d, J = 7.2 Hz).<br>LC/MS (b) Rt = 0.97 min; m/z [M + H]+ 414. |
| 312 |  | $^{1}$H-NMR (CD$_3$OD/CDCl$_3$(1/1)) δ: 8.13 (1H, br s), 7.97 (1H, s), 6.98 (1H, s), 4.52-4.39 (2H, m), 4.35-4.28 (1H, m), 3.62-3.47 (2H, m), 3.30 (3H, s), 3.11-3.03 (1H, m), 2.60 (3H, s), 1.51 (3H, t, J = 7.1 Hz), 1.35 (3H, d, J = 6.6 Hz).<br>LC/MS (a) Rt = 0.73 min; m/z [M + H]+ 414. |
| 313 |  | $^{1}$H-NMR (CD$_3$OD/CDCl$_3$(1/1)) δ: 8.15 (1H, s), 8.14-8.02 (1H, m), 7.10 (1H, s), 4.42-4.09 (1H, m), 3.60-3.45 (4H, m), 3.15-3.05 (1H, m), 2.63 (3H, s), 1.31 (3H, d, J = 6.8 Hz), 1.24-1.14 (3H, m).<br>LC/MS (a) Rt = 0.84 min; m/z [M + H]+ 456. |

TABLE 74-continued

| Example No. | Structural formula | Physical property |
|---|---|---|
| 314 | | ¹H-NMR (CD₃OD/CDCl₃(1/1)) δ: 8.34-8.06 (1H, m), 8.02-7.84 (1H, m), 7.62 (1H, d, J = 9.2 Hz), 7.52-7.35 (2H, m), 7.34-7.17 (4H, m), 4.28-4.19 (1H, m), 4.22 (3H, s), 3.81 (1H, dd, J = 13.9, 4.4 Hz), 3.55-3.44 (1H, m).<br>LC/MS (a) Rt = 0.65 min; m/z [M + H]⁺ 404. |
| 315 | | ¹H-NMR (CD₃OD/CDCl₃(1/1)) δ: 8.08 (1H, d, J = 7.3 Hz), 7.27-7.19 (2H, m), 7.16 (1H, d, J = 3.3 Hz), 6.65 (1H, d, J = 2.9 Hz), 4.31-4.22 (1H, m), 3.86 (3H, s), 3.57-3.50 (2H, m), 3.41 (3H, s), 3.18-3.12 (1H, m), 1.31 (3H, d, J = 6.6 Hz).<br>LC/MS (a) Rt = 0.73 min; m/z [M + H]⁺ 385. |

TABLE 75

| Example No. | Structural formula | Physical property |
|---|---|---|
| 316 | | ¹H-NMR (CD₃OD/CDCl₃(1/1)) δ: 8.54-8.14 (1H, m), 8.07 (1H, s), 7.67 (1H, d, J = 9.0 Hz), 7.28-6.96 (1H, m), 4.48 (2H, q, J = 7.3 Hz), 4.32-4.20 (1H, m), 3.32-3.26 (1H, m), 1.96-1.48 (10H, m), 1.64 (3H, t, J = 7.3 Hz).<br>LC/MS (a) Rt = 0.76 min; m/z [M + H]⁺ 410. |
| 317 | | ¹H-NMR (CD₃OD/CDCl₃(1/1)) δ: 8.23-7.94 (1H, m), 8.19 (1H, s), 7.71-7.52 (1H, m), 4.53 (2H, q, J = 7.3 Hz), 4.37-4.09 (1H, m), 3.55-3.49 (2H, m), 3.36 (3H, s), 3.14-3.08 (1H, m), 1.66 (3H, t, J = 7.3 Hz), 1.30 (3H, d, J = 6.6 Hz).<br>LC/MS (a) Rt = 0.69 min; m/z [M + H]⁺ 434. |

TABLE 75-continued

| Example No. | Structural formula | Physical property |
|---|---|---|
| 318 | | ¹H-NMR (CD₃OD/CDCl₃(1/1)) δ: 8.30-8.03 (1H, m), 7.95 (1H, s), 7.34-7.15 (1H, m), 4.75-4.61 (2H, m), 4.35-4.10 (1H, m), 4.10-4.00 (1H, m), 3.95-3.88 (1H, m), 3.75-3.60 (2H, m), 3.20-3.15 (1H, m), 2.78 (3H, s), 2.05-1.80 (2H, m), 1.50 (3H, t, J = 7.2 Hz).<br>LC/MS (b) Rt = 0.95 min; m/z [M + H]⁺ 412. |
| 319 | | ¹H-NMR (CD₃OD/CDCl₃(1/1)) δ: 8.35-8.20 (1H, m), 8.14 (1H, s), 7.66 (1H, d, J = 9.2 Hz), 7.41-7.35 (1H, m), 5.15-5.06 (1H, m), 4.33-4.22 (1H, m), 3.55-3.43 (2H, m), 3.36 (3H, s), 3.20-3.05 (1H, m), 2.80-2.60 (4H, m), 2.10-1.98 (2H, m), 1.78-1.64 (1H, m), 1.64-1.53 (1H, m), 1.48-1.35 (1H, m), 1.00-0.88 (6H, m).<br>LC/MS (b) Rt = 1.14 min; m/z [M + H]⁺ 468. |
| 320 | | ¹H-NMR (CD₃OD/CDCl₃(1/1)) δ: 8.30-8.10 (1H, m), 7.96 (1H, s), 7.25-7.18 (1H, m), 4.75-4.60 (2H, m), 3.78-3.65 (1H, m), 3.45-3.30 (5H, m), 3.05-2.93 (1H, m), 2.78 (3H, s), 1.50 (3H, t, J = 7.2 Hz), 1.30-1.12 (3H, m).<br>LC/MS (b) Rt = 0.97 min; m/z [M + H]⁺ 414. |

TABLE 76

| Example No. | Structural formula | Physical property |
|---|---|---|
| 321 | | ¹H-NMR (CD₃OD/CDCl₃(1/1)) δ: 8.60-8.32 (1H, m), 8.09 (1H, s), 7.68 (1H, d, J = 8.8 Hz), 7.14-6.98 (1H, m), 4.50 (2H, q, J = 7.2 Hz), 4.42-4.20 (1H, m), 2.90 (1H, dd, J = 13.2, 4.8 Hz), 2.76 (1H, dd, J = 13.2, 7.2 Hz), 1.86-1.70 (1H, m), 1.66 (3H, t, J = 7.2 Hz), 1.62-1.35 (2H, m), 1.05-0.88 (6H, m). LC/MS (b) Rt = 1.06 min; m/z [M + H]⁺ 398. |
| 322 | | ¹H-NMR (CD₃OD/CDCl₃(1/1)) δ: 8.25-8.10 (1H, m), 8.01 (1H, s), 7.25-7.15 (1H, m), 5.25 (1H, septet, J = 6.8 Hz), 3.64 (1H, dd, J = 13.6, 5.2 Hz), 3.59-3.15 (7H, m), 2.78 (3H, s), 1.61 (6H, d, J = 6.8 Hz). LC/MS (b) Rt = 1.02 min; m/z [M + H]⁺ 414. |
| 323 | | ¹H-NMR (CD₃OD/CDCl₃(1/1)) δ: 8.17-8.02 (1H, m), 8.15 (1H, s), 7.12-7.05 (1H, m), 3.64-3.37 (6H, m), 3.28-3.22 (1H, m), 2.63 (3H, s), 1.77 (9H, s), 1.25-1.12 (3H, m). LC/MS (a) Rt = 0.78 min; m/z [M + H]⁺ 442. |
| 324 | | LC/MS (a) Rt = 0.68 min; m/z [M + H]⁺ 368. |

TABLE 76-continued
| Example No. | Structural formula | Physical property |
|---|---|---|
| 325 | 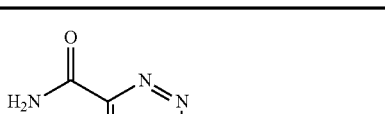 | ¹H-NMR (CD₃OD/CDCl₃(2/1)) δ: 7.77 (1H, d, J = 8.1 Hz), 7.68 (1H, d, J = 7.7 Hz), 7.35 (1H, t, J = 7.5 Hz), 7.28 (1H, t, J = 7.5 Hz), 7.07 (1H, s), 3.85-3.78 (1H, m), 3.64-3.56 (2H, m), 3.54-3.46 (1H, m), 3.44 (3H, s). LC/MS (a) Rt = 0.8 min; m/z [M + H]⁺ 374. |
TABLE 77
| Example No. | Structural formula | Physical property |
|---|---|---|
| 326 | 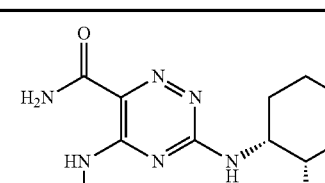 | ¹H-NMR (CD₃OD) δ: 8.29 (1H, s), 8.12-7.95 (1H, br), 7.18-6.95 (1H, m), 5.33-5.18 (2H, m), 4.40-3.05 (6H, m), 2.57 (3H, s), 2.04-1.65 (2H, m). LC/MS (a) Rt = 0.74 min; m/z [M + H]⁺ 466. |
| 327 | 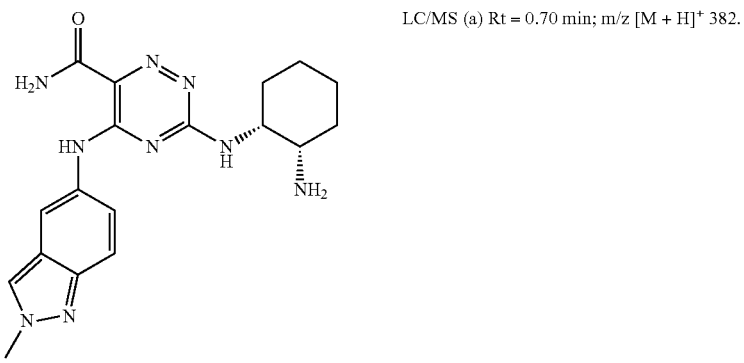 | LC/MS (a) Rt = 0.70 min; m/z [M + H]⁺ 382. |

TABLE 77-continued

| Example No. | Structural formula | Physical property |
|---|---|---|
| 328 | | $^1$H-NMR (CD$_3$OD/CDCl$_3$(1/1)) δ: 8.44 (1H, s), 8.39-8.01 (1H, m), 7.63 (1H, t, J = 60.3 Hz), 7.35-7.08 (1H, m), 4.38-4.10 (1H, m), 4.06-3.99 (1H, m), 3.93-3.86 (1H, m), 3.71-3.61 (2H, m), 3.61-3.51 (2H, m), 3.19-3.16 (1H, m), 2.62 (3H, s), 2.03-1.90 (1H, m), 1.89-1.81 (1H, m).<br>LC/MS (a) Rt = 0.71 min; m/z [M + H]$^+$ 434. |
| 329 | | $^1$H-NMR (CD$_3$OD/CDCl$_3$(1/1)) δ: 8.68-8.41 (1H, m), 8.32-8.13 (1H, m), 7.96 (2H, s), 7.48 (1H, d, J = 8.4 Hz), 4.36-4.02 (1H, m), 3.29-3.24 (1H, m), 1.93-1.47 (8H, m).<br>LC/MS (a) Rt = 0.8 min; m/z [M + H]$^+$ 413415. |
| 330 | | LC/MS (a) Rt = 0.73 min; m/z [M + H]$^+$ 420. |

TABLE 78
| Example No. | Structural formula | Physical property |
|---|---|---|
| 331 | 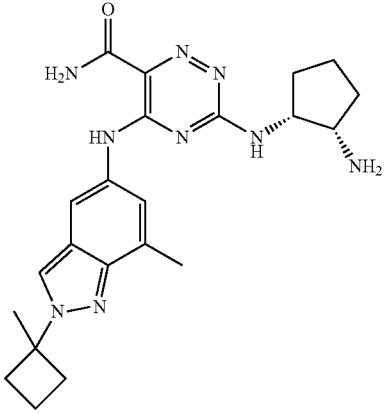 [SMILES: Cc1cc(Nc2nc(N[C@@H]3CCC[C@@H]3N)nnc2C(N)=O)cc2cn(C3(C)CCC3)nc12] | ¹H-NMR (CD₃OD/CDCl₃(1/1)) δ: 8.09-7.89 (2H, m), 7.29-7.03 (1H, m), 4.38-4.10 (1H, m), 3.53-3.46 (1H, m), 2.91-2.80 (2H, m), 2.62 (3H, s), 2.48-2.39 (2H, m), 2.17-1.95 (4H, m), 1.91-1.51 (4H, m), 1.83 (3H, s). LC/MS (a) Rt = 0.8 min; m/z [M + H]⁺ 436. |
| 332 | 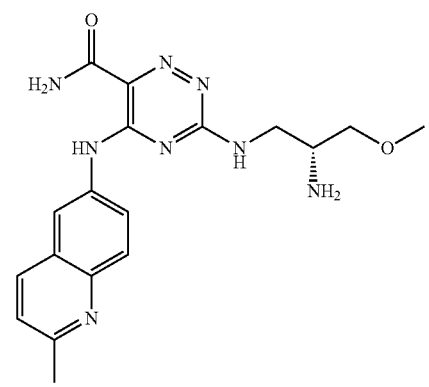 [SMILES: COC[C@H](N)CNc1nnc(C(N)=O)c(Nc2ccc3nc(C)ccc3c2)n1] | ¹H-NMR (CD₃OD/CDCl₃(1/1)) δ: 8.52-8.42 (1H, m), 8.18 (1H, d, J = 8.5 Hz), 7.96 (1H, d, J = 9.3 Hz), 7.87 (1H, d, J = 9.0 Hz), 7.39 (1H, d, J = 8.5 Hz), 3.74-3.66 (1H, m), 3.52-3.26 (4H, m), 3.35 (3H, s), 2.74 (3H, s). LC/MS (a) Rt = 0.57 min; m/z [M + H]⁺ 383. |
| 333 | 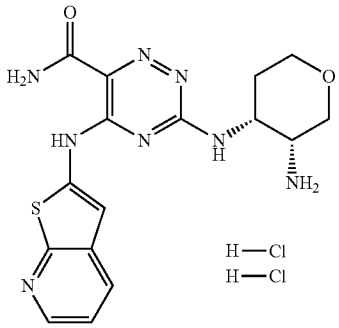 | LC/MS (a) Rt = 0.69 min; m/z [M + H]⁺ 387. |
| 334 | 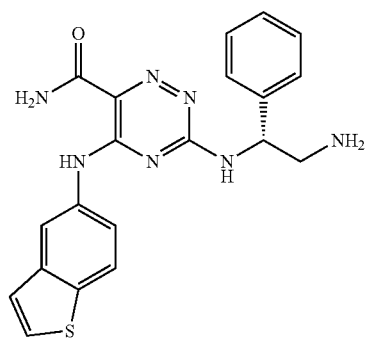 [SMILES: NC[C@H](Nc1nnc(C(N)=O)c(Nc2ccc3sccc3c2)n1)c1ccccc1] | ¹H-NMR (CD₃OD/CDCl₃(1/1)) δ: 8.04-7.97 (1H, m), 7.84-7.76 (1H, m), 7.56 (1H, d, J = 5.5 Hz), 7.43-7.27 (7H, m), 5.03-4.95 (1H, m), 3.10-3.02 (2H, m). LC/MS (a) Rt = 0.84 min; m/z [M + H]⁺ 406. |

TABLE 78-continued
| Example No. | Structural formula | Physical property |
|---|---|---|
| 335 | 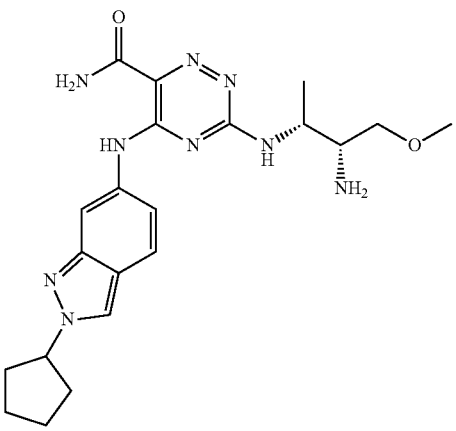 [SMILES: COC[C@H](N)[C@@H](C)Nc1nnc(C(N)=O)c(Nc2ccc3cn(C4CCCC4)nc3c2)n1] | $^1$H-NMR (CD$_3$OD/CDCl$_3$(1/1)) δ: 8.29-8.19 (1H, m), 8.13 (1H, s), 7.64 (1H, d, J = 9.2 Hz), 7.38 (1H, d, J = 9.2 Hz), 5.01-4.94 (1H, m), 4.22-4.14 (1H, m), 3.54-3.48 (2H, m), 3.37 (3H, s), 3.12 (1H, q, J = 5.0 Hz), 2.40-2.30 (2H, m), 2.22-2.12 (2H, m), 2.04-1.94 (2H, m), 1.88-1.78 (2H, m), 1.29 (3H, d, J = 7.0 Hz). LC/MS (a) Rt = 0.75 min; m/z [M + H]$^+$ 440. |
TABLE 79
| Example No. | Structural formula | Physical property |
|---|---|---|
| 336 | 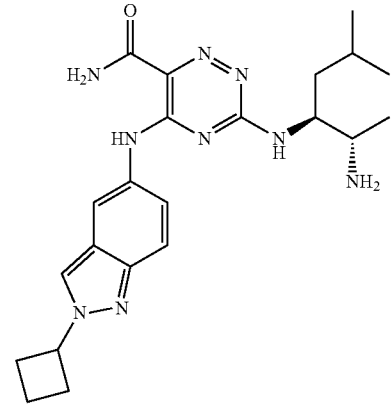 [SMILES: CC(C)C[C@H](Nc1nnc(C(N)=O)c(Nc2ccc3nn(C4CCC4)cc3c2)n1)[C@H](C)N] | LC/MS (a) Rt = 0.82 min; m/z [M + H]$^+$ 438. |
| 337 | 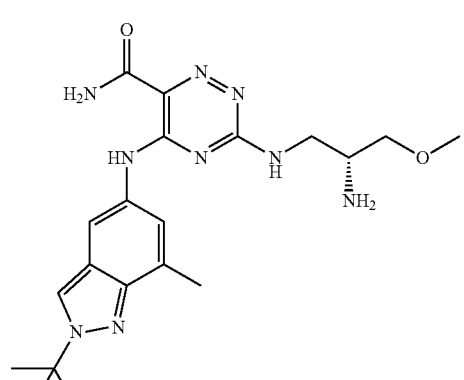 | $^1$H-NMR (CD$_3$OD/CDCl$_3$(1/1)) δ: 8.16 (1H, s), 8.10-8.04 (1H, m), 7.09 (1H, s), 3.64-3.58 (1H, m), 3.50-3.39 (2H, m), 3.35 (3H, s), 3.29-3.23 (2H, m), 2.63 (3H, s), 1.77 (9H, s). LC/MS (a) Rt = 0.75 min; m/z [M + H]$^+$ 428. |

TABLE 79-continued

| Example No. | Structural formula | Physical property |
|---|---|---|
| 338 | | ¹H-NMR (CD₃OD/CDCl₃(1/1)) δ: 7.64-7.59 (2H, m), 7.40 (2H, t, J = 7.7 Hz), 7.30 (1H, d, J = 7.7 Hz), 7.18 (2H, s), 3.77-3.69 (1H, m), 3.61-3.53 (2H, m), 3.48-3.45 (1H, m), 3.41 (3H, s), 3.38-3.33 (1H, m). LC/MS (a) Rt = 0.85 min; m/z [M + H]⁺ 400. |
| 339 | | ¹H-NMR (CD₃OD/CDCl₃(1/1)) δ: 8.10-7.93 (1H, m), 8.06 (1H, s), 4.34-4.08 (1H, m), 4.14 (3H, s), 3.20-3.13 (1H, m), 1.92-1.58 (6H, m), 1.56-1.41 (2H, m). LC/MS (a) Rt = 0.83 min; m/z [M + H]⁺ 450. |
| 340 | | LC/MS (a) Rt = 0.73 min; m/z [M + H]⁺ 386. |

TABLE 80

| Example No. | Structural formula | Physical property |
|---|---|---|
| 341 | 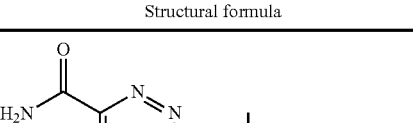 | ¹H-NMR (CD₃OD/CDCl₃(1/1)) δ: 8.30-8.10 (1H, m), 8.00 (1H, s), 7.30-7.10 (1H, m), 5.25 (1H, septet, J = 6.8 Hz), 4.30-4.15 (1H, m), 3.68-3.50 (4H, m), 3.18-3.10 (1H, m), 2.78 (3H, s), 1.61 (6H, d, J = 6.8 Hz), 1.32 (3H, d, J = 6.8 Hz), 1.30-1.12 (3H, m). LC/MS (b) Rt = 1.12 min; m/z [M + H]⁺ 442. |

TABLE 80-continued

| Example No. | Structural formula | Physical property |
|---|---|---|
| 342 | | ¹H-NMR (CD₃OD/CDCl₃(1/1)) δ: 8.05 (1H, d, J = 2.2 Hz), 7.72 (1H, d, J = 2.2 Hz), 7.47 (2H, dt, J = 18.6, 7.6 Hz), 6.80 (1H, s), 4.32-3.95 (1H, m), 3.26-3.19 (1H, m), 1.82-1.42 (8H, m). LC/MS (a) Rt = 0.76 min; m/z[M+H]⁺ 368. |
| 343 | | ¹H-NMR (CD₃OD/CDCl₃(1/1)) δ: 8.30-8.10 (1H, m), 7.97 (1H, s), 7.25-7.10 (1H, m), 4.70-4.60 (2H, m), 3.70-3.25 (7H, m), 2.78 (3H, s), 1.50 (3H, t, J = 7.2 Hz), 1.25-1.10 (3H, m). LC/MS (b) Rt = 0.99 min; m/z [M + H]⁺ 414. |
| 344 | | LC/MS (a) Rt = 0.68 min; m/z [M + H]⁺ 398. |
| 345 | | ¹H-NMR (CD₃OD/CDCl₃(1/1)) δ: 8.25-8.05 (1H, m), 7.20-7.05 (1H, m), 4.52 (2H, q, J = 7.2 Hz), 3.70-3.25 (7H, m), 2.63 (3H, s), 1.66 (3H, t, J = 7.2 Hz), 1.30-1.15 (3H, m). LC/MS (b) Rt = 0.92 min; m/z [M + H]⁺ 414. |

TABLE 81
| Example No. | Structural formula | Physical property |
|---|---|---|
| 346 | 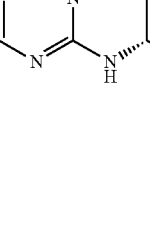 | 1H-NMR (CD₃OD/CDCl₃(1/1)) δ: 8.14 (1H, s), 8.04 (1H, d, J = 7.6 Hz), 7.41 (1H, dd, J = 8.3, 7.6 Hz), 7.19 (1H, d, J = 8.3 Hz), 4.10 (3H, s), 3.46-3.39 (1H, m), 3.26-3.19 (1H, m), 1.87-1.39 (8H, m).<br>LC/MS (a) Rt = 0.75 min; m/z [M + H]⁺ 382. |
| 347 | 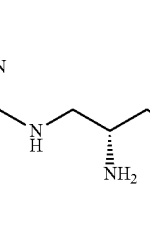 | 1H-NMR (CD₃OD/CDCl₃(1/1)) δ: 8.20-8.10 (1H, m), 8.01 (1H, s), 7.25-7.15 (1H, m), 5.25 (1H, septet, J = 6.8 Hz), 3.70-3.25 (7H, m), 2.78 (3H, s), 1.61 (6H, d, J = 6.8 Hz), 1.30-1.15 (3H, m).<br>LC/MS (b) Rt = 1.08 min; m/z [M + H]⁺ 428. |
| 348 |  | LC/MS (a) Rt = 0.72 min; m/z [M + H]⁺ 452. |
| 349 | 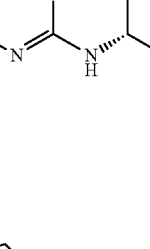 | ¹H-NMR (CD₃OD/CDCl₃(1/1)) δ: 8.48 (1H, s), 8.36-8.19 (1H, m), 7.61 (1H, t, J = 60.1 Hz), 7.16 (1H, s), 3.67-3.47 (5H, m), 3.45-3.39 (1H, m), 3.31-3.25 (1H, m), 2.62 (3H, s), 1.29-1.11 (3H, m).<br>LC/MS (a) Rt = 0.74 min; m/z [M + H]⁺ 436. |

TABLE 81-continued

| Example No. | Structural formula | Physical property |
|---|---|---|
| 350 | | LC/MS (a) Rt = 0.71 min; m/z [M + H]⁺ 424. |

| Example No. | Structural formula | Physical property |
|---|---|---|
| 351 | | ¹H-NMR (CD₃OD/CDCl₃(1/1)) δ: 8.21-8.11 (1H, m), 7.83 (1H, d, J = 8.4 Hz), 7.64-7.56 (3H, m), 7.19 (1H, s), 4.23-4.11 (1H, m), 3.21-3.11 (1H, m), 2.46 (3H, s), 2.00-1.57 (6H, m), 1.55-1.42 (2H, m). LC/MS (a) Rt = 0.84 min; m/z [M + H]⁺ 398. |
| 352 | | ¹H-NMR (CD₃OD/CDCl₃(1/1)) δ: 8.32-8.05 (1H, m), 7.98 (1H, s), 7.28-7.12 (1H, m), 4.70-4.61 (2H, m), 4.35-4.02 (1H, m), 3.72-3.62 (1H, m), 3.36 (3H, s), 3.06-2.98 (1H, m), 2.97-2.88 (1H, m), 2.78 (3H, s), 1.50 (3H, t, J = 7.2 Hz), 1.28-1.18 (3H, m). LC/MS (b) Rt = 1.01 min; m/z [M + H]⁺ 414. |

-continued
| Example No. | Structural formula | Physical property |
|---|---|---|
| 353 | | $^1$H-NMR (CD$_3$OD/CDCl$_3$(1/1)) δ: 8.53-8.41 (1H, m), 8.17 (1H, d, J = 8.5 Hz), 7.96 (1H, d, J = 8.5 Hz), 7.88 (1H, dd, J = 9.1, 2.3 Hz), 7.38 (1H, d, J = 8.5 Hz), 3.68 (1H, dd, J = 13.8, 5.2 Hz), 3.59-3.49 (3H, m), 3.47-3.41 (2H, m), 3.31-3.27 (1H, m), 2.74 (3H, s), 1.28-1.11 (3H, m). LC/MS (a) Rt = 0.57 min; m/z [M + H]$^+$ 397. |
| 354 | | LC/MS (a) Rt = 0.79 min; m/z [M + H]$^+$ 459. |
| 355 | | LC/MS (a) Rt = 0.65 min; m/z [M + H]$^+$ 379. |
TABLE 83
| Example No. | Structural formula | Physical property |
|---|---|---|
| 356 | 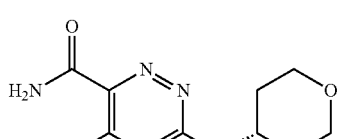 | LC/MS (a) Rt = 0.80 min; m/z [M + H]$^+$ 438. |

TABLE 83-continued

| Example No. | Structural formula | Physical property |
|---|---|---|
| 357 | (structure) | LC/MS (a) Rt = 0.84 min; m/z [M + H]+ 436. |
| 358 | (structure) | LC/MS (a) Rt = 0.63 min; m/z [M + H]+ 368. |
| 359 | (structure) | LC/MS (a) Rt = 0.78 min; m/z [M + H]+ 398. |
| 360 | (structure) | 1H-NMR (CD3OD) δ: 8.50-8.20 (1H, br), 8.08 (1H, s), 7.40-7.15 (1H, m), 5.38-5.15 (2H, m), 4.35-3.00 (6H, m), 2.71 (3H, s), 2.05-1.68 (2H, m). LC/MS (a) Rt = 0.76 min; m/z [M + H]+ 466. |

TABLE 84
| Example No. | Structural formula | Physical property |
|---|---|---|
| 361 | 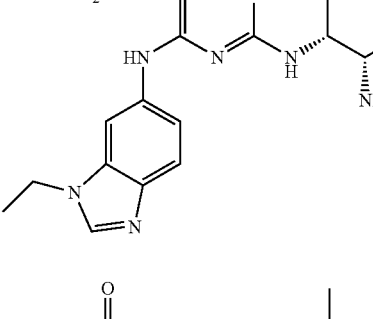 | ¹H-NMR (CD₃OD/CDCl₃(1/1)) δ: 8.06 (1H, s), 8.00 (1H, br s), 7.69 (1H, d, J = 8.4 Hz), 7.50 (1H, d, J = 8.4 Hz), 4.32 (2H, q, J = 7.3 Hz), 4.18-4.09 (1H, m), 3.19-3.11 (1H, m), 1.87-1.63 (6H, m), 1.59 (3H, t, J = 7.3 Hz), 1.53-1.42 (2H, m). LC/MS (a) Rt = 0.59 min; m/z [M + H]⁺ 396. |
| 362 | 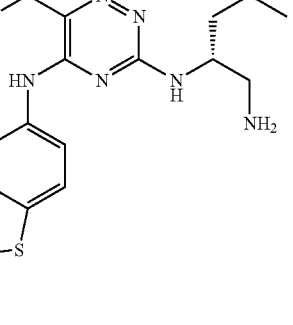 | ¹H-NMR (CD₃OD/CDCl₃(1/1)) δ: 8.45-8.22 (1H, m), 7.88 (1H, d, J = 8.8 Hz), 7.58-7.54 (2H, m), 7.40-7.31 (1H, m), 4.20-4.10 (1H, m), 2.95-2.85 (1H, m), 2.77-2.71 (1H, m), 1.82-1.68 (1H, m), 1.60-1.52 (1H, m), 1.44-1.38 (1H, m), 1.00-0.91 (6H, m). LC/MS (b) Rt = 1.21 min; m/z [M + H]⁺ 386. |
| 363 | 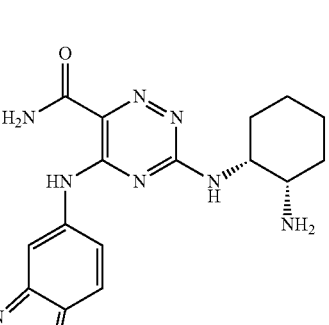 | LC/MS (a) Rt = 0.80 min; m/z [M + H]⁺ 422. |
| 364 | 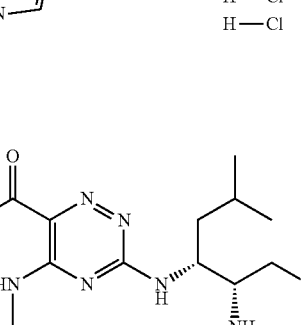 | ¹H-NMR (CD₃OD/CDCl₃(1/1)) δ: 8.58-8.23 (1H, m), 8.09 (1H, s), 7.68 (1H, d, J = 9.2 Hz), 7.20-7.01 (1H, m), 4.50 (2H, q, J = 7.2 Hz), 4.38-4.30 (1H, m), 3.60-3.50 (2H, m), 3.35 (3H, s), 3.20-3.05 (1H, m), 1.80-1.55 (2H, m), 1.66 (3H, t, J = 7.2 Hz), 1.50-1.40 (1H, m), 1.05-0.85 (6H, m). LC/MS (b) Rt=1.09 min ; m/z[M+H]⁺ 442. |

TABLE 84-continued
| Example No. | Structural formula | Physical property |
|---|---|---|
| 365 | 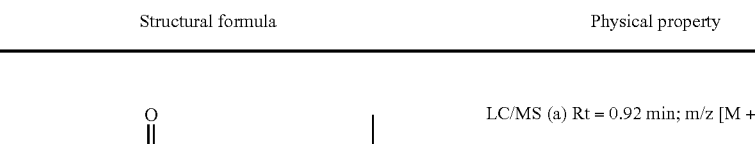 | LC/MS (a) Rt = 0.92 min; m/z [M + H]+ 434. |
TABLE 85
| Example No. | Structural formula | Physical property |
|---|---|---|
| 366 | | LC/MS (a) Rt = 0.70 min; m/z [M + H]+ 420. |
| 367 | 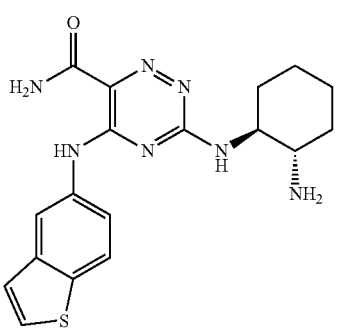 [SMILES: NC(=O)c1nnc(N[C@H]2CCCC[C@@H]2N)nc1Nc1ccc2sccc2c1] | LC/MS (a) Rt = 0.83 min; m/z [M + H]+ 384. |

TABLE 85-continued

| Example No. | Structural formula | Physical property |
|---|---|---|
| 368 | (structure) | $^1$H-NMR (CD$_3$OD/CDCl$_3$(1/1)) δ: 8.19-8.14 (1H, m), 8.03 (1H, dd, J = 7.8,2.9 Hz), 7.43-7.36 (1H, m), 7.29-7.25 (1H, m), 4.73-4.62 (1H, m), 4.23-4.16 (2H, m), 3.70-3.61 (2H, m), 3.58-3.37 (6H, m), 3.32-3.22 (1H, m), 2.50-2.36 (2H, m), 2.06-1.97 (2H, m), 1.26-1.18 (3H, m).<br>LC/MS (a) Rt = 0.95 min; m/z [M + H]$^+$ 456. |
| 369 | (structure) | LC/MS (a) Rt = 0.67 min; m/z [M + H]$^+$ 384. |
| 370 | (structure) | $^1$H-NMR (CD$_3$OD/CDCl$_3$(1/1)) δ: 8.43-8.30 (1H, m), 7.88 (1H, d, J = 8.8 Hz), 7.59-7.52 (2H, m), 7.44-7.31 (1H, m), 4.44-4.05 (1H, m), 3.18-3.08 (1H, m), 1.80-1.68 (1H, m), 1.62-1.50 (1H, m), 1.40-1.25 (1H, m), 1.18-1.12 (3H, m), 0.99 (3H, d, J = 6.8 Hz), 1.00-0.91 (3H, m).<br>LC/MS (b) Rt = 1.24 min; m/z [M + H]$^+$ 400. |

TABLE 86

| Example No. | Structural formula | Physical property |
|---|---|---|
| 371 | (structure) | $^1$H-NMR (CD$_3$OD/CDCl$_3$(1/1)) δ: 8.69-8.45 (2H, m), 7.74 (1H, d, J = 9.9 Hz), 7.64 (1H, t, J = 60.1 Hz), 7.45-7.34 (3H, m), 7.30-7.23 (2H, m), 7.14 (1H, d, J = 9.2 Hz), 4.30-4.23 (1H, m), 3.81 (1H, dd, J = 13.2, 5.9 Hz), 3.70-3.61 (1H, m).<br>LC/MS (a) Rt = 0.77 min; m/z [M + H]$^+$ 440. |

TABLE 86-continued
| Example No. | Structural formula | Physical property |
|---|---|---|
| 372 | 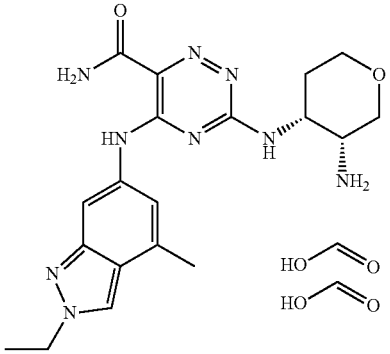 | LC/MS (a) Rt = 0.72 min; m/z [M + H]+ 412. |
| 373 | 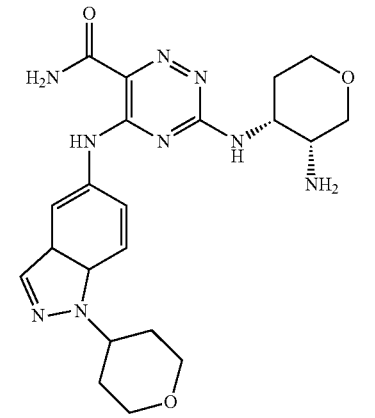 [SMILES: NC(=O)c1nnc(N[C@@H]2CCOC[C@@H]2N)nc1NC1=CC2C=NN(C3CCOCC3)C2C=C1] | LC/MS (a) Rt = 0.68 min; m/z [M + H]+ 454. |
| 374 | 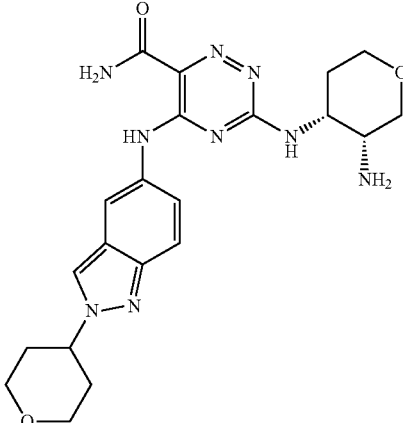 | LC/MS (a) Rt = 0.64 min; m/z [M + H]+ 454. |

TABLE 86-continued

| Example No. | Structural formula | Physical property |
|---|---|---|
| 375 | | LC/MS (a) Rt = 0.97 min; m/z [M + H]+ 381. |

TABLE 87

| Example No. | Structural formula | Physical property |
|---|---|---|
| 376 | | $^1$H-NMR (CD$_3$OD/CDCl$_3$(1/1)) δ: 8.20-8.01 (2H, m), 7.02 (1H, s), 4.04-3.49 (5H, m), 2.64 (3H, s), 1.76 (9H, s). LC/MS (a) Rt = 0.78 min; m/z [M + H]+ 396. |
| 377 | | LC/MS (a) Rt = 0.67 min; m/z [M + H]+ 382. |
| 378 | | LC/MS (a) Rt = 0.60 min; m/z [M + H]+ 370. |

TABLE 87-continued
| Example No. | Structural formula | Physical property |
|---|---|---|
| 379 | | LC/MS (a) Rt = 0.59 min; m/z [M + H]+ 382. |
| 380 | | LC/MS (a) Rt = 0.59 min; m/z [M + H]+ 382. |
TABLE 8
| Example No. | Structural formula | Physical property |
|---|---|---|
| 381 | 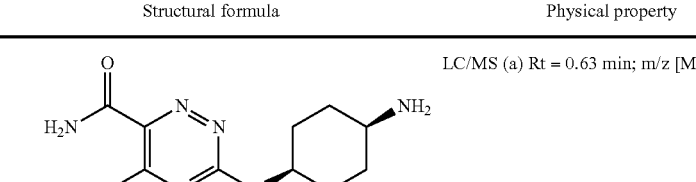 | LC/MS (a) Rt = 0.63 min; m/z [M + H]+ 401. |

TABLE 8-continued

| Example No. | Structural formula | Physical property |
|---|---|---|
| 382 | | LC/MS (a) Rt = 0.69 min; m/z [M + H]+ 401. |
| 383 | | LC/MS (a) Rt = 0.83 min; m/z[M + H]+ 384. |
| 384 | | LC/MS (a) Rt = 0.69 min; m/z [M + H]+ 420. |
| 385 | | LC/MS (a) Rt = 0.74 min; m/z [M + H]+ 404. |

TABLE 89
| Example No. | Structural formula | Physical property |
|---|---|---|
| 386 | 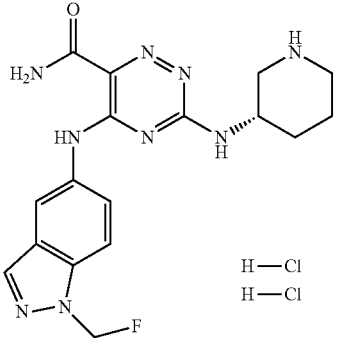 | LC/MS (a) Rt = 0.72 min; m/z [M + H]⁺ 404. |
| 387 |  | LC/MS (a) Rt = 0.69 min; m/z [M + H]⁺ 404. |
| 388 |  | LC/MS (a) Rt = 0.65 min; m/z [M + H]⁺ 440. |

TABLE 89-continued

| Example No. | Structural formula | Physical property |
| --- | --- | --- |
| 389 | | LC/MS (a) Rt = 0.78 min; m/z [M + H]+ 339. |
| 390 | | LC/MS (a) Rt = 0.71 min; m/z [M + H]+ 399. |

TABLE 90

| Example No. | Structural formula | Physical property |
| --- | --- | --- |
| 391 | | LC/MS (a) Rt = 0.88 min; m/z [M + H]+ 445. |

TABLE 90-continued

| Example No. | Structural formula | Physical property |
| --- | --- | --- |
| 392 | | LC/MS (a) Rt = 0.61 min; m/z [M + H]$^+$ 381. |
| 393 | | LC/MS (a) Rt = 0.84 min; m/z [M + H]$^+$ 423. |
| 394 | | LC/MS (a) Rt = 0.65 min; m/z [M + H]$^+$ 398. |
| 395 | | LC/MS (a) Rt = 0.71 min; m/z [M + H]$^+$ 410. |

TABLE 91
| Example No. | Structural formula | Physical property |
|---|---|---|
| 396 | 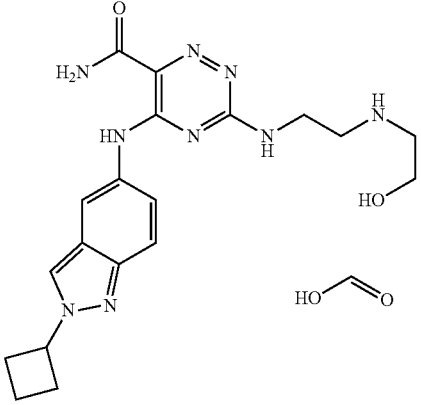 [SMILES: NC(=O)c1nnc(NCCNCCO)nc1Nc1ccc2nn(C3CCC3)cc2c1 ; O=CO] | LC/MS (a) Rt = 0.67 min; m/z [M + H]⁺ 412. |
| 397 | 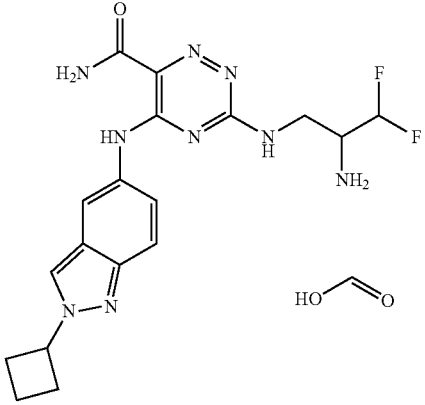 [SMILES: NC(=O)c1nnc(NCC(N)C(F)F)nc1Nc1ccc2nn(C3CCC3)cc2c1 ; O=CO] | $^1$H-NMR (CD$_3$OD) δ: 8.32-8.22 (m, 2H), 8.19 (s, 1H), 7.61 (d, J = 8.8 Hz, 1H), 7.35 (dd, J = 9.2, 1.8 Hz, 1H), 5.99 (br t, J = 53.4 Hz, 1H), 5.12 (quin, J = 8.3 Hz, 1H), 3.90-3.78 (m, 1H), 3.77-3.55 (m, 1H), 2.77-2.53 (m, 4H), 2.07-1.95 (m, 2H). LC/MS (a) Rt = 0.72 min; m/z [M + H]⁺ 418. |
| 398 | 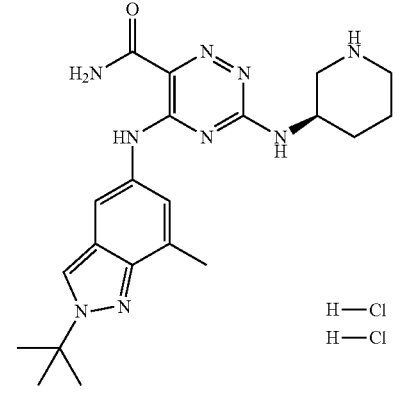 | LC/MS (a) Rt = 0.77 min; m/z [M + H]⁺ 424. |
| 399 | 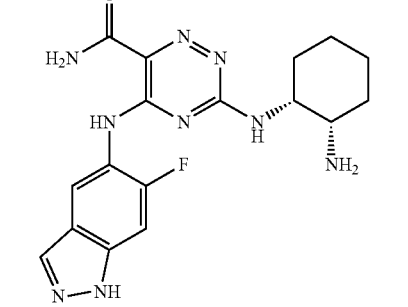 | LC/MS (a) Rt = 0.68 min; m/z [M + H]⁺ 386. |

TABLE 91-continued

| Example No. | Structural formula | Physical property |
|---|---|---|
| 400 |  | ¹H-NMR (CD₃OD/CDCl₃(2/1)) δ: 8.80 (1H, s), 8.10 (1H, s), 7.77 (1H, d, J = 8.4 Hz), 7.61 (1H, t, J = 58.7 Hz), 7.26 (1H, d, J = 6.6 Hz), 3.68 (1H, dd, J = 13.7, 4.6 Hz), 3.57-3.47 (2H, m), 3.43-3.39 (1H, m), 3.36 (3H, s), 3.28-3.23 (1H, m). LC/MS (a) Rt = 0.72 min; m/z [M + H]⁺ 408. |

TABLE 92

| Example No. | Structural formula | Physical property |
|---|---|---|
| 401 | | ¹H-NMR (CD₃OD/CDCl₃(1/1)) δ: 7.64-7.60 (2H, m), 7.40 (2H, t, J = 7.7 Hz), 7.29 (1H, t, J = 7.1 Hz), 7.18 (2H, d, J = 11.0 Hz), 4.32-4.13 (1H, m), 3.54-3.33 (1H, m), 3.02-2.95 (1H, m), 2.74-2.62 (2H, m), 2.23-2.14 (1H, m), 1.91-1.82 (1H, m), 1.74-1.61 (2H, m). LC/MS (a) Rt = 0.83 min; m/z [M + H]⁺ 396. |
| 402 | | ¹H-NMR (CD₃OD/CDCl₃(1/1)) δ: 8.41-8.29 (1H, m), 7.87 (1H, d, J = 8.8 Hz), 7.58-7.53 (2H, m), 7.36-7.31 (1H, m), 3.74-3.60 (2H, m), 2.17-2.06 (2H, m), 1.98-1.86 (2H, m), 1.85-1.68 (2H, m). LC/MS (a) Rt = 0.77 min; m/z [M + H]⁺ 370. |
| 403 | | ¹H-NMR (CD₃OD/CDCl₃(1/1)) δ: 8.73-8.47 (1H, m), 8.49 (1H, s), 7.73 (1H, d, J = 8.8 Hz), 7.63 (1H, t, J = 59.4 Hz), 7.10 (1H, d, J = 7.3 Hz), 3.63 (2H, s), 0.74-0.66 (4H, m). LC/MS (a) Rt = 0.7 min; m/z [M + H]⁺ 390. |

TABLE 92-continued

| Example No. | Structural formula | Physical property |
|---|---|---|
| 404 | (structure: 1,2,4-triazine with CONH₂, NH-benzothiophene, NH-CH(Et)CH₂OH) | ¹H-NMR (CD₃OD/CDCl₃(1/1)) δ: 8.34 (1H, s), 7.86 (1H, d, J = 8.4 Hz), 7.56 (1H, s), 7.54 (1H, d, J = 5.5 Hz), 7.37-7.32 (1H, m), 4.16-3.94 (1H, m), 3.72 (2H, d, J = 4.8 Hz), 1.83-1.73 (1H, m), 1.71-1.63 (1H, m), 1.03 (3H, t, J = 7.3 Hz). LC/MS (a) Rt = 0.89 min; m/z [M + H]⁺ 359. |
| 405 | (structure: 1,2,4-triazine with CONH₂, NH-benzothiophene, NH-(3-hydroxypyrrolidinyl)) | ¹H-NMR (CD₃OD/CDCl₃(1/1)) δ: 8.52-8.39 (1H, m), 7.86 (1H, d, J = 8.1 Hz), 7.55-7.50 (2H, m), 7.43-7.37 (1H, m), 4.32-4.21 (2H, m), 3.53-3.43 (1H, m), 3.12 (1H, dd, J = 12.5, 5.1 Hz), 2.90-2.84 (2H, m). LC/MS (a) Rt = 0.71 min; m/z [M + H]⁺ 372. |

TABLE 93

| Example No. | Structural formula | Physical property |
|---|---|---|
| 406 | (structure: 1,2,4-triazine with CONH₂, NH-(N-methylindol-4-yl), NH-CH(Ph)CH₂NH₂) | ¹H-NMR (CD₃OD/CDCl₃(1/1)) δ: 7.71-7.66 (1H, m), 7.43-7.36 (4H, m), 7.27 (1H, t, J = 7.1 Hz), 7.20-7.16 (2H, m), 7.14-7.11 (1H, m), 6.59-6.56 (1H, m), 5.06-4.99 (1H, m), 3.84 (3H, s), 3.09-3.05 (2H, m). LC/MS (a) Rt = 0.81 min; m/z [M + H]⁺ 403. |
| 407 | (structure: 1,2,4-triazine with CONH₂, NH-(N-(tetrahydrofuran-3-yl)indol-4-yl), NHMe) | LC/MS (a) Rt = 0.82 min; m/z [M + H]⁺ 354. |

TABLE 93-continued

| Example No. | Structural formula | Physical property |
|---|---|---|
| 408 | | LC/MS (a) Rt = 0.90 min; m/z [M + H]+ 368. |
| 409 | | LC/MS (a) Rt = 0.90 min; m/z [M + H]+ 355. |
| 410 | | LC/MS (a) Rt = 0.98 min; m/z [M + H]+ 369. |

TABLE 94

| Example No. | Structural formula | Physical property |
|---|---|---|
| 411 | | LC/MS (a) Rt = 0.87 min; m/z [M + H]+ 369. |
| 412 | | $^1$H-NMR (CD$_3$OD/CDCl$_3$(1/1)) δ: 8.13-8.07 (1H, m), 8.01-7.98 (1H, m), 7.09-7.02 (1H, m), 4.60-4.44 (2H, m), 4.07-3.48 (3H, m), 2.63-2.57 (3H, m), 1.78-1.66 (9H, m).<br>LC/MS (a) Rt = 0.78 min; m/z [M + H]+ 396. |
| 413 | | $^1$H-NMR (CD$_3$OD/CDCl$_3$(1/1)): 8.13-7.85 (2H, m), 7.80-7.64 (1H, m), 3.96-3.83 (1H, m), 3.22-3.08 (1H, m), 1.89-1.19 (17H, m).<br>LC/MS (a) Rt = 0.89 min; m/z [M + H]+ 502/504. |

TABLE 94-continued

| Example No. | Structural formula | Physical property |
| --- | --- | --- |
| 414 | | ¹H-NMR (CD₃OD) δ: 8.29 (3 H, br s), 8.21 (1 H, s), 7.62 (1 H, d, J = 9.2 Hz), 7.36 (1 H, dd, J = 9.2, 1.8 Hz), 5.12 (1 H, quin, J = 8.4 Hz), 4.70 (2 H, br. s.), 4.62 (2 H, br s), 4.15-3.89(2 H, br s), 2.78-2.52 (4 H, m), 2.05-1.94 (2 H, m) LC/MS (a) Rt = 0.69 min; m/z [M + H]⁺ 410. |

TEST EXAMPLES

The biological activity of the present invention was evaluated using the following testing methods.

Test Example 1

Syk Kinase Inhibition Test

The in vitro inhibitory activity of the compound of the present invention against Syk kinase activity was assayed under the following conditions: the purified human Syk protein used in the test were purchased from Carna Biosciences, Inc. For the inhibitory activity assay on the compound, the compound of the present invention was first serially diluted with dimethyl sulfoxide (DMSO). Next, the purified human Syk protein FL-Peptide 22 (final concentration: 1 μM) (Caliper Life Sciences, Inc.), magnesium chloride (final concentration: 5 mM), ATP (final concentration: 30 μM), and each DMSO solution of the compound of the present invention (final concentration of DMSO: 5%) were added into a buffer solution for reaction (20 mM tris-HCl pH 7.5, 20 mM NaCl, 2.5 mM DTT, 0.02% Tween-20, 1% glycerol, 0.01 mM Pefabloc), and the mixture was then incubated at 25° C. for 30 minutes to perform kinase reaction. The kinase reaction was stopped by the addition thereto of EDTA (final concentration: 30 mM) diluted with Separation Buffer (Caliper Life Sciences, Inc.). Finally, phosphorylated peptides and non-phosphorylated peptides were separated therebetween using LabChip™ 3000 system (Caliper Life Sciences, Inc., excitation wavelength: 488 nm, detection wavelength: 530 nm). Their respective amounts were measured, and the rate of phosphorylation reaction was then determined from the ratio between the amounts. The concentration at which the compound can inhibit 50% phosphorylation reaction is defined as an IC₅₀ value (μM).

Also, known 1,2,4-triazine-6-carboxamide derivatives A, B, and C (WO2000/075113 (A: compound No. 121 and B: compound No. 154) and WO2000/076980 (C: compound No. 39)) were synthesized as control compounds. Their IC₅₀ values (μM) were calculated in the same way as above and then compared with that of the compound of the present invention.

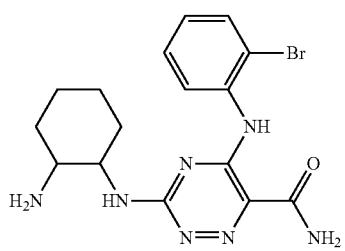

A

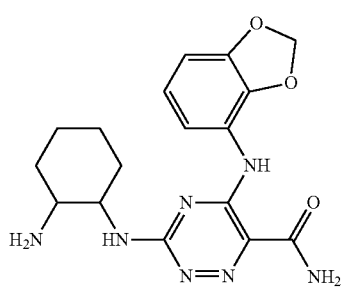

B

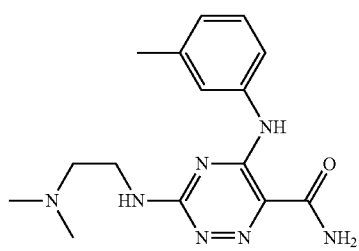

C

Test Example 2

Cell Growth Inhibition Test

The in vitro cell growth inhibition of SU-DHL-6 cells (diffuse large-cell lymphoma cell line) was tested under the following conditions:

SU-DHL-6 cells (ATCC, Cat#: CRL-2959) suspended in an RPMI1640 medium (ATCC, Cat#: 30-2001) containing 10% FBS were inoculated at a density of 8×10³ cells (100 μl)/well to a 96-well flat-bottomed microplate (NUNC, Cat#:

165305) and then cultured at 37° C. for 1 day in an incubator containing 5% $CO_2$. The compound of the present invention was serially diluted with dimethyl sulfoxide and then added to an RPMI1640 medium containing 10% FBS. Each resulting solution was added at a concentration of 100 μl/well to the preceding SU-DHL-6 cell culture plate (final concentration of the compound: 10, 3, 1, 0.3, 0.1, 0.03, 0.01, and 0.003 μM). The cells were cultured at 37° C. for 3 days in an incubator containing 5% $CO_2$. The cells thus cultured were left at room temperature for 30 minutes and then centrifuged at 1500 rpm for 3 minutes using a centrifuge (Hitachi Koki Co., Ltd., Himac CF7D2). A 100 μl aliquot of the supernatant was removed from each well to allow 100 μl of the cell culture solution to remain therein. This 100 μl of the remaining cell culture solution was supplemented with an equal amount of CellTiter-Glo Luminescent Cell Viability Assay (Promega KK, Cat#: G7573), and the mixture was then shaken for 1 minute using a plate mixer. The reaction solution was left in the dark for 10 minutes. Then, luminescence intensity derived from live cells of each well was measured using a microplate reader (PerkinElmer Inc., ARVOsx). The rate of cell growth inhibition was calculated according to the expression shown below to determine the concentration at which the compound of the present invention inhibited 50% cell growth ($IC_{50}$ value (μM))

Likewise, the $IC_{50}$ values (μM) of the control compounds were also calculated and then compared with that of the compound of the present invention.

Rate of cell growth inhibition(%)=$(C-T)/C$×100

T: luminescence intensity (count per second) of a well supplemented with the test compound
C: luminescence intensity (count per second) of a well non-supplemented with the test compound Tables 95 and 96 show the results of testing the inhibition of Syk kinase and the cell growth inhibition of SU-DHL6 cells by representative compounds according to the present invention and the control compounds.

TABLE 95

| Example No. | SYK inhibitory activity IC50 (nM) |
|---|---|
| 1 | 0.40 |
| 2 | 0.46 |
| 3 | 0.36 |
| 5 | 0.52 |
| 7 | 0.92 |
| 9 | 0.90 |
| 11 | 0.47 |
| 13 | 0.49 |
| 16 | 0.94 |
| 17 | 0.21 |
| 24 | 0.53 |
| 25 | 0.36 |
| 26 | 0.22 |
| 33 | 0.71 |
| 34 | 0.42 |
| 35 | 0.51 |
| 48 | 0.27 |
| 50 | 0.42 |
| 56 | 0.50 |
| 57 | 0.52 |
| 60 | 0.33 |
| 61 | 0.37 |
| 62 | 0.37 |
| 65 | 0.23 |
| 66 | 0.61 |
| 67 | 0.26 |

TABLE 95-continued

| Example No. | SYK inhibitory activity IC50 (nM) |
|---|---|
| 73 | 0.37 |
| 76 | 0.55 |
| 77 | 0.42 |
| 78 | 0.53 |
| 79 | 0.37 |
| 91 | 0.26 |
| 93 | 0.67 |
| 97 | 0.39 |
| 99 | 0.63 |
| 100 | 0.41 |
| 106 | 0.85 |
| 107 | 0.61 |
| 154 | 0.43 |
| 160 | 0.38 |
| 161 | 0.28 |
| 164 | 0.29 |
| 165 | 0.36 |
| 170 | 0.58 |
| 184 | 0.38 |
| 208 | 0.40 |
| 209 | 0.33 |
| 212 | 0.29 |
| 220 | 0.26 |
| 245 | 0.35 |
| 256 | 0.35 |
| 257 | 0.38 |
| 258 | 0.29 |
| 259 | 0.33 |
| 265 | 0.50 |
| 267 | 0.41 |
| 274 | 0.95 |
| 277 | 0.41 |
| 282 | 0.48 |
| 284 | 0.34 |
| 310 | 0.59 |
| 311 | 0.55 |
| 316 | 0.31 |
| 354 | 0.89 |
| 359 | 0.37 |
| A | 33 |
| B | 6.8 |
| C | 620 |

TABLE 96

| Example No. | Cell growth inhibition IC50 (nM) |
|---|---|
| 3 | 91 |
| 7 | 174 |
| 17 | 76 |
| 24 | 152 |
| 25 | 100 |
| 26 | 41 |
| 34 | 65 |
| 35 | 107 |
| 57 | 179 |
| 60 | 106 |
| 61 | 164 |
| 65 | 24 |
| 67 | 49 |
| 73 | 53 |
| 77 | 82 |
| 78 | 85 |
| 79 | 93 |
| 91 | 138 |
| 93 | 149 |
| 97 | 191 |
| 154 | 138 |
| 160 | 165 |
| 161 | 27 |

TABLE 96-continued

| Example No. | Cell growth inhibition IC50 (nM) |
|---|---|
| 164 | 92 |
| 165 | 177 |
| 170 | 178 |
| 212 | 128 |
| 220 | 180 |
| 245 | 158 |
| 256 | 157 |
| 257 | 49 |
| 258 | 60 |
| 259 | 75 |
| 265 | 125 |
| 267 | 128 |
| 274 | 155 |
| 277 | 181 |
| A | 2000 |
| B | 1900 |
| C | >10000 |

As is evident from Tables 95 and 96, the compound of the present invention has stronger Syk inhibitory activity and cell growth inhibitory effect than those of the control compounds A, B, and C. This result demonstrated that the compound represented by the general formula (I) which has been found by the present invention is a stronger Syk inhibitor than known triazine derivatives.

Test Example 3

Confirmation of KDR Kinase Activity Inhibitory Effect

Conditions for assaying the in vitro inhibitory activity of the compound against KDR kinase activity were set with reference to the statement in the LabChip™ series reagent supplies price list of Caliper Life Sciences, Inc. that FL-Peptide 22 is adaptable as a substrate peptide to KDR kinase activity assay. The purified recombinant human KDR protein used in the test is a house purified product. For the inhibitory activity assay on the compound, the compound of the present invention was first serially diluted with dimethyl sulfoxide (DMSO). Next, the purified human KDR protein FL-Peptide 22 (final concentration: 1.5 μM), magnesium chloride (final concentration: 10 mM), ATP (final concentration: 200 μM), and each DMSO solution of the compound of the present invention (final concentration of DMSO: 5%) were added into a buffer solution for reaction (100 mM HEPES pH 7.5, 1 mM DTT, 0.003% Brij 35, 0.04% Tween-20, 0.05% CHAPSO) supplemented with a phosphatase inhibitor cocktail (PhosSTOP, F. Hoffmann-La Roche Ltd.) and a protease inhibitor cocktail (Complete Mini, EDTA-free, F. Hoffmann-La Roche Ltd) at recommended concentrations. The mixture was incubated at 30° C. for 180 minutes to perform kinase reaction. The kinase reaction was stopped by the addition thereto of EDTA (final concentration: 30 mM) diluted with Separation Buffer manufactured by Caliper Life Sciences, Inc. Finally, phosphorylated peptides and non-phosphorylated peptides were separated therebetween using LabChip™ 3000 system (Caliper Life Sciences, Inc., excitation wavelength: 488 nm, detection wavelength: 530 nm). Their respective amounts were measured, and the rate of phosphorylation reaction was then determined from the ratio between the amounts. The concentration at which the compound can inhibit 50% phosphorylation reaction is defined as an $IC_{50}$ value (nM) and shown in Table 97 below. Likewise, the $IC_{50}$ value (μM) of an existing Syk inhibitor R406 (Rigel Pharmaceuticals, Inc.) was also calculated as a control compound and then compared with that of the compound of the present invention.

Test Example 4

Confirmation of Aurora B Kinase Activity Inhibitory Effect

The in vitro inhibitory activity of the compound against Aurora B kinase activity was assayed with reference to a method described in patent publication (JP-A-2008-81492). The purified recombinant human Aurora B protein used in the test was purchased from Carna Biosciences, Inc. For the inhibitory activity assay on the compound, the compound of the present invention was first serially diluted with dimethyl sulfoxide (DMSO). Next, the purified human Aurora B protein FL-Peptide 21 (Caliper Life Sciences, Inc., final concentration: 100 nM), magnesium chloride (final concentration: 1 mM), ATP (final concentration: 40 μM), and each DMSO solution of the compound of the present invention (final concentration of DMSO: 5%) were added into a buffer solution for reaction (20 mM HEPES pH 7.4, 2 mM DTT, 0.01% Tween-20), and the mixture was then incubated at 25° C. for 60 minutes to perform kinase reaction. The kinase reaction was stopped by the addition thereto of IMAP™ Progressive Binding Reagent diluted 500-fold with IMAP™ Progressive Binding Buffer A manufactured by Molecular Devices, LLC. The reaction solution was left standing in the dark at room temperature for 120 minutes. Then, fluorescence polarization values obtained by measurement using PHERAstar (BMG LABTECH JAPAN Ltd., excitation wavelength: 485 nm, detection wavelength: 520 nm) were used to determine the rate of phosphorylation reaction. The concentration at which the compound can inhibit 50% phosphorylation reaction is defined as an $IC_{50}$ value (nM) and shown in Table 97 below. Likewise, the $IC_{50}$ value (μM) of an existing Syk inhibitor R406 (Rigel Pharmaceuticals, Inc.) was also calculated as a control compound and then compared with that of the compound of the present invention.

TABLE 97

| Example No. | SYK inhibitory activity IC50 (nM) | KDR inhibitory activity IC50 (nM)/ Selectivity for Syk | AuroraB inhibitory activity IC50 (nM)/ Selectivity for Syk |
|---|---|---|---|
| 24 | 0.53 | >10000 (>20000 times) | >10000 (>20000 times) |
| 160 | 0.38 | 1400 (4400 times) | 1300 (4100 times) |
| 161 | 0.28 | >2000 (>7000 times) | 420 (1500 times) |
| R406 | 5.5 | 10 (1.8 times) | 110 (20 times) |

As is evident from Table 97, the compound of the present invention, compared with the control compound, has remarkable Syk selectivity without the inhibition of other kinases which is responsible for potential adverse effects. This result showed that the compound represented by the general formula (I) which has been found by the present invention has fewer adverse effects than those of known Syk inhibitors.

The invention claimed is:
1. A compound of formula (I) or a salt thereof:

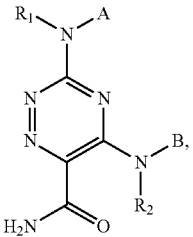

wherein
R₁ represents a hydrogen atom or an optionally $R_a$-substituted $C_1$-$C_6$ alkyl group;
A represents an optionally $R_a$-substituted $C_1$-$C_8$ alkyl group, an optionally $R_a$-substituted $C_2$-$C_6$ alkenyl group, an optionally $R_a$-substituted $C_2$-$C_6$ alkynyl group, an optionally $R_b$-substituted $C_3$-$C_{10}$ cycloalkyl group, an optionally $R_b$-substituted $C_6$-$C_{14}$ aromatic hydrocarbon group, an optionally $R_b$-substituted 4- to 10-membered unsaturated heterocyclic group, or an optionally $R_b$-substituted 4- to 10-membered saturated heterocyclic group, or optionally forms a 4- to 10-membered unsaturated heterocyclic ring or a 4- to 10-membered saturated heterocyclic ring together with R₁ and a nitrogen atom bonded thereto, wherein the 4- to 10-membered unsaturated heterocyclic ring and the 4- to 10-membered saturated heterocyclic ring are each optionally substituted by $R_b$;
$R_a$ represents a heavy hydrogen atom, a halogen atom, a cyano group, a nitro group, —C(=O)OR$_x$, —C(=O)SR$_x$, —C(=S)OR$_x$, —N(R$_x$)(R$_y$), —NR$_x$C(=O)R$_y$, —NR$_x$SO$_2$R$_y$, —NR$_x$C(=O)OR$_y$, —NR$_x$C(=O)N(R$_y$)(R$_z$), —NR$_x$SO$_2$N(R$_y$)(R$_z$), —N(R$_x$)—OR$_y$, =NR$_x$, =N—OR$_x$, —OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —SO$_2$R$_x$, —SO$_2$N(R$_x$)(R$_y$), a $C_3$-$C_{10}$ cycloalkyl group, a $C_6$-$C_{14}$ aromatic hydrocarbon group, a 4- to 10-membered unsaturated heterocyclic group, or a 4- to 10-membered saturated heterocyclic group, wherein the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each independently optionally substituted by substituent(s) selected from the group consisting of a heavy hydrogen atom, a halogen atom, a hydroxyl group, a cyano group, a nitro group, an amino group, an oxo group, an oxide group, an imino group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group;
$R_b$ represents a heavy hydrogen atom, a halogen atom, a cyano group, a nitro group, an oxo group, an oxide group, —C(=O)OR$_x$, —C(=O)SR$_x$, —C(=S)OR$_x$, —N(R$_x$)(R$_y$), —NR$_x$C(=O)R$_y$, —NR$_x$SO$_2$R$_y$, —NR$_x$C(=O)OR$_y$, —NR$_x$C(=O)N(R$_y$)(R$_x$), —NR$_x$SO$_2$N(R$_y$)(R$_x$), —N(R$_x$)—OR$_y$, =NR$_x$, =N—OR$_x$, —OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —SO$_2$R$_x$, —SO$_2$N(R$_x$)(R$_y$), a $C_1$-$C_6$ alkyl group, a $C_1$-$C_6$ haloalkyl group, a $C_1$-$C_6$ deuterated alkyl group, a $C_2$-$C_6$ alkenyl group, or a $C_2$-$C_6$ alkynyl group;
R₂ represents a hydrogen atom or an optionally $R_a$-substituted $C_1$-$C_6$ alkyl group;
B represents an optionally $R_c$-substituted unsaturated heterocyclic group, with the proviso that B is not a 3,4-methylenedioxyphenyl group;
$R_c$ represents a heavy hydrogen atom, a halogen atom, a cyano group, a nitro group, an oxo group, an oxide group, —C(=O)R$_x$, —C(=O)OR$_x$, —C(=O)N(R$_x$)(R$_y$), —C(=O)SR$_x$, —C(=S)OR$_x$, —N(R$_x$)(R$_y$), —NR$_x$C(=O)R$_y$, —NR$_x$SO$_2$R$_y$, —NR$_x$C(=O)OR$_y$, —NR$_x$C(=O)N(R$_y$)(R$_z$), —NR$_x$SO$_2$N(R$_y$)(R$_z$), —N(R$_x$)—OR$_y$, =NR$_x$, =N—OR$_x$, —OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —SO$_2$R$_x$, —SO$_2$N(R$_x$)(R$_y$), a $C_1$-$C_6$ alkyl group, a $C_1$-$C_6$ haloalkyl group, a $C_1$-$C_6$ deuterated alkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, a 4- to 10-membered unsaturated heterocyclic group, or a 4- to 10-membered saturated heterocyclic group, wherein the $C_1$-$C_6$ alkyl group, the $C_1$-$C_6$ haloalkyl group, the $C_1$-$C_6$ deuterated alkyl group, the $C_2$-$C_6$ alkenyl group, and the $C_2$-$C_6$ alkynyl group are each independently optionally substituted by substituent(s) selected from the group consisting of a cyano group, a nitro group, —N(R$_x$)(R$_y$), and —OR$_x$, and the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each independently optionally substituted by substituent(s) selected from the group consisting of $R_d$, an oxo group, an oxide group, a $C_1$-$C_6$ alkyl group, a $C_1$-$C_6$ haloalkyl group, a $C_1$-$C_6$ deuterated alkyl group, a $C_2$-$C_6$ alkenyl group, and a $C_2$-$C_6$ alkynyl group;
$R_d$ represents a heavy hydrogen atom, a halogen atom, a cyano group, a nitro group, —C(=O)R$_x$, —C(=O)OR$_x$, —C(=O)N(R$_x$)(R$_y$), —C(=O)SR$_x$, —C(=S)OR$_x$, —C(=O)ON(R$_x$)(R$_y$), —N(R$_x$)(R$_y$), —NR$_x$C(=O)R$_y$, —NR$_x$SO$_2$R$_y$, —NR$_x$C(=O)OR$_y$, —NR$_x$C(=O)N(R$_y$)(R$_z$), —NR$_x$SO$_2$N(R$_y$)(R$_z$), —N(R$_x$)—OR$_y$, =NR$_x$, =N—OR$_x$, —OR$_x$, —OC(=O)R$_x$, —OC(=S)R$_x$, —OC(=O)OR$_x$, —OC(=O)N(R$_x$)(R$_y$), —OC(=S)OR$_x$, —SR$_x$, —SO$_2$R$_x$, or —SO$_2$N(R$_x$)(R$_y$); and
$R_x$, $R_y$, and $R_z$ are the same as or different from each other and each represent a hydrogen atom, a $C_1$-$C_6$ alkyl group, a $C_1$-$C_6$ haloalkyl group, a $C_1$-$C_6$ deuterated alkyl group, a $C_2$-$C_6$ alkenyl group, a $C_2$-$C_6$ alkynyl group, a $C_3$-$C_{10}$ cycloalkyl group, a $C_6$-$C_{14}$ aromatic hydrocarbon group, a 4- to 10-membered unsaturated heterocyclic group, or a 4- to 10-membered saturated heterocyclic group.

2. The compound or the salt thereof according to claim 1, wherein R₁ is a hydrogen atom or a $C_1$-$C_6$ alkyl group, and R₂ is a hydrogen atom.

3. The compound or the salt thereof according to claim 1, wherein A is a $C_1$-$C_8$ alkyl group optionally substituted by 1 to 5 identical or different $R_a$, a $C_3$-$C_{10}$ cycloalkyl group optionally substituted by 1 to 3 identical or different $R_b$, or a 4- to 10-membered saturated heterocyclic group optionally substituted by 1 to 3 identical or different $R_b$, or forms a 4- to 10-membered unsaturated heterocyclic ring or a 4- to 10-membered saturated heterocyclic ring together with R₁ and the nitrogen atom bonded thereto, wherein the 4- to 10-membered unsaturated heterocyclic ring and the 4- to 10-membered saturated heterocyclic ring are each optionally substituted by $R_b$.

4. The compound or the salt thereof according to claim 1, wherein B is an optionally $R_c$-substituted 5- or 6-membered monocyclic unsaturated heterocyclic group having 1 to 3 heteroatoms selected from N, S, and O or an optionally $R_c$-substituted 9- or 10-membered bicyclic unsaturated heterocyclic group having 1 to 3 heteroatoms selected from N, S, and O.

5. The compound or the salt thereof according to claim 1, wherein B is a 5- or 6-membered monocyclic unsaturated heterocyclic group having 1 to 3 heteroatoms selected from N, S, and O or a 9- or 10-membered bicyclic unsaturated heterocyclic group having 1 to 3 heteroatoms selected from N, S, and O, wherein the unsaturated heterocyclic group is optionally substituted by 1 to 5 identical or different substituents selected from the group consisting of a halogen atom, a cyano group, an oxide group, a $C_1$-$C_6$ alkyl group, —C(=O) $R_x$, —C(=O)$OR_x$, —C(=O)N($R_x$)($R_y$), a $C_3$-$C_{10}$ cycloalkyl group, a $C_6$-$C_{14}$ aromatic hydrocarbon group, a 4- to 10-membered unsaturated heterocyclic group, or a 4- to 10-membered saturated heterocyclic group, wherein the $C_1$-$C_6$ alkyl group is optionally substituted by $R_d$, and the $C_3$-$C_{10}$ cycloalkyl group, the $C_6$-$C_{14}$ aromatic hydrocarbon group, the 4- to 10-membered unsaturated heterocyclic group, and the 4- to 10-membered saturated heterocyclic group are each optionally substituted by identical or different substituent(s) selected from the group consisting of $R_d$, an oxo group, an oxide group, a $C_1$-$C_6$ alkyl group, a $C_1$-$C_6$ haloalkyl group, a $C_1$-$C_6$ deuterated alkyl group, a $C_1$-$C_6$ alkoxy group, a $C_2$-$C_6$ alkenyl group, and a $C_2$-$C_6$ alkynyl group.

6. The compound or the salt thereof according to claim 1, wherein $R_1$ is a hydrogen atom, A is a $C_1$-$C_8$ alkyl group optionally substituted by 1 to 5 identical or different substituents selected from the group consisting of an amino group and a $C_1$-$C_6$ alkoxy group; a $C_3$-$C_{10}$ cycloalkyl group optionally substituted by an amino group; or a 4- to 10-membered saturated heterocyclic group optionally substituted by an amino group, $R_2$ is a hydrogen atom, B is a halogen atom; a $C_1$-$C_6$ alkyl group optionally substituted by 1 to 5 identical or different substituents selected from the group consisting of a heavy hydrogen atom, a halogen atom, and a hydroxyl group; a $C_3$-$C_{10}$ cycloalkyl group optionally substituted by 1 to 3 hydroxyl groups; a $C_6$-$C_{14}$ aromatic hydrocarbon group; a 4- to 10-membered unsaturated heterocyclic group optionally substituted by 1 to 3 $C_1$-$C_6$ alkyl groups; or a thienyl group, an indolyl group, an indazolyl group, a benzothienyl group, or a quinolyl group optionally substituted by 1 to 5 identical or different substituents selected from the group consisting of a 4- to 10-membered saturated heterocyclic group.

7. The compound or the salt thereof according to claim 1, wherein the compound is selected from the group consisting of:

3-((1R,2S)-2-aminocyclohexylamino)-5-(2-cyclobutyl-2H-indazol-5-ylamino)-1,2,4-triazine-6-carboxamide;

3-(((3R,4R)-3-aminotetrahydro-2H-pyran-4-yl)amino)-5-((2-(tert-butyl)-7-methyl-2H-indazol-5-yl)amino)-1,2,4-triazine-6-carboxamide;

3-(((1R,2S)-2-aminocyclohexyl)amino)-5-((2-(difluoromethyl)-7-methyl-2H-indazol-5-yl)amino)-1,2,4-triazine-6-carboxamide;

3-(((1R,2S)-2-aminocyclohexyl)amino)-5-((1-(1-methyl-1H-pyrazol-4-yl)-1H-indol-4-yl)amino)-1,2,4-triazine-6-carboxamide;

3-(((1R,2S)-2-aminocyclohexyl)amino)-5-((4-(pyrimidin-2-yl)thiophen-2-yl)amino)-1,2,4-triazine-6-carboxamide;

3-(((1R,2S)-2-aminocyclohexyl)amino)-5-((1-(trans-4-hydroxycyclohexyl)-6-methyl-1H-indol-4-yl)amino)-1,2,4-triazine-6-carboxamide;

3-(((1R,2S)-2-aminocyclohexyl)amino)-5-((1-(2-hydroxyethyl)-1H-indol-4-yl)amino)-1,2,4-triazine-6-carboxamide;

3-(((1R,2S)-2-aminocyclohexyl)amino)-5-((1-ethyl-4-methyl-1H-indazol-6-yl)amino)-1,2,4-triazine-6-carboxamide;

3-(((3R,4R)-3-aminotetrahydro-2H-pyran-4-yl)amino)-5-((2-(tert-butyl)-7-chloro-2H-indazol-5-yl)amino)-1,2,4-triazine-6-carboxamide;

3-(((2R,3R)-3-amino-4-methoxybutan-2-yl)amino)-5-((1,6-dimethyl-1H-indol-4-yl)amino)-1,2,4-triazine-6-carboxamide;

3-(((3R,4R)-3-aminotetrahydro-2H-pyran-4-yl)amino)-5-((2-methyl-7-phenyl-2H-indazol-5-yl)amino)-1,2,4-triazine-6-carboxamide;

3-(((1R,2S)-2-aminocyclohexyl)amino)-5-((8-methylquinolin-6-yl)amino)-1,2,4-triazine-6-carboxamide;

3-(((1R,2S)-2-aminocyclohexyl)amino)-5-((2-(difluoromethyl)-4-methyl-2H-indazol-6-yl)amino)-1,2,4-triazine-6-carboxamide;

3-(((2R,3R)-3-amino-4-methoxybutan-2-yl)amino)-5-((1-ethyl-7-methyl-1H-indazol-5-yl)amino)-1,2,4-triazine-6-carboxamide;

3-(((1R,2S)-2-aminocycloheptyl)amino)-5-((2-ethyl-2H-indazol-6-yl)amino)-1,2,4-triazine-6-carboxamide; and 3-(((3R,4R)-3-aminotetrahydro-2H-pyran-4-yl)amino)-5-((7-methylbenzo[b]thiophen-5-yl)amino)-1,2,4-triazine-6-carboxamide.

8. A pharmaceutical composition, comprising:

the compound or the salt thereof according to claim 1 and a pharmaceutically acceptable carrier.

9. A method for treating blood cancer, the method comprising:

administering a therapeutically effective amount of the compound or the salt thereof according to claim 1 to a subject in need thereof.

10. The compound or the salt thereof according to claim 1, which is a salt of a compound selected from the group consisting of:

3-((1R,2S)-2-aminocyclohexylamino)-5-(2-cyclobutyl-2H-indazol-5-ylamino)-1,2,4-triazine-6-carboxamide;

3-(((3R,4R)-3-aminotetrahydro-2H-pyran-4-yl)amino)-5-((2-(tert-butyl)-7-methyl-2H-indazol-5-yl)amino)-1,2,4-triazine-6-carboxamide;

3-(((1R,2S)-2-aminocyclohexyl)amino)-5-((2-(difluoromethyl)-7-methyl-2H-indazol-5-yl)amino)-1,2,4-triazine-6-carboxamide;

3-(((1R,2S)-2-aminocyclohexyl)amino)-5-((1-(1-methyl-1H-pyrazol-4-yl)-1H-indol-4-yl)amino)-1,2,4-triazine-6-carboxamide;

3-(((1R,2S)-2-aminocyclohexyl)amino)-5-((4-(pyrimidin-2-yl)thiophen-2-yl)amino)-1,2,4-triazine-6-carboxamide;

3-(((1R,2S)-2-aminocyclohexyl)amino)-5-((1-(trans-4-hydroxycyclohexyl)-6-methyl-1H-indol-4-yl)amino)-1,2,4-triazine-6-carboxamide;

3-(((1R,2S)-2-aminocyclohexyl)amino)-5-((1-(2-hydroxyethyl)-1H-indol-4-yl)amino)-1,2,4-triazine-6-carboxamide;

3-(((1R,2S)-2-aminocyclohexyl)amino)-5-((1-ethyl-4-methyl-1H-indazol-6-yl)amino)-1,2,4-triazine-6-carboxamide;

3-(((3R,4R)-3-aminotetrahydro-2H-pyran-4-yl)amino)-5-((2-(tert-butyl)-7-chloro-2H-indazol-5-yl)amino)-1,2,4-triazine-6-carboxamide;

3-(((2R,3R)-3-amino-4-methoxybutan-2-yl)amino)-5-((1,6-dimethyl-1H-indol-4-yl)amino)-1,2,4-triazine-6-carboxamide;

3-(((3R,4R)-3-aminotetrahydro-2H-pyran-4-yl)amino)-5-(2-methyl-7-phenyl-2H-indazol-5-yl)amino)-1,2,4-triazine-6-carboxamide;

3-(((1R,2S)-2-aminocyclohexyl)amino)-5-((8-methylquinolin-6-yl)amino)-1,2,4-triazine-6-carboxamide;

3-(((1R,2S)-2-aminocyclohexyl)amino)-5-((2-(difluoromethyl)-4-methyl-2H-indazol-6-yl)amino)-1,2,4-triazine-6-carboxamide;

3-(((2R,3R)-3-amino-4-methoxybutan-2-yl)amino)-5-((1-ethyl-7-methyl-1H-indazol-5-yl)amino)-1,2,4-triazine-6-carboxamide;

3-(((1R,2S)-2-aminocycloheptyl)amino)-5-((2-ethyl-2H-indazol-6-yl)amino)-1,2,4-triazine-6-carboxamide; and 3-(((3R,4R)-3-aminotetrahydro-2H-pyran-4-yl)amino)-5-((7-methylbenzo[b]thiophen-5-yl)amino)-1,2,4-triazine-6-carboxamide.

\* \* \* \* \*